United States Patent
Ackermann et al.

(10) Patent No.: US 7,645,776 B2
(45) Date of Patent: Jan. 12, 2010

(54) HETEROARYL SUBSTITUTED PIPERIDINE DERIVATIVES WHICH ARE L-CPT1 INHIBITORS

(75) Inventors: Jean Ackermann, Riehen (CH); Konrad Bleicher, Freiburg (DE); Simona M. Ceccarelli Grenz, Basel (CH); Odile Chomienne, Altkirch (FR); Patrizio Mattei, Riehen (CH); Tanja Schulz-Gasch, Liestal (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 416 days.

(21) Appl. No.: 11/605,904

(22) Filed: Nov. 29, 2006

(65) Prior Publication Data

US 2007/0129544 A1   Jun. 7, 2007

(30) Foreign Application Priority Data

Dec. 1, 2005   (EP)   ................... 05111560

(51) Int. Cl.
  *C07D 417/14*   (2006.01)
  *C07D 413/12*   (2006.01)
  *A61K 31/541*   (2006.01)
  *A61K 31/5377*   (2006.01)

(52) U.S. Cl. ............ 514/326; 546/209; 546/210
(58) Field of Classification Search ........... 546/209, 546/210; 514/326
    See application file for complete search history.

(56) References Cited

U.S. PATENT DOCUMENTS 5,196,418 A    3/1993   Gandour et al.

FOREIGN PATENT DOCUMENTS

WO    WO 98/00389 A1    1/1998
WO    WO 99/65881 A1    12/1999

OTHER PUBLICATIONS

Jackson et al., 1999, *Biochem. J.* 341, 483-489.
Jackson et al., 2000, *J. Biol. Chem.* 275, 19560-19566.
Anichkov, S.V., et al., Chemical Abstracts XP002420469 & Khimiko-Farmatsevticheskii Zhurnal, vol. 11, No. 1, pp. 35-38 (1977).

*Primary Examiner*—Kahsay T Habte
(74) *Attorney, Agent, or Firm*—George W. Johnston; Dennis P. Tramaloni; Samuel H. Megerditchian

(57) ABSTRACT

The invention is concerned with novel substituted piperidine derivatives of formula (I)

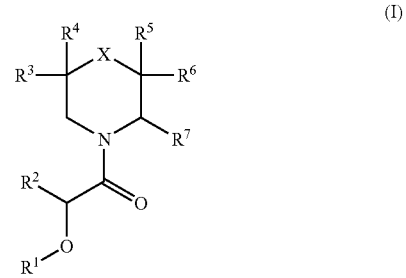

wherein $R^1$, $R^2$, $R^3$, $R^4$, $R^5$, $R^6$, $R^7$ and X are as defined in the description and in the claims, as well as physiologically acceptable salts and esters thereof. These compounds inhibit L-CPT1 and can be used as medicaments.

38 Claims, No Drawings

HETEROARYL SUBSTITUTED PIPERIDINE DERIVATIVES WHICH ARE L-CPT1 INHIBITORS

PRIORITY TO RELATED APPLICATIONS

This application claims the benefit of European Application No. 05111560.8, filed Dec. 1, 2005, which is hereby incorporated by reference in its entirety.

FIELD OF THE INVENTION

The invention is concerned with novel substituted piperidine derivatives of the formula (I)

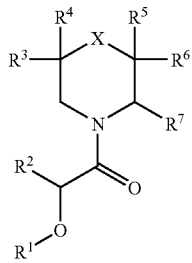

and pharmaceutically acceptable salts and esters thereof.

Further, the invention is concerned with a process for the manufacture of the above compounds, pharmaceutical preparations which contain such compounds as well as the use of these compounds for the production of pharmaceutical preparations.

All documents cited or relied upon below are expressly incorporated herein by reference.

BACKGROUND

High levels of free fatty acids (FFA) lead to an increase of liver mitochondrial β-oxidation, which is crucial to drive efficient gluconeogenesis. The mitochondrial oxidation of long-chain FFA requires the intervention of two membrane-bound carnitine-dependent palmitoyltransferases (CPTs). CPT1, the outer mitochondrial membrane enzyme, catalyzes the formation of long-chain acylcarnitines. Liver (L-CPT1) and muscle (M-CPT1) CPT1 isoforms are encoded by two different genes and inhibited by malonyl-CoA. The N-ter domain of L-CPT1 confers its lower sensitivity to malonyl CoA. CPT2, the inner mitochondrial membrane enzyme, reconverts long-chain acylcarnitines into long-chain acyl CoA esters. Long-chain acyl-CoAs are then β-oxidized to acetyl-CoA, which activates the pyruvate carboxylase and gluconeogenesis. According to the mechanism of action described above, pharmaceutically active substances which inhibit L-CPT1 reduce liver β-oxidation, consequently inhibit gluconeogenesis and therefore counteract hyperglycemia.

SUMMARY OF THE INVENTION

In an embodiment of the present invention, provided is a compound of formula (I):

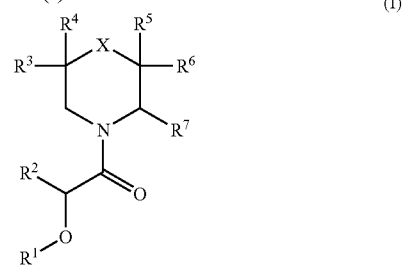

wherein:

X is $C(R^8R^9)$, $NR^{10}$, O, S, S(O), $S(O_2)$;

$R^1$ is phenyl optionally substituted with 1 to 3 substituents selected from the group consisting of halogen, hydroxy, lower-alkyl, hydroxy-lower-alkyl, fluoro-lower-alkyl, lower-alkoxy and CN;

$R^2$ is hydrogen or lower-alkyl;

$R^3$ and $R^4$ independently from each other are hydrogen, halogen, lower-alkyl or lower-alkoxy, or $R^3$ and $R^4$ together are =O to form a carbonyl group together with the carbon atom to which they are attached;

$R^5$ and $R^6$ independently from each other are hydrogen, halogen, lower-alkyl or lower-alkoxy, or $R^5$ and $R^6$ together are =O to form a carbonyl group together with the carbon atom to which they are attached;

$R^7$ is an oxadiazolyl or triazolyl, which oxadiazolyl or triazolyl is substituted with $R^{11}$ and optionally substituted with $R^{12}$;

$R^8$ and $R^9$ independently from each other are hydrogen, halogen, hydroxy, lower-alkyl, lower-alkoxy; or $R^8$ and $R^9$ are bound together and —$R^8$—$R^9$— is —$(CH_2)_{2-7}$— to form a ring together with the carbon atom to which they are attached;

$R^{10}$ is hydrogen, lower-alkyl, lower-alkyl-carbonyl or lower-alkyl-sulfonyl;

$R^{11}$ is aryl or a heteroaryl selected from the group consisting of pyridinyl, pyrazinyl, pyrimidinyl, pyridinyl-2-one, oxadiazolyl, indazolyl, 1,3-dihydro-benzimidazol-2-one, 1,3-dihydro-indol-2-one, benztriazolyl, imidazopyridinyl, triazolepyridinyl, tetrazolepyridinyl, benzimidazolyl, 2-oxo-2,3-dihydro-1H-indol-5-yl, pyrimidin-4-one, furanyl, thiadiazolyl, pyrazolyl, isoxazolyl, pyrimidine-2,4-dione, benzooxazin-3-one, 1,4-dihydro-benzooxazin-2-one, indolyl, thiophenyl, oxazolyl, benzooxazin-2-one, 3,4-dihydro-quinazolin-2-one, pyridazinyl, quinoxalinyl, benzothiazolyl, benzothiadiazolyl, naphthyridinyl, cinnolinyl, 1,4-dihydro-quinoxaline-2,3-dione and 1,2-dihydro-indazol-3-one, which aryl or heteroaryl is optionally substituted with 1 to 3 substituents selected from the group consisting of lower-alkyl, hydroxy, $B(OH)_2$, carboxy-lower-alkoxy, carbamoyl-lower-alkoxy, cyano, hydroxy-lower-alkyl, fluoro-lower-alkyl, lower-alkoxy, halogen, $S(O_2)R^{13}$, $C(O)R^{14}$, $NO_2$, $NR^{15}R^{16}$, imidazolyl, pyrazolyl, tetrazolyl, pyrrolyl, phenyl-lower-alkoxy, [1,3,4] oxadiazol-2-one, oxadiazolyl, triazolyl and isoxazolyl, which imidazolyl is optionally substituted with lower-alkyl, and which phenyl-lower-alkoxy is optionally substituted with hydroxy, halogen, lower-alkyl, lower-alkoxy or fluoro-lower-alkyl, and which pyrazolyl is optionally substituted with lower-alkyl, and which isoxazolyl is optionally substituted with lower-alkyl;

$R^{12}$ is hydrogen or lower-alkyl;

$R^{13}$ is lower-alkyl, $NR^{17}R^{18}$ or fluoro-lower-alkyl;

$R^{14}$ is OH, $NR^{19}R^{20}$, lower-alkoxy, lower-alkenyl-oxy or lower-alkyl;

$R^{15}$ and $R^{16}$ independently from each other are hydrogen, lower-alkyl, lower-alkyl-carbonyl, lower-alkyl-$SO_2$, lower-alkenyl-oxy-carbonyl, $NH_2$-carbonyl, lower-alkyl-NH-carbonyl, (lower-alkyl)$_2$N-carbonyl or phenyl-lower-alkyl, which phenyl-lower-alkyl is optionally substituted with hydroxy, halogen, lower-alkyl, lower-alkoxy or fluoro-lower-alkyl; or $NR^{15}R^{16}$ is a heterocyclyl selected from the group consisting of morpholinyl, thiomorpholinyl, 1,1-dioxo-thiomorpholinyl, piperidinyl, piperidin-2-one, piperazin-2-one, 8-oxa-3-aza-bicyclo[3.2.1]octyl, piperazinyl, pyrrolidinyl, 1,1-dioxo-isothiazolidinyl, pyrrolidin-2-one, imidazolidine-2,4-dione, 2,4-dihydro[1,2,4]triazol-3-one, pyrrolidine-2,5-dione, azetidin-2-one and 1,3-dihydro-imidazol-2-one, which heterocyclyl is optionally substituted with hydroxy-lower-alkyl or lower-alkyl-carbonyl;

$R^{17}$ and $R^{18}$ independently from each other are hydrogen, lower-alkyl, hydroxy-lower-alkyl, lower-alkoxy-lower-alkyl; or $NR^{17}R^{18}$ is morpholinyl;

$R^{19}$ and $R^{20}$ independently from each other are hydrogen, lower-alkyl, cycloalkyl, hydroxy-lower-alkyl, lower-alkoxy-lower-alkyl, (lower-alkyl)$_2$N-lower-alkyl, pyridinyl-lower-alkyl or cyano-lower-alkyl; or $NR^{19}R^{20}$ is a heterocyclyl selected from the group consisting of morpholinyl, pyrrolidinyl, 8-oxa-3-aza-bicyclo[3.2.1] octyl, piperidinyl, piperazinyl, piperazin-2-one, thiazolidinyl, thiomorpholinyl, 1,3,8-triaza-spiro[4,5]decane-2,4-dione and spiro(1-phtalan)-piperidine-4-yl, which heterocyclyl is optionally substituted with hydroxy, lower-alkyl-S($O_2$), lower-alkyl, lower-alkyl-carbonyl, carboxy, carbamoyl, lower-alkoxy-carbonyl, cyano, phenyl, pyridinyl or lower-alkoxy;

and pharmaceutically acceptable salts and esters thereof.

In another embodiment of the present invention, provided is a process for the manufacture of a compound according to formula (I), comprising the step of reacting a compound of formula (II)

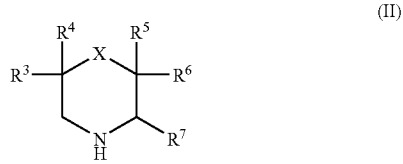

(II)

with a compound of formula (III)

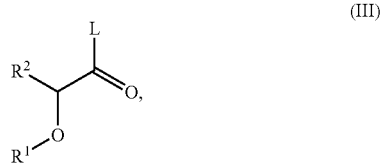

(III)

wherein $R^1$, $R^2$, $R^3$, $R^4$, $R^5$, $R^6$, $R^7$, and X are as defined in the compound of formula (I) and L is halogen.

In a further embodiment of the present invention, provided is a pharmaceutical composition, comprising a therapeutically effective amount of a compound according to formula (I) and a pharmaceutically acceptable carrier and/or adjuvant.

In a still another embodiment of the present invention, provided is a method for the treatment of diseases which are modulated by L-CPT1 inhibitors, comprising the step of administering a therapeutically effective amount of a compound according to formula (I) to a human being or animal in need thereof.

DETAILED DESCRIPTION

The present invention relates to novel compounds which inhibit liver carnitine palmitoyl transferase 1 (L-CPT1) activity. The compounds of the present invention can be used as pharmaceutically active agents which are useful in the prevention and/or treatment of diseases which are modulated by L-CPT1 inhibitors, particularly diseases which are related to hyperglycemia and/or glucose tolerance disorders. Such diseases include e.g. diabetes and associated pathologies, non insulin dependent diabetes mellitus (also referred to as diabetes type II), obesity, hypertension, insulin resistance syndrome, metabolic syndrome, hyperlipidemia, hypercholesterolemia, fatty liver disease, atherosclerosis, congestive heart failure and renal failure.

Unless otherwise indicated, the following definitions are set forth to illustrate and define the meaning and scope of the various terms used to describe the invention herein.

In this specification the term "lower" is used to mean a group consisting of one to seven, preferably of one to four carbon atom(s).

The term "halogen" refers to fluorine, chlorine, bromine and iodine, with fluorine, chlorine and bromine being preferred.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms. Lower-alkyl groups as described below also are preferred alkyl groups.

The term "lower-alkyl", alone or in combination with other groups, refers to a branched or straight-chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the like. The term "hydroxy-lower-alkyl" refers to a lower-alkyl group which is substituted with hydroxy.

The term "fluoro-lower-alkyl" refers to lower-alkyl groups which are mono- or multiply substituted with fluorine. Examples of fluoro-lower-alkyl groups are e.g. $CFH_2$, $CF_2H$, $CF_3$, $CF_3CH_2$, $CF_3(CH_2)_2$, $(CF_3)_2CH$ and $CF_2H-CF_2$.

The term "alkoxy" refers to the group R'—O—, wherein R' is an alkyl. The term "lower-alkoxy" refers to the group R'—O—, wherein R' is a lower-alkyl.

The term "fluoro-lower-alkoxy" refers to the group R"—O—, wherein R" is fluoro-lower-alkyl.

Examples of fluoro-lower-alkoxy groups are e.g. $CFH_2$—O, $CF_2H$—O, $CF_3$—O, $CF_3CH_2$—O, $CF_3(CH_2)_2$—O, $(CF_3)_2CH$—O, and $CF_2H$—$CF_2$—O.

The term "alkenyl", alone or in combination with other groups, stands for a straight-chain or branched hydrocarbon residue comprising an olefinic bond and up to 20, preferably up to 16 carbon atoms. The term "lower-alkenyl" refers to a straight-chain or branched hydrocarbon residue comprising an olefinic bond and up to 7, preferably up to 4 carbon atoms, such as e.g. 2-propenyl.

The term "alkinyl", alone or in combination with other groups, stands for a straight-chain or branched hydrocarbon residue comprising a triple bond and up to 20, preferably up to 16 carbon atoms. The term "lower-alkinyl" refers to a straight-chain or branched hydrocarbon residue comprising a triple bond and up to 7, preferably up to 4 carbon atoms, such as e.g. 2-propinyl.

The term "alkylene" refers to a straight chain or branched divalent saturated aliphatic hydrocarbon group of 1 to 20 carbon atoms, preferably 1 to 16 carbon atoms, more preferably up to 10 carbon atoms. Lower-alkylene groups as described below also are preferred alkylene groups.

The term "lower-alkylene" refers to a straight chain or branched divalent saturated aliphatic hydrocarbon group of 1 to 7, preferably 1 to 6 or 3 to 6 carbon atoms. Straight chain alkylene or lower-alkylene groups are preferred.

The term "cycloalkyl" refers to a monovalent carbocyclic radical of 3 to 10 carbon atoms, preferably 3 to 6 carbon atoms, such as cyclopropyl, cyclobutyl, cyclopentyl, or cyclohexyl.

The term "aryl", alone or in combination, relates to the phenyl or naphthyl group, preferably the phenyl group, which can optionally be substituted by 1 to 5, preferably 1 to 3, substituents independently selected from the group consisting of halogen, hydroxy, amino, $NO_2$, lower-alkyl, hydroxy-lower-alkyl, lower-alkoxy, carboxy, carboxy-lower-alkyl, lower-alkoxy-carbonyl, lower-alkoxy-carbonyl-lower-alkyl, lower-alkylcarbonyl, lower-alkylcarbonyloxy, lower-alkyl-carbonyl-NH, $H_2NC(O)$, (H,lower-alkyl)NC(O), (lower-alkyl)$_2$NC(O), $H_2NC(O)$-lower-alkyl, (H,lower-alkyl)NC(O)-lower-alkyl, (lower-alkyl)$_2$NC(O)-lower-alkyl, fluoro-lower-alkyl, fluoro-lower-alkoxy, $H_2N$-lower-alkyl, (H,lower-alkyl)N-lower-alkyl, (lower-alkyl)$_2$N-lower-alkyl, lower-alkyl-$SO_2$, lower-alkyl-$SO_2O$, lower-alkyl-$SO_2$—NH, lower-alkyl-$SO_2$—N(lower-alkyl), $H_2NSO_2$, (H,lower-alkyl)$NSO_2$, (lower-alkyl)$_2NSO_2$, dioxo-lower-alkylene (forming e.g. a benzodioxyl group), cyano, heteroaryl, cycloalkyl, lower-alkoxy-lower-alkyl, lower-alkenyl, lower-alkinyl, phenyl and phenyloxy. Of the above mentioned substituents, halogen, lower-alkyl, fluoro-lower-alkyl, lower-alkoxy and fluoro-lower-alkoxy are preferred. Furthermore and more preferably, aryl groups can be substituted as described in the description below.

The term "heteroaryl" refers to an aromatic 5 to 6 membered monocyclic ring or 9 to 10 membered bicyclic ring which can comprise 1, 2 or 3 atoms selected from nitrogen, oxygen and/or sulphur, such as furyl, pyridinyl, pyridazinyl, pyrimidinyl, pyrazinyl, thienyl, isoxazolyl, oxazolyl, oxadiazolyl, imidazolyl, pyrrolyl, pyrazolyl, triazolyl, tetrazolyl, thiazolyl, isothiazolyl, 1,2,3-thiadiazolyl, benzimidazolyl, indolyl, indazolyl, benzoisothiazolyl, benzoxazolyl, benzoisoxazolyl, pyridinyl-2-one, oxadiazolyl, 1,3-dihydro-benzimidazol-2-one, 1,3-dihydro-indol-2-one, benztriazolyl, imidazopyridinyl, triazolepyridinyl and tetrazolepyridinyl. Other possible heteroaryl are 2-oxo-2,3-dihydro-1H-indol-5-yl, pyrimidin-4-one, furanyl, thiadiazolyl, pyrazolyl, isoxazolyl, pyrimidine-2,4-dione, benzooxazin-3-one, 1,4-dihydro-benzooxazin-2-one, indolyl, thiophenyl, oxazolyl, benzooxazin-2-one, 3,4-dihydro-quinazolin-2-one, pyridazinyl, quinoxalinyl, benzothiazolyl, benzothiadiazolyl, naphthyridinyl, cinnolinyl, 1,4-dihydro-quinoxaline-2,3-dione and 1,2-dihydro-indazol-3-one. A heteroaryl group may optionally have a substitution pattern as described earlier in connection with the term "aryl". Furthermore, heteroaryl groups can preferably be substituted as described in the description below.

The term "heterocyclyl" refers to 5 to 6 membered monocyclic ring or 8 to 14, preferably 8 to 10, membered bi- or tricyclic ring which can comprise 1, 2 or 3 atoms selected from nitrogen, oxygen and/or sulphur, such as morpholinyl, thiomorpholinyl, 1,1-dioxo-thiomorpholinyl, piperidinyl, piperidin-2-one, piperazin-2-one, 8-oxa-3-aza-bicyclo[3.2.1]octyl, piperazinyl and pyrrolidinyl. Other possible heterocyclyl are 1,1-dioxo-isothiazolidinyl, pyrrolidin-2-one, imidazolidine-2,4-dione, 2,4-dihydro[1,2,4]triazol-3-one, pyrrolidine-2,5-dione, azetidin-2-one, 1,3-dihydro-imidazol-2-one, thiazolidinyl, 1,3,8-triaza-spiro[4,5]decane-2,4-dione and spiro(1-phtalan)-piperidine-4-yl. A heterocyclyl may optionally have a substitution pattern as described earlier in connection with the term "aryl". Furthermore, heterocyclyl groups can preferably be substituted as described in the description below.

Compounds of formula (I) wherein an amino group is present can form pharmaceutically acceptable acid addition salts. Examples of such pharmaceutically acceptable salts are salts of compounds of formula (I) with physiologically compatible mineral acids, such as hydrochloric acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts. Compounds of formula (I) in which a COOH group is present can further form salts with bases. Examples of such salts are alkaline, earth-alkaline and ammonium salts such as e.g. Na—, K—, Ca— and Trimethylammonium salt. The term "pharmaceutically acceptable salts" also refers to such salts. Salts obtained by the addition of an acid are preferred.

The term "pharmaceutically acceptable esters" embraces derivatives of the compounds of formula (I), in which a carboxy group has been converted to an ester. Lower-alkyl, hydroxy-lower-alkyl, lower-alkoxy-lower-alkyl, amino-lower-alkyl, mono- or di-lower-alkyl-amino-lower-alkyl, morpholino-lower-alkyl, pyrrolidino-lower-alkyl, piperidino-lower-alkyl, piperazino-lower-alkyl, lower-alkyl-piperazino-lower-alkyl and aralkyl esters are examples of suitable esters. The methyl, ethyl, propyl, butyl and benzyl esters are preferred esters. The term "pharmaceutically acceptable esters" furthermore embraces compounds of formula (I) in which hydroxy groups have been converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

In detail, the present invention relates to compounds of formula (I)

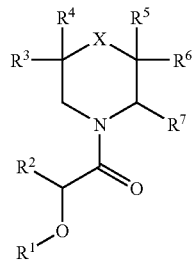

wherein

X is C(R$^8$R$^9$), NR$^{10}$, O, S, S(O), S(O$_2$);
R$^1$ is phenyl optionally substituted with 1 to 3 substituents selected from the group consisting of halogen, hydroxy, lower-alkyl, hydroxy-lower-alkyl, fluoro-lower-alkyl, lower-alkoxy and CN;
R$^2$ is hydrogen or lower-alkyl;
R$^3$ and R$^4$ independently from each other are hydrogen, halogen, lower-alkyl or lower-alkoxy, or R$^3$ and R$^4$ together are =O to form a carbonyl group together with the carbon atom to which they are attached;
R$^5$ and R$^6$ independently from each other are hydrogen, halogen, lower-alkyl or lower-alkoxy, or R$^5$ and R$^6$ together are =O to form a carbonyl group together with the carbon atom to which they are attached;
R$^7$ is an oxadiazolyl or triazolyl, which oxadiazolyl or triazolyl is substituted with R$^{11}$ and optionally substituted with R$^{12}$;
R$^8$ and R$^9$ independently from each other are hydrogen, halogen, hydroxy, lower-alkyl, lower-alkoxy; or
R$^8$ and R$^9$ are bound together and —R$^8$—R$^9$— is —(CH$_2$)$_{2-7}$— to form a ring together with the carbon atom to which they are attached;
R$^{10}$ is hydrogen, lower-alkyl, lower-alkyl-carbonyl or lower-alkyl-sulfonyl;
R$^{11}$ is aryl or a heteroaryl selected from the group consisting of pyridinyl, pyrazinyl, pyrimidinyl, pyridinyl-2-one, oxadiazolyl, indazolyl, 1,3-dihydro-benzimidazol-2-one, 1,3-dihydro-indol-2-one, benztriazolyl, imidazopyridinyl, triazolepyridinyl,tetrazolepyridinyl, benzimidazolyl, 2-oxo-2,3-dihydro-1H-indol-5-yl, pyrimidin-4-one, furanyl, thiadiazolyl, pyrazolyl, isoxazolyl, pyrimidine-2,4-dione, benzooxazin-3-one, 1,4-dihydro-benzooxazin-2-one, indolyl, thiophenyl, oxazolyl, benzooxazin-2-one, 3,4-dihydro-quinazolin-2-one, pyridazinyl, quinoxalinyl, benzothiazolyl, benzothiadiazolyl, naphthyridinyl, cinnolinyl, 1,4-dihydro-quinoxaline-2,3-dione and 1,2-dihydro-indazol-3-one, which aryl or heteroaryl is optionally substituted with 1 to 3 substituents selected from the group consisting of lower-alkyl, hydroxy, B(OH)$_2$, carboxy-lower-alkoxy, carbamoyl-lower-alkoxy, cyano, hydroxy-lower-alkyl, fluoro-lower-alkyl, lower-alkoxy, halogen, S(O$_2$)R$^{13}$, C(O)R$^{14}$, NO$_2$, NR$^{15}$R$^{16}$, imidazolyl, pyrazolyl, tetrazolyl, pyrrolyl, phenyl-lower-alkoxy, [1,3,4]oxadiazol-2-one, oxadiazolyl, triazolyl and isoxazolyl, which imidazolyl is optionally substituted with lower-alkyl, and which phenyl-lower-alkoxy is optionally substituted with hydroxy, halogen, lower-alkyl, lower-alkoxy or fluoro-lower-alkyl, and which pyrazolyl is optionally substituted with lower-alkyl, and which isoxazolyl is optionally substituted with lower-alkyl;
R$^{12}$ is hydrogen or lower-alkyl;
R$^{13}$ is lower-alkyl, NR$^{17}$R$^{18}$ or fluoro-lower-alkyl;
R$^{14}$ is OH, NR$^{19}$R$^{20}$, lower-alkoxy, lower-alkenyl-oxy or lower-alkyl;
R$^{15}$ and R$^{16}$ independently from each other are hydrogen, lower-alkyl, lower-alkyl-carbonyl, lower-alkyl-SO$_2$, lower-alkenyl-oxy-carbonyl, NH$_2$-carbonyl, lower-alkyl-NH-carbonyl, (lower-alkyl)$_2$N-carbonyl or phenyl-lower-alkyl, which phenyl-lower-alkyl is optionally substituted with hydroxy, halogen, lower-alkyl, lower-alkoxy or fluoro-lower-alkyl; or
NR$^{15}$R$^{16}$ is a heterocyclyl selected from the group consisting of morpholinyl, thiomorpholinyl, 1,1-dioxo-thiomorpholinyl, piperidinyl, piperidin-2-one, piperazin-2-one, 8-oxa-3-aza-bicyclo[3.2.1]octyl, piperazinyl, pyrrolidinyl, 1,1-dioxo-isothiazolidinyl, pyrrolidin-2-one, imidazolidine-2,4-dione, 2,4-dihydro[1,2,4]triazol-3-one, pyrrolidine-2,5-dione, azetidin-2-one and 1,3-dihydro-imidazol-2-one, which heterocyclyl is optionally substituted with hydroxy-lower-alkyl or lower-alkyl-carbonyl;
R$^{17}$ and R$^{18}$ independently from each other are hydrogen, lower-alkyl, hydroxy-lower-alkyl, lower-alkoxy-lower-alkyl; or
NR$^{17}$R$^{18}$ is morpholinyl;
R$^{19}$ and R$^{20}$ independently from each other are hydrogen, lower-alkyl, cycloalkyl, hydroxy-lower-alkyl, lower-alkoxy-lower-alkyl, (lower-alkyl)$_2$N-lower-alkyl, pyridinyl-lower-alkyl or cyano-lower-alkyl; or
NR$^{19}$R$^{20}$ is a heterocyclyl selected from the group consisting of morpholinyl, pyrrolidinyl, 8-oxa-3-aza-bicyclo[3.2.1]octyl, piperidinyl, piperazinyl, piperazin-2-one, thiazolidinyl, thiomorpholinyl, 1,3,8-triaza-spiro[4,5]decane-2,4-dione and spiro(1-phtalan)-piperidine-4-yl, which heterocyclyl is optionally substituted with hydroxy, lower-alkyl-S(O$_2$), lower-alkyl, lower-alkyl-carbonyl, carboxy, carbamoyl, lower-alkoxy-carbonyl, cyano, phenyl, pyridinyl or lower-alkoxy;

and pharmaceutically acceptable salts and esters thereof.

Compounds of formula (I) are individually preferred and physiologically acceptable salts thereof are individually preferred and pharmaceutically acceptable esters thereof are individually preferred, with the compounds of formula (I) being particularly preferred.

The compounds of formula (I) can have one or more asymmetric C atoms and can therefore exist as an enantiomeric mixture, mixture of stereoisomers or as optically pure compounds.

Preferred compounds of formula (I) as described above are those, wherein

X is C(R$^8$R$^9$), NR$^{10}$, O, S, S(O), S(O$_2$);
R$^1$ is phenyl optionally substituted with 1 to 3 substituents selected from the group consisting of halogen, hydroxy, lower-alkyl, hydroxy-lower-alkyl, fluoro-lower-alkyl, lower-alkoxy and CN;
R$^2$ is hydrogen or lower-alkyl;
R$^3$ and R$^4$ independently from each other are hydrogen, halogen, lower-alkyl or lower-alkoxy, or R$^3$ and R$^4$ together are =O to form a carbonyl group together with the carbon atom to which they are attached;
R$^5$ and R$^6$ independently from each other are hydrogen, halogen, lower-alkyl or lower-alkoxy, or R$^5$ and R$^6$ together are =O to form a carbonyl group together with the carbon atom to which they are attached;

R$^7$ is an oxadiazolyl or triazolyl, which oxadiazolyl or triazolyl is substituted with R$^{11}$ and optionally substituted with R$^{12}$;

R$^8$ and R$^9$ independently from each other are hydrogen, halogen, hydroxy, lower-alkyl, lower-alkoxy; or R$^8$ and R$^9$ are bound together and —R$^8$—R$^9$— is —(CH$_2$)$_{2-7}$— to form a ring together with the carbon atom to which they are attached;

R$^{10}$ is hydrogen, lower-alkyl, lower-alkyl-carbonyl or lower-alkyl-sulfonyl;

R$^{11}$ is aryl or a heteroaryl selected from the group consisting of pyridinyl, pyrazinyl, pyrimidinyl, pyridinyl-2-one, oxadiazolyl, indazolyl, 1,3-dihydro-benzimidazol-2-one, 1,3-dihydro-indol-2-one, benztriazolyl, imidazopyridinyl, triazolepyridinyl, tetrazolepyridinyl and benzimidazolyl, which aryl or heteroaryl is optionally substituted with 1 to 3 substituents selected from the group consisting of lower-alkyl, hydroxy-lower-alkyl, fluoro-lower-alkyl, lower-alkoxy, halogen, S(O$_2$)R$^{13}$, C(O)R$^{14}$, NO$_2$, NR$^{15}$R$^{16}$, imidazolyl, pyrazolyl, tetrazolyl, pyrrolyl, and phenyl-lower-alkoxy, which imidazolyl is optionally substituted with lower-alkyl and which phenyl-lower-alkoxy is optionally substituted with hydroxy, halogen, lower-alkyl, lower-alkoxy or fluoro-lower-alkyl;

R$^{12}$ is hydrogen or lower-alkyl;

R$^{13}$ is lower-alkyl, NR$^{17}$R$^{18}$ or fluoro-lower-alkyl;

R$^{14}$ is OH, NR$^{19}$R$^{20}$, lower-alkoxy or lower-alkenyl-oxy;

R$^{15}$ and R$^{16}$ independently from each other are hydrogen, lower-alkyl, lower-alkyl-carbonyl, lower-alkyl-SO$_2$, lower-alkenyl-oxy-carbonyl, NH$_2$-carbonyl, lower-alkyl-NH-carbonyl, (lower-alkyl)$_2$N-carbonyl or phenyl-lower-alkyl, which phenyl-lower-alkyl is optionally substituted with hydroxy, halogen, lower-alkyl, lower-alkoxy or fluoro-lower-alkyl; or NR$^{15}$R$^{16}$ is a heterocyclyl selected from the group consisting of morpholinyl, thiomorpholinyl, 1,1-dioxo-thiomorpholinyl, piperidinyl, piperidin-2-one, piperazin-2-one, 8-oxa-3-aza-bicyclo[3.2.1]octyl, piperazinyl and pyrrolidinyl, which heterocyclyl is optionally substituted with hydroxy-lower-alkyl or lower-alkyl-carbonyl;

R$^{17}$ and R$^{18}$ independently from each other are hydrogen, lower-alkyl, hydroxy-lower-alkyl, lower-alkoxy-lower-alkyl; or NR$^{17}$R$^{18}$ is morpholinyl;

R$^{19}$ and R$^{20}$ independently from each other are hydrogen, lower-alkyl, cycloalkyl, hydroxy-lower-alkyl or lower-alkoxy-lower-alkyl; or NR$^{19}$R$^{20}$ is a heterocyclyl selected from the group consisting of morpholinyl, pyrrolidinyl and 8-oxa-3-aza-bicyclo[3.2.1]octyl, which heterocyclyl is optionally substituted with hydroxy or lower-alkyl-S(O$_2$);

and pharmaceutically acceptable salts and esters thereof.

Preferred compounds of formula (I) as described above are those, wherein R$^1$ is phenyl optionally substituted with halogen, hydroxy, hydroxy-lower-alkyl or CN, more preferably those wherein R$^1$ is phenyl.

Other preferred compounds are those, wherein R$^2$ is hydrogen. Further preferred compounds are those, wherein R$^3$ is hydrogen. Still other preferred compounds are those, wherein R$^4$ is hydrogen. Other preferred compounds are those, wherein R$^5$ is hydrogen. Compounds wherein R$^6$ is hydrogen are also preferred.

Preferably, R$^7$ which are an oxadiazolyl are not substituted with R$^{12}$. In a preferred embodiment of the present invention, R$^7$ is

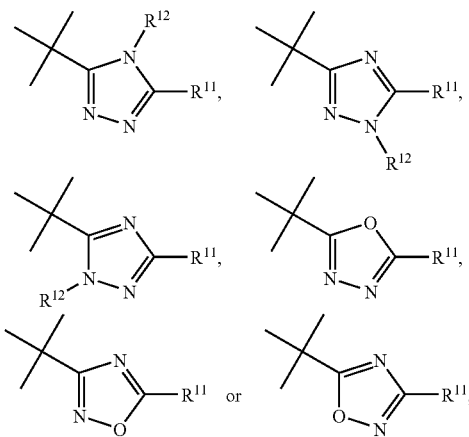

wherein R$^{11}$ and R$^{12}$ are as defined above. Preferably, R$^7$ is

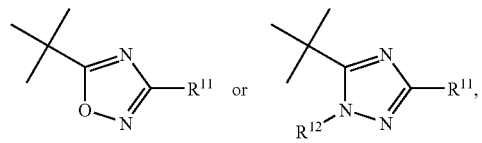

wherein R$^{11}$ and R$^{12}$ are as defined in claim 1.

Furthermore, it is preferred that R$^7$ is

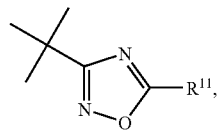

wherein R$^{11}$ is as defined above.

Preferred compounds of formula (I) as described above are those, wherein X is C(R$^8$R$^9$), NR$^{10}$, O or S, wherein R$^8$, R$^9$ and R$^{10}$ are as defined above. Preferably, X is C(R$^8$R$^9$) or NR$^{10}$, wherein R$^8$, R$^9$ and R$^{10}$ are as defined above.

In the compounds as defined above, it is preferred that R$^8$ is hydrogen. Preferably, R$^9$ is hydrogen. It is also preferred, that R$^{10}$ is hydrogen.

Another preferred embodiment of the present invention refers to compounds as defined above, wherein R$^{11}$ is phenyl or a heteroaryl selected from the group consisting of pyridinyl, pyrazinyl, pyridinyl-2-one, indazolyl, 1,3-dihydro-benzimidazol-2-one, 1,3-dihydro-indol-2-one, benztriazolyl and benzimidazolyl, which phenyl or heteroaryl is optionally substituted with 1 to 2 substituents selected from the group consisting of lower-alkyl, hydroxy-lower-alkyl, fluoro-lower-alkyl, lower-alkoxy, halogen, S(O$_2$)R$^{13}$, C(O)R$^{14}$, NO$_2$, NR$^{15}$R$^{16}$, imidazolyl, pyrazolyl, tetrazolyl, pyrrolyl, and phenyl-lower-alkoxy, which imidazolyl is optionally substituted with lower-alkyl, wherein R$^{13}$, R$^{14}$, R$^{15}$ and R$^{16}$ are as defined above.

Preferably, R$^{11}$ is phenyl or a heteroaryl selected from the group consisting of pyridinyl, pyridinyl-2-one, indazolyl, 1,3-dihydro-benzimidazol-2-one, 1,3-dihydro-indol-2-one, benztriazolyl and benzimidazolyl, which phenyl or heteroaryl is optionally substituted with 1 to 2 substituents selected from the group consisting of fluoro-lower-alkyl, halogen, C(O)R$^{14}$ and NR$^{15}$R$^{16}$, wherein R$^{14}$, R$^{15}$ and R$^{16}$ are as defined above.

More preferably, R$^{11}$ is 1H-Indazol-5-yl, 1H-Indazol-6-yl, 1,3-dihydro-indol-2-one-6-yl, 1,3-dihydro-benzoimidazol-2-one-5-yl, 1,3-dihydro-indol-2-one-5-yl, 1H-Benzotriazol-5-yl, 1H-Benzoimidazol-5-yl, 1H-pyridin-2-one-4-yl, 4-Fluoro-phenyl, 3-trifluoromethyl-phenyl, 1H-Benzoimidazol-5-yl, 3-benzamide, 5-nicotinamide, 3-(N-acetamide)-phenyl or 3-(N-methanesulfonamide)-phenyl.

Another preferred embodiment of the present invention refers to compounds as defined above, wherein R$^{11}$ is phenyl or a heteroaryl selected from the group consisting of 2-oxo-2,3-dihydro-1H-indol-5-yl, pyrimidin-4-one, furanyl, thiadiazolyl, pyrazolyl, isoxazolyl, pyrimidine-2,4-dione, benzooxazin-3-one, 1,4-dihydro-benzooxazin-2-one, indolyl, thiophenyl, oxazolyl, benzooxazin-2-one, 3,4-dihydro-quinazolin-2-one, pyridazinyl, quinoxalinyl, benzothiazolyl, benzothiadiazolyl, naphthyridinyl, cinnolinyl, 1,4-dihydro-quinoxaline-2,3-dione and 1,2-dihydro-indazol-3-one, which phenyl or heteroaryl is optionally substituted with 1 to 3 substituents selected from the group consisting of hydroxy, B(OH)$_2$, carboxy-lower-alkoxy, carbamoyl-lower-alkoxy, cyano, [1,3,4]oxadiazol-2-one, oxadiazolyl, triazolyl and isoxazolyl, which pyrazolyl is optionally substituted with lower-alkyl, and which isoxazolyl is optionally substituted with lower-alkyl.

Preferably, R$^{11}$ is phenyl or a heteroaryl selected from the group consisting of pyridinyl, 1,3-dihydro-indol-2-one, 1H-benzimidazolyl, 3H-pyrimidin-4-one, 1H-pyrazolyl, isoxazolyl and 4H-benzo[1,4]oxazin-3-one, which phenyl or heteroaryl is optionally substituted with 1 to 3 substituents selected from the group consisting of lower-alkyl, hydroxy, halogen and NR$^{15}$R$^{16}$, wherein R$^{14}$ and R$^{15}$ are as defined in claim 1.

More preferably, R$^{11}$ is 2-methyl-3H-pyrimidin-4-one, 5-methyl-isoxazol-3-yl, 1H-pyrazol-3-yl, 6-amino-pyridin-3-yl, 1,3-dihydro-indol-2-one, 2-amino-pyridin-4-yl, 4H-benzo[1,4]oxazin-3-one, 1H-benzimidazol-5-yl, 3-(N-acetamide)-4-fluoro-phenyl or 2-hydroxy-pyridin-4-yl.

Preferably, R$^{12}$ is hydrogen. Compounds as defined above, wherein R$^{13}$ is lower-alkyl are also preferred. Other preferred compounds are those, wherein R$^{14}$ is NR$^{19}$R$^{20}$, wherein R$^{19}$ and R$^{20}$ are as defined above. Other preferred compounds are those, wherein R$^{14}$ is lower-alkyl.

Another preferred embodiment of the present invention refers to compounds as defined above, wherein R$^{15}$ and R$^{16}$ independently from each other are hydrogen, lower-alkyl, lower-alkyl-carbonyl, lower-alkyl-SO$_2$, lower-alkenyl-oxycarbonyl or lower-alkyl-NH-carbonyl; or NR$^{15}$R$^{16}$ is a heterocyclyl selected from the group consisting of morpholinyl, thiomorpholinyl, 1,1-dioxo-thiomorpholinyl, piperidinyl, piperidin-2-one, piperazin-2-one, piperazinyl and pyrrolidinyl, which heterocyclyl is optionally substituted with hydroxy-lower-alkyl or lower-alkyl-carbonyl. More preferably, R$^{15}$ and R$^{16}$ independently from each other are hydrogen, lower-alkyl-carbonyl or lower-alkyl-SO$_2$.

Other preferred compounds are those, wherein NR$^{15}$R$^{16}$ is a heterocyclyl selected from the group consisting of 1,1-dioxo-isothiazolidinyl, pyrrolidin-2-one, imidazolidine-2,4-dione, 2,4-dihydro[1,2,4]triazol-3-one, pyrrolidine-2,5-dione, azetidin-2-one and 1,3-dihydro-imidazol-2-one, which heterocyclyl is optionally substituted with hydroxy-lower-alkyl or lower-alkyl-carbonyl.

Other preferred compounds are those, wherein R$^{17}$ and R$^{18}$ independently from each other are hydrogen or lower-alkyl; or NR$^{17}$R$^{18}$ is morpholinyl.

Further preferred compounds as defined above are those, wherein R$^{19}$ and R$^{20}$ independently from each other are hydrogen, lower-alkyl, cycloalkyl, hydroxy-lower-alkyl, lower-alkoxy-lower-alkyl; or NR$^{19}$R$^{20}$ is a heterocyclyl selected from the group consisting of morpholinyl or pyrrolidinyl, which heterocyclyl is optionally substituted with hydroxy or lower-alkyl-S(O$_2$). More preferably, R$^{19}$ and R$^{20}$ are hydrogen.

Other preferred compounds are those, wherein R$^{19}$ and R$^{20}$ independently from each other are (lower-alkyl)$_2$N-lower-alkyl, pyridinyl-lower-alkyl or cyano-lower-alkyl; or NR$^{19}$R$^{20}$ is a heterocyclyl selected from the group consisting of piperidinyl, piperazinyl, piperazin-2-one, thiazolidinyl, thiomorpholinyl, 1,3,8-triaza-spiro[4,5]decane-2,4-dione and spiro(1-phtalan)-piperidine-4-yl, which heterocyclyl is optionally substituted with hydroxy, lower-alkyl-S(O$_2$), lower-alkyl, lower-alkyl-carbonyl, carboxy, carbamoyl, lower-alkoxy-carbonyl, cyano, phenyl, pyridinyl or lower-alkoxy.

Preferred compounds of formula (I) as defined above are those, which are R-isomers and which are characterised by formula (Ia)

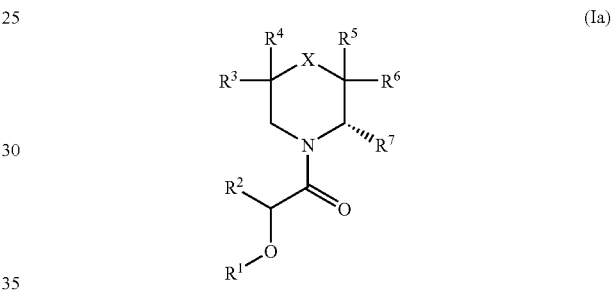

(Ia)

wherein R$^1$, R$^2$, R$^3$, R$^4$, R$^5$, R$^6$, R$^7$ and X are as defined above.

In particular, preferred compounds are the compounds of formula (I) described in the examples as individual compounds as well as pharmaceutically acceptable salts as well as pharmaceutically acceptable esters thereof.

Preferred compounds of formula (I) are those selected from the group consisting of:
(R)-1-{2-[3-(4-Methoxy-phenyl)-[1,2,4]oxadiazol-5-yl]-piperidin-1-yl}-2-phenoxy-ethanone,
(R)-3-(2-{2-[3-(4-Methoxy-phenyl)[1,2,4]oxadiazol-5-yl]-piperidin-1-yl}-2-oxo-ethoxy) benzonitrile,
(R) 1-{2-[3-(4-Methoxy-phenyl)-[1,2,4]oxadiazol-5-yl]-piperidin-1-yl}-2-phenoxy-propan-1-one,
(R)-1-{2-[3-(4-Bromo-phenyl)[1,2,4]oxadiazol-5-yl]-piperidin-1-yl}-2-phenoxy-ethanone,
(R)-2-(4-Hydroxy-phenoxy)-1-{2-[3-(4-methoxy-phenyl)-[1,2,4]oxadiazol-5-yl]-piperidin-1-yl}-ethanone,
(R)-2-(4-Chloro-phenoxy)-1-{2-[3-(4-methoxy-phenyl)-[1,2,4]oxadiazol-5-yl]-piperidin-1-yl}-ethanone,
(R)-2-(4-Hydroxymethyl-phenoxy)-1-{2-[3-(4-methoxy-phenyl)-[1,2,4]oxadiazol-5-yl]-piperidin-1-yl}-ethanone,
(R)-2-(3-Chloro-phenoxy)-1-{2-[3-(4-methoxy-phenyl)-[1,2,4]oxadiazol-5-yl]-piperidin-1-yl}-ethanone,
(R)-2-(4-Fluoro-phenoxy)-1-{2-[3-(4-methoxy-phenyl)-[1,2,4]oxadiazol-5-yl]-piperidin-1-yl}-ethanone,
(R)-1-{2-[3-(4-Fluoro-phenyl)-[1,2,4]oxadiazol-5-yl]-piperidin-1-yl}-2-phenoxy-ethanone,
(R)-1-{2-[3-(4-Methane-sulfonyl-phenyl)-[1,2,4]oxadiazol-5-yl]-piperidin-1-yl}-2-phenoxy-ethanone, (R)-4-{5-[1-(2-Phenoxy-acetyl)-piperidin-2-yl]-[1,2,4]oxadiazol-3-yl}-benzenesulfonamide,
(R)-2-(4-Fluoro-phenoxy)-1-[2-(3-pyridin-4-yl-[1,2,4]oxadiazol-5-yl)-piperidin-1-yl]-ethanone,
(R)-3-{5-[1-(2-Phenoxy-acetyl)-piperidin-2-yl]-[1,2,4]oxadiazol-3-yl}-benzoic acid methyl ester,
(R)-1-{2-[3-(3-Nitro-phenyl)-[1,2,4]oxadiazol-5-yl]-piperidin-1-yl}-2-phenoxy-ethanone,
(R)-1-{2-[3-(4-Nitro-phenyl)-[1,2,4]oxadiazol-5-yl]-piperidin-1-yl}-2-phenoxy-ethanone,
(R)-3-{5-[1-(2-Phenoxy-acetyl)-piperidin-2-yl]-[1,2,4]oxadiazol-3-yl}-benzenesulfonamide,
(R)-2-Phenoxy-1-[2-(3-pyrazin-2-yl-[1,2,4]oxadiazol-5-yl)-piperidin-1-yl]-ethanone,
(R)-1-(2-{3-[4-(Morpholine-4-sulfonyl)-phenyl]-[1,2,4]oxadiazol-5-yl}-piperidin-1-yl)-2-phenoxy-ethanone,
(R)-1-{2-[3-(6-Methoxy-pyridin-3-yl)-[1,2,4]oxadiazol-5-yl]-piperidin-1-yl}-2-phenoxy-ethanone,
(R)-1-{2-[3-(3-Hydroxymethyl-phenyl)-[1,2,4]oxadiazol-5-yl]-piperidin-1-yl}-2-phenoxy-ethanone,
(R)-6-{5-[1-(2-Phenoxy-acetyl)-piperidin-2-yl]-[1,2,4]oxadiazol-3-yl}-nicotinic acid allyl ester,
(R)-1-{2-[3-(4-Imidazol-1-yl-phenyl)-[1,2,4]oxadiazol-5-yl]-piperidin-1-yl}-2-phenoxy-ethanone,
(R)-N-Methyl-4-{5-[1-(2-phenoxy-acetyl)-piperidin-2-yl]-[1,2,4]oxadiazol-3-yl}-benzenesulfonamide,
(R)-1-{2-[3-(6-Morpholin-4-yl-pyridin-3-yl)-[1,2,4]oxadiazol-5-yl]-piperidin-1-yl}-2-phenoxy-ethanone,
(R)-2-Phenoxy-1-{2-[3-(4-trifluoromethanesulfonyl-phenyl)-[1,2,4]oxadiazol-5-yl]-piperidin-1-yl}-ethanone,
(R)-2-Phenoxy-1-{2-[3-(4-trifluoromethyl-phenyl)-[1,2,4]oxadiazol-5-yl]-piperidin-1-yl}-ethanone,
(R)-1-{2-[3-(4-Chloro-phenyl)-[1,2,4]oxadiazol-5-yl]-piperidin-1-yl}-2-phenoxy-ethanone,
(R)-N-(4-{5-[1-(2-Phenoxy-acetyl)-piperidin-2-yl]-[1,2,4]oxadiazol-3-yl}-2-trifluoromethyl-phenyl)-acetamide,
(R)-1-{2-[3-(3-Methanesulfonyl-phenyl)-[1,2,4]oxadiazol-5-yl]-piperidin-1-yl}-2-phenoxy-ethanone,
(R)-1-{2-[3-(4-Methyl-3-nitro-phenyl)-[1,2,4]oxadiazol-5-yl]-piperidin-1-yl}-2-phenoxy-ethanone,
(R)-1-{2-[3-(4-Methoxy-3-nitro-phenyl)-[1,2,4]oxadiazol-5-yl]-piperidin-1-yl}-2-phenoxy-ethanone,
(R)-N-(2-Hydroxy-ethyl)-4-{5-[1-(2-phenoxy-acetyl)-piperidin-2-yl]-[1,2,4]oxadiazol-3-yl}-benzenesulfonamide,
(R)-N-(2-Methoxy-ethyl)-N-methyl-4-{5-[1-(2-phenoxy-acetyl)-piperidin-2-yl]-[1,2,4]oxadiazol-3-yl}-benzenesulfonamide,
(R)-N,N-Dimethyl-4-{5-[1-(2-phenoxy-acetyl)-piperidin-2-yl]-[1,2,4]oxadiazol-3-yl}-benzenesulfonamide,
(R)-N,N-Diethyl-4-{5-[1-(2-phenoxy-acetyl)-piperidin-2-yl]-[1,2,4]oxadiazol-3-yl}-benzenesulfonamide,
(R)-1-{2-[3-(2-Morpholin-4-yl-pyridin-4-yl)-[1,2,4]oxadiazol-5-yl]-piperidin-1-yl}-2-phenoxy-ethanone,
(R)-2-Phenoxy-1-{2-[3-(3,4,5,6-tetrahydro-2H-[1,2']bipyridinyl-4'-yl)-[1,2,4]oxadiazol-5-yl]-piperidin-1-yl}-ethanone,
(R)-2-Phenoxy-1-{2-[3-(2-thiomorpholin-4-yl-pyridin-4-yl)-[1,2,4]oxadiazol-5-yl]-piperidin-1-yl}-ethanone,
(R)-1-{2-[3-(2-Diethylamino-pyridin-4-yl)-[1,2,4]oxadiazol-5-yl]-piperidin-1-yl}-2-phenoxy-ethanone,
(R)-4-{5-[1-(2-Phenoxy-acetyl)-piperidin-2-yl]-[1,2,4]oxadiazol-3-yl}-pyridine-2-carboxylic acid ethyl ester,
(R)-1-(2-{3-[6-(4-Acetyl-piperazin-1-yl)-pyridin-3-yl]-[1,2,4]oxadiazol-5-yl}-piperidin-1-yl)-2-phenoxy-ethanone,
(R)-1-{2-[3-(2-Imidazol-1-yl-pyridin-4-yl)-[1,2,4]oxadiazol-5-yl]-piperidin-1-yl}-2-phenoxy-ethanone,
(R)-1-(3-{5-[1-(2-Phenoxy-acetyl)-piperidin-2-yl]-[1,2,4]oxadiazol-3-yl}-phenyl)-piperidin-2-one,
(R)-1-(2-{3-[4-(3H-Imidazol-4-yl)-phenyl]-[1,2,4]oxadiazol-5-yl}-piperidin-1-yl)-2-phenoxy-ethanone,
(R)-1-(2-{3-[4-(2-Methyl-imidazol-1-yl)-phenyl]-[1,2,4]oxadiazol-5-yl}-piperidin-1-yl)-2-phenoxy-ethanone,
(R)-2-Phenoxy-1-{2-[3-(2-pyrazol-1-yl-pyridin-4-yl)-[1,2,4]oxadiazol-5-yl]-piperidin-1-yl}-ethanone,
(R)-4-(5-{5-[1-(2-Phenoxy-acetyl)-piperidin-2-yl]-[1,2,4]oxadiazol-3-yl}-pyridin-2-yl)-piperazin-2-one,
(R)-2-Phenoxy-1-(2-{3-[4-(1H-tetrazol-5-yl)-phenyl]-[1,2,4]oxadiazol-5-yl}-piperidin-1-yl)-ethanone,
(R)-1-{2-[3-(1H-Indazol-5-yl)-[1,2,4]oxadiazol-5-yl]-piperidin-1-yl}-2-phenoxy-ethanone,
(R)-1-{2-[3-(1H-Indazol-6-yl)-[1,2,4]oxadiazol-5-yl]-piperidin-1-yl}-2-phenoxy-ethanone,
(R)-1-{2-[3-(4-Fluoro-3-trifluoromethyl-phenyl)-[1,2,4]oxadiazol-5-yl]-piperidin-1-yl}-2-phenoxy-ethanone,
(R)-6-{5-[1-(2-Phenoxy-acetyl)-piperidin-2-yl]-[1,2,4]oxadiazol-3-yl}-1,3-dihydro-indol-2-one,
(R)-5-{5-[1-(2-Phenoxy-acetyl)-piperidin-2-yl]-[1,2,4]oxadiazol-3-yl}-1,3-dihydro-benzoimidazol-2-one,
(R)-5-{5-[1-(2-Phenoxy-acetyl)-piperidin-2-yl]-[1,2,4]oxadiazol-3-yl}-1,3-dihydro-indol-2-one,
(R)-1-{2-[3-(1H-Benzotriazol-5-yl)-[1,2,4]oxadiazol-5-yl]-piperidin-1-yl}-2-phenoxy-ethanone,
(R)-1-{2-[3-(1H-Benzoimidazol-5-yl)-[1,2,4]oxadiazol-5-yl]-piperidin-1-yl}-2-phenoxy-ethanone,
(R)-1-(2-{3-[6-(1,1-Dioxo-thiomorpholin-4-yl)-pyridin-3-yl]-[1,2,4]oxadiazol-5-yl}-piperidin-1-yl)-2-phenoxy-ethanone,
(R)-N-(4-{5-[1-(2-Phenoxy-acetyl)-piperidin-2-yl]-[1,2,4]oxadiazol-3-yl}-pyridin-2-yl)-acetamide,
(R)-1-{2-[3-(6-Benzyloxy-pyridin-3-yl)-[1,2,4]oxadiazol-5-yl]-piperidin-1-yl}-2-phenoxy-ethanone,
(R)-5-{5-[1-(2-Phenoxy-acetyl)-piperidin-2-yl]-[1,2,4]oxadiazol-3-yl}-nicotinic acid ethyl ester,
(R)-4-{5-[4-(2-Phenoxy-acetyl)-morpholin-3-yl]-[1,2,4]oxadiazol-3-yl}-1H-pyridin-2-one,
(R)-5-{5-[1-(2-Phenoxy-acetyl)-piperidin-2-yl]-[1,2,4]oxadiazol-3-yl}-1H-pyridin-2-one,
(R)-2-Phenoxy-1-[2-(5-phenyl-2H-[1,2,4]triazol-3-yl)-piperidin-1-yl]-ethanone,
(R)-1-{2-[5-(4-Methanesulfonyl-phenyl)-2H-[1,2,4]triazol-3-yl]-piperidin-1-yl}-2-phenoxy-ethanone,
(R)-1-{2-[5-(3,4-Dimethoxy-phenyl)-2H-[1,2,4]triazol-3-yl]-piperidin-1-yl}-2-phenoxy-ethanone,
(R)-1-{2-[5-(3,4-Dichloro-phenyl)-2H-[1,2,4]triazol-3-yl]-piperidin-1-yl}-2-phenoxyethanone,
(R)-1-{2-[5-(4-Fluoro-phenyl)-2H-[1,2,4]triazol-3-yl]-piperidin-1-yl}-2-phenoxy-ethanone,
(R)-2-Phenoxy-1-{2-[5-(3-trifluoromethyl-phenyl)-2H-[1,2,4]triazol-3-yl]-piperidin-1-yl}-ethanone,
(R)-1-{2-[5-(4-Methoxy-phenyl)-2H-[1,2,4]triazol-3-yl]-piperidin-1-yl}-2-phenoxy-ethanone,
(R)-1-{2-[5-(3-Nitro-phenyl)-2H-[1,2,4]triazol-3-yl]-piperidin-1-yl}-2-phenoxy-ethanone,
(R)-3-{5-[1-(2-Phenoxy-acetyl)-piperidin-2-yl]-1H-[1,2,4]triazol-3-yl}-benzoic acid methyl ester,
(R)-1-{2-[5-(4-Fluoro-3-trifluoromethyl-phenyl)-2H-[1,2,4]triazol-3-yl]-piperidin-1-yl}-2-phenoxy-ethanone,
(R)-6-{5-[1-(2-Phenoxy-acetyl)-piperidin-2-yl]-1H-[1,2,4]triazol-3-yl}-1,3-dihydro-indol-2-one,
1-{3-[3-(4-Methoxy-phenyl)-[1,2,4]oxadiazol-5-yl]-morpholin-4-yl}-2-phenoxy-ethanone,
1-{3-[3-(4-Methanesulfonyl-phenyl)-[1,2,4]oxadiazol-5-yl]-morpholin-4-yl}-2-phenoxy-ethanone, 4-{5-[4-(2-Phenoxy-acetyl)-morpholin-3-yl]-[1,2,4]oxadiazol-3-yl}-benzenesulfonamide, 1-(3-{3-[6-(1,1-Dioxo-thiomorpholin-4-yl)-pyridin-3-yl]-[1,2,4]oxadiazol-5-yl}-morpholin-4-yl)-2-phenoxy-ethanone, N-(4-{5-[4-(2-Phenoxy-acetyl)-morpholin-3-yl]-[1,2,4]oxadiazol-3-yl}-pyridin-2-yl)-acetamide, 1-{3-[5-(4-Methanesulfonyl-phenyl)-2H-[1,2,4]triazol-3-yl]-morpholin-4-yl}-2-phenoxy-ethanone, 2-Phenoxy-1-{3-[5-(3-trifluoromethyl-phenyl)-2H-[1,2,4]triazol-3-yl]-morpholin-4-yl}-ethanone, (R)-4-{5-[4-(2-Phenoxy-acetyl)-morpholin-3-yl]-[1,2,4]oxadiazol-3-yl}-1H-pyridin-2-one, 1-{3-[3-(4-Methoxy-phenyl)-[1,2,4]oxadiazol-5-yl]-thiomorpholin-4-yl}-2-phenoxy-ethanone, 1-{3-[3-(4-Methanesulfonyl-phenyl)-[1,2,4]oxadiazol-5-yl]-thiomorpholin-4-yl}-2-phenoxy-ethanone, 4-{5-[4-(2-Phenoxy-acetyl)-thiomorpholin-3-yl]-[1,2,4]oxadiazol-3-yl}-benzenesulfonamide, 2-Phenoxy-1-[3-(3-pyridin-4-yl-[1,2,4]oxadiazol-5-yl)-thiomorpholin-4-yl]-ethanone, 1-{2-[3-(4-Methoxy-phenyl)-[1,2,4]oxadiazol-5-yl]-piperazin-1-yl}-2-phenoxy-ethanone, N-(5-{5-[1-(2-Phenoxy-acetyl)-piperazin-2-yl]-[1,2,4]oxadiazol-3-yl}-pyridin-2-yl)-acetamide, 1-{2-[3-(2-Imidazol-1-yl-pyridin-4-yl)-[1,2,4]oxadiazol-5-yl]-piperazin-1-yl}-2-phenoxy-ethanone, N,N-Diethyl-4-{5-[1-(2-phenoxy-acetyl)-piperazin-2-yl]-[1,2,4]oxadiazol-3-yl}-benzenesulfonamide, N,N-Dimethyl-4-{5-[1-(2-phenoxy-acetyl)-piperazin-2-yl]-[1,2,4]oxadiazol-3-yl}-benzenesulfonamide, 4-{5-[1-(2-Phenoxy-acetyl)-piperazin-2-yl]-[1,2,4]oxadiazol-3-yl}-benzenesulfonamide, 1-{2-[3-(4-Methanesulfonyl-phenyl)-[1,2,4]oxadiazol-5-yl]-piperazin-1-yl}-2-phenoxy-ethanone, 2-Phenoxy-1-[2-(3-pyridin-4-yl-[1,2,4]oxadiazol-5-yl)-piperazin-1-yl]-ethanone, 1-{2-[3-(2,4-Dichloro-phenyl)-[1,2,4]oxadiazol-5-yl]-piperazin-1-yl}-2-phenoxy-ethanone, 2-Phenoxy-1-[2-(3-pyridin-2-yl-[1,2,4]oxadiazol-5-yl)-piperazin-1-yl]-ethanone, 2-Phenoxy-1-[2-(3-pyridin-2-yl-[1,2,4]oxadiazol-5-yl)-piperazin-2-yl]-ethanone, 1-{2-[3-(4-Nitro-phenyl)-[1,2,4]oxadiazol-5-yl]-piperazin-1-yl}-2-phenoxy-ethanone, 1-{2-[3-(6-Methoxy-pyridin-3-yl)-[1,2,4]oxadiazol-5-yl]-piperazin-1-yl}-2-phenoxy-ethanone, 1-{2-[3-(6-Morpholin-4-yl-pyridin-3-yl)-[1,2,4]oxadiazol-5-yl]-piperazin-1-yl}-2-phenoxy-ethanone, 1-{2-[3-(6-Morpholin-4-yl-pyridin-3-yl)-[1,2,4]oxadiazol-5-yl]-piperazin-1-yl}-2-phenoxy-ethanone, 1-{2-[3-(3-Hydroxymethyl-phenyl)-[1,2,4]oxadiazol-5-yl]-piperazin-1-yl}-2-phenoxy-ethanone, 1-{2-[3-(4-Diethylamino-phenyl)-[1,2,4]oxadiazol-5-yl]-piperazin-1-yl}-2-phenoxy-ethanone, 1-(2-{3-[4-(Morpholine-4-sulfonyl)-phenyl]-[1,2,4]oxadiazol-5-yl}-piperazin-1-yl)-2-phenoxy-ethanone, N-Methyl-4-{5-[1-(2-phenoxy-acetyl)-piperazin-2-yl]-[1,2,4]oxadiazol-3-yl}-benzenesulfonamide, N-(2-Methoxy-ethyl)-N-methyl-4-{5-[1-(2-phenoxy-acetyl)-piperazin-2-yl]-[1,2,4]oxadiazol-3-yl}-benzenesulfonamide, 1-{2-[3-(4-Chloro-phenyl)-[1,2,4]oxadiazol-5-yl]-piperazin-1-yl}-2-phenoxy-ethanone, N-(4-{5-[1-(2-Phenoxy-acetyl)-piperazin-2-yl]-[1,2,4]oxadiazol-3-yl}-2-trifluoromethyl-phenyl)-acetamide, 4-{5-[1-(2-Phenoxy-acetyl)-piperazin-2-yl]-[1,2,4]oxadiazol-3-yl}-benzoic acid allyl ester, 1-{2-[3-(4-Methyl-3-nitro-phenyl)-[1,2,4]oxadiazol-5-yl]-piperazin-1-yl}-2-phenoxy-ethanone, 1-{2-[3-(4-Methoxy-3-nitro-phenyl)-[1,2,4]oxadiazol-5-yl]-piperazin-1-yl}-2-phenoxy-ethanone, 1-{2-[3-(4-Chloro-3-nitro-phenyl)-[1,2,4]oxadiazol-5-yl]-piperazin-1-yl}-2-phenoxy-ethanone, 3-Fluoro-4-{5-[1-(2-phenoxy-acetyl)-piperazin-2-yl]-[1,2,4]oxadiazol-3-yl}-benzoic acid methyl ester, 4-{5-[1-(2-Phenoxy-acetyl)-piperazin-2-yl]-[1,2,4]oxadiazol-3-yl}-pyridine-2-carboxylic acid ethyl ester, 2-Phenoxy-1-{2-[3-(4-piperidin-1-yl-phenyl)-[1,2,4]oxadiazol-5-yl]-piperazin-1-yl}-ethanone, 1-{2-[3-(4-Morpholin-4-yl-phenyl)-[1,2,4]oxadiazol-5-yl]-piperazin-1-yl}-2-phenoxy-ethanone, 1-(2-{3-[4-(2-Methyl-imidazol-1-yl)-phenyl]-[1,2,4]oxadiazol-5-yl}-piperazin-1-yl)-2-phenoxy-ethanone, 1-(2-{3-[4-(3H-Imidazol-4-yl)-phenyl]-[1,2,4]oxadiazol-5-yl}-piperazin-1-yl)-2-phenoxy-ethanone, 4-(5-{5-[1-(2-Phenoxy-acetyl)-piperazin-2-yl]-[1,2,4]oxadiazol-3-yl}-pyridin-2-yl)-piperazin-2-one, 1-{2-[3-(6-Imidazol-1-yl-pyridin-3-yl)-[1,2,4]oxadiazol-5-yl]-piperazin-1-yl}-2-phenoxy-ethanone, 1-(2-{3-[6-(4-Acetyl-piperazin-1-yl)-pyridin-3-yl]-[1,2,4]oxadiazol-5-yl}-piperazin-1-yl)-2-phenoxy-ethanone, 2-Phenoxy-1-{2-[3-(4-pyrrol-1-yl-phenyl)-[1,2,4]oxadiazol-5-yl]-piperazin-1-yl}-ethanone, 2-Phenoxy-1-{2-[3-(4-trifluoromethanesulfonyl-phenyl)-[1,2,4]oxadiazol-5-yl]-piperazin-1-yl}-ethanone, 1-{2-[3-(2-Morpholin-4-yl-pyridin-4-yl)-[1,2,4]oxadiazol-5-yl]-piperazin-1-yl}-2-phenoxy-ethanone, 2-Phenoxy-1-{2-[3-(2-thiomorpholin-4-yl-pyridin-4-yl)-[1,2,4]oxadiazol-5-yl]-piperazin-1-yl}-ethanone, 1-(2-{3-[6-(3-Hydroxymethyl-pyrrolidin-1-yl)-pyridin-3-yl]-[1,2,4]oxadiazol-5-yl}-piperazin-1-yl)-2-phenoxy-ethanone, (R)-1-{2-[3-(6-Methoxy-pyridin-3-yl)-[1,2,4]oxadiazol-5-yl]-piperazin-1-yl}-2-phenoxy-ethanone, (R)-1-{2-[3-(6-Morpholin-4-yl-pyridin-3-yl)-[1,2,4]oxadiazol-5-yl]-piperazin-1-yl}-2-phenoxy-ethanone, (R)-N-(4-{5-[1-(2-Phenoxy-acetyl)-piperazin-2-yl]-[1,2,4]oxadiazol-3-yl}-2-trifluoromethyl-phenyl)-acetamide, (R)-1-{2-[3-(4-Methyl-3-nitro-phenyl)-[1,2,4]oxadiazol-5-yl]-piperazin-1-yl}-2-phenoxy-ethanone, (R)-1-{2-[3-(4-Methyl-3-nitro-phenyl)-[1,2,4]oxadiazol-5-yl]-piperazin-1-yl}-2-phenoxy-ethanone, (R)-1-{2-[3-(4-Morpholin-4-yl-phenyl)-[1,2,4]oxadiazol-5-yl]-piperazin-1-yl}-2-phenoxy-ethanone, (R)-1-(2-{3-[4-(3H-Imidazol-4-yl)-phenyl]-[1,2,4]oxadiazol-5-yl}-piperazin-1-yl)-2-phenoxy-ethanone, (R)-1-(2-{3-[6-(3-Hydroxymethyl-pyrrolidin-1-yl)-pyridin-3-yl]-[1,2,4]oxadiazol-5-yl}-piperazin-1-yl)-2-phenoxy-ethanone, (R)-1-(2-{3-[6-(4-Acetyl-piperazin-1-yl)-pyridin-3-yl]-[1,2,4]oxadiazol-5-yl}-piperazin-1-yl)-2-phenoxy-ethanone, (R)-N-(3-{5-[1-(2-Phenoxy-acetyl)-piperazin-2-yl]-[1,2,4]oxadiazol-3-yl}-phenyl)-acetamide hydrochloride, (R)-1-{2-[3-(1H-Benzoimidazol-5-yl)-[1,2,4]oxadiazol-5-yl]-piperazin-1-yl}-2-phenoxy-ethanone, (R)-1-{2-[3-(1H-Benzotriazol-5-yl)-[1,2,4]oxadiazol-5-yl]-piperazin-1-yl}-2-phenoxy-ethanone, (R)-1-{2-[3-(1H-Indazol-5-yl)-[1,2,4]oxadiazol-5-yl]-piperazin-1-yl}-2-phenoxy-ethanone hydrochloride, (R)-5-{5-[1-(2-Phenoxy-acetyl)-piperazin-2-yl]-[1,2,4]oxadiazol-3-yl}-1,3-dihydro-benzoimidazol-2-one, (R)-1-(2-{3-[6-(1,1-Dioxo-thiomorpholin-4-yl)-pyridin-3-yl]-[1,2,4]oxadiazol-5-yl}-piperazin-1-yl)-2-phenoxy-ethanone hydrochloride,
(R)-1-{2-[3-(3-Nitro-phenyl)-[1,2,4]oxadiazol-5-yl]-piperazin-1-yl}-2-phenoxy-ethanone,
(R)-1-{2-[3-(4-Fluoro-phenyl)-[1,2,4]oxadiazol-5-yl]-piperazin-1-yl}-2-phenoxy-ethanone,
(R)-4-{5-[1-(2-Phenoxy-acetyl)-piperazin-2-yl]-[1,2,4]oxadiazol-3-yl}-1H-pyridin-2-one,
1-{4-Acetyl-2-[3-(4-methoxy-phenyl)-[1,2,4]oxadiazol-5-yl]-piperazin-1-yl}-2-phenoxy-ethanone,
1-{4-Acetyl-2-[3-(4-methanesulfonyl-phenyl)-[1,2,4]oxadiazol-5-yl]-piperazin-1-yl}-2-phenoxy-ethanone,
4-{5-[4-Acetyl-1-(2-phenoxy-acetyl)-piperazin-2-yl]-[1,2,4]oxadiazol-3-yl}-benzenesulfonamide,
1-[4-Acetyl-2-(3-pyridin-4-yl-[1,2,4]oxadiazol-5-yl)-piperazin-1-yl]-2-phenoxy-ethanone,
1-{4-Methanesulfonyl-2-[3-(4-methoxy-phenyl)-[1,2,4]oxadiazol-5-yl]-piperazin-1-yl}-2-phenoxy-ethanone,
(R)-1-{2-[5-(4-Fluoro-phenyl)-2H-[1,2,4]triazol-3-yl]-piperazin-1-yl}-2-phenoxy-ethanone,
(R)-2-Phenoxy-1-{2-[5-(3-trifluoromethyl-phenyl)-2H-[1,2,4]triazol-3-yl]-piperazin-1-yl}-ethanone,
1-{2-[5-(4-Fluoro-3-trifluoromethyl-phenyl)-2H-[1,2,4]triazol-3-yl]-piperazin-1-yl}-2-phenoxy-ethanone,
1-{2-[5-(4-Methanesulfonyl-phenyl)-2H-[1,2,4]triazol-3-yl]-piperazin-1-yl}-2-phenoxy-ethanone,
2-Phenoxy-1-{2-[5-(3-trifluoromethyl-phenyl)-2H-[1,2,4]triazol-3-yl]-piperazin-1-yl}-ethanone,
2-Phenoxy-1-[2-(5-p-tolyl-2H-[1,2,4]triazol-3-yl)-piperazin-1-yl]-ethanone,
2-Phenoxy-1-{2-[5-(4-trifluoromethyl-phenyl)-2H-[1,2,4]triazol-3-yl]-piperazin-1-yl}-ethanone,
1-{2-[5-(4-Methoxy-phenyl)-2H-[1,2,4]triazol-3-yl]-piperazin-1-yl}-2-phenoxy-ethanone,
1-{2-[5-(4-Fluoro-phenyl)-2H-[1,2,4]triazol-3-yl]-piperazin-1-yl}-2-phenoxy-ethanone,
1-{2-[5-(4-Fluoro-phenyl)-2H-[1,2,4]triazol-3-yl]-piperazin-1-yl}-2-phenoxy-ethanone,
1-{2-[5-(3,4-Dimethoxy-phenyl)-2H-[1,2,4]triazol-3-yl]-piperazin-1-yl}-2-phenoxy-ethanone,
1-{2-[5-(3,4-Dichloro-phenyl)-2H-[1,2,4]triazol-3-yl]-piperazin-1-yl}-2-phenoxy-ethanone,
1-{2-[5-(2-Fluoro-phenyl)-2H-[1,2,4]triazol-3-yl]-piperazin-1-yl}-2-phenoxy-ethanone,
1-{2-[5-(2-Fluoro-phenyl)-2H-[1,2,4]triazol-3-yl]-piperazin-1-yl}-2-phenoxy-ethanone,
4-{5-[4-Methyl-1-(2-phenoxy-acetyl)-piperazin-2-yl]-[1,2,4]oxadiazol-3-yl}-benzamide,
(R)-1-{2-[3-(1H-Indazol-5yl)-[1,2,4]oxadiazol-5-yl]-4-methyl-piperazin-1-yl}-2-phenoxy-ethanone,
(R)-1-{2-[3-(4-Fluoro-phenyl)-[1,2,4]oxadiazol-5-yl]-4-methyl-piperazin-1-yl}-2-phenoxy-ethanone,
(R)-5-{5-[4-Methyl-1-(2-phenoxy-acetyl)-piperazin-2-yl]-[1,2,4]oxadiazol-3-yl}-1,3-dihydro-indol-2-one,
(R)-5-{5-[4-Methyl-1-(2-phenoxy-acetyl)-piperazin-2-yl]-[1,2,4]oxadiazol-3-yl}-1,3-dihydro-benzoimidazol-2-one,
(R)-1-{2-[3-(1H-Benzoimidazol-5-yl)-[1,2,4]oxadiazol-5-yl]-4-methyl-piperazin-1-yl}-2-phenoxy-ethanone,
(R)-1-{2-[3-(1H-Benzotriazol-5-yl)-[1,2,4]oxadiazol-5-yl]-4-methyl-piperazin-1-yl}-2-phenoxy-ethanone,
(R)-1-{4-Methyl-2-[5-(3-trifluoromethyl-phenyl)-2H-[1,2,4]triazol-3-yl]-piperazin-1-yl}-2-phenoxy-ethanone,
(R)-1-{2-[5-(4-Methoxy-phenyl)-2H-[1,2,4]triazol-3-yl]-4-methyl-piperazin-1-yl}-2-phenoxy-ethanone,
(R)-1-{2-[5-(4-Fluoro-phenyl)-2H-[1,2,4]triazol-3-yl]-4-methyl-piperazin-1-yl}-2-phenoxy-ethanone,
(R)-1-{2-[5-(4-Methanesulfonyl-phenyl)-2H-[1,2,4]triazol-3-yl]-4-methyl-piperazin-1-yl}-2-phenoxy-ethanone,
(R)-4-{5-[4-Methyl-1-(2-phenoxy-acetyl)-piperazin-2-yl]-1H-[1,2,4]triazol-3-yl}-benzoic acid methyl ester,
(R)-N-(3-{5-[4-Methyl-1-(2-phenoxy-acetyl)-piperazin-2-yl]-1H-[1,2,4]triazol-3-yl}-phenyl)-acetamide,
(R)-N-(3-{5-[4-Methyl-1-(2-phenoxy-acetyl)-piperazin-2-yl]-1H-[1,2,4]triazol-3-yl}-phenyl)-methanesulfonamide,
(R)-4-{5-[4-Methyl-1-(2-phenoxy-acetyl)-piperazin-2-yl]-1H-[1,2,4]triazol-3-yl}-benzamide,
(R)-4-{5-[1-(2-Phenoxy-acetyl)-piperidin-2-yl]-[1,2,4]oxadiazol-3-yl}-benzoic acid,
(R)-3-{5-[1-(2-Phenoxy-acetyl)-piperidin-2-yl]-[1,2,4]oxadiazol-3-yl}-benzoic acid,
(R)-6-{5-[1-(2-Phenoxy-acetyl)-piperidin-2-yl]-[1,2,4]oxadiazol-3-yl}-nicotinic acid,
(R)-2-Fluoro-4-{5-[1-(2-phenoxy-acetyl)-piperidin-2-yl]-[1,2,4]oxadiazol-3-yl}-benzoic acid,
(R)-5-{5-[1-(2-Phenoxy-acetyl)-piperidin-2-yl]-[1,2,4]oxadiazol-3-yl}-pyridine-2-carboxylic acid,
(R)-4-{5-[1-(2-Phenoxy-acetyl)-piperidin-2-yl]-[1,2,4]oxadiazol-3-yl}-pyridine-2-carboxylic acid,
(R)-3-{5-[1-(2-Phenoxy-acetyl)-piperidin-2-yl]-1H-[1,2,4]triazol-3-yl}-benzoic acid,
3-{5-[4-(2-Phenoxy-acetyl)-morpholin-3-yl]-[1,2,4]oxadiazol-3-yl}-benzoic acid,
3-{5-[4-(2-Phenoxy-acetyl)-morpholin-3-yl]-[1,2,4]oxadiazol-3-yl}-benzoic acid,
4-{5-[4-(2-Phenoxy-acetyl)-thiomorpholin-3-yl]-[1,2,4]oxadiazol-3-yl}-benzamide,
4-{5-[4-(2-Phenoxy-acetyl)-thiomorpholin-3-yl]-[1,2,4]oxadiazol-4-yl}-benzamide,
3-{5-[4-Acetyl-1-(2-phenoxy-acetyl)-piperazin-2-yl]-[1,2,4]oxadiazol-3-yl}-benzoic acid,
4-{5-[4-Acetyl-1-(2-phenoxy-acetyl)-piperazin-2-yl]-[1,2,4]oxadiazol-3-yl}-benzoic acid,
(R)-4-{5-[4-Methyl-1-(2-phenoxy-acetyl)-piperazin-2-yl]-1H-[1,2,4]triazol-3-yl}-benzoic acid,
(R)-5-{5-[1-(2-Phenoxy-acetyl)-piperidin-2-yl]-[1,2,4]oxadiazol-3-yl}-nicotinic acid,
1-(2-{3-[4-(Morpholine-4-carbonyl)-phenyl]-[1,2,4]oxadiazol-5-yl}-piperidin-1-yl)-2-phenoxy-ethanone,
(R)-1-(2-{3-[4-(3-Hydroxy-pyrrolidine-1-carbonyl)-phenyl]-[1,2,4]oxadiazol-5-yl}-piperidin-1-yl)-2-phenoxy-ethanone,
(R)-N,N-Diethyl-4-{5-[1-(2-phenoxy-acetyl)-piperidin-2-yl]-[1,2,4]oxadiazol-3-yl}-benzamide,
(R)-N-Methyl-4-{5-[1-(2-phenoxy-acetyl)-piperidin-2-yl]-[1,2,4]oxadiazol-3-yl}-benzamide,
(R)-N,N-Dimethyl-4-{5-[1-(2-phenoxy-acetyl)-piperidin-2-yl]-[1,2,4]oxadiazol-3-yl}-benzamide,
(R)-N-Ethyl-4-{5-[1-(2-phenoxy-acetyl)-piperidin-2-yl]-[1,2,4]oxadiazol-3-yl}-benzamide,
(R)-N-Cyclopropyl-4-{5-[1-(2-phenoxy-acetyl)-piperidin-2-yl]-[1,2,4]oxadiazol-3-yl}-benzamide,
(R)-N-(2-Hydroxy-ethyl)-4-{5-[1-(2-phenoxy-acetyl)-piperidin-2-yl]-[1,2,4]oxadiazol-3-yl}-benzamide,
(R)-N-(2-Methoxy-ethyl)-N-methyl-4-{5-[1-(2-phenoxy-acetyl)-piperidin-2-yl]-[1,2,4]oxadiazol-3-yl}-benzamide,
(R)-N-Methyl-3-{5-[1-(2-phenoxy-acetyl)-piperidin-2-yl]-[1,2,4]oxadiazol-3-yl}-benzamide,
(R)-N,N-Dimethyl-3-{5-[1-(2-phenoxy-acetyl)-piperidin-2-yl]-[1,2,4]oxadiazol-3-yl}-benzamide, (R)-N-Ethyl-3-{5-[1-(2-phenoxy-acetyl)-piperidin-2-yl]-[1,2,4]oxadiazol-3-yl}-benzamide,
(R)-N-Cyclopropyl-3-{5-[1-(2-phenoxy-acetyl)-piperidin-2-yl]-[1,2,4]oxadiazol-3-yl}-benzamide,
(R)-N-(2-Hydroxy-ethyl)-3-{5-[1-(2-phenoxy-acetyl)-piperidin-2-yl]-[1,2,4]oxadiazol-3-yl}-benzamide,
(R)-N-(2-Methoxy-ethyl)-N-methyl-3-{5-[1-(2-phenoxy-acetyl)-piperidin-2-yl]-[1,2,4]oxadiazol-3-yl}-benzamide,
(R)-1-(2-{3-[3-(Morpholine-4-carbonyl)-phenyl]-[1,2,4]oxadiazol-5-yl}-piperidin-1-yl)-2-phenoxy-ethanone,
(R)-1-(2-{3-[3-(3-Hydroxy-pyrrolidine-1-carbonyl)-phenyl]-[1,2,4]oxadiazol-5-yl}-piperidin-1-yl)-2-phenoxy-ethanone,
(R)-N,N-Diethyl-3-{5-[1-(2-phenoxy-acetyl)-piperidin-2-yl]-[1,2,4]oxadiazol-3-yl}-benzamide,
(R)-4-{5-[1-(2-Phenoxy-acetyl)-piperidin-2-yl]-[1,2,4]oxadiazol-3-yl}-pyridine-2-carboxylic acid methylamide,
(R)-4-{5-[1-(2-Phenoxy-acetyl)-piperidin-2-yl]-[1,2,4]oxadiazol-3-yl}-pyridine-2-carboxylic acid dimethylamide,
(R)-4-{5-[1-(2-Phenoxy-acetyl)-piperidin-2-yl]-[1,2,4]oxadiazol-3-yl}-pyridine-2-carboxylic acid ethylamide,
(R)-4-{5-[1-(2-Phenoxy-acetyl)-piperidin-2-yl]-[1,2,4]oxadiazol-3-yl}-pyridine-2-carboxylic acid diethylamide,
(R)-1-(2-{3-[2-(Morpholine-4-carbonyl)-pyridin-4-yl]-[1,2,4]oxadiazol-5-yl}-piperidin-1-yl)-2-phenoxy-ethanone,
(R)-1-(2-{3-[2-(3-Methanesulfonyl-pyrrolidine-1-carbonyl)-pyridin-4-yl]-[1,2,4]oxadiazol-5-yl}-piperidin-1-yl)-2-phenoxy-ethanone,
(R)-5-{5-[1-(2-Phenoxy-acetyl)-piperidin-2-yl]-[1,2,4]oxadiazol-3-yl}-pyridine-2-carboxylic acid methylamide,
(R)-N-Methyl-3-{5-[1-(2-phenoxy-acetyl)-piperidin-2-yl]-1H-[1,2,4]triazol-3-yl}-benzamide,
1N,N-Diethyl-4-{5-[1-(2-phenoxy-acetyl)-piperazin-2-yl]-[1,2,4]oxadiazol-3-yl}-benzamide,
1-(2-{3-[4-(Morpholine-4-carbonyl)-phenyl]-[1,2,4]oxadiazol-5-yl}-piperazin-1-yl)-2-phenoxy-ethanone,
N-Methyl-4-{5-[1-(2-phenoxy-acetyl)-piperazin-2-yl]-[1,2,4]oxadiazol-3-yl}-benzamide,
(R)-N-Methyl-5-{5-[1-(2-phenoxy-acetyl)-piperidin-2-yl]-[1,2,4]oxadiazol-3-yl}-nicotinamide,
(R)-N-Ethyl-5-{5-[1-(2-phenoxy-acetyl)-piperidin-2-yl]-[1,2,4]oxadiazol-3-yl}-nicotinamide,
(R)-N-Diethyl-5-{5-[1-(2-phenoxy-acetyl)-piperidin-2-yl]-[1,2,4]oxadiazol-3-yl}-nicotinamide,
(R)-N-Diethyl-5-{5-[1-(2-phenoxy-acetyl)-piperidin-2-yl]-[1,2,4]oxadiazol-3-yl}-nicotinamide,
(R)-N-(2-Hydroxy-ethyl)-5-{5-[1-(2-phenoxy-acetyl)-piperidin-2-yl]-[1,2,4]oxadiazol-3-yl}-nicotinamide,
(R)-N-(2-Methoxy-ethyl)-N-methyl-5-{5-[1-(2-phenoxy-acetyl)-piperidin-2-yl][1,2,4]oxadiazol-3-yl}-nicotinamide,
(R)-N-Cyclopropyl-5-{5-[1-(2-phenoxy-acetyl)-piperidin-2-yl]-[1,2,4]oxadiazol-3-yl}-nicotinamide,
(R)-1-(2-{3-[5-(3-Hydroxy-pyrrolidine-1-carbonyl)-pyridin-3-yl]-[1,2,4]oxadiazol-5-yl}-piperidin-1-yl)-2-phenoxy-ethanone,
(R)-4-{5-[1-(2-Phenoxy-acetyl)-piperidin-2-yl]-[1,2,4]oxadiazol-3-yl}-benzamide,
(R)-3-{5-[1-(2-Phenoxy-acetyl)-piperidin-2-yl]-[1,2,4]oxadiazol-3-yl}-benzamide,
(R)-4-{5-[1-(2-Phenoxy-acetyl)-piperidin-2-yl]-[1,2,4]oxadiazol-3-yl}-pyridine-2-carboxylic acid amide,
(R)-3-{5-[1-(2-Phenoxy-acetyl)-piperidin-2-yl]-1H-[1,2,4]triazol-3-yl}-benzamide,
4-{5-[4-(2-Phenoxy-acetyl)-morpholin-3-yl]-[1,2,4]oxadiazol-3-yl}-benzamide,
4-{5-[4-(2-Phenoxy-acetyl)-thiomorpholin-3yl]-[1,2,4]oxadiazol-3yl}-benzamide,
4-{5-[1-(2-Phenoxy-acetyl)-piperazin-2-yl]-[1,2,4]oxadiazol-3-yl}-benzamide,
5-{5-[1-(2-Phenoxy-acetyl)-piperidin-2-yl]-[1,2,4]oxadiazol-3-yl}-nicotinamide,
(R)-1-{2-[3-(3-Amino-phenyl)-[1,2,4]oxadiazol-5-yl]-piperidin-1-yl}-2-phenoxy-ethanone,
(R)-1-{2-[3-(4-Amino-phenyl)-[1,2,4]oxadiazol-5-yl]-piperidin-1-yl}-2-phenoxy-ethanone,
(R)-1-{2-[5-(3-Amino-phenyl)-2H-[1,2,4]triazol-3-yl]-piperidin-1-yl}-2-phenoxy-ethanone,
(R)-N-(3-{5-[1-(2-Phenoxy-acetyl)-piperidin-2-yl]-[1,2,4]oxadiazol-3-yl}-phenyl)-acetamide,
(R)-N-(4-{5-[1-(2-Phenoxy-acetyl)-piperidin-2-yl]-[1,2,4]oxadiazol-3-yl}-phenyl)-acetamide,
(R)-N-(5-{5-[1-(2-Phenoxy-acetyl)-piperidin-2-yl]-[1,2,4]oxadiazol-3-yl}-pyridin-2-yl)-acetamide,
(R)-N-(3-{5-[1-(2-Phenoxy-acetyl)-piperidin-2-yl]-1H-[1,2,4]triazol-3-yl}-phenyl)-acetamide,
(R)-N-(3-{5-[1-(2-Phenoxy-acetyl)-piperidin-2-yl]-[1,2,4]oxadiazol-3-yl}-phenyl)-methanesulfonamide,
(R)-N-(4-{5-[1-(2-Phenoxy-acetyl)-piperidin-2-yl]-[1,2,4]oxadiazol-3-yl}-phenyl)-methanesulfonamide,
(R)-(3-{5-[1-(2-Phenoxy-acetyl)-piperidin-2-yl]-[1,2,4]oxadiazol-3-yl}-phenyl)-carbamic acid allyl ester,
(R)-(4-{5-[1-(2-Phenoxy-acetyl)-piperidin-2-yl]-[1,2,4]oxadiazol-3-yl}-phenyl)-carbamic acid allyl ester,
(R)-N-(3-{5-[1-(2-Phenoxy-acetyl)-piperidin-2-yl]-1H-[1,2,4]triazol-3-yl}-phenyl)-methanesulfonamide,
(R)-1-Ethyl-3-(3-{5-[1-(2-phenoxy-acetyl)-piperidin-2-yl]-1H-[1,2,4]triazol-3-yl}-phenyl)-urea,
(R)-3-{5-[1-(2-Phenoxy-acetyl)-piperidin-2-yl]-1H-[1,2,4]triazol-3-yl}-benzonitrile, and
(R)-5-{5-[1-(2-Phenoxy-acetyl)-piperidin-2-yl]-[1,2,4]oxadiazol-3-yl}-nicotinonitrile, and pharmaceutically acceptable salts and esters thereof.

Particularly preferred compounds of formula (I) are those selected from the group consisting of:

(R)-1-{2-[3-(1H-Indazol-5-yl)-[1,2,4]oxadiazol-5-yl]-piperidin-1-yl}-2-phenoxy-ethanone,
(R)-1-{2-[3-(1H-Indazol-6-yl)-[1,2,4]oxadiazol-5-yl]-piperidin-1-yl}-2-phenoxy-ethanone,
(R)-6-{5-[1-(2-Phenoxy-acetyl)-piperidin-2-yl]-[1,2,4]oxadiazol-3-yl}-1,3-dihydro-indol-2-one,
(R)-5-{5-[1-(2-Phenoxy-acetyl)-piperidin-2-yl]-[1,2,4]oxadiazol-3-yl}-1,3-dihydro-benzoimidazol-2-one,
(R)-5-{5-[1-(2-Phenoxy-acetyl)-piperidin-2-yl]-[1,2,4]oxadiazol-3-yl}-1,3-dihydro-indol-2-one,
(R)-1-{2-[3-(1H-Benzotriazol-5-yl)-[1,2,4]oxadiazol-5-yl]-piperidin-1-yl}-2-phenoxy-ethanone,
(R)-1-{2-[3-(1H-Benzoimidazol-5-yl)-[1,2,4]oxadiazol-5-yl]-piperidin-1-yl}-2-phenoxy-ethanone,
(R)-4-{5-[4-(2-Phenoxy-acetyl)-morpholin-3-yl]-[1,2,4]oxadiazol-3-yl}-1H-pyridin-2-one,
(R)-1-{2-[5-(4-Fluoro-phenyl)-2H-[1,2,4]triazol-3-yl]-piperidin-1-yl}-2-phenoxy-ethanone,
(R)-2-Phenoxy-1-{2-[5-(3-trifluoromethyl-phenyl)-2H-[1,2,4]triazol-3-yl]-piperidin-1-yl}-ethanone,
(R)-1-{2-[3-(1H-Benzoimidazol-5-yl)-[1,2,4]oxadiazol-5-yl]-piperazin-1-yl}-2-phenoxy-ethanone,
(R)-3-{5-[1-(2-Phenoxy-acetyl)-piperidin-2-yl]-[1,2,4]oxadiazol-3-yl}-benzamide,
5-{5-[1-(2-Phenoxy-acetyl)-piperidin-2-yl]-[1,2,4]oxadiazol-3-yl}-nicotinamide, (R)-N-(3-{5-[1-(2-Phenoxy-acetyl)-piperidin-2-yl]-1H-[1,2,4]triazol-3-yl}-phenyl)-acetamide, and
(R)-N-(3-{5-[1-(2-Phenoxy-acetyl)-piperidin-2-yl]-1H-[1,2,4]triazol-3-yl}-phenyl)-methanesulfonamide, and pharmaceutically acceptable salts and esters thereof.

Other preferred compounds of formula (I) are those selected from the group consisting of:

1-{(R)-2-[3-(2-Methyl-1H-benzoimidazol-5-yl)-[1,2,4]oxadiazol-5-yl]-piperidin-1-yl}-2-phenoxy-ethanone,
1-{(R)-2-[3-(2-Amino-pyridin-4-yl)-[1,2,4]oxadiazol-5-yl]-piperidin-1-yl}-2-phenoxy-ethanone,
1-{(R)-2-[3-(3-Hydroxy-phenyl)-[1,2,4]oxadiazol-5-yl]-piperidin-1-yl}-2-phenoxy-ethanone,
4-{5-[(R)-1-(2-Phenoxy-acetyl)-piperidin-2-yl]-[1,2,4]oxadiazol-3-yl}-1H-pyridin-2-one,
1-{(R)-2-[3-(4-Hydroxy-phenyl)-[1,2,4]oxadiazol-5-yl]-piperidin-1-yl}-2-phenoxy-ethanone,
3-{5-[1-(2-Phenoxy-acetyl)-piperidin-2-yl]-[1,2,4]oxadiazol-3-yl}-phenylboronic acid,
4-(2-Oxo-2-{(R)-2-[3-(2-oxo-2,3-dihydro-1H-indol-5-yl)-[1,2,4]oxadiazol-5-yl]-piperidin-1-yl}-ethoxy)-benzonitrile,
4-(2-{(R)-2-[3-(4-Methoxy-phenyl)-[1,2,4]oxadiazol-5-yl]-piperidin-1-yl}-2-oxo-ethoxy)-benzonitrile,
2-Methyl-5-{5-[(R)-1-(2-phenoxy-acetyl)-piperidin-2-yl]-[1,2,4]oxadiazol-3-yl}-3H-pyrimidin-4-one,
1-[(R)-2-(3-Furan-2-yl-[1,2,4]oxadiazol-5-yl)-piperidin-1-yl]-2-phenoxy-ethanone,
1-[(R)-2-(3-Imidazo[1,2-a]pyridin-2-yl-[1,2,4]oxadiazol-5-yl)-piperidin-1-yl]-2-phenoxy-ethanone,
1-{(R)-2-[3-(4-Methyl-[1,2,3]thiadiazol-5-yl)-[1,2,4]oxadiazol-5-yl]-piperidin-1-yl}-2-phenoxy-ethanone,
1-{(R)-2-[3-(2,5-Dimethyl-2H-pyrazol-3-yl)-[1,2,4]oxadiazol-5-yl]-piperidin-1-yl}-2-phenoxy-ethanone,
2-Phenoxy-1-{(R)-2-[3-(1H-pyrazol-4-yl)-[1,2,4]oxadiazol-5-yl]-piperidin-1-yl}-ethanone,
1-{(R)-2-[3-(5-Methyl-isoxazol-3-yl)-[1,2,4]oxadiazol-5-yl]-piperidin-1-yl}-2-phenoxy-ethanone,
2-Phenoxy-1-{(R)-2-[3-(1H-pyrazol-3-yl)-[1,2,4]oxadiazol-5-yl]-piperidin-1-yl}-ethanone,
5-{5-[(R)-1-(2-Phenoxy-acetyl)-piperidin-2-yl]-[1,2,4]oxadiazol-3-yl}-1H-pyrimidine-2,4-dione,
1-{(R)-2-[3-(6-Amino-pyridin-3-yl)-[1,2,4]oxadiazol-5-yl]-piperidin-1-yl}-2-phenoxy-ethanone,
1-[(R)-2-(3-Imidazo[1,2-a]pyridin-6-yl-[1,2,4]oxadiazol-5-yl)-piperidin-1-yl]-2-phenoxy-ethanone,
6-{5-[(R)-1-(2-Phenoxy-acetyl)-piperidin-2-yl]-[1,2,4]oxadiazol-3-yl}-4H-benzo[1,4]oxazin-3-one,
6-{5-[(R)-1-(2-Phenoxy-acetyl)-piperidin-2-yl]-[1,2,4]oxadiazol-3-yl}-1,4-dihydro-benzo[d][1,3]oxazin-2-one,
1-((R)-2-{3-[3-(1,1-Dioxo-1λ6-isothiazolidin-2-yl)-phenyl]-[1,2,4]oxadiazol-5-yl}-piperidin-1-yl)-2-phenoxy-ethanone,
1-(3-{5-[(R)-1-(2-Phenoxy-acetyl)-piperidin-2-yl]-[1,2,4]oxadiazol-3-yl}-phenyl)-pyrrolidin-2-one,
1-(3-{5-[(R)-1-(2-Phenoxy-acetyl)-piperidin-2-yl]-[1,2,4]oxadiazol-3-yl}-phenyl)-imidazolidine-2,4-dione,
4-(3-{5-[(R)-1-(2-Phenoxy-acetyl)-piperidin-2-yl]-[1,2,4]oxadiazol-3-yl}-phenyl)-2,4-dihydro-[1,2,4]triazol-3-one,
1-(3-Fluoro-5-{5-[(R)-1-(2-phenoxy-acetyl)-piperidin-2-yl]-[1,2,4]oxadiazol-3-yl}-phenyl)-pyrrolidine-2,5-dione,
5-{5-[(R)-1-(2-Phenoxy-acetyl)-piperidin-2-yl]-1H-[1,2,4]triazol-3-yl}-1,3-dihydro-indol-2-one,
1-{(R)-2-[5-(1H-Indazol-5-yl)-2H-[1,2,4]triazol-3-yl]-piperidin-1-yl}-2-phenoxy-ethanone,
1-{(R)-2-[5-(1H-Indol-5-yl)-2H-[1,2,4]triazol-3-yl]-piperidin-1-yl}-2-phenoxy-ethanone,
1-{(R)-2-[5-(3H-Benzotriazol-5-yl)-2H-[1,2,4]triazol-3-yl]-piperidin-1-yl}-2-phenoxy-ethanone,
5-{5-[(R)-1-(2-Phenoxy-acetyl)-piperidin-2-yl]-1H-[1,2,4]triazol-3-yl}-1,3-dihydro-benzoimidazol-2-one,
1-{(R)-2-[5-(2-Methyl-1H-benzoimidazol-5-yl)-2H-[1,2,4]triazol-3-yl]-piperidin-1-yl}-2-phenoxy-ethanone,
1-{(R)-2-[5-(2-Amino-pyridin-4-yl)-2H-[1,2,4]triazol-3-yl]-piperidin-1-yl}-2-phenoxy-ethanone,
5-(3-{5-[(R)-1-(2-Phenoxy-acetyl)-piperidin-2-yl]-1H-[1,2,4]triazol-3-yl}-phenyl)-3H-[1,3,4]oxadiazol-2-one,
1-{(R)-2-[5-(3-[1,3,4]Oxadiazol-2-yl-phenyl)-2H-[1,2,4]triazol-3-yl]-piperidin-1-yl}-2-phenoxy-ethanone,
3-{5-[1-(2-Phenoxy-acetyl)-piperidin-2-yl]-1H-[1,2,4]triazol-3-yl}-phenylboronic acid,
6-{5-[(R)-1-(2-Phenoxy-acetyl)-piperidin-2-yl]-1H-[1,2,4]triazol-3-yl}-4H-benzo[1,4]oxazin-3-one,
1-[(R)-2-(5-Imidazo[1,2-a]pyridin-6-yl-2H-[1,2,4]triazol-3-yl)-piperidin-1-yl]-2-phenoxy-ethanone,
1-{(R)-2-[5-(6-Amino-pyridin-3-yl)-2H-[1,2,4]triazol-3-yl]-piperidin-1-yl}-2-phenoxy-ethanone,
1-{(R)-2-[5-(1H-Benzoimidazol-5-yl)-2H-[1,2,4]triazol-3-yl]-piperidin-1-yl}-2-phenoxy-ethanone,
2-Phenoxy-1-[(R)-2-(5-pyridin-3-yl-2H-[1,2,4]triazol-3-yl)-piperidin-1-yl]-ethanone,
1-{(R)-2-[5-(3,5-Dimethyl-isoxazol-4-yl)-2H-[1,2,4]triazol-3-yl]-piperidin-1-yl}-2-phenoxy-ethanone,
2-Phenoxy-1-[(R)-2-(5-thiophen-2-yl-2H-[1,2,4]triazol-3-yl)-piperidin-1-yl]-ethanone,
2-Phenoxy-1-[(R)-2-(5-pyrimidin-2-yl-2H-[1,2,4]triazol-3-yl)-piperidin-1-yl]-ethanone,
1-{(R)-2-[5-(4-Methyl-oxazol-5-yl)-2H-[1,2,4]triazol-3-yl]-piperidin-1-yl}-2-phenoxy-ethanone,
2-Phenoxy-1-[(R)-2-(5-pyrazin-2-yl-2H-[1,2,4]triazol-3-yl)-piperidin-1-yl]-ethanone,
1-{(R)-2-[5-(2-Fluoro-phenyl)-2H-[1,2,4]triazol-3-yl]-piperidin-1-yl}-2-phenoxy-ethanone,
1-{(R)-2-[5-(3,5-Difluoro-phenyl)-2H-[1,2,4]triazol-3-yl]-piperidin-1-yl}-2-phenoxy-ethanone,
1-{(R)-2-[5-(2-Methyl-pyridin-4-yl)-2H-[1,2,4]triazol-3-yl]-piperidin-1-yl}-2-phenoxy-ethanone,
1-{(R)-2-[5-(3-Fluoro-phenyl)-2H-[1,2,4]triazol-3-yl]-piperidin-1-yl}-2-phenoxy-ethanone,
1-{(R)-2-[5-(3,4-Difluoro-phenyl)-2H-[1,2,4]triazol-3-yl]-piperidin-1-yl}-2-phenoxy-ethanone,
6-{5-[(R)-1-(2-Phenoxy-acetyl)-piperidin-2-yl]-1H-[1,2,4]triazol-3-yl}-1,4-dihydro-benzo[d][1,3]oxazin-2-one,
7-{5-[(R)-1-(2-Phenoxy-acetyl)-piperidin-2-yl]-1H-[1,2,4]triazol-3-yl}-3,4-dihydro-1H-quinazolin-2-one,
1-(3-{5-[(R)-1-(2-Phenoxy-acetyl)-piperidin-2-yl]-1H-[1,2,4]triazol-3-yl}-phenyl)-imidazolidine-2,4-dione,
1-{(R)-3-[3-(2-Amino-pyridin-4-yl)-[1,2,4]oxadiazol-5-yl]-morpholin-4-yl}-2-phenoxy-ethanone,
1-{(R)-3-[3-(1H-Benzoimidazol-5-yl)-[1,2,4]oxadiazol-5-yl]-morpholin-4-yl}-2-phenoxy-ethanone,
1-{(R)-2-[3-(1H-Benzoimidazol-5-yl)-[1,2,4]oxadiazol-5-yl]-piperazin-1-yl}-2-phenoxy-ethanone,
5-{5-[(R)-1-(2-Phenoxy-acetyl)-piperazin-2-yl]-[1,2,4]oxadiazol-3-yl}-1,3-dihydro-indol-2-one,
1-{(R)-2-[3-(2-Amino-pyridin-4-yl)-[1,2,4]oxadiazol-5-yl]-piperazin-1-yl}-2-phenoxy-ethanone,
(3-{5-[(R)-1-(2-Phenoxy-acetyl)-piperidin-2-yl]-[1,2,4]oxadiazol-3-yl}-phenoxy)-acetic acid,
2-Phenoxy-1-((R)-2-{5-[3-(piperidine-1-carbonyl)-phenyl]-2H-[1,2,4]triazol-3-yl}-piperidin-1-yl)-ethanone, 1-((R)-2-{5-[3-(Morpholine-4-carbonyl)-phenyl]-2H-[1,2,4]triazol-3-yl}-piperidin-1-yl)-2-phenoxy-ethanone,
1-((R)-2-{5-[3-(4-Methyl-piperazine-1-carbonyl)-phenyl]-2H-[1,2,4]triazol-3-yl}-piperidin-1-yl)-2-phenoxy-ethanone,
4-(3-{5-[(R)-1-(2-Phenoxy-acetyl)-piperidin-2-yl]-1H-[1,2,4]triazol-3-yl}-benzoyl)-piperazin-2one,
N-(2-Methoxy-ethyl)-N-methyl-3-{5-[(R)-1-(2-phenoxy-acetyl)-piperidin-2-yl]-1H-[1,2,4]triazol-3-yl}-benzamide,
1-((R)-2-{5-[3-(4-Acetyl-piperazine-1-carbonyl)-phenyl]-2H-[1,2,4]triazol-3-yl}-piperidin-1-yl)-2-phenoxy-ethanone,
1-(3-{5-[(R)-1-(2-Phenoxy-acetyl)-piperidin-2-yl]-1H-[1,2,4]triazol-3-yl}-benzoyl)-piperidine-4-carboxylic acid,
1-(3-{5-[(R)-1-(2-Phenoxy-acetyl)-piperidin-2-yl]-1H-[1,2,4]triazol-3-yl}-benzoyl)-piperidine-4-carboxylic acid amide,
2-Phenoxy-1-((R)-2-{5-[3-(thiazolidine-3-carbonyl)-phenyl]-2H-[1,2,4]triazol-3-yl}-piperidin-1-yl)-ethanone,
N-(2-Dimethylamino-ethyl)-N-methyl-3-{5-[(R)-1-(2-phenoxy-acetyl)-piperidin-2-yl]-1H-[1,2,4]triazol-3-yl}-benzamide,
2-Phenoxy-1-((R)-2-{5-[3-(thiomorpholine-4-carbonyl)-phenyl]-2H-[1,2,4]triazol-3-yl}-piperidin-1-yl)-ethanone,
4-(3-{5-[(R)-1-(2-Phenoxy-acetyl)-piperidin-2-yl]-1H-[1,2,4]triazol-3-yl}-benzoyl)-piperazine-1-carboxylic acid ethyl ester,
N-(2-Hydroxy-ethyl)-3-{5-[(R)-1-(2-phenoxy-acetyl)-piperidin-2-yl]-1H-[1,2,4]triazol-3-yl}-benzamide,
N-Methyl-3-{5-[(R)-1-(2-phenoxy-acetyl)-piperidin-2-yl]-1H-[1,2,4]triazol-3-yl}-N-(2-pyridin-2-yl-ethyl)-benzamide,
N-(2-Cyano-ethyl)-N-cyclopropyl-3-{5-[(R)-1-(2-phenoxy-acetyl)-piperidin-2-yl]-1H-[1,2,4]triazol-3-yl}-benzamide,
1-(3-{5-[(R)-1-(2-Phenoxy-acetyl)-piperidin-2-yl]-1H-[1,2,4]triazol-3-yl}-benzoyl)-4-phenyl-piperidine-4-carbonitrile,
1-((R)-2-{5-[3-(4-Hydroxy-piperidine-1-carbonyl)-phenyl]-2H-[1,2,4]triazol-3-yl}-piperidin-1-yl)-2-phenoxy-ethanone,
8-(3-{5-[(R)-1-(2-Phenoxy-acetyl)-piperidin-2-yl]-1H-[1,2,4]triazol-3-yl}-benzoyl)-1,3,8-triaza-spiro[4.5]decane-2,4-dione,
1-(2-{5-[3-(Spiro(1-Phtalan)-piperidine-4-carbonyl)-phenyl]-2H-[1,2,4]triazol-3-yl}-piperidin-1-yl)-2-phenoxy-ethanone,
2-Phenoxy-1-((R)-2-{5-[3-(3-pyridin-4-yl-pyrrolidine-1-carbonyl)-phenyl]-2H-[1,2,4]triazol-3-yl}-piperidin-1-yl)-ethanone,
1-((R)-2-{5-[3-(3-Methanesulfonyl-pyrrolidine-1-carbonyl)-phenyl]-2H-[1,2,4]triazol-3-yl}-piperidin-1-yl)-2-phenoxy-ethanone,
1-((R)-2-{5-[3-((S)-3-Ethoxy-pyrrolidine-1-carbonyl)-phenyl]-2H-[1,2,4]triazol-3-yl}-piperidin-1-yl)-2-phenoxy-ethanone,
1-((R)-2-{5-[3-((S)-3-Hydroxy-pyrrolidine-1-carbonyl)-phenyl]-2H-[1,2,4]triazol-3-yl}-piperidin-1-yl)-2-phenoxy-ethanone,
5-{5-[(R)-1-(2-Phenoxy-acetyl)-piperidin-2-yl]-1H-[1,2,4]triazol-3-yl}-nicotinamide,
2-(3-{5-[1-(2-Phenoxy-acetyl)-piperidin-2-yl]-[1,2,4]oxadiazol-3-yl}-phenoxy)-acetamide,
N-(3-Fluoro-5-{5-[(R)-1-(2-phenoxy-acetyl)-piperidin-2-yl]-[1,2,4]oxadiazol-3-yl}-phenyl)-acetamide,
N-(2-Fluoro-5-{5-[(R)-1-(2-phenoxy-acetyl)-piperidin-2-yl]-[1,2,4]oxadiazol-3-yl}-phenyl)-acetamide,
N-(3-{5-[(R)-1-(2-Phenoxy-acetyl)-piperidin-2-yl]-1H-[1,2,4]triazol-3-yl}-phenyl)-propionamide,
N-(3-{5-[(R)-1-(2-Phenoxy-acetyl)-piperidin-2-yl]-1H-[1,2,4]triazol-3-yl}-phenyl)-isobutyramide,
N-(4-Fluoro-3-{5-[(R)-1-(2-phenoxy-acetyl)-piperidin-2-yl]-1H-[1,2,4]triazol-3-yl}-phenyl)-acetamide,
N-(3-Fluoro-5-{5-[(R)-1-(2-phenoxy-acetyl)-piperidin-2-yl]-1H-[1,2,4]triazol-3-yl}-phenyl)-acetamide,
N-(2-Fluoro-5-{5-[(R)-1-(2-phenoxy-acetyl)-piperidin-2-yl]-1H-[1,2,4]triazol-3-yl}-phenyl)-acetamide,
N-(4-{5-[(R)-1-(2-Phenoxy-acetyl)-piperidin-2-yl]-1H-[1,2,4]triazol-3-yl}-pyridin-2-yl)-acetamide,
1-(3-{5-[(R)-1-(2-Phenoxy-acetyl)-piperidin-2-yl]-1H-[1,2,4]triazol-3-yl}-phenyl)-azetidin-2-one,
1-(3-{5-[1-(2-Phenoxy-acetyl)-piperidin-2-yl]-1H-[1,2,4]triazol-3-yl}-phenyl)-pyrrolidine-2,5-dione,
2-Phenoxy-1-[(R)-2-(5-pyridazin-4-yl-[1,2,4]oxadiazol-3-yl)-piperidin-1-yl]-ethanone,
4-{3-[(R)-1-(2-Phenoxy-acetyl)-piperidin-2-yl]-[1,2,4]oxadiazol-5-yl}-benzonitrile,
1-{(R)-2-[5-(3-Amino-pyrazin-2-yl)-[1,2,4]oxadiazol-3-yl]-piperidin-1-yl}-2-phenoxy-ethanone,
3-{3-[(R)-1-(2-Phenoxy-acetyl)-piperidin-2-yl]-[1,2,4]oxadiazol-5-yl}-benzonitrile,
1-{(R)-2-[5-(2-Hydroxy-pyridin-3-yl)-[1,2,4]oxadiazol-3-yl]-piperidin-1-yl}-2-phenoxy-ethanone,
1-{(R)-2-[5-(5-Amino-pyridin-3-yl)-[1,2,4]oxadiazol-3-yl]-piperidin-1-yl}-2-phenoxy-ethanone,
1-{(R)-2-[5-(2-Hydroxy-pyridin-4-yl)-[1,2,4]oxadiazol-3-yl]-piperidin-1-yl}-2-phenoxy-ethanone,
1-{(R)-2-[5-(2-Hydroxy-6-methyl-pyridin-4-yl)-[1,2,4]oxadiazol-3-yl]-piperidin-1-yl}-2-phenoxy-ethanone,
1-{(R)-2-[5-(4-Hydroxy-pyridin-2-yl)-[1,2,4]oxadiazol-3-yl]-piperidin-1-yl}-2-phenoxy-ethanone,
1-{(R)-2-[5-(2-Amino-5-chloro-pyrimidin-4-yl)-[1,2,4]oxadiazol-3-yl]-piperidin-1-yl}-2-phenoxy-ethanone,
2-Phenoxy-1-[(R)-2-(5-pyrazin-2-yl-[1,2,4]oxadiazol-3-yl)-piperidin-1-yl]-ethanone,
2-Phenoxy-1-{(R)-2-[5-(4-[1,2,4]triazol-1-yl-phenyl)-[1,2,4]oxadiazol-3-yl]-piperidin-1-yl}-ethanone,
2-Phenoxy-1-{(R)-2-[5-(4-tetrazol-1-yl-phenyl)-[1,2,4]oxadiazol-3-yl]-piperidin-1-yl}-ethanone,
1-{(R)-2-[5-(1H-Benzoimidazol-4-yl)-[1,2,4]oxadiazol-3-yl]-piperidin-1-yl}-2-phenoxy-ethanone,
1-{(R)-2-[5-(4-Acetyl-phenyl)-[1,2,4]oxadiazol-3-yl]-piperidin-1-yl}-2-phenoxy-ethanone,
1-{(R)-2-[5-(6-Hydroxy-pyridin-2-yl)-[1,2,4]oxadiazol-3-yl]-piperidin-1-yl}-2-phenoxy-ethanone,
1-{(R)-2-[5-(5-Methyl-pyrazin-2-yl)-[1,2,4]oxadiazol-3-yl]-piperidin-1-yl}-2-phenoxy-ethanone,
2-Phenoxy-1-[(R)-2-(5-quinoxalin-2-yl-[1,2,4]oxadiazol-3-yl)-piperidin-1-yl]-ethanone,
1-{(R)-2-[5-(3-Methanesulfonyl-phenyl)-[1,2,4]oxadiazol-3-yl]-piperidin-1-yl}-2-phenoxy-ethanone,
1-{(R)-2-[5-(6-Chloro-pyridin-3-yl)-[1,2,4]oxadiazol-3-yl]-piperidin-1-yl}-2-phenoxy-ethanone,
1-[(R)-2-(5-Benzothiazol-6-yl-[1,2,4]oxadiazol-3-yl)-piperidin-1-yl]-2-phenoxy-ethanone,
2-Phenoxy-1-{(R)-2-[5-(2,4,5-trifluoro-phenyl)-[1,2,4]oxadiazol-3-yl]-piperidin-1-yl}-ethanone,
2-Phenoxy-1-{(R)-2-[5-(6-trifluoromethyl-pyridin-3-yl)-[1,2,4]oxadiazol-3-yl]-piperidin-1-yl}-ethanone,
1-[(R)-2-(5-Benzo[1,2,3]thiadiazol-5-yl-[1,2,4]oxadiazol-3-yl)-piperidin-1-yl]-2-phenoxy-ethanone, 1-[(R)-2-(5-[1,8]Naphthyridin-2-yl-[1,2,4]oxadiazol-3-yl)-piperidin-1-yl]-2-phenoxy-ethanone,
1-[(R)-2-(5-[1,6]Naphthyridin-2-yl-[1,2,4]oxadiazol-3-yl)-piperidin-1-yl]-2-phenoxy-ethanone,
1-[(R)-2-(5-Cinnolin-4-yl-[1,2,4]oxadiazol-3-yl)-piperidin-1-yl]-2-phenoxy-ethanone,
1-{(R)-2-[5-(1H-Benzotriazol-5-yl)-[1,2,4]oxadiazol-3-yl]-piperidin-1-yl}-2-phenoxy-ethanone,
1-{(R)-2-[5-(1H-Benzoimidazol-5-yl)-[1,2,4]oxadiazol-3-yl]-piperidin-1-yl}-2-phenoxy-ethanone,
1-{(R)-2-[5-(3,6-Dichloro-pyridazin-4-yl)-[1,2,4]oxadiazol-3-yl]-piperidin-1-yl}-2-phenoxy-ethanone,
6-{3-[(R)-1-(2-Phenoxy-acetyl)-piperidin-2-yl]-[1,2,4]oxadiazol-5-yl}-4H-benzo[1,4]oxazin-3-one,
1-{(R)-2-[5-(3H-Imidazo[4,5-b]pyridin-6-yl)-[1,2,4]oxadiazol-3-yl]-piperidin-1-yl}-2-phenoxy-ethanone,
N-(4-{3-[(R)-1-(2-Phenoxy-acetyl)-piperidin-2-yl]-[1,2,4]oxadiazol-5-yl}-pyridin-2-yl)-acetamide,
1-{(R)-2-[5-(6-Chloro-3-hydroxy-pyridazin-4-yl)-[1,2,4]oxadiazol-3-yl]-piperidin-1-yl}-2-phenoxy-ethanone,
6-{3-[(R)-1-(2-Phenoxy-acetyl)-piperidin-2-yl]-[1,2,4]oxadiazol-5-yl}-1,4-dihydro-quinoxaline-2,3-dione,
1-{(R)-2-[5-(6-Hydroxy-pyridin-3-yl)-[1,2,4]oxadiazol-3-yl]-piperidin-1-yl}-2-phenoxy-ethanone,
7-{3-[(R)-1-(2-Phenoxy-acetyl)-piperidin-2-yl]-[1,2,4]oxadiazol-5-yl}-3,4-dihydro-1H-quinoxalin-2-one,
1-{(R)-2-[5-(6-Amino-pyridin-2-yl)-[1,2,4]oxadiazol-3-yl]-piperidin-1-yl}-2-phenoxy-ethanone,
6-{3-[(R)-1-(2-Phenoxy-acetyl)-piperidin-2-yl]-[1,2,4]oxadiazol-5-yl}-nicotinonitrile,
5-{3-[(R)-1-(2-Phenoxy-acetyl)-piperidin-2-yl]-[1,2,4]oxadiazol-5-yl}-pyridine-2-carbonitrile,
4-{3-[(R)-1-(2-Phenoxy-acetyl)-piperidin-2-yl]-[1,2,4]oxadiazol-5-yl}-1,2-dihydro-indazol-3-one,
1-{(R)-2-[5-(2-Amino-pyridin-4-yl)-[1,2,4]oxadiazol-3-yl]-piperidin-1-yl}-2-phenoxy-ethanone,
1-{(R)-2-[5-(6-Hydroxy-pyrimidin-4-yl)-[1,2,4]oxadiazol-3-yl]-piperidin-1-yl}-2-phenoxy-ethanone,
4-(3-{3-[(R)-1-(2-Phenoxy-acetyl)-piperidin-2-yl]-[1,2,4]oxadiazol-5-yl}-phenyl)-2,4-dihydro-[1,2,4]triazol-3-one,
1-(3-{3-[(R)-1-(2-Phenoxy-acetyl)-piperidin-2-yl]-[1,2,4]oxadiazol-5-yl}-phenyl)-imidazolidine-2,4-dione,
1-((R)-2-{5-[3-(1,1-Dioxo-1λ6-isothiazolidin-2-yl)-phenyl]-[1,2,4]oxadiazol-3-yl}-piperidin-1-yl)-2-phenoxy-ethanone,
1-(3-{3-[(R)-1-(2-Phenoxy-acetyl)-piperidin-2-yl]-[1,2,4]oxadiazol-5-yl}-phenyl)-pyrrolidin-2-one,
1-(3-{3-[(R)-1-(2-Phenoxy-acetyl)-piperidin-2-yl]-[1,2,4]oxadiazol-5-yl}-phenyl)-1,3-dihydro-imidazol-2-one,
3-(3-{3-[(R)-1-(2-Phenoxy-acetyl)-piperidin-2-yl]-[1,2,4]oxadiazol-5-yl}-phenyl)-imidazolidine-2,4-dione,
1-{(R)-2-[5-(1-Methyl-1H-pyrazol-3-yl)-[1,2,4]oxadiazol-3-yl]-piperidin-1-yl}-2-phenoxy-ethanone,
2-Phenoxy-1-{(R)-2-[5-(1H-pyrazol-3-yl)-[1,2,4]oxadiazol-3-yl]-piperidin-1-yl}-ethanone,
1-{(R)-2-[5-(5-Methyl-isoxazol-3-yl)-[1,2,4]oxadiazol-3-yl]-piperidin-1-yl}-2-phenoxy-ethanone,
1-{(R)-2-[5-(2,5-Dimethyl-2H-pyrazol-3-yl)-[1,2,4]oxadiazol-3-yl]-piperidin-1-yl}-2-phenoxy-ethanone,
1-{(R)-2-[5-(5-Methyl-2H-pyrazol-3-yl)-[1,2,4]oxadiazol-3-yl]-piperidin-1-yl}-2-phenoxy-ethanone, and
1-{(R)-2-[5-(3-Methyl-isoxazol-5-yl)-[1,2,4]oxadiazol-3-yl]-piperidin-1-yl}-2-phenoxy-ethanone, and pharmaceutically acceptable salts and esters thereof.

Other particularly preferred compounds of formula (I) are those selected from the group consisting of:

2-Methyl-5-{5-[(R)-1-(2-phenoxy-acetyl)-piperidin-2-yl]-[1,2,4]oxadiazol-3-yl}-3H-pyrimidin-4-one,
1-{(R)-2-[3-(5-Methyl-isoxazol-3-yl)-[1,2,4]oxadiazol-5-yl]-piperidin-1-yl}-2-phenoxy-ethanone,
2-Phenoxy-1-{(R)-2-[3-(1H-pyrazol-3-yl)-[1,2,4]oxadiazol-5-yl]-piperidin-1-yl}-ethanone,
1-{(R)-2-[3-(6-Amino-pyridin-3-yl)-[1,2,4]oxadiazol-5-yl]-piperidin-1-yl}-2-phenoxy-ethanone,
5-{5-[(R)-1-(2-Phenoxy-acetyl)-piperidin-2-yl]-1H-[1,2,4]triazol-3-yl}-1,3-dihydro-indol-2-one,
1-{(R)-2-[5-(2-Amino-pyridin-4-yl)-2H-[1,2,4]triazol-3-yl]-piperidin-1-yl}-2-phenoxy-ethanone,
6-{5-[(R)-1-(2-Phenoxy-acetyl)-piperidin-2-yl]-1H-[1,2,4]triazol-3-yl}-4H-benzo[1,4]oxazin-3-one,
1-{(R)-2-[5-(6-Amino-pyridin-3-yl)-2H-[1,2,4]triazol-3-yl]-piperidin-1-yl}-2-phenoxy-ethanone,
1-{(R)-2-[5-(1H-Benzoimidazol-5-yl)-2H-[1,2,4]triazol-3-yl]-piperidin-1-yl}-2-phenoxy-ethanone,
N-(2-Fluoro-5-{5-[(R)-1-(2-phenoxy-acetyl)-piperidin-2-yl]-1H-[1,2,4]triazol-3-yl}-phenyl)-acetamide, and
1-{(R)-2-[5-(2-Hydroxy-pyridin-4-yl)-[1,2,4]oxadiazol-3-yl]-piperidin-1-yl}-2-phenoxy-ethanone, and pharmaceutically acceptable salts and esters thereof.

It will be appreciated that the compounds of general formula (I) in this invention may be derivatised at functional groups to provide derivatives which are capable of conversion back to the parent compound in vivo.

The invention further relates to a process for the manufacture of compounds of formula (I) as defined above, which process comprises reacting a compound of formula (II)

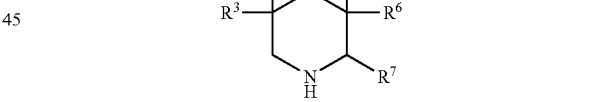

(II)

with a compound of formula (III)

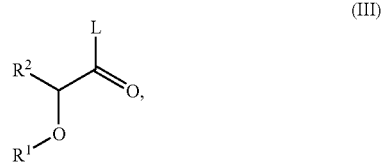

(III)

wherein $R^1$, $R^2$, $R^3$, $R^4$, $R^5$, $R^6$, $R^7$, and X are as defined in any of claims 1-22 and L is halogen.

The reaction of a compound of formula (II) with a compound of formula (III) can be carried out under conditions well known to the person skilled in the art. Such reactions can conveniently be carried out for example by mixing a compound of formula (II) with e.g. an acid chloride of formula (III) or alternatively with an activated ester thereof a compound of formula (III) in a solvent such as e.g. DMF at appropriate temperatures between 25° C. and 120° C., optionally in the presence of diisopropylethylamine. Preferably, L is Cl. Alternatively, L can be an active ester. Such active esters as well as their use to form amide bonds are well known to the person skilled in the art.

The present invention also relates to compounds of formula (I) as defined above, when prepared by a process as described above.

The compounds of formula (I), (II) and (III) can be prepared by methods known in the art or as described below or in analogy thereto. Unless otherwise indicated, $R^1$, $R^2$, $R^3$, $R^4$, $R^5$, $R^6$, $R^7$ and X are as described above.

Compounds of formula (I), can be prepared according to the following general methods.

Compounds of general formula 1 are dissolved preferably in DMF and 1 equivalent of activation reagent such as TBTU is added. The reaction is stirred at room temperature for 10 min and the corresponding hydroxyamidine (compound 2) added to result in compounds of general formula 3. The reaction mixture is heated to 80° C. and stirred overnight of treated under microwave conditions at 120° C. for 15-30 minutes to result in 4. After evaporation of the solvent and extracted from ethylactate/water the crude material is treated with neat trifluoroacetic acid or 4N HCL in Dioxan to result in compounds of general formula 5. The final product is obtained by treating these intermediates either with phenoxyl chloride and derivatives thereof or its corresponding active esters.

The corresponding N-methylpiperazine derivatives were generated from the piperazines as indicated in scheme 2.

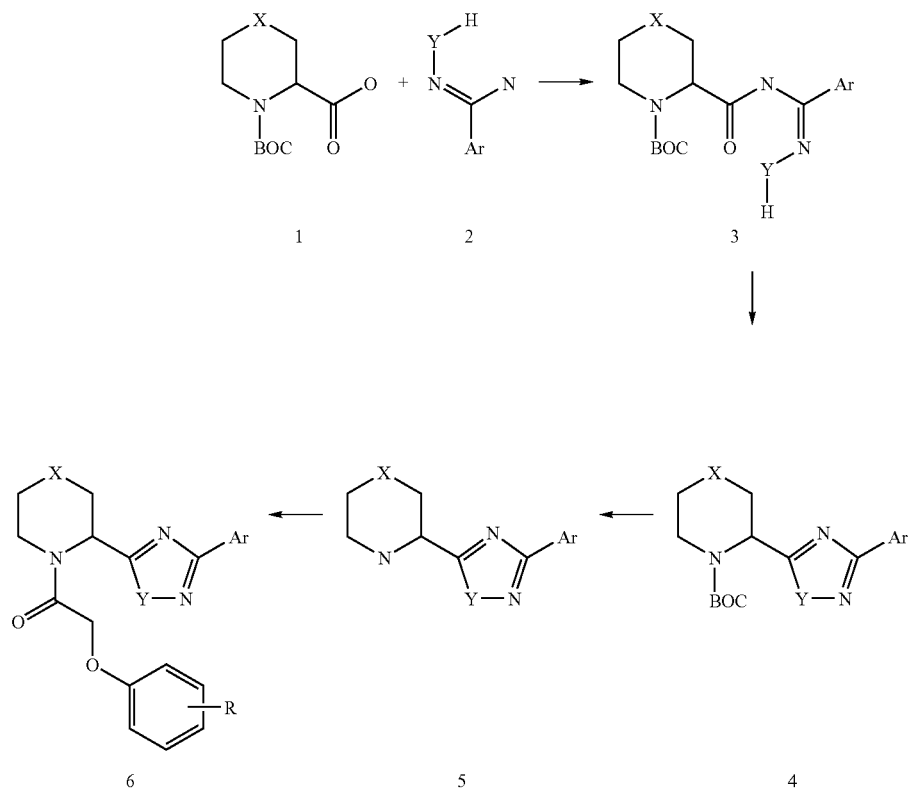

X = CH2, O, S, NAc, NMes
Y = O, NH

Scheme 2

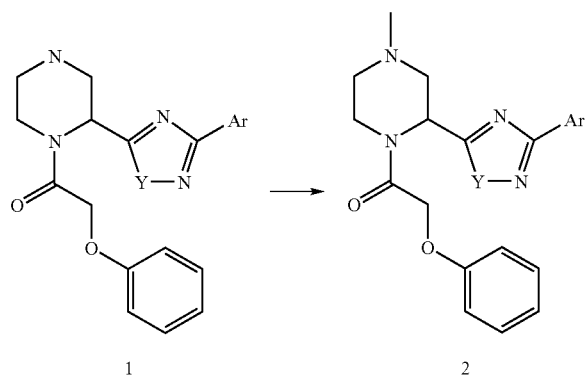

Compounds of type 1 are dissolved preferably in DMF and treated with an excess of formaldehyde and catalytic amount of acetic acid. The reaction mixture is stirred at room temperature for 30 minutes and 1 equivalent of NaBH3CN added. The reaction is stirred at room temperature for 16 h and the product isolated by chromatography.

The carboxylic acid analogues were generated from the corresponding esters through classical saponification with NaOH or LiOH or by catalytic debenzylation procedures where the starting material is typically dissolved in methanol and an aqueous solution of NaOH or LiOH is added.

The reaction is stirred preferably for 2 h at room temperature and the product extracted form ethylacetate/water after acidification of the reaction mixture.

The carboxyamide analogues were generated from the corresponding carboxylates by preactivation with reagents such as TBTU in DMF. The reaction mixtures are usually stirred at room temperature overnight.

The primary carboxyamide analogues were generated from the corresponding carboxylates through coupling on Rink-resin and subsequent cleavage with TFA by preactivating the starting material with reagents such as TBTU. The reaction mixture is usually stirred at room temperature overnight. After excessive washing of the resins with solvents such as DMF, methanol and methylenchloride the solid phase material is treated with TFA at room temperature for 2 h. After evaporation the product is isolated by chromatography.

The amino derivatives were generated from the corresponding nitro analogues through a Zink mediated reduction where the starting material is dissolved preferably in ethanol and saturated aqueous ammonium chloride. An excess of zinc powder is added, the reaction briefly heated to reflux and then stirred at room temperature for 16 h. The product is isolated by extraction from ethylacetate/water and final chromatography The following N-amides, -sulfonamides, -carbamates and -ureas were all generated from the corresponding amino-derivatives where the amino-derivatives are dissolved preferably in DMF and the corresponding acetyl chlorides or activate esters, sulfonyl chlorides or isocyanates are added. The reactions proceed at room temperature. The products are isolated by chromatography.

The benzonitriles were generated from the corresponding primary benzamides by treatment of the latter with neat trifluoroacetic anhydride at room temperature for preferably 16 h.

The non-commercially available aminoacids were generated from Piperazine-1,2-dicarboxylic acid 1-tert-butyl ester 2-methyl ester by coupling with either acetyl chloride or methylsulfonyl chloride in THF at room temperature followed by saponification as described above.

The non-commercially available hydroxyamidines were generated from the corresponding nitriles by the addition of 5 equivalents of hydroxylamine mono hydrochloride and 2.5 equivanents sodium carbonate in a mixture of ethanol/water (7:3). The reaction mixture was heated to 80° C. for usually 2 h. The product was isolated by extraction from ethylacetate/water.

The non-commercially available sulfonamido hydroxyamidines were generated by coupling of 4-cyanobenzen-1-sulfonylchloride with 2 equivalents of the corresponding amine in THF at room temperature for 16 h. After evaporation of the solvent the product is extracted from ethylacetate/water. The crude nitril is treated with hydrazine as described above.

The non-commercially available 2-aminopyridino hydroxyamidines were generated from the corresponding nitriles as described above. The nitriles were obtained from the corresponding chlorocyanopyridines after dissolving in DMF and adding 2 equivalents of the amine. The reaction mixture was heated to 120° C. under microwave conditions usually for 30 min. The product was isolated by extraction from ethylacetate/water after evaporation of the reaction solvent.

The aminoamidines were generated from the corresponding imidoethers by addition of 1 equivalent of hydrazine monohydrate in methanol. The product was isolated by precipitation when adding 1.25M HCl/methanol. The iminoethers were obtained from the corresponding nitriles after suspending in methylenchloride and saturation with HCl gas at 0° C. for 30 min. The reaction mixture was stirred for 16 h at room temperature and the product filtered off after addition of diethylether.

The non-commercially available nitrites were generated from the corresponding primary amides by the addition of neat trifluoroaceticacid anhydride at room temperature preferably for 16 h.

Scheme 3

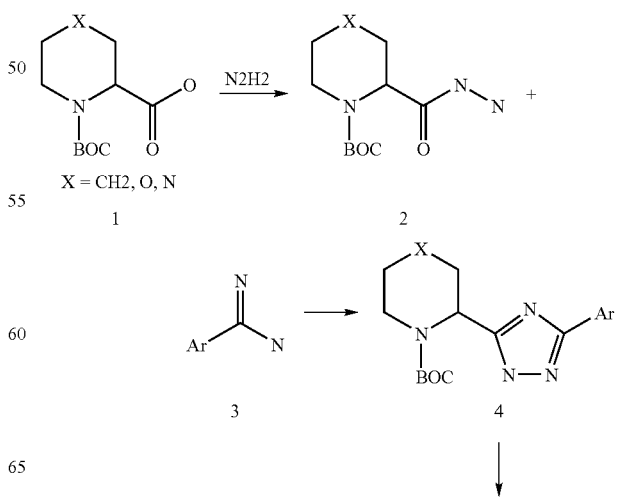

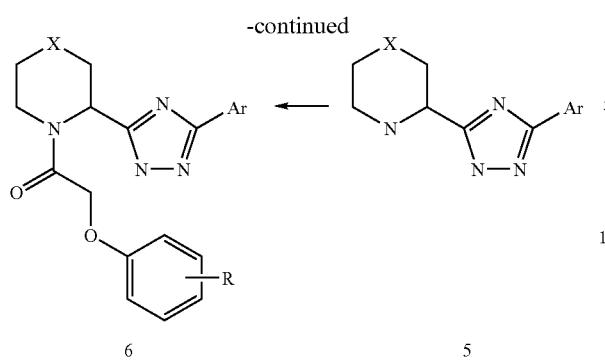

Furthermore, as outlined in scheme 3, compounds of general formula 1 can be dissolved preferably in DMF and 1 equivalent of activation reagent such as TBTU is added in addition to 1 equivalent of a base such as DIPEA. The reaction is cooled to 0° C. and an excess of hydrazine added. The reaction is warmed up and stirred at ambient temperature to result in compound 2. After evaporation of the solvent and extraction from ethylactate/water the crude material is treated with 1 equivalent of the corresponding amidine in DMF. Catalytic amount of acetic acid is added and the reaction heated to 120° C. overnight to result in compounds of general formula 4. After evaporation of the solvent and extraction from ethylactate/water neat trifluoroacetic acid or 4N HCL in Dioxan is added to generate compounds of general formula 5. The final product is obtained by treating these intermediates either with phenoxyacetyl chloride and derivatives thereof or its corresponding active esters.

their corresponding acetyl chlorides in solvents such as DMF to result in compounds with the general formula 3. Cyclisation to the corresponding oxadiazole occurs under elevated temperature either using conventional or microwave heating. Boc cleavage is usually performed using either neat TFA or 4N HCl in Dioxan to result in compounds of general formula 5. The final product is obtained by treating these intermediates either with phenoxyacetyl chloride and derivatives thereof or its corresponding active esters.

The corresponding salts can be obtained by standard methods known to the person skilled in the art, e.g. by dissolving the compound of formula(I) in a suitable solvent such as e.g. dioxan or THF and adding an appropriate amount of the corresponding acid. The products can usually be isolated by filtration or by chromatography.

The conversion of compounds of formula (I) into pharmaceutically acceptable esters can be carried out e.g. by treatment of a suitable carboxy group present in the molecule with a suitable alcohol using e.g. a condensating reagent such as benzotriazol-1-yloxytris(dimethylamino)phosphonium hexafluorophosphate (BOP), N,N-dicyclohexylcarbodiimide (DCC), N-(3-dimethylaminopropyl)-N'-ethylcarbodiimide hydrochloride (EDCI) or O-(1,2-dihydro-2-oxo-1-pyridyl)-N,N,N,N-tetra-methyluronium-tetrafluorborate (TPTU). Pharmaceutically acceptable esters can furthermore be prepared by treatment of a suitable hydroxy group present in the molecule with a suitable acid, optionally or if necessary in the presence of a condensating agent as described above.

Insofar as their preparation is not described in the examples, the compounds of formula (I) as well as all intermediate products can be prepared according to analogous methods or according to the methods set forth above. Starting

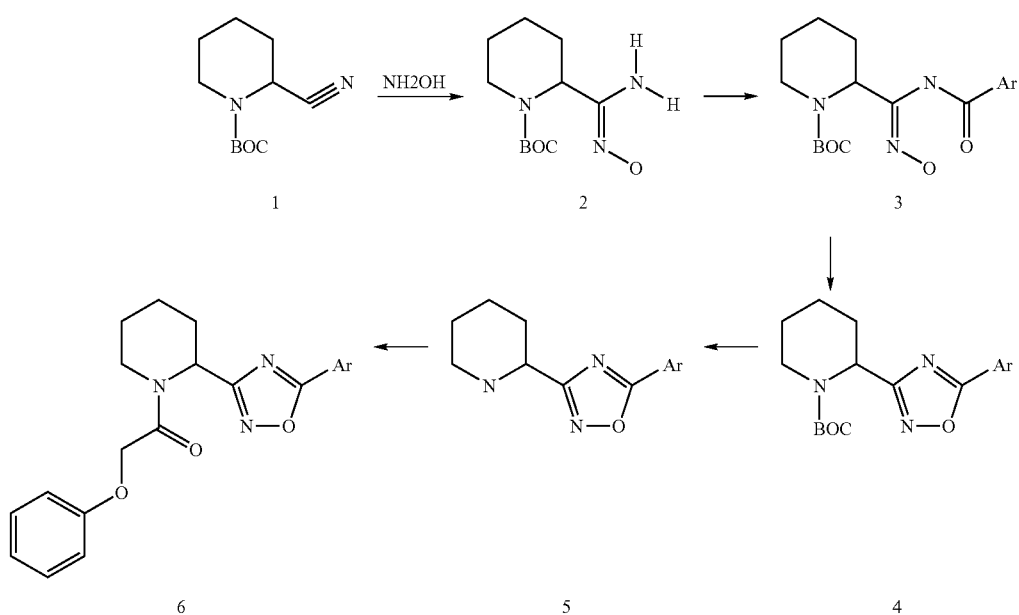

Furthermore, as outlined in scheme 4, compound 1 can be dissolved preferably in aqueous ethanol and treated with an excess of hydrazine hydrochloride and a base such as sodium carbonate to result in compound 2. This intermediate can be coupled with 1 equivalent of pre-activated carboxylates or materials are commercially available, known in the art or can be prepared by methods known in the art or in analogy thereto.

As described above, the novel compounds of the present invention have been found to inhibit liver carnitine palmitoyl transferase 1 (L-CPT1) activity. The compounds of the present invention can therefore be used in the treatment and/or prophylaxis of diseases which are modulated by L-CPT1 inhibitors, particularly diseases which are related to hyperglycemia and/or glucose tolerance disorders. Such diseases include e.g. diabetes and associated pathologies, non insulin dependent diabetes mellitus, obesity, hypertension, insulin resistance syndrome, metabolic syndrome, hyperlipidemia, hypercholesterolemia, fatty liver disease, atherosclerosis, congestive heart failure and renal failure.

The invention therefore also relates to pharmaceutical compositions comprising a compound as defined above and a pharmaceutically acceptable carrier and/or adjuvant.

The invention likewise embraces compounds as described above for use as therapeutically active substances, especially as therapeutically active substances for the treatment and/or prophylaxis of diseases which are modulated by L-CPT1 inhibitors, particularly as therapeutically active substances for the treatment and/or prophylaxis of hyperglycemia, glucose tolerance disorders, diabetes and associated pathologies, non insulin dependent diabetes mellitus, obesity, hypertension, insulin resistance syndrome, metabolic syndrome, hyperlipidemia, hypercholesterolemia, fatty liver disease, atherosclerosis, congestive heart failure and renal failure.

In another preferred embodiment, the invention relates to a method for the therapeutic and/or prophylactic treatment of diseases which are modulated by L-CPT1 inhibitors, particularly for the therapeutic and/or prophylactic treatment of hyperglycemia, glucose tolerance disorders, diabetes and associated pathologies, non insulin dependent diabetes mellitus, obesity, hypertension, insulin resistance syndrome, metabolic syndrome, hyperlipidemia, hypercholesterolemia, fatty liver disease, atherosclerosis, congestive heart failure and renal failure, which method comprises administering a compound as defined above to a human being or animal.

The invention also embraces the use of compounds as defined above for the therapeutic and/or prophylactic treatment of diseases which are modulated by L-CPT1 inhibitors, particularly for the therapeutic and/or prophylactic treatment of hyperglycemia, glucose tolerance disorders, diabetes and associated pathologies, non insulin dependent diabetes mellitus, obesity, hypertension, insulin resistance syndrome, metabolic syndrome, hyperlipidemia, hypercholesterolemia, fatty liver disease, atherosclerosis, congestive heart failure and renal failure.

The invention also relates to the use of compounds as described above for the preparation of medicaments for the therapeutic and/or prophylactic treatment of diseases which are modulated by L-CPT1 inhibitors, particularly for the therapeutic and/or prophylactic treatment of hyperglycemia, glucose tolerance disorders, diabetes and associated pathologies, non insulin dependent diabetes mellitus, obesity, hypertension, insulin resistance syndrome, metabolic syndrome, hyperlipidemia, hypercholesterolemia, fatty liver disease, atherosclerosis, congestive heart failure and renal failure. Such medicaments comprise a compound as described above.

Prevention and/or treatment of hyperglycemia and non insulin dependent diabetes mellitus is the preferred indication.

The following tests were carried out in order to determine the activity of the compounds of the present invention. Background information on the performed assays can be found in: Jackson et al., 1999, *Biochem. J.* 341, 483-489 and Jackson et al., 2000, *J. Biol. Chem.* 275, 19560-19566.

Human liver and muscle CPT1 cDNAs and rat CPT2 cDNA were subcloned in pGAPZB or pGAPZA, respectively. These plasmids were used to transform *P. pastoris* strain X-33 via electroporation after the preparation of electrocompetent cells. High copy number clones were selected where necessary using 0.5 or 1 mg/ml Zeocin. Cultures for activity measurements were induced for 16 h in YPD medium (1% yeast extract, 2% peptone, 2% glucose). Crude cell extracts were prepared by disrupting the cells with glass beads or French Press, depending on fermenter sizes. After centrifugation, the cell-free extracts were resuspended in cell breaking buffer (50 mM Tris, pH7.4, 100 mM KCl, 1 mM EDTA) in the presence of a protease inhibitor cocktail, before aliquoting and freezing at −20° C.

CPT activity was measured using a spectrophotometric assay using 5,5'-dithio-bis-(2-nitrobenzoic acid) (DTNB) also called Ellman's reagent. The HS-CoA released on the formation of acylcarnitine from carnitine (500 µM) and palmitoyl-CoA (80 µM) reduced DTNB (300 µM) forming 5-mercapto-(2-nitrobenzoic acid) which absorbed at 410 nm with a molar coefficient extinction of 13600 $M^{-1}.cm^{-1}$. The assay buffer contained 120 mM KCl, 25 mM Tris, pH 7.4, 1 mM EDTA. This assay was used for the identification of selective inhibitors of the liver CPT1 isoform versus the muscle CPT1 and CPT2 isoforms.

The compounds according to formula (I) preferably have an IC50 value below 10 µM, preferably 10 nM to 10 µM, more preferably 10 nM to 5 µM. The following table shows data for some examples.

| Example | L-CPT1 inhibition $IC_{50}$ [µmol/l] |
| --- | --- |
| 1 | 0.066 |
| 10 | 0.260 |
| 172 | 0.242 |

The compounds of formula I and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or suspensions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 2000 mg, especially about 1 to 500 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-500 mg, preferably 1-200 mg, of a compound of formula I.

The following Examples serve to illustrate the present invention in more detail. They are, however, not intended to limit its scope in any manner.

EXAMPLES

Example 1

(R)-1-{2-[3-(4-Methoxy-phenyl)-[1,2,4]oxadiazol-5-yl]-piperidin-1-yl}-2-phenoxy-ethanone Step 1:

(R)-2-{[Hydroxyimino-(4-methoxy-phenyl)-methyl]-carbamoyl}-piperidine-1-carboxylic acid tert-butyl ester 23 mg (0.1 mmol) of Boc-D-Pipecolic Acid were treated with 0.1 mmol [Dimethylamino-([1,2,3]triazolo[4,5-b]pyridin-3-yloxy)-methylene]-dimethyl-ammonium hexafluorophosphate (HATU) and Diisopropylamine (DIPEA) in 1 ml Dimethylforamide (DMF) for 10 min. 17 mg (0.1 mmol) of N-Hydroxy-4-methoxy-benzamidine were added and the reaction stirred at room temperature for 20 min. The product was not further characterized.

Step 2:

(R)-2-[3-(4-Methoxy-phenyl)-[1,2,4]oxadiazol-5-yl]-piperidine-1-carboxylic acid tert-butyl ester Crude material from step 1 was either treated at 80° C. for 16 h or briefly heated to 120° C. under microwave conditions (10 min). The DMF was evaporated and the product extracted from ethylacetate/water. The product was not further characterized.

Step 3:

(R)-2-[3-(4-Methoxy-phenyl)-[1,2,4]oxadiazol-5-yl]-piperidine trifluoroacetate

Crude material from step 2 was treated with neat trifluoroacetic acid (TFA) at room temperature for 1 h. The TFA was evaporated. The crude product not further characterized.

Step 4:

(R)-1-{2-[3-(4-Methoxy-phenyl)-[1,2,4]oxadiazol-5-yl]-piperidin-1-yl}-2-phenoxy-ethanone Crude material from step 3 was dissolved in 1 ml DMF and 0.1 mmol DIPEA. Either 0.1 mmol phenoxyacetyl chloride were added and the reaction stirred at room temperature for 30 min, or the corresponding phenoxyacetic acid derivatives were pre-activated with HATU/DIPEA in DMF for 10min and added to the crude material from step 3. The product was isolated via preparative high performance liquid chromatography (HPLC).

MS(ISO): 394.4 (MH+)

The following compounds were prepared in analogy.

TABLE 1

| Example | Compound name | Starting materials | MH+ (found) |
|---|---|---|---|
| 2 | (R)-3-(2-{2-[3-(4-Methoxy-phenyl)[1,2,4]oxadiazol-5-yl]-piperidin-1-yl}-2-oxo-ethoxy)benzonitrile | Boc-D-Pipecolic Acid, N-Hydroxy-4-methoxy-benzamidine and 3-Cyanophenoxy-acetyl chloride | 419.5 |
| 3 | (R)-1-{2-[3-(4-Methoxy-phenyl)-[1,2,4]oxadiazol-5-yl]-piperidin-1-yl}-2-phenoxy-propan-1-one | Boc-D-Pipecolic Acid, N-Hydroxy-4-methoxy-benzamidine and 2-Phenoxy-propionic acid | 408.5 |
| 4 | (R)-1-{2-[3-(4-Bromo-phenyl)[1,2,4]oxadiazol-5-yl]-piperidin-1-yl}-2-phenoxy-ethanone | Boc-D-Pipecolic Acid, N-Hydroxy-4-bromo-benzamidine and phenoxyacetyl chloride | 442.2 |
| 5 | (R)-2-(4-Hydroxy-phenoxy)-1-{2-[3-(4-methoxy-phenyl)-[1,2,4]oxadiazol-5-yl]-piperidin-1-yl}-ethanone | Boc-D-Pipecolic Acid, N-Hydroxy-4-methoxy-benzamidine and 4-Hydroxy-phenoxyacetic acid | 410.5 |
| 6 | (R)-2-(4-Chloro-phenoxy)-1-{2-[3-(4-methoxy-phenyl)-[1,2,4]oxadiazol-5-yl]-piperidin-1-yl}-ethanone | Boc-D-Pipecolic Acid, N-Hydroxy-4-methoxy-benzamidine and 4-Chlorophenoxy-acetic acid | 428.5 |

TABLE 1-continued

| Example | Compound name | Starting materials | MH+ (found) |
|---|---|---|---|
| 7 | (R)-2-(4-Hydroxymethyl-phenoxy)-1-{2-[3-(4-methoxy-phenyl)-[1,2,4]oxadiazol-5-yl]-piperidin-1-yl}-ethanone | Boc-D-Pipecolic Acid, N-Hydroxy-4-methoxy-benzamidine and 4-Hydroxymethylphenoxy-acetic acid | 424.2 |
| 8 | (R)-2-(3-Chloro-phenoxy)-1-{2-[3-(4-methoxy-phenyl)-[1,2,4]oxadiazol-5-yl]-piperidin-1-yl}-ethanone | Boc-D-Pipecolic Acid, N-Hydroxy-4-methoxy-benzamidine and 3-Chlorophenoxy-acetic acid | 428.5 |
| 9 | (R)-2-(4-Fluoro-phenoxy)-1-{2-[3-(4-methoxy-phenyl)-[1,2,4]oxadiazol-5-yl]-piperidin-1-yl}-ethanone | Boc-D-Pipecolic Acid, N-Hydroxy-4-methoxy-benzamidine and 4-Fluorophenoxy-acetic acid | 412.4 |
| 10 | (R)-1-{2-[3-(4-Fluoro-phenyl)-[1,2,4]oxadiazol-5-yl]-piperidin-1-yl}-2-phenoxy-ethanone | Boc-D-Pipecolic Acid, N-Hydroxy-4-fluoro-benzamidine and phenoxyacetyl chloride | 382.5 |
| 11 | (R)-1-{2-[3-(4-Methane-sulfonyl-phenyl)-[1,2,4]oxadiazol-5-yl]-piperidin-1-yl}-2-phenoxy-ethanone | Boc-D-Pipecolic Acid, N-Hydroxy-4-methane-sulfonylbenzamidine and phenoxyacetyl chloride | 442.5 |
| 12 | (R)-4-{5-[1-(2-Phenoxy-acetyl)-piperidin-2-yl]-[1,2,4]oxadiazol-3-yl}-benzenesulfonamide | Boc-D-Pipecolic Acid, N-Hydroxy-4-sulfamoyl-benzamidine and phenoxyacetyl chloride | 443.5 |
| 13 | (R)-2-(4-Fluoro-phenoxy)-1-[2-(3-pyridin-4-yl-[1,2,4]oxadiazol-5-yl)-piperidin-1-yl]-ethanone | Boc-D-Pipecolic Acid, N-Hydroxy-isonicotinamidine and phenoxyacetyl chloride | 383.4 |
| 14 | (R)-3-{5-[1-(2-Phenoxy-acetyl)-piperidin-2-yl]-[1,2,4]oxadiazol-3-yl}-benzoic acid methyl ester | Boc-D-Pipecolic Acid, 3-(N-Hydroxycarb-imidoyl)-benzoic acid methyl ester and phenoxyacetyl chloride | 422.5 |
| 15 | (R)-1-{2-[3-(3-Nitro-phenyl)-[1,2,4]oxadiazol-5-yl]-piperidin-1-yl}-2-phenoxy-ethanone | Boc-D-Pipecolic Acid, N-Hydroxy-3-nitro-benzamidine and phenoxyacetyl chloride | 409.5 |
| 16 | (R)-1-{2-[3-(4-Nitro-phenyl)-[1,2,4]oxadiazol-5-yl]-piperidin-1-yl}-2-phenoxy-ethanone | Boc-D-Pipecolic Acid, N-Hydroxy-4-nitro-benzamidine and phenoxyacetyl chloride | 409.5 |
| 17 | (R)-3-{5-[1-(2-Phenoxy-acetyl)-piperidin-2-yl]-[1,2,4]oxadiazol-3-yl}-benzenesulfonamide | Boc-D-Pipecolic Acid, N-Hydroxy-3-sulfamoyl-benzamidine and phenoxyacetyl chloride | 443.5 |
| 18 | (R)-2-Phenoxy-1-[2-(3-pyrazin-2-yl-[1,2,4]oxadiazol-5-yl)-piperidin-1-yl]-ethanone | Boc-D-Pipecolic Acid, N-Hydroxy-pyrazine-2-carboxamidine and phenoxyacetyl chloride | 366.5 |
| 19 | (R)-1-(2-{3-[4-(Morpholine-4-sulfonyl)-phenyl]-[1,2,4]oxadiazol-5-yl}-piperidin-1-yl)-2-phenoxy-ethanone | Boc-D-Pipecolic Acid, N-Hydroxy-4-N-acetyl-benzamidine and phenoxyacetyl chloride | 513.6 |
| 20 | (R)-1-{2-[3-(6-Methoxy-pyridin-3-yl)-[1,2,4]oxadiazol-5-yl]-piperidin-1-yl}-2-phenoxy-ethanone | Boc-D-Pipecolic Acid, N-Hydroxy-6-methoxy-nicotinamidine and phenoxyacetyl chloride | 395.5 |
| 21 | (R)-1-{2-[3-(3-Hydroxymethyl-phenyl)-[1,2,4]oxadiazol-5-yl]-piperidin-1-yl}-2-phenoxy-ethanone | Boc-D-Pipecolic Acid, N-Hydroxy-3-hydroxymethyl benzamidine and phenoxyacetyl chloride | 394.5 |
| 22 | (R)-6-{5-[1-(2-Phenoxy-acetyl)-piperidin-2-yl]-[1,2,4]oxadiazol-3-yl}-nicotinic acid allyl ester | Boc-D-Pipecolic Acid, 6-(N-Hydroxycarb-amimidoyl)-nicotinic acid allyl ester and phenoxyacetyl chloride | 449.1 |
| 23 | (R)-1-{2-[3-(4-Imidazol-1-yl-phenyl)-[1,2,4]oxadiazol-5-yl]-piperidin-1-yl}-2-phenoxy-ethanone | Boc-D-Pipecolic Acid, N-Hydroxy-4-imidazol-1-yl-benzamidine and phenoxyacetyl chloride | 430.5 |

TABLE 1-continued

| Example | Compound name | Starting materials | MH+ (found) |
|---|---|---|---|
| 24 | (R)-N-Methyl-4-{5-[1-(2-phenoxy-acetyl)-piperidin-2-yl]-[1,2,4]oxadiazol-3-yl}-benzenesulfonamide | Boc-D-Pipecolic Acid, N-Hydroxy-4-methylsulfamoyl-benzamidine and phenoxyacetyl chloride | 457.5 |
| 25 | (R)-1-{2-[3-(6-Morpholin-4-yl-pyridin-3-yl)-[1,2,4]oxadiazol-5-yl]-piperidin-1-yl}-2-phenoxy-ethanone | Boc-D-Pipecolic Acid, N-Hydroxy-6-morpholin-4-yl-nicotinamidine and phenoxy-acetyl chloride | 450.5 |
| 26 | (R)-2-Phenoxy-1-{2-[3-(4-trifluoromethanesulfonyl-phenyl)-[1,2,4]oxadiazol-5-yl]-piperidin-1-yl}-ethanone | Boc-D-Pipecolic Acid, N-Hydroxy-4-trifluoromethanesulfonyl-benzamidine and phenoxyacetyl chloride | 496.5 |
| 27 | (R)-2-Phenoxy-1-{2-[3-(4-trifluoromethyl-phenyl)-[1,2,4]oxadiazol-5-yl]-piperidin-1-yl}-ethanone | Boc-D-Pipecolic Acid, N-Hydroxy-4-trifluoromethyl-benzamidine and phenoxyacetyl chloride | 432.5 |
| 28 | (R)-1-{2-[3-(4-Chloro-phenyl)-[1,2,4]oxadiazol-5-yl]-piperidin-1-yl}-2-phenoxy-ethanone | Boc-D-Pipecolic Acid, N-Hydroxy-4-chloro-benzamidine and phenoxyacetyl chloride | 398.4 |
| 29 | (R)-N-(4-{5-[1-(2-Phenoxy-acetyl)-piperidin-2-yl]-[1,2,4]oxadiazol-3-yl}-2-trifluoromethyl-phenyl)-acetamide | Boc-D-Pipecolic Acid, N-[4-(N-Hydroxycarb-amimidoyl)-2-trifluoro-methyl-phenyl]-acetamide and phenoxyacetyl chloride | 489.5 |
| 30 | (R)-1-{2-[3-(3-Methanesulfonyl-phenyl)-[1,2,4]oxadiazol-5-yl]-piperidin-1-yl}-2-phenoxy-ethanone | Boc-D-Pipecolic Acid, N-Hydroxy-3-methanesulfonyl-benzamidine and phenoxyacetyl chloride | 442.5 |
| 31 | (R)-1-{2-[3-(4-Methyl-3-nitro-phenyl)-[1,2,4]oxadiazol-5-yl]-piperidin-1-yl}-2-phenoxy-ethanone | Boc-D-Pipecolic Acid, N-Hydroxy-4-methyl-3-nitro-benzamidine and phenoxyacetyl chloride | 423.5 |
| 32 | (R)-1-{2-[3-(4-Methoxy-3-nitro-phenyl)-[1,2,4]oxadiazol-5-yl]-piperidin-1-yl}-2-phenoxy-ethanone | Boc-D-Pipecolic Acid, N-Hydroxy-4-methoxy-3-nitro-benzamidine and phenoxyacetyl chloride | 439.5 |
| 33 | (R)-N-(2-Hydroxy-ethyl)-4-{5-[1-(2-phenoxy-acetyl)-piperidin-2-yl]-[1,2,4]oxadiazol-3-yl}-benzenesulfonamide | Boc-D-Pipecolic Acid, N-Hydroxy-4-(2-hydroxy-ethylsulfamoyl)-benzamidine and phenoxyacetyl chloride | 487.5 |
| 34 | (R)-N-(2-Methoxy-ethyl)-N-methyl-4-{5-[1-(2-phenoxy-acetyl)-piperidin-2-yl]-[1,2,4]oxadiazol-3-yl}-benzenesulfonamide | Boc-D-Pipecolic Acid, N-Hydroxy-4-[(2-methoxy-ethyl)-methyl-suifamoyl]-benzamidine and phenoxyacetyl chloride | 515.5 |
| 35 | (R)-N,N-Dimethyl-4-{5-[1-(2-phenoxy-acetyl)-piperidin-2-yl]-[1,2,4]oxadiazol-3-yl}-benzenesulfonamide | Boc-D-Pipecolic Acid, 4-Dimethylsulfamoyl-N-hydroxy-benzamidine and phenoxyacetyl chloride | 471.5 |
| 36 | (R)-N,N-Diethyl-4-{5-[1-(2-phenoxy-acetyl)-piperidin-2-yl]-(1,2,4]oxadiazol-3-yl}-benzenesulfonamide | Boc-D-Pipecolic Acid, 4-Diethylsulfamoyl-N-hydroxy-benzamidine and phenoxyacetyl chloride | 499.6 |
| 37 | (R)-1-{2-[3-(2-Morpholin-4-yl-pyridin-4-yl)-[1,2,4]oxadiazol-5-yl]-piperidin-1-yl}-2-phenoxy-ethanone | Boc-D-Pipecolic Acid, N-Hydroxy-2-morpholin-4-yl-isonicotinamidine and phenoxyacetyl chloride | 450.5 |
| 38 | (R)-2-Phenoxy-1-{2-[3-(3,4,5,6-tetrahydro-2H-[1,2']bipyridinyl-4'-yl)-[1,2,4]oxadiazol-5-yl]-piperidin-1-yl}-ethanone | Boc-D-Pipecolic Acid, N-Hydroxy-3,4,5,6-tetrahydro-2H-[1,2']bipyridinyl-4'-carboxamidine and phenoxyacetyl chloride | 448.5 |
| 39 | (R)-2-Phenoxy-1-{2-[3-(2-thiomorpholin-4-yl-pyridin-4-yl)-[1,2,4]oxadiazol-5-yl]-piperidin-1-yl}-ethanone | Boc-D-Pipecolic Acid, N-Hydroxy-2-thiomorpholin-4-yl-isonicotinamidine and phenoxyacetyl chloride | 466.5 |

TABLE 1-continued

| Example | Compound name | Starting materials | MH+ (found) |
|---|---|---|---|
| 40 | (R)-1-{2-[3-(2-Diethylamino-pyridin-4-yl)-[1,2,4]oxadiazol-5-yl]-piperidin-1-yl}-2-phenoxy-ethanone | Boc-D-Pipecolic Acid, 2-Diethylamino-N-hydroxy-isonicotin amidine and phenoxyacetyl chloride | 436.5 |
| 41 | (R)-4-{5-[1-(2-Phenoxy-acetyl)-piperidin-2-yl]-[1,2,4]oxadiazol-3-yl}-pyridine-2-carboxylic acid ethyl ester | Boc-D-Pipecolic Acid, 4-(N-Hydroxycarbamimidoyl)-pyridine-2-carboxylic acid ethyl esterand phenoxyacetyl chloride | 437.5 |
| 42 | (R)-1-(2-{3-[6-(4-Acetyl-piperazin-1-yl)-pyridin-3-yl]-[1,2,4]oxadiazol-5-yl}-piperidin-1-yl)-2-phenoxy-ethanone | Boc-D-Pipecolic Acid, 6-(4-Acetyl-piperazin-1yl)-N-hydroxy-nicotinamidine and phenoxyacetyl chloride | 491.5 |
| 43 | (R)-1-{2-[3-(2-Imidazol-1-yl-pyridin-4-yl)-[1,2,4]oxadiazol-5-yl]-piperidin-1-yl}-2-phenoxy-ethanone | Boc-D-Pipecolic Acid, N-Hydroxy-2-imidazol-1-yl isonicotinamidine and phenoxyacetyl chloride | 431.5 |
| 44 | (R)-1-(3-{5-[1-(2-Phenoxy-acetyl)-piperidin-2-y]-[1,2,4]oxadiazol-3-yl}-phenyl)-piperidin-2-one | Boc-D-Pipecolic Acid, N-Hydroxy-3-(2-oxo-piperidin-1-yl)-benzamidine and phenoxy-acetyl chloride | 461.5 |
| 45 | (R)-1-(2-{3-[4-(3H-Imidazol-4-yl)-phenyl]-[1,2,4]oxadiazol-5-yl}-piperidin-1-yl)-2-phenoxy-ethanone | Boc-D-Pipecolic Acid, N-Hydroxy-4-(3H-imidazol-4-yl)-benzamidine and phenoxy-acetyl chloride | 430.5 |
| 46 | (R)-1-(2-{3-[4-(2-Methyl-imidazol-1-yl)-phenyl]-[1,2,4]oxadiazol-5-yl}-piperidin-1-yl)-2-phenoxy-ethanone | Boc-D-Pipecolic Acid, N-Hydroxy-4-(2-methyl-imidazol-1-yl)-benzamidine and phenoxy-acetyl chloride | 444.5 |
| 47 | (R)-2-Phenoxy-1-{2-[3-(2-pyrazol-1-yl-pyridin-4-yl)-[1,2,4]oxadiazol-5-yl]-piperidin-1-yl}-ethanone | Boc-D-Pipecohc Acid, N-Hydroxy-2-pyrazol-1-yl-isonicotin amidine and phenoxy-acetyl chloride | 431.5 |
| 48 | (R)-4-(5-{5-[1-(2-Phenoxy-acetyl)-piperidin-2-yl]-[1,2,4]oxadiazol-3-yl}-pyridin-2-yl)-piperazin-2-one | Boc-D-Pipecolic Acid, N-Hydroxy-6-(3-oxo-piperazin-1-yl)-nicotinamidine and phenoxyacetyl chloride | 463.5 |
| 49 | (R)-2-Phenoxy-1-(2-{3-[4-(1H-tetrazol-5-yl)-phenyl]-[1,2,4]oxadiazol-5-yl}-piperidin-1-yl)-ethanone | Boc-D-Pipecolic Acid, N-Hydroxy-4-(1H-tetrazol-5-yl)-benzamidine and phenoxyacetyl chloride | 430.1(M − H+) |
| 50 | (R)-1-{2-[3-(1H-Indazol-5-yl)-[1,2,4]oxadiazol-5-yl]-piperidin-1-yl}-2-phenoxy-ethanone | Boc-D-Pipecolic Acid, N-Hydroxy-1H-indazole-5-carboxamidine and phenoxyacetyl chloride | 404.5 |
| 51 | (R)-1-{2-[3-(1H-Indazol-6-yl)-[1,2,4]oxadiazol-5-yl]-piperidin-1-yl}-2-phenoxy-ethanone | Boc-D-Pipecolic Acid, N-Hydroxy-1H-indazole-5-carboxamidine and phenoxyacetyl chloride | 404.1 |
| 52 | (R)-1-{2-[3-(4-Fluoro-3-trifluoromethyl-phenyl)-[1,2,4]oxadiazol-5-yl]-piperidin-1-yl}-2-phenoxy-ethanone | Boc-D-Pipecolic Acid, 4-Fluoro-N-hydroxy-3-trifluoromethyl-benzamidine and phenoxyacetyl chloride | 450.4 |
| 53 | (R)-6-{5-[1-(2-Phenoxy-acetyl)-piperidin-2-yl]-[1,2,4]oxadiazol-3-yl}-1,3-dihydro-indol-2-one | Boc-D-Pipecolic Acid, N-Hydroxy-2-oxo-2,3-dihydro-1H-indole-6-carboxamidine and phenoxyacetyl chloride | 419.3 |
| 54 | (R)-5-{5-[1-(2-Phenoxy-acetyl)-piperidin-2-yl]-[1,2,4]oxadiazol-3-yl}-1,3-dihydro-benzoimidazol-2-one | Boc-D-Pipecolic Acid, N-Hydroxy-2-oxo-2,3-dihydro-1H-benzoimidazole-5-carboxamidine and phenoxyacetyl chloride | 420.4 |
| 55 | (R)-5-{5-[1-(2-Phenoxy-acetyl)-piperidin-2-yl]-[1,2,4]oxadiazol-3-yl}-1,3-dihydro-indol-2-one | Boc-D-Pipecolic Acid, N-Hydroxy-2-oxo-2,3-dihydro-1H-indole-5-carboxamidine and phenoxyacetyl chloride | 419.4 |
| 56 | (R)-1-{2-[3-(1H-Benzotriazol-5-yl)-[1,2,4]oxadiazol-5-yl]-piperidin-1-yl}-2-phenoxy-ethanone | Boc-D-Pipecolic Acid, N-Hydroxy-1H-benzotriazole-5-carboxamidine and phenoxyacetyl chloride | 405.4 |

TABLE 1-continued

| Example | Compound name | Starting materials | MH+ (found) |
|---|---|---|---|
| 57 | (R)-1-{2-[3-(1H-Benzoimidazol-5-yl)-[1,2,4]oxadiazol-5-yl]-piperidin-1-yl}-2-phenoxy-ethanone | Boc-D-Pipecolic Acid, N-Hydroxy-1H-benzoimidazole-5-carboxamidine and phenoxyacetyl chloride | 404.5 |
| 58 | (R)-1-(2-{3-[6-(1,1-Dioxo-thiomorpholin-4-yl)-pyridin-3-yl]-[1,2,4]oxadiazol-5-yl}-piperidin-1-yl)-2-phenoxy-ethanone | Boc-D-Pipecolic Acid, 6-(1,1-Dioxo-thiomorpholin-4-yl)-N-hydroxy-nicotinamidine and phenoxyacetyl chloride | 498.5 |
| 59 | (R)-N-(4-{5-[1-(2-Phenoxy-acetyl)-piperidin-2-yl]-[1,2,4]oxadiazol-3-yl}-pyridin-2-yl)-acetamide | Boc-D-Pipecolic Acid, N-[4-(N-Hydroxy-carbamimidoyl)-pyridin-2-yl]-acetamide and phenoxyacetyl chloride | 422.5 |
| 60 | (R)-1-{2-[3-(6-Benzyloxy-pyridin-3-yl)-[1,2,4]oxadiazol-5-yl]-piperidin-1-yl}-2-phenoxy-ethanone | Boc-D-Pipecolic Acid, 6-Benzyloxy-N-hydroxy-nicotinamidine and phenoxyacetyl chloride | 470.8 |
| 61 | (R)-5-{5-[1-(2-Phenoxy-acetyl)-piperidin-2-yl]-[1,2,4]oxadiazol-3-yl}-nicotinic acid ethyl ester | Boc-D-Pipecolic Acid, 5-(N-Hydroxy-carbamimidoyl)-nicotinic acid ethyl ester and phenoxyacetyl chloride | 337.5 |
| 62 | (R)-4-{5-[1-(2-Phenoxy-acetyl)-piperidin-2-yl]-[1,2,4]oxadiazol-3-yl}-1H-pyridin-2-one | Boc-D-Pipecolic Acid, N-Hydroxy-2-oxo-1,2-dihydro-pyridine-4-carboxamidine and phenoxyacetyl chloride | 381.5 |
| 63 | (R)-5-{5-[1-(2-Phenoxy-acetyl)-piperidin-2-yl]-[1,2,4]oxadiazol-3-yl}-1H-pyridin-2-one | Boc-D-Pipecolic Acid, N-Hydroxy-6-oxo-1,6-dihydro-pyridine-3-carboxamidine and phenoxyacetyl chloride | 381.5 |
| 64 | (R)-2-Phenoxy-1-[2-(5-phenyl-2H-[1,2,4]triazol-3-yl)-piperidin-1-yl]-ethanone | Boc-D-Pipecolic Acid, N-Amino-benzamidine and phenoxyacetic acid | 363.5 |
| 65 | (R)-1-{2-[5-(4-Methanesulfonyl-phenyl)-2H-[1,2,4]triazol-3-yl]-piperidin-1-yl}-2-phenoxy-ethanone | Boc-D-Pipecolic Acid, N-Amino-4-methanesulfonyl-benzamidine and phenoxyacetic acid | 441.5 |
| 66 | (R)-1-{2-[5-(3,4-Dimethoxy-phenyl)-2H-[1,2,4]triazol-3-yl]-piperidin-1-yl}-2-phenoxy-ethanone | Boc-D-Pipecolic Acid, N-Amino-3,4-Dimethoxy-benzamidine and phenoxyacetic acid | 423.5 |
| 67 | (R)-1-{2-[5-(3,4-Dichloro-phenyl)-2H-[1,2,4]triazol-3-yl]-piperidin-1-yl}-2-phenoxyethanone | Boc-D-Pipecolic Acid, N-Amino-3,4-Dichloro-benzamidine and phenoxyacetic acid | 431.4 |
| 68 | (R)-1-{2-[5-(4-Fluoro-phenyl)-2H-[1,2,4]triazol-3-yl]-piperidin-1-yl}-2-phenoxy-ethanone | Boc-D-Pipecolic Acid, N-Amino-4-Fluoro-benzamidine and phenoxyacetic acid | 381.5 |
| 69 | (R)-2-Phenoxy-1-{2-[5-(3-trifluoromethyl-phenyl)-2H-[1,2,4]triazol-3-yl]-piperidin-1-yl}-ethanone | Boc-D-Pipecolic Acid, N-Amino-3-Trifluoromethyl-benzamidine and phenoxyacetic acid | 431.5 |
| 70 | (R)-1-{2-[5-(4-Methoxy-phenyl)-2H-[1,2,4]triazol-3-yl]-piperidin-1-yl}-2-phenoxy-ethanone | Boc-D-Pipecolic Acid, N-Amino-4-Methoxy-benzamidine and phenoxyacetic acid | 393.5 |
| 71 | (R)-1-{2-[5-(3-Nitro-phenyl)-2H-[1,2,4]triazol-3-yl]-piperidin-1-yl}-2-phenoxy-ethanone | Boc-D-Pipecolic Acid, N-Amino-3-Nitro-benzamidine and phenoxyacetic acid | 408.5 |
| 72 | (R)-3-{5-[1-(2-Phenoxy-acetyl)-piperidin-2-yl]-1H-[1,2,4]triazol-3-yl}-benzoic acid methyl ester | Boc-D-Pipecolic Acid, N-Amino-3-Benzoic Acidmethylester-benzamidine and phenoxyacetic acid | 421.5 |
| 73 | (R)-1-{2-[5-(4-Fluoro-3-trifluoromethyl-phenyl)-2H-[1,2,4]triazol-3-yl]-piperidin-1-yl}-2-phenoxy-ethanone | Boc-D-Pipecolic Acid, N-Amino-4-Fluoro-3-trifluoromethyl-benzamidine and phenoxyacetic acid | 449.0 |
| 74 | (R)-6-{5-[1-(2-Phenoxy-acetyl)-piperidin-2-yl]-1H-[1,2,4]triazol-3-yl}-1,3-dihydro-indol-2-one | Boc-D-Pipecolic Acid, N-Amino-2-Oxo-2,3-dihydro-1H-indole-6-carboxamidine benzamidine and phenoxyacetic acid | 418.5 |

TABLE 1-continued

| Example | Compound name | Starting materials | MH+ (found) |
|---|---|---|---|
| 75 | 1-{3-[3-(4-Methoxy-phenyl)-[1,2,4]oxadiazol-5-yl]-morpholin-4-yl}-2-phenoxy-ethanone | Morpholine-3,4-dicarboxylic acid 4-tert-butyl ester, N-Hydroxy-4-methoxy-benzamidine and phenoxyacetyl chloride | 396.4 |
| 76 | 1-{3-[3-(4-Methanesulfonyl-phenyl)-[1,2,4]oxadiazol-5-yl]-morpholin-4-yl}-2-phenoxy-ethanone | Morpholine-3,4-dicarboxylic acid 4-tert-butyl ester, N-Hydroxy-4-methanesulfonyl-benzamidine and phenoxyacetyl chloride | 444.5 |
| 77 | 4-{5-[4-(2-Phenoxy-acetyl)-morpholin-3-yl]-[1,2,4]oxadiazol-3-yl}-benzenesulfonamide | Morpholine-3,4-dicarboxylic acid 4-tert-butyl ester, N-Hydroxy-4-sulfamoyl-benzamidine and phenoxyacetyl chloride | 445.5 |
| 78 | 1-(3-{3-[6-(1,1-Dioxo-thiomorpholin-4-yl)-pyridin-3-yl]-[1,2,4]oxadiazol-5-yl}-morpholin-4-yl)-2-phenoxy-ethanone | Morpholine-3,4-dicarboxylic acid 4-tert-butyl ester, 6-(1,1-Dioxo-thiomorpholin-4-yl)-N-hydroxy-nicotinamidine and phenoxyacetyl chloride | 500.5 |
| 79 | N-(4-{5-[4-(2-Phenoxy-acetyl)-morpholin-3-yl]-[1,2,4]oxadiazol-3-yl}-pyridin-2-yl)-acetamide | Morpholine-3,4-dicarboxylic acid 4-tert-butyl ester, N-[4-(N-Hydroxycarbamimidoyl)-pyridin-2-yl]-acetamide and phenoxyacetyl chloride | 424.6 |
| 80 | 1-{3-[5-(4-Methanesulfonyl-phenyl)-2H-[1,2,4]triazol-3-yl]-morpholin-4-yl}-2-phenoxy-ethanone | Morpholine-3,4-dicarboxylic acid 4-tert-butyl ester, 4-Methanesulfonyl-N-amino-benzamidine and phenoxyacetyl chloride | 443.4 |
| 81 | 2-Phenoxy-1-{3-[5-(3-trifluoromethyl-phenyl)-2H-[1,2,4]triazol-3-yl]-morpholin-4-yl}-ethanone | Morpholine-3,4-dicarboxylic acid 4-tert-butyl ester, 3-Trifluoromethyl-N-amino-benzamidine and phenoxyacetyl chloride | 433.4 |
| 82 | (R)-4-{5-[4-(2-Phenoxy-acetyl)-morpholin-3-yl]-[1,2,4]oxadiazol-3-yl}-1H-pyridin-2-one | (R)-Morpholine-3,4-dicarboxylic acid 4-tert-butyl ester, N-Hydroxy-2-oxo-1,2-dihydro-pyridine-4-carboxamidine and phenoxyacetyl chloride | 383.4 |
| 83 | 1-{3-[3-(4-Methoxy-phenyl)-[1,2,4]oxadiazol-5-yl]-thiomorpholin-4-yl}-2-phenoxy-ethanone | 4-(2-tert-Butoxy-acetyl)-thiomorpholine-3-carboxylic acid, N-Hydroxy-4-methoxy-benzamidine and phenoxyacetyl chloride | 412.5 |
| 84 | 1-{3-[3-(4-Methanesulfonyl-phenyl)-[1,2,4]oxadiazol-5-yl]-thiomorpholin-4-yl}-2-phenoxy-ethanone | 4-(2-tert-Butoxy-acetyl)-thiomorpholine-3-carboxylic acid, N-Hydroxy-4-methane-sulfonyl-benzamidine and phenoxyacetyl chloride | 460.4 |
| 85 | 4-{5-[4-(2-Phenoxy-acetyl)-thiomorpholin-3-yl]-[1,2,4]oxadiazol-3-yl}-benzenesulfonamide | 4-(2-tert-Butoxy-acetyl)-thiomorpholine-3-carboxylic acid, N-Hydroxy-4-sulfamoyl-benzamidine and phenoxyacetyl chloride | 461.4 |
| 86 | 2-Phenoxy-1-[3-(3-pyridin-4-yl-[1,2,4]oxadiazol-5-yl)-thiomorpholin-4-yl]-ethanone | 4-(2-tert-Butoxy-acetyl)-thiomorpholine-3-carboxylic acid, N-Hydroxy-isonicotinamidine and phenoxyacetyl chloride | 383.4 |
| 87 | 1-{2-[3-(4-Methoxy-phenyl)-[1,2,4]oxadiazol-5-yl]-piperazin-1-yl}-2-phenoxy-ethanone | Piperazine-1,3-dicarboxylic acid 1-tert-butyl ester, N-Hydroxy-4-methoxy-benzamidine and phenoxyacetic acid | 395.5 |
| 88 | N-(5-{5-[1-(2-Phenoxy-acetyl)-piperazin-2-yl]-[1,2,4]oxadiazol-3-yl}-pyridin-2-yl)-acetamide | Piperazine-1,3-dicarboxylic acid 1-tert-butyl ester, N-[5-(N-Hydroxycarbamimidoyl)-pyridin-2-yl]-acetamide and phenoxyacetic | 423.5 |
| 89 | 1-{2-[3-(2-Imidazol-1-yl-pyridin-4-yl)-[1,2,4]oxadiazol-5-yl]-piperazin-1-yl}-2-phenoxy-ethanone | Piperazine-1,3-dicarboxylic acid 1-tert-butyl ester, N-Hydroxy-2-imidazol-1-yl-isonicotinamidine and phenoxyacetic | 432.5 |

TABLE 1-continued

| Example | Compound name | Starting materials | MH+ (found) |
|---|---|---|---|
| 90 | N,N-Diethyl-4-{5-[1-(2-phenoxy-acetyl)-piperazin-2-yl]-[1,2,4]oxadiazol-3-yl}-benzenesulfonamide | Piperazine-1,3-dicarboxylic acid 1-tert-butyl ester, 4-Diethylsulfamoyl-N-hydroxybenzamidine and phenoxyacetic acid | 500.5 |
| 91 | N,N-Dimethyl-4-{5-[1-(2-phenoxy-acetyl)-piperazin-2-yl]-[1,2,4]oxadiazol-3-yl}-benzenesulfonamide | Piperazine-1,3-dicarboxylic acid 1-tert-butyl ester, 4-Dimethylsulfamoyl-N-hydroxybenzamidine and phenoxyacetic acid | 472.5 |
| 92 | 4-{5-[1-(2-Phenoxy-acetyl)-piperazin-2-yl]-[1,2,4]oxadiazol-3-yl}-benzenesulfonamide | Piperazine-1,3-dicarboxylic acid 1-tert-butyl ester, N-Hydroxy-4-sulfamoyl-benzamidine and phenoxyacetic acid | 444.4 |
| 93 | 1-{2-[3-(4-Methanesulfonyl-phenyl)-[1,2,4]oxadiazol-5-yl]-piperazin-1-yl}-2-phenoxy-ethanone | Piperazine-1,3-dicarboxylic acid 1-tert-butyl ester, N-Hydroxy-4-methane-sulfonyl-benzamidine and phenoxyacetic acid | 443.5 |
| 94 | 2-Phenoxy-1-[2-(3-pyridin-4-yl-[1,2,4]oxadiazol-5-yl)-piperazin-1-yl]-ethanone | Piperazine-1,3-dicarboxylic acid 1-tert-butyl ester, N-Hydroxyisonicotin-amidine and phenoxyacetic acid | 366.4 |
| 95 | 1-{2-[3-(2,4-Dichloro-phenyl)-[1,2,4]oxadiazol-5-yl]-piperazin-1-yl}-2-phenoxy-ethanone | Piperazine-1,3-dicarboxylic acid 1-tert-butyl ester, 2,4-Dichloro-N-hydroxy-benzamidine and phenoxyacetic acid | 433.3 |
| 96 | 2-Phenoxy-1-[2-(3-pyridin-2-yl-[1,2,4]oxadiazol-5-yl)-piperazin-1-yl]-ethanone | Piperazine-1,3-dicarboxylic acid 1-tert-butyl ester, N-Hydroxy-pyridine-2-carboxamidine and phenoxyacetic acid | 366.4 |
| 97 | 2-Phenoxy-1-[2-(3-pyridin-2-yl-[1,2,4]oxadiazol-5-yl)-piperazin-2-yl]-ethanone | Piperazine-1,3-dicarboxylic acid 1-tert-butyl ester, N-Hydroxy-pyridine-3-carboxamidine and phenoxyacetic acid | 366.4 |
| 98 | 1-{2-[3-(4-Nitro-phenyl)-[1,2,4]oxadiazol-5-yl]-piperazin-1-yl}-2-phenoxy-ethanone | Piperazine-1,3-dicarboxylic acid 1-tert-butyl ester, N-Hydroxy-4-nitro-benzamidine nd phenoxyacetic acid | 410.4 |
| 99 | 1-{2-[3-(6-Methoxy-pyridin-3-yl)-[1,2,4]oxadiazol-5-yl]-piperazin-1-yl}-2-phenoxy-ethanone | Piperazine-1,3-dicarboxylic acid 1-tert-butyl ester, N-Hydroxy-6-methoxy-nicotinamidine and phenoxyacetic acid | 396.4 |
| 100 | 1-{2-[3-(6-Morpholin-4-yl-pyridin-3-yl)-[1,2,4]oxadiazol-5-yl]-piperazin-1-yl}-2-phenoxy-ethanone | Piperazine-1,3-dicarboxylic acid 1-tert-butyl ester, N-Hydroxy-6-morpholin-4-yl-nicotinamidine and phenoxy acetic acid | 451.5 |
| 101 | 1-{2-[3-(6-Morpholin-4-yl-pyridin-3-yl)-[1,2,4]oxadiazol-5-yl]-piperazin-1-yl}-2-phenoxy-ethanone | Piperazine-1,3-dicarboxylic acid 1-tert-butyl ester, N-Hydroxy-pyrazine-2-carboxamidine and phenoxy-acetic acid | 367.4 |
| 102 | 1-{2-[3-(3-Hydroxymethyl-phenyl)-[1,2,4]oxadiazol-5-yl]-piperazin-1-yl}-2-phenoxy-ethanone | Piperazine-1,3-dicarboxylic acid 1-tert-butyl ester, N-Hydroxy-3-hydroxy-methyl-benzamidine and phenoxy-acetic acid | 395.4 |
| 103 | 1-{2-[3-(4-Diethylamino-phenyl)-[1,2,4]oxadiazol-5-yl]-piperazin-1-yl}-2-phenoxy-ethanone | Piperazine-1,3-dicarboxylic acid 1-tert-butyl ester, 4-Diethylamino-N-hydroxy-benzamidine and phenoxy-acetic acid | 436.5 |
| 104 | 1-(2-{3-[4-(Morpholine-4-sulfonyl)-phenyl]-[1,2,4]oxadiazol-5-yl}-piperazin-1-yl)-2-phenoxy-ethanone | Piperazine-1,3-dicarboxylic acid 1-tert-butyl ester, N-Hydroxy-4-(morpholine-4-sulfonyl)-benzamidine and phenoxyacetic acid | 514.6 |
| 105 | N-Methyl-4-{5-[1-(2-phenoxy-acetyl)-piperazin-2-yl]-[1,2,4]oxadiazol-3-yl}-benzenesulfonamide | Piperazine-1,3-dicarboxylic acid 1-tert-butyl ester, N-Hydroxy-4-methylsulfamoyl-benzamidine and phenoxyacetic acid | 458.4 |
| 106 | N-(2-Methoxy-ethyl)-N-methyl-4-{5-[1-(2-phenoxy-acetyl)-piperazin-2-yl]-[1,2,4]oxadiazol-3-yl}-benzenesulfonamide | Piperazine-1,3-dicarboxylic acid 1-tert-butyl ester, N-Hydroxy-4-[(2-methoxy-ethyl)-methyl-sulfamoyl]-benzamidine and phenoxy-acetic acid | 516.4 |

TABLE 1-continued

| Example | Compound name | Starting materials | MH+ (found) |
|---|---|---|---|
| 107 | 1-{2-[3-(4-Chloro-phenyl)-[1,2,4]oxadiazol-5-yl]-piperazin-1-yl}-2-phenoxy-ethanone | Piperazine-1,3-dicarboxylic acid 1-tert-butyl ester, 4-Chloro-N-hydroxy-benzamidine and phenoxyacetic acid | 399.3 |
| 108 | N-(4-{5-[1-(2-Phenoxy-acetyl)-piperazin-2-yl]-[1,2,4]oxadiazol-3-yl}-2-trifluoromethyl-phenyl)-acetamide | Piperazine-1,3-dicarboxylic acid 1-tert-butyl ester, N-[4-(N-Hydroxycarbamimidoyl)-2-trifluoro-methyl-phenyl]-acetamide and phenoxyacetic acid | 490.4 |
| 109 | 4-{5-[1-(2-Phenoxy-acetyl)-piperazin-2-yl]-[1,2,4]oxadiazol-3-yl}-benzoic acid allyl ester | Piperazine-1,3-dicarboxylic acid 1-tert-butyl ester, 4-(N-Hydroxycarbamimidoyl)-benzoic acid allyl ester and phenoxyacetic acid | 449.4 |
| 110 | 1-{2-[3-(4-Methyl-3-nitro-phenyl)-[1,2,4]oxadiazol-5-yl]-piperazin-1-yl}-2-phenoxy-ethanone | Piperazine-1,3-dicarboxylic acid 1-tert-butyl ester, N-Hydroxy-4-methyl-3-nitro-benzamidine and phenoxyacetic acid | 424.4 |
| 111 | 1-{2-[3-(4-Methoxy-3-nitro-phenyl)-[1,2,4]oxadiazol-5-yl]-piperazin-1-yl}-2-phenoxy-ethanone | Piperazine-1,3-dicarboxylic acid 1-tert-butyl ester, N-Hydroxy-4-methoxy-3-nitro-benzamidine and phenoxyacetic acid | 440.4 |
| 112 | 1-{2-[3-(4-Chloro-3-nitro-phenyl)-[1,2,4]oxadiazol-5-yl]-piperazin-1-yl}-2-phenoxy-ethanone | Piperazine-1,3-dicarboxylic acid 1-tert-butyl ester, 4-Chloro-N-hydroxy-3-nitro-benzamidine and phenoxyacetic acid | 444.8 |
| 113 | 3-Fluoro-4-{5-[1-(2-phenoxy-acetyl)-piperazin-2-yl]-[1,2,4]oxadiazol-3-yl}-benzoic acid methyl ester | Piperazine-1,3-dicarboxylic acid 1-tert-butyl ester, 3-Fluoro-4-(N-hydroxy-carbamimidoyl)-benzoic acid methyl ester and phenoxyacetic acid | 441.4 |
| 114 | 4-{5-[1-(2-Phenoxy-acetyl)-piperazin-2-yl]-[1,2,4]oxadiazol-3-yl}-pyridine-2-carboxylic acid ethyl ester | Piperazine-1,3-dicarboxylic acid 1-tert-butyl ester, 4-(N-Hydroxycarbamimidoyl)-pyridine-2-carboxylic acid ethyl ester and phenoxyacetic acid | 438.4 |
| 115 | 2-Phenoxy-1-{2-[3-(4-piperidin-1-yl-phenyl)-[1,2,4]oxadiazol-5-yl]-piperazin-1-yl}-ethanone | Piperazine-1,3-dicarboxylic acid 1-tert-butyl ester, N-Hydroxy-4-piperidin-1-yl-benzamidine and phenoxyacetic acid | 448.5 |
| 116 | 1-{2-[3-(4-Morpholin-4-yl-phenyl)-[1,2,4]oxadiazol-5-yl]-piperazin-1-yl}-2-phenoxy-ethanone | Piperazine-1,3-dicarboxylic acid 1-tert-butyl ester, N-Hydroxy-4-morpholin-4-yl-benzamidine and phenoxyacetic acid | 450.4 |
| 117 | 1-(2-{3-[4-(2-Methyl-imidazol-1-yl)-phenyl]-[1,2,4]oxadiazol-5-yl}-piperazin-1-yl)-2-phenoxy-ethanone | Piperazine-1,3-dicarboxylic acid 1-tert-butyl ester, N-Hydroxy-4-(2-methyl-imidazol-1-yl)-benzamidine and phenoxyacetic acid | 445.4 |
| 118 | 1-(2-{3-[4-(3H-Imidazol-4-yl)-phenyl]-[1,2,4]oxadiazol-5-yl}-piperazin-1-yl)-2-phenoxy-ethanone | Piperazine-1,3-dicarboxylic acid 1-tert-butyl ester, N-Hydroxy-4-(3H-imidazol-4-yl)-benzamidine and phenoxyacetic acid | 431.4 |
| 119 | 4-(5-{5-[1-(2-Phenoxy-acetyl)-piperazin-2-yl]-[1,2,4]oxadiazol-3-yl}-pyridin-2-yl)-piperazin-2-one | Piperazine-1,3-dicarboxylic acid 1-tert-butyl ester, N-Hydroxy-6-(3-oxo-piperazin-1-yl)-nicotinamidine and phenoxyacetic acid | 464.4 |
| 120 | 1-{2-[3-(6-Imidazol-1-yl-pyridin-3-yl)-[1,2,4]oxadiazol-5-yl]-piperazin-1-yl}-2-phenoxy-ethanone | Piperazine-1,3-dicarboxylic acid 1-tert-butyl ester, N-Hydroxy-6-imidazol-1-yl-nicotinamidine and phenoxyacetic acid | 432.4 |
| 121 | 1-(2-{3-[6-(4-Acetyl-piperazin-1-yl)-pyridin-3-yl]-[1,2,4]oxadiazol-5-yl}-piperazin-1-yl)-2-phenoxy-ethanone | Piperazine-1,3-dicarboxylic acid 1-tert-butyl ester, 6-(4-Acetyl-piperazin-1-yl)-N-hydroxy-nicotinamidine and phenoxyacetic acid | 492.4 |
| 122 | 2-Phenoxy-1-{2-[3-(4-pyrrol-1-yl-phenyl)-[1,2,4]oxadiazol-5-yl]-piperazin-1-yl}-ethanone | Piperazine-1,3-dicarboxylic acid 1-tert-butyl ester, N-Hydroxy-4-pyrrol-1-yl-benzamidine and phenoxyacetic acid | 430.4 |
| 123 | 2-Phenoxy-1-{2-[3-(4 trifluoromethanesulfonyl- | Piperazine-1,3-dicarboxylic acid 1-tert-butyl ester, N-Hydroxy- | 497.4 |

TABLE 1-continued

| Example | Compound name | Starting materials | MH+ (found) |
|---|---|---|---|
| | phenyl)-[1,2,4]oxadiazol-5-yl]-piperazin-1-yl}-ethanone | 4-trifluoromethane-sulfonyl-benzamidine and phenoxyacetic acid | |
| 124 | 1-{2-[3-(2-Morpholin-4-yl-pyridin-4-yl)-[1,2,4]oxadiazol-5-yl]-piperazin-1-yl}-2-phenoxy-ethanone | Piperazine-1,3-dicarboxylic acid 1-tert-butyl ester, N-Hydroxy-2-morpholin-4-yl-isonicotinamidine and phenoxyacetic acid | 451.4 |
| 125 | 2-Phenoxy-1-{2-[3-(2-thiomorpholin-4-yl-pyridin-4-yl)-[1,2,4]oxadiazol-5-yl]-piperazin-1-yl}-ethanone | Piperazine-1,3-dicarboxylic acid 1-tert-butyl ester, N-Hydroxy-2-thiomorpholin-4-yl-isonicotinamidine and phenoxyacetic acid | 467.4 |
| 126 | 1-(2-{3-[6-(3-Hydroxymethyl-pyrrolidin-1-yl)-pyridin-3-yl]-[1,2,4]oxadiazol-5-yl}-piperazin-1-yl)-2-phenoxy-ethanone | Piperazine-1,3-dicarboxylic acid 1-tert-butyl ester, N-Hydroxy-6-(3-hydroxymethyl-pyrrolidin-1-yl)-nicotinamidine and phenoxyacetic acid | 465.4 |
| 127 | (R)-1-{2-[3-(6-Methoxy-pyridin-3-yl)-[1,2,4]oxadiazol-5-yl]-piperazin-1-yl}-2-phenoxy-ethanone | D-Piperazine-1,3-dicarboxylic acid 1-tert-butyl ester, N-Hydroxy-6-methoxy-nicotinamidine and phenoxyacetic acid | 396.4 |
| 128 | (R)-1-{2-[3-(6-Morpholin-4-yl-pyridin-3-yl)-[1,2,4]oxadiazol-5-yl]-piperazin-1-yl}-2-phenoxy-ethanone | D-Piperazine-1,3-dicarboxylic acid 1-tert-butyl ester, N-Hydroxy-6-morpholin-4-yl-nicotinamidine and phenoxyacetic acid | 451.4 |
| 129 | (R)-N-(4-{5-[1-(2-Phenoxy-acetyl)-piperazin-2-yl]-[1,2,4]oxadiazol-3-yl}-2-trifluoromethyl-phenyl)-acetamide | D-Piperazine-1,3-dicarboxylic acid 1-tert-butyl ester, N-[4-(N-Hydroxycarbamimidoyl)-2-trifluoromethyl-phenyl]-acetamide and phenoxyacetic acid | 490.4 |
| 130 | (R)-1-{2-[3-(4-Methyl-3-nitro-phenyl)-[1,2,4]oxadiazol-5-yl]-piperazin-1-yl}-2-phenoxy-ethanone | D-Piperazine-1,3-dicarboxylic acid 1-tert-butyl ester, N-Hydroxy-4-methyl-3-nitro-benzamidine and phenoxyacetic acid | 424.4 |
| 131 | (R)-1-{2-[3-(4-Methyl-3-nitro-phenyl)-[1,2,4]oxadiazol-5-yl]-piperazin-1-yl}-2-phenoxy-ethanone | D-Piperazine-1,3-dicarboxylic acid 1-tert-butyl ester, 1-{2-[3-(4-Methoxy-3-nitro-phenyl)-[1,2,4]oxadiazol-5-yl]-piperazin-1-yl}-2-phenoxy-ethanone and phenoxyacetic acid | 440.4 |
| 132 | (R)-1-{2-[3-(4-Morpholin-4-yl-phenyl)-[1,2,4]oxadiazol-5-yl]-piperazin-1-yl}-2-phenoxy-ethanone | D-Piperazine-1,3-dicarboxylic acid 1-tert-butyl ester, N-Hydroxy-4-morpholin-4-yl-benzamidine and phenoxyacetic acid | 450.4 |
| 133 | (R)-1-(2-{3-[4-(3H-Imidazol-4-yl)-phenyl]-[1,2,4]oxadiazol-5-yl]-piperazin-1-yl)-2-phenoxy-ethanone | D-Piperazine-1,3-dicarboxylic acid 1-tert-butyl ester, N-Hydroxy-4-(3H-imidazol-4-yl)-benzamidine and phenoxyacetic acid | 431.4 |
| 134 | (R)-1-(2-{3-[6-(3-Hydroxymethyl-pyrrolidin-1-yl)-pyridin-3-yl]-[1,2,4]oxadiazol-5-yl}-piperazin-1-yl)-2-phenoxy-ethanone | D-Piperazine-1,3-dicarboxylic acid 1-tert-butyl ester, N-Hydroxy-6-(3-hydroxymethyl-pyrrolidin-1-yl)-nicotinamidine and phenoxyacetic acid | 465.4 |
| 135 | (R)-1-(2-{3-[6-(4-Acetyl-piperazin-1-yl)-pyridin-3-yl]-[1,2,4]oxadiazol-5-yl}-piperazin-1-yl)-2-phenoxy-ethanone | D-Piperazine-1,3-dicarboxylic acid 1-tert-butyl ester, 6-(4-Acetyl-piperazin-1-yl)-N-hydroxy-nicotinamidine and phenoxyacetic acid | 492.5 |
| 136 | (R)-N-(3-{5-[1-(2-Phenoxy-acetyl)-piperazin-2-yl]-[1,2,4]oxadiazol-3-yl}-phenyl)-acetamide hydrochloride | D-Piperazine-1,3-dicarboxylic acid 1-tert-butyl ester, N-[3-(N-Hydroxycarbamimidoyl)-phenyl]-acetamide and phenoxyacetic acid | 422.4 |

TABLE 1-continued

| Example | Compound name | Starting materials | MH+ (found) |
|---|---|---|---|
| 137 | (R)-1-{2-[3-(1H-Benzoimidazol-5-yl)-[1,2,4]oxadiazol-5-yl]-piperazin-1-yl}-2-phenoxy-ethanone | D-Piperazine-1,3-dicarboxylic acid 1-tert-butyl ester, N-Hydroxy-1H-benzoimidazole-5-carboxamidine and phenoxyacetic acid | 405.5 |
| 138 | (R)-1-{2-[3-(1H-Benzotriazol-5-yl)-[1,2,4]oxadiazol-5-yl]-piperazin-1-yl}-2-phenoxy-ethanone | D-Piperazine-1,3-dicarboxylic acid 1-tert-butyl ester, N-Hydroxy-1H-benzotriazole-5-carboxamidine and phenoxyacetic acid | 406.4 |
| 139 | (R)-1-{2-[3-(1H-Indazol-5-yl)-[1,2,4]oxadiazol-5-yl]-piperazin-1-yl}-2-phenoxy-ethanone hydrochloride | D-Piperazine-1,3-dicarboxylic acid 1-tert-butyl ester, N-Hydroxy-1H-indazole-5-carboxamidine and phenoxyacetic acid | 405.4 |
| 140 | (R)-5-{5-[1-(2-Phenoxy-acetyl)-piperazin-2-yl]-[1,2,4]oxadiazol-3-yl}-1,3-dihydro-benzoimidazol-2-one | D-Piperazine-1,3-dicarboxylic acid 1-tert-butyl ester, N-Hydroxy-2-oxo-2,3-dihydro-1H-benzoimidazole-5-carboxamidine and phenoxyacetic acid | 421.5 |
| 141 | (R)-1-(2-{3-[6-(1,1-Dioxo-thiomorpholin-4-yl)-pyridin-3-yl]-[1,2,4]oxadiazol-5-yl}-piperazin-1-yl)-2-phenoxy-ethanone hydrochloride | D-Piperazine-1,3-dicarboxylic acid 1-tert-butyl ester, 6-(1,1-Dioxo-thiomorpholin-4-yl)-N-hydroxy-nicotinamidine and phenoxyacetic acid | 499.1 |
| 142 | (R)-1-{2-[3-(3-Nitro-phenyl)-[1,2,4]oxadiazol-5-yl]-piperazin-1-yl}-2-phenoxy-ethanone | D-Piperazine-1,3-dicarboxylic acid 1-tert-butyl ester, N-Hydroxy-3-nitro-benzamidine and phenoxyacetic acid | 410.1 |
| 143 | (R)-1-{2-[3-(4-Fluoro-phenyl)-[1,2,4]oxadiazol-5-yl]-piperazin-1-yl}-2-phenoxy-ethanone | D-Piperazine-1,3-dicarboxylic acid 1-tert-butyl ester, 4-Fluoro-N-hydroxy-benzamidine and phenoxyacetic acid | 383.4 |
| 144 | (R)-4-{5-[1-(2-Phenoxy-acetyl)-piperazin-2-yl]-[1,2,4]oxadiazol-3-yl}-1H-pyridin-2-one | D-Piperazine-1,3-dicarboxylic acid 1-tert-butyl ester, N-Hydroxy-2-oxo-1,2-dihydro-pyridine-4-carboxamidine and phenoxyacetic acid | 382.4 |
| 145 | 1-{4-Acetyl-2-[3-(4-methoxy-phenyl)-[1,2,4]oxadiazol-5-yl]-piperazin-1-yl}-2-phenoxy-ethanone | 4-Acetyl-piperazine-1,2-dicarboxylic acid 1-tert-butyl ester, N-Hydroxy-4-methoxy-benzamidine and phenoxyacetic acid | 437.5 |
| 146 | 1-{4-Acetyl-2-[3-(4-methanesulfonyl-phenyl)-[1,2,4]oxadiazol-5-yl]-piperazin-1-yl}-2-phenoxy-ethanone | 4-Acetyl-piperazine-1,2-dicarboxylic acid 1-tert-butyl ester, N-Hydroxy-4-methanesulfonyl-benzamidine and phenoxyacetic acid | 485.5 |
| 147 | 4-{5-[4-Acetyl-1-(2-phenoxy-acetyl)-piperazin-2-yl]-[1,2,4]oxadiazol-3-yl}-benzenesulfonamide | 4-Acetyl-piperazine-1,2-dicarboxylic acid 1-tert-butyl ester, N-Hydroxy-4-sulfamoyl-benzamidine and phenoxyacetic acid | 486.5 |
| 148 | 1-[4-Acetyl-2-(3-pyridin-4-yl-[1,2,4]oxadiazol-5-yl)-piperazin-1-yl]-2-phenoxy-ethanone | 4-Acetyl-piperazine-1,2-dicarboxylic acid 1-tert-butyl ester, N-Hydroxy-isonicotinamidine and phenoxyacetic acid | 408.5 |
| 149 | 1-{4-Methanesulfonyl-2-[3-(4-methoxy-phenyl)-[1,2,4]oxadiazol-5-yl]-piperazin-1-yl}-2-phenoxy-ethanone | 4-Methanesulfonyl-piperazine-1,2-dicarboxylic acid 1-tert-butyl ester, N-Hydroxy-4-Methoxy-benzamidine and phenoxyacetic acid | 473.2 |
| 150 | (R)-1-{2-[5-(4-Fluoro-phenyl)-2H-[1,2,4]triazol-3-yl]-piperazin-1-yl}-2-phenoxy-ethanone | D-Piperazine-1,3-dicarboxylic acid 1-tert-butyl ester, 4-Fluoro-N-amino-benzamidine and phenoxyacetic acid | 382.4 |
| 151 | (R)-2-Phenoxy-1-{2-[5-(3-trifluoromethyl-phenyl)-2H-[1,2,4]triazol-3-yl]-piperazin-1-yl}-ethanone | D-Piperazine-1,3-dicarboxylic acid 1-tert-butyl ester, 3-Trifluoromethyl-N-amino-benzamidine and phenoxyacetic acid | 432.4 |

TABLE 1-continued

| Example | Compound name | Starting materials | MH+ (found) |
|---|---|---|---|
| 152 | 1-{2-[5-(4-Fluoro-3-trifluoromethyl-phenyl)-2H-[1,2,4]triazol-3-yl]-piperazin-1-yl}-2-phenoxy-ethanone | Piperazine-1,3-dicarboxylic acid 1-tert-butyl ester, 4-Fluoro-3-trifluoromethyl-N-amino-benzamidine and phenoxyacetic acid | 450.4 |
| 153 | 1-{2-[5-(4-Methanesulfonyl-phenyl)-2H-[1,2,4]triazol-3-yl]-piperazin-1-yl}-2-phenoxy-ethanone | Piperazine-1,3-dicarboxylic acid 1-tert-butyl ester, 4-Methanesulfonyl-N-amino-benzamidine and phenoxyacetic acid | 442.4 |
| 154 | 2-Phenoxy-1-{2-[5-(3-trifluoromethyl-phenyl)-2H-[1,2,4]triazol-3-yl]-piperazin-1-yl}-ethanone | Piperazine-1,3-dicarboxylic acid 1-tert-butyl ester, 3-Trifluoromethyl-N-amino-benzamidine and phenoxyacetic acid | 432.4 |
| 155 | 2-Phenoxy-1-[2-(5-p-tolyl-2H-[1,2,4]triazol-3-yl)-piperazin-1-yl]-ethanone | Piperazine-1,3-dicarboxylic acid 1-tert-butyl ester, 4-Methyl-N-amino-benzamidine and phenoxyacetic acid | 378.4 |
| 156 | 2-Phenoxy-1-{2-[5-(4 trifluoromethyl-phenyl)-2H-[1,2,4]triazol-3-yl]-piperazin-1-yl}-ethanone | Piperazine-1,3-dicarboxylic acid 1-tert-butyl ester, 4-Trifluoromethyl-N-amino-benzamidine and phenoxyacetic acid | 432.4 |
| 157 | 1-{2-[5-(4-Methoxy-phenyl)-2H-[1,2,4]triazol-3-yl]-piperazin-1-yl}-2-phenoxy-ethanone | Piperazine-1,3-dicarboxylic acid 1-tert-butyl ester, 4-Methoxy-N-amino-benzamidine and phenoxyacetic acid | 394.4 |
| 158 | 1-{2-[5-(4-Fluoro-phenyl)-2H-[1,2,4]triazol-3-yl]-piperazin-1-yl}-2-phenoxy-ethanone | Piperazine-1,3-dicarboxylic acid 1-tert-butyl ester, 4-Fluoro-N-amino-benzamidine and phenoxyacetic acid | 382.4 |
| 159 | 1-{2-[5-(4-Fluoro-phenyl)-2H-[1,2,4]triazol-3-yl]-piperazin-1-yl}-2-phenoxy-ethanone | Piperazine-1,3-dicarboxylic acid 1-tert-butyl ester, 2,4-Difluoro-N-amino-benzamidine and phenoxyacetic acid | 400.4 |
| 160 | 1-{2-[5-(3,4-Dimethoxy-phenyl)-2H-[1,2,4]triazol-3-yl]-piperazin-1-yl}-2-phenoxy-ethanone | Piperazine-1,3-dicarboxylic acid 1-tert-butyl ester, 3,4-Dimethoxy-N-amino-benzamidine and phenoxyacetic acid | 424.4 |
| 161 | 1-{2-[5-(3,4-Dichloro-phenyl)-2H-[1,2,4]triazol-3-yl]-piperazin-1-yl}-2-phenoxy-ethanone | Piperazine-1,3-dicarboxylic acid 1-tert-butyl ester, 3,4-Dichloro-N-amino-benzamidine and phenoxyacetic acid | 432.4 |
| 162 | 1-{2-[5-(2-Fluoro-phenyl)-2H-[1,2,4]triazol-3-yl]-piperazin-1-yl}-2-phenoxy-ethanone | Piperazine-1,3-dicarboxylic acid 1-tert-butyl ester, 3-Fluoro-N-amino-benzamidine and phenoxyacetic acid | 382.4 |
| 163 | 1-{2-[5-(2-Fluoro-phenyl)-2H-[1,2,4]triazol-3-piperazin-1-yl}-2-phenoxy-ethanone | Piperazine-1,3-dicarboxylic acid 1-tert-butyl ester, 2-Fluoro-N-amino-benzamidine and phenoxyacetic acid | 382.4 |

Example 164

4-{5-[4-Methyl-1-(2-phenoxy-acetyl)-piperazin-2-yl]-[1,2,4]oxadiazol-3-yl}-benzamide 0.1 mmol of 4-{5-[1-(2-Phenoxy-acetyl)-piperazin-2-yl]-[1,2,4]oxadiazol-3-yl}-benzamide are dissolved in 1 ml DMF and 1 eq. DIPEA and $Na_2CO_3$ added. To the suspension 1 eq. of MeI is added and the reaction stirred at room temperature overnight. The product is isolated via preparative HPLC.

MS(ISO): 422.4 (MH+)

The following compounds have been prepared in analogy:

TABLE 2

| Example | Compound name | Starting material | MH+ (found) |
|---|---|---|---|
| 165 | (R)-1-{2-[3-(1H-Indazol-5yl)-[1,2,4]oxadiazol-5-yl]-4-methyl-piperazin-1-yl}-2-phenoxy-ethanone | (R)-1-{2-[3-(1H-Indazol-5 yl)-[1,2,4]oxadiazol-5 yl]-piperazin-1-yl}-2-phenoxy-ethanone | 419.5 |

TABLE 2-continued

| Example | Compound name | Starting material | MH+ (found) |
|---|---|---|---|
| 166 | (R)-1-{2-[3-(4-Fluoro-phenyl)-[1,2,4]oxadiazol-5-yl]-4-methyl-piperazin-1-yl}-2-phenoxy-ethanone | (R)-1-{2-[3-(4-Fluoro-phenyl)-[1,2,4]oxadiazol-5-yl]-piperazin1-yl}-2-phenoxy-ethanone | 397.4 |
| 167 | (R)-5-{5-[4-Methyl-1-(2-phenoxy-acetyl)-piperazin-2-yl]-[1,2,4]oxadiazol-3-yl}-1,3-dihydro-indol-2-one | (R)-5-{5-[1-(2-Phenoxy-acetyl)-piperazin-2-yl]-[1,2,4]oxadiazol-3-yl}-1,3-dihydro-indol-2-one | 434.5 |
| 168 | (R)-5-{5-[4-Methyl-1-(2-phenoxy-acetyl)-piperazin-2-yl]-[1,2,4]oxadiazol-3-yl}-1,3-dihydro-benzoimidazol-2-one | (R)-5-{5-[1-(2-Phenoxy-acetyl)-piperazin-2-yl]-[1,2,4]oxadiazol-3-yl}-1,3-dihydro-benzoimidazol-2-one | 435.5 |
| 169 | (R)-1-{2-[3-(1H-Benzoimidazol-5-yl)-[1,2,4]oxadiazol-5-yl]-4-methyl-piperazin-1-yl}-2-phenoxy-ethanone | (R)-1-{2-[3-(1H-Benzoimidazol-5-yl)-[1,2,4]oxadiazol-5-yl]-piperazin-1-yl}-2-phenoxy-ethanone | 419.5 |
| 170 | (R)-1-{2-[3-(1H-Benzotriazol-5-yl)-[1,2,4]oxadiazol-5-yl]-4-methyl-piperazin-1-yl}-2-phenoxy-ethanone | (R)-1-{2-[3-(1H-Benzotriazol-5-yl)-[1,2,4]oxadiazol-5-yl]-piperazin-1-yl}-2-phenoxy-ethanone | 420.5 |
| 171 | (R)-1-{4-Methyl-2-[5-(3-trifluoromethyl-phenyl)-2H-[1,2,4]triazol-3-yl]-piperazin-1-yl}-2-phenoxy-ethanone | (R)-2-Phenoxy-1-{2-[5-(3-trifluoromethyl-phenyl)-2H-[1,2,4]triazol-3-yl]-piperazin 1-yl}-ethanone | 446.4 |
| 172 | (R)-1-{2-[5-(4-Methoxy-phenyl)-2H-[1,2,4]triazol-3-yl]-4-methyl-piperazin-1-yl}-2-phenoxy-ethanone | (R)-1-{2-[5-(4-Methoxy-phenyl)-2H-[1,2,4]triazol-3-yl]-piperazin}-yl}-2-phenoxy-ethanone | 408.4 |
| 173 | (R)-1-{2-[5-(4-Fluoro-phenyl)-2H-[1,2,4]triazol-3-yl]-4-methyl-piperazin-1-yl}-2-phenoxy-ethanone | (R)-1-{2-[5-(4-Fluoro-phenyl)-2H-[1,2,4]triazol-3-yl]-piperazin1-yl}-2-phenoxy-ethanone | 396.4 |
| 174 | (R)-1-{2-[5-(4-Methanesulfonyl-phenyl)-2H-[1,2,4]triazol-3-yl]-4-methyl-piperazin-1-yl}-2-phenoxy-ethanone | (R)-1-{2-[5-(4-Methanesulfonyl-phenyl)-2H-[1,2,4]triazol-3-yl]-piperazin-1-yl}-2-phenoxy-ethanone | 456.4 |
| 175 | (R)-4-{5-[4-Methyl-1-(2-phenoxy-acetyl)-piperazin-2-yl]-1H-[1,2,4]triazol-3-yl}-benzoic acid methyl ester | (R)-4-{5-[1-(2-Phenoxy-acetyl)-piperazin-2-yl]-1H-[1,2,4]triazol-3-yl}-benzoic acid methyl ester | 436.5 |
| 176 | (R)-N-(3-{5-[4-Methyl-1-(2-phenoxy-acetyl)-piperazin-2-yl]-1H-[1,2,4]triazol-3-yl}-phenyl)-acetamide | (R)-N-(3-{5-[1-(2-Phenoxy-acetyl)-piperazin-2-yl]-1H-[1,2,4]triazol-3-yl}-phenyl)-acetamide | 435.5 |
| 177 | (R)-N-(3-{5-[4-Methyl-1-(2-phenoxy-acetyl)-piperazin-2-yl]-1H-[1,2,4]triazol-3-yl}-phenyl)-methanesulfonamide | (R)-N-(3-{5-[1-(2-Phenoxy-acetyl)-piperazin-2-yl]-1H-[1,2,4]triazol-3-yl}-phenyl)methanesulfonamide | 471.5 |
| 178 | (R)-4-{5-[4-Methyl-1-(2-phenoxy-acetyl)-piperazin-2-yl]-1H-[1,2,4]triazol-3-yl}-benzamide | (R)-4-{5-[1-(2-Phenoxy-acetyl)-piperazin-2-yl]-1H-[1,2,4]triazol-3-yl}-benzamide | 421.5 |

Example 179

(R)-4-{5-[1-(2-Phenoxy-acetyl)-piperidin-2-yl]-[1,2,4]oxadiazol-3-yl}-benzoic acid 4 mmol of (R)-4-{5-[1-(2-Phenoxy-acetyl)-piperidin-2-yl]-[1,2,4]oxadiazol-3-yl}-benzoic acid benzyl ester were dissolved in MeOH and treated with Pd/C and flushed with hydrogen (3 bar) and stirred for 30 min. The catalyst was filtered off and the solvent evaporated. After extraction from ethylacetate/water the resulting oil was purified via preperative HPLC. The corresponding alkylesters were treated with aq. 2N NaOH or LiOH in methanol at room temperature. The allylester can be cleaved using Pd(Ph3)4 as catalyst and morpholine as a nucleophile.

MS(ISO): 408.5 (MH+)

The following compounds have been prepared in analogy:

TABLE 3

| Example | Compound name | Starting material | MH+ (found) |
|---|---|---|---|
| 180 | (R)-3-{5-[1-(2-Phenoxy-acetyl)-piperidin-2-yl]-[1,2,4]oxadiazol-3-yl}-benzoic acid | (R)-3-{5-[1-(2-Phenoxy-acetyl)-piperidin-2-yl]-[1,2,4]oxadiazol-3-yl}-benzoic acid methyl ester | 408.5 |
| 181 | (R)-6-{5-[1-(2-Phenoxy-acetyl)-piperidin-2-yl]-[1,2,4]oxadiazol-3-yl}-nicotinic acid | (R)-6-{5-[1-(2-Phenoxy-acetyl)-piperidin-2-yl]-[1,2,4]oxadiazol-3-yl}-nicotinic acid methylester | 409.4 |
| 182 | (R)-2-Fluoro-4-{5-[1-(2-phenoxy-acetyl)-piperidin-2-yl]-[1,2,4]oxadiazol-3-yl}-benzoic acid | (R)-2-Fluoro-4-{5-[1-(2-phenoxy-acetyl)-piperidin-2-yl]-[1,2,4]oxadiazol-3-yl}-benzoic acid methyl ester | 426.5 |
| 183 | (R)-5-{5-[1-(2-Phenoxy-acetyl)-piperidin-2-yl]-[1,2,4]oxadiazol-3-yl}-pyridine-2-carboxylic acid | (R)-5-{5-[1-(2-Phenoxy-acetyl)-piperidin-2-yl]-[1,2,4]oxadiazol-3-yl}-pyridine-2-carboxylic acid methyl ester | 409.4 |
| 184 | (R)-4-{5-[1-(2-Phenoxy-acetyl)-piperidin-2-yl]-[1,2,4]oxadiazol-3-yl}-pyridine-2-carboxylic acid | (R)-4-{5-[1-(2-Phenoxy-acetyl)-piperidin-2-yl]-[1,2,4]oxadiazol-3-yl}-pyridine-2-carboxylic acid ethyl ester | 409.4 |
| 185 | (R)-3-{5-[1-(2-Phenoxy-acetyl)-piperidin-2-yl]-1H-[1,2,4]triazol-3-yl}-benzoic acid | (R)-3-{5-[1-(2-Phenoxy-acetyl)-piperidin-2-yl]-1H-[1,2,4]triazol-3-yl}-benzoic acid methyl ester | 407.4 |
| 186 | 3-{5-[4-(2-Phenoxy-acetyl)-morpholin-3-yl]-[1,2,4]oxadiazol-3-yl}-benzoic acid | 3-{5-[4-(2-Phenoxy-acetyl)-morpholin-3-yl]-[1,2,4]oxadiazol-3-yl}-benzoic acid methyl ester | 410.5 |
| 187 | 3-{5-[4-(2-Phenoxy-acetyl)-morpholin-3-yl]-[1,2,4]oxadiazol-3-yl}-benzoic acid | 3-{5-[4-(2-Phenoxy-acetyl)-morpholin-3-yl]-[1,2,4]oxadiazol-3-yl}-benzoic acid methyl ester | 410.5 |
| 188 | 4-{5-[4-(2-Phenoxy-acetyl)-thiomorpholin-3-yl]-[1,2,4]oxadiazol-3-yl}-benzamide | 4-{5-[4-(2-Phenoxy-acetyl)-thiomorpholin-3-yl]-[1,2,4]oxadiazol-3-yl}-benzamide methyl ester | 426.4 |
| 189 | 4-{5-[4-(2-Phenoxy-acetyl)-thiomorpholin-3-yl]-[1,2,4]oxadiazol-4-yl}-benzamide | 4-{5-[4-(2-Phenoxy-acetyl)-thiomorpholin-3-yl]-[1,2,4]oxadiazol-4-yl}-benzamide methyl ester | 426.4 |
| 190 | 3-{5-[4-Acetyl-1-(2-phenoxy-acetyl)-piperazin-2-yl]-[1,2,4]oxadiazol-3-yl}-benzoic acid | 3-{5-[4-Acetyl-1-(2-phenoxy-acetyl)-piperazin-2-yl]-[1,2,4]oxadiazol-3-yl}-benzoic acid methyl ester | 451.5 |
| 191 | 4-{5-[4-Acetyl-1-(2-phenoxy-acetyl)-piperazin-2-yl]-[1,2,4]oxadiazol-3-yl}-benzoic acid | 4-{5-[4-Acetyl-1-(2-phenoxy-acetyl)-piperazin-2-yl]-[1,2,4]oxadiazol-3-yl}-benzoic acid methyl ester | 451.5 |
| 192 | (R)-4-{5-[4-Methyl-1-(2-phenoxy-acetyl)-piperazin-2-yl]-1H-[1,2,4]triazol-3-yl}-benzoic acid | (R)-4-{5-[1-(2-Phenoxy-acetyl)-piperazin-2-yl]-1H-[1,2,4]triazol-3-yl}-benzoic acid methyl ester | 422.5 |
| 193 | (R)-5-{5-[1-(2-Phenoxy-acetyl)-piperidin-2-yl]-[1,2,4]oxadiazol-3-yl}-nicotinic acid | (R)-5-{5-[1-(2-Phenoxy-acetyl)-piperidin-2-yl]-[1,2,4]oxadiazol-3-yl}-nicotinic acid ethyl ester | 409.5 |

Example 194
(R)-1-(2-{3-[4-(Morpholine-4-carbonyl)-phenyl]-[1,2,4]oxadiazol-5-yl}-piperidin-1-yl)-2-phenoxy-ethanone 0.07 mmol of (R)-4-{5-[1-(2-Phenoxy-acetyl)-piperidin-2-yl]-[1,2,4]oxadiazol-3-yl}-benzoic acid were treated with 1 eq. of TBTU/DIPEA in 1 ml DMF for 10 min and 2 eq. of Morpholine added. Ther reaction is stirred overnight at room temperature and the product isolated via preperative HPLC.

MS(ISO): 477.6 (MH+)

The following compounds have been prepared in analogy:

TABLE 4

| Example | Compound name | Starting material | MH+ (found) |
|---|---|---|---|
| 195 | (R)-1-(2-{3-[4-(3-Hydroxy-pyrrolidine-1-carbonyl)-phenyl]-[1,2,4]oxadiazol-5-yl}-piperidin-1-yl)-2-phenoxy-ethanone | (R)-4-{5-[1-(2-Phenoxy-acetyl)-piperidin-2-yl]-[1,2,4]oxadiazol-3-yl}-benzoic acid and pyrrolidin-3-ol | 477.6 |
| 196 | (R)-N,N-Diethyl-4-{5-[1-(2-phenoxy-acetyl)-piperidin-2-yl]-[1,2,4]oxadiazol-3-yl}-benzamide | (R)-4-{5-[1-(2-Phenoxy-acetyl)-piperidin-2-yl]-[1,2,4]oxadiazol-3-yl}-benzoic acid and diethylamine | 463.6 |
| 197 | (R)-N-Methyl-4-{5-[1-(2-phenoxy-acetyl)-piperidin-2-yl]-[1,2,4]oxadiazol-3-yl}-benzamide | (R)-4-{5-[1-(2-Phenoxy-acetyl)-piperidin-2-yl]-[1,2,4]oxadiazol-3-yl}-benzoic acid and methylamine | 421.5 |
| 198 | (R)-N,N-Dimethyl-4-{5-[1-(2-phenoxy-acetyl)-piperidin-2-yl]-[1,2,4]oxadiazol-3-yl}-benzamide | (R)-4-{5-[1-(2-Phenoxy-acetyl)-piperidin-2-yl]-[1,2,4]oxadiazol-3-yl}-benzoic acid and dimethylamine | 435.5 |
| 199 | (R)-N-Ethyl-4-{5-[1-(2-phenoxy-acetyl)-piperidin-2-yl]-[1,2,4]oxadiazol-3-yl}-benzamide | (R)-4-{5-[1-(2-Phenoxy-acetyl)-piperidin-2-yl]-[1,2,4]oxadiazol-3-yl}-benzoic acid and ethylamine | 435.5 |
| 200 | (R)-N-Cyclopropyl-4-{5-[1-(2-phenoxy-acetyl)-piperidin-2-yl]-[1,2,4]oxadiazol-3-yl}-benzamide | (R)-4-{5-[1-(2-Phenoxy-acetyl)-piperidin-2-yl]-[1,2,4]oxadiazol-3-yl}-benzoic acid and cyclopropylamine | 447.5 |
| 201 | (R)-N-(2-Hydroxy-ethyl)-4-{5-[1-(2-phenoxy-acetyl)-piperidin-2-yl]-[1,2,4]oxadiazol-3-yl}-benzamide | (R)-4-{5-[1-(2-Phenoxy-acetyl)-piperidin-2-yl]-[1,2,4]oxadiazol-3-yl}-benzoic acid and ethanolamine | 451.5 |
| 202 | (R)-N-(2-Methoxy-ethyl)-N-methyl-4-{5-[1-(2-phenoxy-acetyl)-piperidin-2-yl]-[1,2,4]oxadiazol-3-yl}-benzamide | (R)-4-{5-[1-(2-Phenoxy-acetyl)-piperidin-2-yl]-[1,2,4]oxadiazol-3-yl}-benzoic acid and (2-methoxy-ethyl)-methyl-amine | 479.5 |
| 203 | (R)-N-Methyl-3-{5-[1-(2-phenoxy-acetyl)-piperidin-2-yl]-[1,2,4]oxadiazol-3-yl}-benzamide | (R)-3-{5-[1-(2-Phenoxy-acetyl)-piperidin-2-yl]-[1,2,4]oxadiazol-3-yl}-benzoic acid and methylamine | 421.5 |
| 204 | (R)-N,N-Dimethyl-3-{5-[1-(2-phenoxy-acetyl)-piperidin-2-yl]-[1,2,4]oxadiazol-3-yl}-benzamide | (R)-3-{5-[1-(2-Phenoxy-acetyl)-piperidin-2-yl]-[1,2,4]oxadiazol-3-yl}-benzoic acid and dimethylamine | 435.5 |
| 205 | (R)-N-Ethyl-3-{5-[1-(2-phenoxy-acetyl)-piperidin-2-yl]-[1,2,4]oxadiazol-3-yl}-benzamide | (R)-3-{5-[1-(2-Phenoxy-acetyl)-piperidin-2-yl]-[1,2,4]oxadiazol-3-yl}-benzoic acid and ethylamine | 435.5 |
| 206 | (R)-N-Cyclopropyl-3-{5-[1-(2-phenoxy-acetyl)-piperidin-2-yl]-[1,2,4]oxadiazol-3-yl}-benzamide | (R)-3-{5-[1-(2-Phenoxy-acetyl)-piperidin-2-yl]-[1,2,4]oxadiazol-3-yl}-benzoic acid and cyclopropylamine | 447.5 |
| 207 | (R)-N-(2-Hydroxy-ethyl)-3-{5-[1-(2-phenoxy-acetyl)-piperidin-2-yl]-[1,2,4]oxadiazol-3-yl}-benzamide | (R)-3-{5-[1-(2-Phenoxy-acetyl)-piperidin-2-yl]-[1,2,4]oxadiazol-3-yl}-benzoic acid and ethanolamine | 451.5 |
| 208 | (R)-N-(2-Methoxy-ethyl)-N-methyl-3-{5-[1-(2-phenoxy-acetyl)-piperidin-2-yl]-[1,2,4]oxadiazol-3-yl}-benzamide | (R)-3-{5-[1-(2-Phenoxy-acetyl)-piperidin-2-yl]-[1,2,4]oxadiazol-3-yl}-benzoic acid and (2-methoxy-ethyl)-methyl-amine | 479.5 |
| 209 | (R)-1-(2-{3-[3-(Morpholine-4-carbonyl)-phenyl]-[1,2,4]oxadiazol-5-yl}-piperidin-1-yl)-2-phenoxy-ethanone | (R)-3-{5-[1-(2-Phenoxy-acetyl)-piperidin-2-yl]-[1,2,4]oxadiazol-3-yl}-benzoic acid and morpholine | 477.6 |
| 210 | (R)-1-(2-{3-[3-(3-Hydroxy-pyrrolidine-1-carbonyl)-phenyl]-[1,2,4]oxadiazol-5-yl}-piperidin-1-yl)-2-phenoxy-ethanone | (R)-3-{5-[1-(2-Phenoxy-acetyl)-piperidin-2-yl]-[1,2,4]oxadiazol-3-yl}-benzoic acid and pyrrolidin-3-ol | 477.6 |
| 211 | (R)-N,N-Diethyl-3-{5-[1-(2-phenoxy-acetyl)-piperidin-2-yl]-[1,2,4]oxadiazol-3-yl}-benzamide | (R)-3-{5-[1-(2-Phenoxy-acetyl)-piperidin-2-yl]-[1,2,4]oxadiazol-3-yl}-benzoic acid and diethylamine | 463.6 |

TABLE 4-continued

| Example | Compound name | Starting material | MH+ (found) |
|---|---|---|---|
| 212 | (R)-4-{5-[1-(2-Phenoxy-acetyl)-piperidin-2-yl]-[1,2,4]oxadiazol-3-yl}-pyridine-2-carboxylic acid methylamide | (R)-4-{5-[1-(2-Phenoxy-acetyl)-piperidin-2-yl]-[1,2,4]oxadiazol-3-yl}-pyridine-2-carboxylic acid and methylamine | 422.5 |
| 213 | (R)-4-{5-[1-(2-Phenoxy-acetyl)-piperidin-2-yl]-[1,2,4]oxadiazol-3-yl}-pyridine-2-carboxylic acid dimethylamide | (R)-4-{5-[1-(2-Phenoxy-acetyl)-piperidin-2-yl]-[1,2,4]oxadiazol-3-yl}-pyridine-2-carboxylic acid and dimethylamine | 436.5 |
| 214 | (R)-4-{5-[1-(2-Phenoxy-acetyl)-piperidin-2-yl]-[1,2,4]oxadiazol-3-yl}-pyridine-2-carboxylic acid ethylamide | (R)-4-{5-[1-(2-Phenoxy-acetyl)-piperidin-2-yl]-[1,2,4]oxadiazol-3-yl}-pyridine-2-carboxylic acid and ethylamine | 436.5 |
| 215 | (R)-4-{5-[1-(2-Phenoxy-acetyl)-piperidin-2-yl]-[1,2,4]oxadiazol-3-yl}-pyridine-2-carboxylic acid diethylamide | (R)-4-{5-[1-(2-Phenoxy-acetyl)-piperidin-2-yl]-[1,2,4]oxadiazol-3-yl}-pyridine-2-carboxylic acid and diethylamine | 464.5 |
| 216 | (R)-1-(2-{3-[2-(Morpholine-4-carbonyl)-pyridin-4-yl]-[1,2,4]oxadiazol-5-yl}-piperidin-1-yl)-2-phenoxy-ethanone | (R)-4-{5-[1-(2-Phenoxy-acetyl)-piperidin-2-yl]-[1,2,4]oxadiazol-3-yl}-pyridine-2-carboxylic acid and morpholine | 478.5 |
| 217 | (R)-1-(2-{3-[2-(3-Methanesulfonyl-pyrrolidine-1-carbonyl)-pyridin-4-yl]-[1,2,4]oxadiazol-5-yl}-piperidin-1-yl)-2-phenoxy-ethanone | (R)-4-{5-[1-(2-Phenoxy-acetyl)-piperidin-2-yl]-[1,2,4]oxadiazol-3-yl}-pyridine-2-carboxylic acid and 3-methanesulfonyl-pyrrolidine | 540.5 |
| 218 | (R)-5-{5-[1-(2-Phenoxy-acetyl)-piperidin-2-yl]-[1,2,4]oxadiazol-3-yl}-pyridine-2-carboxylic acid methylamide | (R)-5-{5-[1-(2-Phenoxy-acetyl)-piperidin-2-yl]-[1,2,4]oxadiazol-3-yl}-pyridine-2-carboxylic acid and methylamine | 422.4 |
| 219 | (R)-N-Methyl-3-{5-[1-(2-phenoxy-acetyl)-piperidin-2-yl]-1H-[1,2,4]triazol-3-yl}-benzamide | (R)-3-{5-[1-(2-Phenoxy-acetyl)-piperidin-2-yl]-1H-[1,2,4]triazol-3-yl}-benzoic acid and methylamine | 420.4 |
| 220 | 1N,N-Diethyl-4-{5-[1-(2-phenoxy-acetyl)-piperazin-2-yl]-[1,2,4]oxadiazol-3-yl}-benzamide | 3-[3-(4-Carboxy-phenyl)-[1,2,4]oxadiazol-5-yl]-4-(2-phenoxy-acetyl)-piperazine-1-carboxylic acid tert-butyl ester and diethylamine | 464.3 |
| 221 | 1-(2-{3-[4-(Morpholine-4-carbonyl)-phenyl]-[1,2,4]oxadiazol-5-yl}-piperazin-1-yl)-2-phenoxy-ethanone | 3-[3-(4-Carboxy-phenyl)-[1,2,4]oxadiazol-5-yl]-4-(2-phenoxy-acetyl)-piperazine-1-carboxylic acid tert-butyl ester and morpholine | 478.0 |
| 222 | N-Methyl-4-{5-[1-(2-phenoxy-acetyl)-piperazin-2-yl]-[1,2,4]oxadiazol-3-yl}-benzamide | 3-[3-(4-Carboxy-phenyl)-[1,2,4]oxadiazol-5-yl]-4-(2-phenoxy-acetyl)-piperazine-1-carboxylic acid tert-butyl ester and methylamine | 422.4 |
| 223 | (R)-N-Methyl-5-{5-[1-(2-phenoxy-acetyl)-piperidin-2-yl]-[1,2,4]oxadiazol-3-yl}-nicotinamide | (R)-5-{5-[1-(2-Phenoxy-acetyl)-piperidin-2-yl]-[1,2,4]oxadiazol-3-yl}-nicotinic acid and methylamine | 422.4 |
| 224 | (R)-N-Ethyl-5-{5-[1-(2-phenoxy-acetyl)-piperidin-2-yl]-[1,2,4]oxadiazol-3-yl}-nicotinamide | (R)-5-{5-[1-(2-Phenoxy-acetyl)-piperidin-2-yl]-[1,2,4]oxadiazol-3-yl}-nicotinic acid and ethylamine | 436.5 |
| 225 | (R)-N-Diethyl-5-{5-[1-(2-phenoxy-acetyl)-piperidin-2-yl]-[1,2,4]oxadiazol-3-yl}-nicotinamide | (R)-5-{5-[1-(2-Phenoxy-acetyl)-piperidin-2-yl]-[1,2,4]oxadiazol-3-yl}-nicotinic acid and diethylamine | 436.5 |
| 226 | (R)-N-Diethyl-5-{5-[1-(2-phenoxy-acetyl)-piperidin-2-yl]-[1,2,4]oxadiazol-3-yl}-nicotinamide | (R)-5-{5-[1-(2-Phenoxy-acetyl)-piperidin-2-yl]-[1,2,4]oxadiazol-3-yl}-nicotinic acid and diethylamine | 464.5 |
| 227 | (R)-N-(2-Hydroxy-ethyl)-5-{5-[1-(2-phenoxy-acetyl)-piperidin-2-yl]-[1,2,4]oxadiazol-3-yl}-nicotinamide | (R)-5-{5-[1-(2-Phenoxy-acetyl)-piperidin-2-yl]-[1,2,4]oxadiazol-3-yl}-nicotinic acid and aminoethanol | 452.5 |

TABLE 4-continued

| Example | Compound name | Starting material | MH+ (found) |
|---|---|---|---|
| 228 | (R)-N-(2-Methoxy-ethyl)-N-methyl-5-{5-[1-(2-phenoxy-acetyl)-piperidin-2-yl]-[1,2,4]oxadiazol-3-yl}-nicotinamide | (R)-5-{5-[1-(2-Phenoxy-acetyl)-piperidin-2-yl]-[1,2,4]oxadiazol-3-yl}-nicotinic acid and (2-Methoxy-ethyl)-methyl-amine | 480.6 |
| 229 | (R)-N-Cyclopropyl-5-{5-[1-(2-phenoxy-acetyl)-piperidin-2-yl]-[1,2,4]oxadiazol-3-yl}-nicotinamide | (R)-5-{5-[1-(2-Phenoxy-acetyl)-piperidin-2-yl]-[1,2,4]oxadiazol-3-yl}-nicotinic acid and cyclopropylamine | 448.5 |
| 230 | (R)-1-(2-{3-[5-(3-Hydroxy-pyrrolidine-1-carbonyl)-pyridin-3-yl]-[1,2,4]oxadiazol-5-yl}-piperidin-1-yl)-2-phenoxy-ethanone | (R)-5-{5-[1-(2-Phenoxy-acetyl)-piperidin-2-yl]-[1,2,4]oxadiazol-3-yl}-nicotinic acid and Pyrrolidin-3-ol | 478.5 |

Example 231

(R)-4-{5-[1-(2-Phenoxy-acetyl)-piperidin-2-yl]-[1,2,4]oxadiazol-3-yl}-benzamide 34 mg of (R)-4-{5-[1-(2-Phenoxy-acetyl)-piperidin-2-yl]-[1,2,4]oxadiazol-3-yl}-benzoic acid were treated with 1 eq HATU/DIPEA in DMF and added to 1 eq of Rink-Resin. The reaction was shaken overnight at room temperature. The resin was washed with DMF, MeOH, DCM (3 times each) and then treated with TFA/DCM (1:1) for 2 h. The resulting yellow oil was purified via preparative HPLC.

MS(ISO): 407.5 (MH+)

The following compounds have been prepared in analogy:

Example 239

(R)-1-{2-[3-(3-Amino-phenyl)-[1,2,4]oxadiazol-5-yl]-piperidin-1-yl}-2-phenoxy-ethanone (R)-1-{2-[3-(3-Nitro-phenyl)-[1,2,4]oxadiazol-5-yl]-piperidin-1-yl}-2-phenoxy-ethanone were dissolved in 100 ml MeOH. 50 ml sat. NH$_4$Cl and Zn-powder were added. The suspension was briefly heated to reflux and stirred for 30 min. After filtration the MeOH was evaporated and the product isolated via extraction ethylacetate/water.

MS(ISO): 379.5 (MH+)

TABLE 5

| Example | Compound name | Starting materials | MH+ (found) |
|---|---|---|---|
| 232 | (R)-3-{5-[1-(2-Phenoxy-acetyl)-piperidin-2-yl]-[1,2,4]oxadiazol-3-yl}-benzamide | (R)-3-{5-[1-(2-Phenoxy-acetyl)-piperidin-2-yl]-[1,2,4]oxadiazol-3-yl}-benzoic acid and Rink resin | 407.4 |
| 233 | (R)-4-{5-[1-(2-Phenoxy-acetyl)-piperidin-2-yl]-[1,2,4]oxadiazol-3-yl}-pyridine-2-carboxylic acid amide | (R)-4-{5-[1-(2-Phenoxy-acetyl)-piperidin-2-yl]-[1,2,4]oxadiazol-3-yl}-pyridine-2-carboxylic acid and Rink resin | 408.4 |
| 234 | (R)-3-{5-[1-(2-Phenoxy-acetyl)-piperidin-2-yl]-1H-[1,2,4]triazol-3-yl}-benzamide | (R)-3-{5-[1-(2-Phenoxy-acetyl)-piperidin-2-yl]-1H-[1,2,4]triazol-3-yl}-benzoic acid and Rink resin | 406.4 |
| 235 | 4-{5-[4-(2-Phenoxy-acetyl)-morpholin-3-yl]-[1,2,4]oxadiazol-3-yl}-benzamide | 4-{5-[4-(2-Phenoxy-acetyl)-morpholin-3-yl]-[1,2,4]oxadiazol-3-yl}-benzoic acid and Rink resin | 409.5 |
| 236 | 4-{5-[4-(2-Phenoxy-acetyl)-thiomorpholin-3 yl]-[1,2,4]oxadiazol-3yl}-benzamide | 4-{5-[4-(2-Phenoxy-acetyl)-thiomorpholin-3 yl]-[1,2,4]oxadiazol-3yl}-benzoic acid and Rink resin | 425.5 |
| 237 | 4-{5-[1-(2-Phenoxy-acetyl)-piperazin-2-yl]-[1,2,4]oxadiazol-3-yl}-benzamide | 3-[3-(4-Carboxy-phenyl)-[1,2,4]oxadiazol-5-yl]-4-(2-phenoxy-acetyl)-piperazine-1-carboxylic acid tert-butyl ester and Rink resin | 408.3 |
| 238 | (R)-5-{5-[1-(2-Phenoxy-acetyl)-piperidin-2-yl]-[1,2,4]oxadiazol-3-yl}-nicotinamide | (R)-5-{5-[1-(2-Phenoxy-acetyl)-piperidin-2-yl]-[1,2,4]oxadiazol-3-yl}-nicotinic acid and Rink resin | 408.5 |

Example 240

(R)-1-{2-[3-(4-Amino-phenyl)-[1,2,4]oxadiazol-5-yl]-piperidin-1-yl}-2-phenoxy-ethanone (R)-1-{2-[3-(4-Nitro-phenyl)-[1,2,4]oxadiazol-5-yl]-piperidin-1-yl}-2-phenoxy-ethanone were dissolved in 100 ml MeOH. 50 ml sat. NH₄Cl and Zn-powder were added. The suspension was briefly heated to reflux and stirred for 30 min. After filtration the MeOH was evaporated and the product isolated via extraction ethylacetate/water.

MS(ISO): 379.5 (MH+)

Example 241

(R)-1-{2-[5-(3-Amino-phenyl)-2H-[1,2,4]triazol-3-yl]-piperidin-1-yl}-2-phenoxy-ethanone (R)-1-{2-[5-(3-Nitro-phenyl)-2H-[1,2,4]triazol-3-yl]-piperidin-1-yl}-2-phenoxy-ethanone were dissolved in 100 ml MeOH. 50 ml sat. NH₄Cl and Zn-powder were added. The suspension was briefly heated to reflux and stirred for 30 min. After filtration the MeOH was evaporated and the product isolated via extraction ethylacetate/water.

MS(ISO): 378.5 (MH+)

Example 242

(R)-N-(3-{5-[1-(2-Phenoxy-acetyl)-piperidin-2-yl]-[1,2,4]oxadiazol-3-yl}-phenyl)-acetamide 1 mmol (R)-1-{2-[3-(3-Amino-phenyl)-[1,2,4]oxadiazol-5-yl]-piperidin-1-yl}-2-phenoxy ethanone were dissolved in THF. 2 eq. of DIPEA were added. The reaction was cooled to 0° C. 1 eq. of acetylchloride in THF was added dropwise and the reaction stirred for 30 min. The product was isolated by extraction from ethylactetade/water and subsequent purification via preparative HPLC.

MS(ISO): 421.5 (MH+)

The following compounds have been generated in analogy by using either acetyl chloride, mesylchloride, chloroformic acid allyl ester or ethylisocyanate as the reagent:

TABLE 6

| Example | Compound name | Starting materials | MH+ (found) |
|---|---|---|---|
| 243 | (R)-N-(4-{5-[1-(2-Phenoxy-acetyl)-piperidin-2-yl]-[1,2,4]oxadiazol-3-yl}-phenyl)-acetamide | (R)-1-{2-[3-(4-Amino-phenyl)-[1,2,4]oxadiazol-5-yl]-piperidin-1-yl}-2-phenoxy-ethanone and acetyl chloride | 421.5 |
| 244 | (R)-N-(5-{5-[1-(2-Phenoxy-acetyl)-piperidin-2-yl]-[1,2,4]oxadiazol-3-yl}-pyridin-2-yl)-acetamide | (R)-1-{2-[3-(6-Amino-pyridin-3-yl)-[1,2,4]oxadiazol-5-yl]-piperidin-1-yl}-2-phenoxy-ethanone and acytyl chloride | 422.5 |
| 245 | (R)-N-(3-{5-[1-(2-Phenoxy-acetyl)-piperidin-2-yl]-1H-[1,2,4]triazol-3-yl}-phenyl)-acetamide | (R)-1-{2-[5-(3-Amino-phenyl)-2H-[1,2,4]triazol-3-yl]-piperidin-1-yl}-2-phenoxy-ethanone and acytyl chloride | 420.5 |
| 246 | (R)-N-(3-{5-[1-(2-Phenoxy-acetyl)-piperidin-2-yl]-[1,2,4]oxadiazol-3-yl}-phenyl)-methanesulfonamide | (R)-1-{2-[3-(3-Amino-phenyl)-[1,2,4]oxadiazol-5-yl]-piperidin-1yl}-2 phenoxy-ethanone and mesyl chloride | 457.4 |
| 247 | (R)-N-(4-{5-[1-(2-Phenoxy-acetyl)-piperidin-2-yl]-[1,2,4]oxadiazol-3-yl}-phenyl)-methane-sulfonamide | (R)-1-{2-[3-(4-Amino-phenyl)-[1,2,4]oxadiazol-5-yl]-piperidin-1-yl}-2-phenoxy-ethanone and mesylchloride | 457.4 |
| 248 | (R)-(3-{5-[1-(2-Phenoxy-acetyl)-piperidin-2-yl]-[1,2,4]oxadiazol-3-yl}-phenyl)-carbamic acid allyl ester | (R)-1-{2-[3-(3-Amino-phenyl)-[1,2,4]oxadiazol-5-yl]-piperidin-1yl}-2 phenoxy-ethanone acid allyl ester | 463.5 |
| 249 | (R)-(4-{5-[1-(2-Phenoxy-acetyl)-piperidin-2-yl]-[1,2,4]oxadiazol-3-yl}-phenyl)-carbamic acid allyl ester | (R)-1-{2-[3-(4-Amino-phenyl)-[1,2,4]oxadiazol-5-yl]-piperidin-1-yl}-2-phenoxy-ethanone and chloroformic acid allyl ester | 463.5 |
| 250 | (R)-N-(3-{5-[1-(2-Phenoxy-acetyl)-piperidin-2-yl]-1H-[1,2,4]triazol-3-yl}-phenyl)-methanesulfonamide | (R)-1-{2-[5-(3-Amino-phenyl)-2H-[1,2,4]triazol-3-yl]-piperidin-1-yl}-2-phenoxy-ethanone and mesyl chloride | 456.5 |
| 251 | (R)-1-Ethyl-3-(3-{5-[1-(2-phenoxy-acetyl)-piperidin-2-yl-1H-[1,2,4]triazol-3-yl}-phenyl)-urea | (R)-1-{2-[5-(3-Amino-phenyl)-2H-[1,2,4]triazol-3-yl]-piperidin-1-yl}-2-phenoxy-ethanone and ethylisocyanate | 449.5 |

Example 252

(R)-3-{5-[1-(2-Phenoxy-acetyl)-piperidin-2-yl]-1H-[1,2,4]triazol-3-yl}-benzonitrile 1.3 mmol (R)-3-{5-[1-(2-Phenoxy-acetyl)-piperidin-2-yl]-1H-[1,2,4]triazol-3-yl}-benzamide were treated with neat trifluoroacetic anhydride at room temperature overnight. The reaction was quenched with aqueous NaHCO$_3$ and product extracted with ethylacetate twice. The organic layers were washed with water/NaCl, combined, dried over Na2SO4 and the solvent evaporated. The product was purified via preparative HPLC.

MS(ISO): 388.5 (MH+)

Example 253

(R)-5-{5-[1-(2-Phenoxy-acetyl)-piperidin-2-yl]-[1,2,4]oxadiazol-3-yl}-nicotinonitrile 0.15 mmol of 5-{5-[1-(2-Phenoxy-acetyl)-piperidin-2-yl]-[1,2,4]oxadiazol-3-yl}-nicotinamide are treated with trifluoracetic anhydride at room temperature over night. The reaction was quenched with aqueous NaHCO$_3$ and product extracted with ethylacetate twice. The organic layers were washed with water/NaCl, combined, dried over Na2SO4 and the solvent evaporated. The product was purified via preparative HPLC.

MS(ISO): 390.4 (MH+)

Example 254

4-Acetyl-piperazine-1,2-dicarboxylic acid 1-tert-butyl ester 10 mmol of Piperazine-1,2-dicarboxylic acid 1-tert-butyl ester 2-methyl ester were dissolved in 20 ml methylenchloride. 1.05 eq of DIPEA and acetychloride were added. The reaction mixture was stirred at room temperature for 30 min. The product was extracted from etylacetate/water. The crude material was re-dissolved in methanol and treated with 2N NaOH. The reaction mixture was stirred at room temperature for 2 h. The mixture was neutralized with HCl and the product isolated via extraction from ethylacetate/water.

MS(ISO): 271.3 (M–H+)

Example 255

4-Methanesulfonyl-piperazine-1,2-dicarboxylic acid 1-tert-butyl ester 10 mmol of Piperazine-1,2-dicarboxylic acid 1-tert-butyl ester 2-methyl ester were dissolved in 20 ml methylenchloride. 1.05 eq of DIPEA and mesylchloride were added. The reaction mixture was stirred at room temperature for 30 min. The product was extracted from etylacetate/water. The crude material was redissolved in methanol and treated with 2N NaOH. The reaction mixture was stirred at room temperature for 2 h. The mixture was neutralized with HCl and the product isolated via extraction from ethylacetate/water.

MS(ISO): 307.4 (M–H+)

Example 256

N-Hydroxy-4-sulfamoyl-benzamidine 1 mmol of 4-Cyano-benzenesulfonamide are dissolved in a mixture of ethanol/water (7:3) and 5 eq of hydroxylamine hydrochloride and 2.5 eq. Na2CO3 added. The suspension is heated to 80° C. for 2 h. After evaporation of the solvent mixture the resulting material is extracted from ethylacetate/water. The product was not further characterized.

MS(ISO): 216.3 (MH+)

All following compounds were prepared in analogy:

TABLE 7

| Example | Compound name | Starting materials |
|---|---|---|
| 257 | 3-(N-Hydroxy-carbamimidoyl)-benzoic acid methyl ester | 3-Cyano-benzoic acid methyl ester and hydroxylamine |
| 258 | 4-(N-Hydroxycarbamimidoyl)-pyridine-2-carboxylic acid ethyl ester | 4-Cyano-pyridine-2-carboxylic acid ethyl ester |
| 259 | 3-Fluoro-4-(N-hydroxycarbamimidoyl)-benzoic acid methyl ester | 4-Cyano-3-fluoro-benzoic acid methyl ester |
| 260 | N-Hydroxy-4-nitro-benzamidine | 4-Nitro-benzonitrile and hydroxylamine |
| 261 | N-Hydroxy-3-sulfamoyl-benzamidine | 3-Cyano-benzenesulfonamide and hydroxylamine |
| 262 | N-Hydroxy-6-methoxy-nicotinamidine | 6-Methoxy-nicotinonitrile and hydroxylamine |
| 263 | N-Hydroxy-3-hydroxymethyl-benzamidine | 3-Hydroxymethyl-benzonitrile and hydroxylamine |
| 264 | N-Hydroxy-4-imidazol-1-yl-benzamidine | 4-Imidazol-1-yl-benzonitrile and hydroxylamine |
| 265 | N-Hydroxy-6-morpholin-4-yl-nicotinamidine | 6-Morpholin-4-yl-nicotinonitrile and hydroxylamine |
| 266 | N-Hydroxy-4-trifluoromethanesulfonyl-benzamidine | 4-Trifluoromethanesulfonyl-benzonitrile and hydroxylamine |
| 267 | N-Hydroxy-4-trifluoromethyl-benzamidine | 4-Trifluoromethyl-benzonitrile and hydroxylamine |
| 268 | 4-Chloro-N-hydroxy-benzamidine | 4-Chloro-benzonitrile and hydroxylamine |
| 269 | N-[4-(N-Hydroxycarbamimidoyl)-2-trifluoromethyl-phenyl]-acetamide | N-(4-Cyano-2-trifluoromethyl-phenyl)-acetamide and hydroxylamine |

TABLE 7-continued

| Example | Compound name | Starting materials |
| --- | --- | --- |
| 270 | N-Hydroxy-3-methanesulfonyl-benzamidine | 3-Methanesulfonyl-benzonitrile and hydroxylamine |
| 271 | N-Hydroxy-4-methyl-3-nitro-benzamidine | 4-Methyl-3-nitro-benzonitrile and hydroxylamine |
| 272 | N-Hydroxy-4-methoxy-3-nitro-benzamidine | 4-Methoxy-3-nitro-benzonitrile and hydroxylamine |
| 273 | N-Hydroxy-2-oxo-1,2-dihydro-pyridine-4-carboxamidine | 2-Oxo-1,2-dihydro-pyridine-4-carbonitrile |
| 274 | N-Hydroxy-6-oxo-1,6-dihydro-pyridine-3-carboxamidine | 6-Oxo-1,6-dihydro-pyridine-3-carbonitrile |
| 275 | N-Hydroxy-4-(1H-tetrazol-5-yl)-benzamidine | 4-(1H-Tetrazol-5-yl)-benzonitrile and hydroxylamine |
| 276 | N-Hydroxy-1H-indazole-5-carboxamidine | 1H-Indazole-5-carbonitrile and hydroxylamine |
| 277 | N-Hydroxy-1H-indazole-6-carboxamidine | 1H-Indazole-6-carbonitrile and hydroxylamine |
| 278 | 4-Fluoro-N-hydroxy-3-trifluoromethyl-benzamidine | 4-Fluoro-3-trifluoro-methyl-benzonitrile and hydroxylamine |
| 279 | N-Hydroxy-2-oxo-2,3-dihydro-1H-indole-6-carboxamidine | 2-Oxo-2,3-dihydro-1H-indole-6-carbonitrile and hydroxylamine |
| 280 | N-Hydroxy-2-oxo-2,3-dihydro-1H-benzoimidazole-5-carboxamidine | 2-Oxo-2,3-dihydro-1H-benzoimidazole-5-carbonitrile and hydroxylamine |
| 281 | N-Hydroxy-2-oxo-2,3-dihydro-1H-indole-5-carboxamidine | 2-Oxo-2,3-dihydro-1H-indole-5-carbonitrile and hydroxylamine |
| 282 | N-Hydroxy-pyridine-2-carboxamidine | Pyridine-2-carbonitrile and hydroxylamine |
| 283 | N-Hydroxy-pyridine-3-carboxamidine | Pyridine-3-carbonitrile and hydroxylamine |
| 284 | 4-Diethylamino-N-hydroxy-benzamidine | 4-Diethylamino-benzonitrile and hydroxylamine |
| 285 | N-[4-(N-Hydroxycarbamimidoyl)-2-trifluoromethyl-phenyl]-acetamide | N-(4-Cyano-2-trifluoromethyl-phenyl)-acetamide and hydroxylamine |
| 286 | 4-Chloro-N-hydroxy-3-nitro-benzamidine | 4-Chloro-3-nitro-benzonitrile and hydroxylamine |
| 287 | N-Hydroxy-4-pyrrol-1yl-benzamidine | 4-Pyrrol-1-yl-benzonitrile and hydroxylamine |
| 288 | 2,4-Dichloro-N-hydroxy-benzamidine | 2,4-Dichloro-benzonitrile and hydroxylamine |
| 289 | N-Hydroxy-3-(2-oxo-piperidin-1-yl)-benzamidine | 3-(2-Oxo-piperidin-1-yl)-benzonitrile and hydroxylamine |
| 290 | N-Hydroxy-1H-benzoimidazole-5-carboxamidine | 1H-Benzoimidazole-5-carbonitrile |
| 291 | 6-(N-Hydroxy-carbamimidoyl)-nicotinic acid allyl ester | 6-Cyano-nicotinic acid allyl ester and hydroxylamine |
| 292 | 4-(N-Hydroxycarbamimidoyl)-pyridine-2-carboxylic acid ethyl ester | 4-Cyano-pyridine-2-carboxylic acid ethyl ester and hydroxylamine |
| 293 | 3-Fluoro-4-(N-hydroxycarbamimidoyl)-benzoic acid methyl ester | 4-Cyano-3-fluoro-benzoic acid methyl ester and bydroxylamine |
| 294 | N-Hydroxy-1H-benzotriazole-5-carboxamidine | 1H-Benzotriazole-5-carbonitrile |
| 294 | 6-Benzyloxy-N-hydroxy-nicotinamidine | 6-Benzyloxy-nicotinonitrile |
| 295 | N-[5-(N-Hydroxycarbamimidoyl)-pyridin-2-yl]-acetamide | N-(5-Cyano-pyridin-2-yl)-acetamide |
| 296 | N-[4-(N-Hydroxycarbamimidoyl)-pyridin-2-yl]-acetamide | N-(4-Cyano-pyridin-2-yl)-acetamide |

Example 297

N-Hydroxy-4-methylsulfamoyl-benzamidine 5 mmol of 4-Cyano-benzenesulfonyl chloride were dissolved in 10 ml THF. 10 ml of a 2M methylamine/THF solution was added dropwise. The reaction was stirred at room temperature overnight. The solvent was evaporated and the product extracted from ethylacetate/water. The nitril obtained was treated analogously to example 231.

MS(ISO): 230.5 (MH+)

All following compounds were prepared in analogy:

TABLE 8

| Example | Compound name | Starting materials |
|---|---|---|
| 298 | N-Hydroxy-4-(morpholine-4-sulfonyl)-benzamidine | 4-Cyano-benzenesulfonyl chloride and morpholine |
| 299 | N-Hydroxy-4-(2-hydroxy-ethylsulfamoyl)-benzamidine | 4-Cyano-benzenesulfonyl chloride and ethanolamine |
| 300 | N-Hydroxy-4-[(2-methoxy-ethyl)-methyl-sulfamoyl]-benzamidine | 4-Cyano-benzenesulfonyl chloride and (2-Methoxy-ethyl)-methylamine |
| 301 | 4-Dimethylsulfamoyl-N-hydroxy-benzamidine | 4-Cyano-benzenesulfonyl chloride and dimethylamine |
| 302 | 4-Diethylsulfamoyl-N-hydroxy-benamidine | 4-Cyano-benzenesulfonyl chloride and diethylamine |

Example 303

6-(1,1-Dioxo-thiomorpholin-4-yl)-N-hydroxy-nicotinamidine 10 mmol of 6-Cl-4-CN-pyridine are dissolved in 10 ml DMF. 20 mmol of morpholine are added and the reaction heated to 120° C. under microwave conditions for 20 min. The DMF is evaporated and the crude extracted from ethylacetate/water. After evaporation the resulting solid was treated with 30 mmol of metha-chloroperbenzoic acid in DCM at room temperature overnight and the resulting precipitate filtered off and recrystalized from MeOH. The nitril obtained was treated analogously to example 231.
MS(ISO): 271.5 (MH+)
The following compounds were prepared in analogy.

TABLE 9

| Example | Compound name | Starting materials |
|---|---|---|
| 304 | N-Hydroxy-2-morpholin-4-yl-isonicotinamidine | 2-Chloroisonicotinonitrile and morpholin |
| 305 | N-Hydroxy-3,4,5,6-tetrahydro-2H-[1,2']bipyridinyl-4'-carboxamidine | 2-Chloroisonicotinonitrile and piperidin |
| 306 | N-Hydroxy-2-thiomorpholin-4-yl-isonicotinamidine | 2-Chloroisonicotinonitrile and thiomorpholin |
| 307 | 2-Diethylamino-N-hydroxy-isonicotinamidine | 2-Chloroisonicotinonitrile and diethylamine |
| 308 | N-Hydroxy-6-(3-oxo-piperazin-1-yl)-nicotinamidine | 2-Chloronicotinonitrile and Piperazin-2-one |
| 309 | 6-(4-Acetyl-piperazin-1-yl)-N-hydroxy-nicotinamidine | 2-Chloronicotinonitrile and 1-acetylpiperazin |
| 310 | N-Hydroxy-6-(3-hydroxymethyl-pyrrolidin-1-yl)-nicotinamidine | 2-Chloronicotinonitrile and Pyrrolidin-3-yl-methanol |
| 311 | N-Hydroxy-6-morpholin-4-yl-nicotinamidine | 2-Chloronicotinonitrile and morpholin |

Example 312

4-Fluoro-N-amino-benzamidine hydrochloride 82 mmol of 3-Cyano-benzoic acid methyl ester were dissolved in 50 ml of an HCl-saturated methylenchloride solution and 50 ml of methanol. Under ice-bath cooling HCl-gas was bubbled through the solution to keep the temperature under 20° C. The reaction mixture was stirred overnight at room temperature. l00ml of diethylether were added and the resulting solid filtered off, washed with diethylether and dried under vaccum. The resulting imidoether was extracted from ethylacetate/aq. sodiumbicarbonate to result in an oily residue. This was taken up in 25 ml methanol and treated with 1 ml hydrazin monohydrate at room temperature overnight. The solution was slowly added to a cold solution of 4N HCl/dioxan. 80 ml of diethylether were added and the suspension stirred at room temperature for 30 min. The solid was filtered off and washed with diethylether and dried under vacuum. The product was confirmed by MS.
MS(ISO): 194.4 (MH+)

The following compounds were prepared in analogy:

TABLE 10

| Example | Compound name | Starting materials |
| --- | --- | --- |
| 313 | 4-Fluoro-N-amino-3-trifluoromethyl-benzamidine hydrochloride | 4-Fluoro-3-trifluoromethyl-benzonitrile and hydrazine |
| 314 | N-Amino-4-methanesulfonyl-benzamidine hydrochloride | 4-Methanesulfonyl-benzonitril and hydrazine |
| 315 | N-Amino-3-trifluoromethyl-benzamidine hydrochloride | m-Trifluoromethyl-benzonitril and hydrazine |
| 316 | N-Amino-4-methyl-benzamidine hydrochloride | p-Tolunitril and hydrazine |
| 317 | N-Amino-4-trifluoromethyl-benzamidine hydrochloride | p-Trifluoromethyl-benzonitril and hydrazine |
| 318 | N-Amino-4-methoxy-benzamidine hydrochloride | 4-Methoxybenzonitrile and hydrazine |
| 319 | N-Amino-2,4-difluoro-benzamidine hydrochloride | 2,4-Difluorobenzonitrile and hydrazine |
| 320 | N-Amino-3,4-dimethoxy-benzamidine hydrochloride | 3,4-Dimethoxybenzonitrile and hydrazine |
| 321 | N-Amino-3,4-dichloro-benzamidine hydrochloride | 3,4-Dichlorobenzonitrile and hydrazine |
| 322 | N-Amino-benzamidine hydrochloride | Benzonitrile and hydrazine |
| 323 | N-Amino-3-Nitro-benzamidine hydrochloride | 3-Nitrobenzonitrile and hydrazine |
| 324 | N-Amino-3-methylester-benzamidine hydrochloride | 3-Cyano-benzoic acid methyl ester and hydrazine |
| 325 | N-Amino-2-oxo-2,3-dihydro-1H-indole-6-carboxamidine | 2-Oxo-2,3-dihydro-1H-indole-6-carbonitrile and hydrazine |
| 326 | N-Amino-2-fluoro-benzamidine hydrochloride | 2-Fluorobenzonitrile and hydrazine |

Example 327

6-Cyano-nicotinic acid allyl ester 4 mmol of 6-Cyanonicotinic acid were dissolved in THF. 1.5 eq. of Cs2CO3 were added he reaction stirred for 10 min. 1.5 eq allylbromide and a catalytic amount of KI were added he reaction heated to 100° C. for 4 h. The product was isolated via extraction from cetate/water.
MS(ISO): 222.5 (MH+)

Example 328

1H-Benzotriazole-5-carbonitrile 10 mmol of 3,4-Diamino-benzonitrile were suspended in water/acetic acid (4:1) and cooled to 0° C. 1.05 eq of NaNO2 were dissolved in water and added inert 30 min. The reaction was stirred at room temperature overnight. The precipitate was filtered off, washed with ether and dried under vacuum. The intermediate was not further characterized.

Example 329

6-Benzyloxy-nicotinonitrile 20 mmol of 6-Chloro-nicotinonitrile were dissolved in THF. 1.1 eq. of benzyl alcohol were added. The reaction mixture was cooled to 0° C. and flushed with argon. 4 eq of NaH were added slowly. After 15 min the product was isolated via extraction from ethylacetate/water.
MS(ISO): 211.5 (MH+)

Example 330

N-(5-Cyano-pyridin-2-yl)-acetamide 8 mmol of 6-Amino-nicotinonitrile were dissolved in THF. 2 eq of DIPEA were added. The reaction mixture was cooled to 0° C. and 1.0 eq of acetylchloride in THF added dropwise and the reaction stirred for 2 h. The product was isolated by extraction from ethylacetate/water.
MS(ISO): 162.2 (MH+)

Example 331

N-(4-Cyano-pyridin-2-yl)-acetamide 8 mmol of 2-Amino-isonicotinonitrile were dissolved in THF. 2 eq of DIPEA were added. The reaction mixture was cooled to 0° C. and 1.0 eq of acetylchloride in THF added dropwise and the reaction stirred for 2 h. The product was isolated by extraction from ethylacetate/water.
MS(ISO): 162.2 (MH+)

The following compounds were generated in analogy to example 1

| Example | Compound name | Starting materials | MH+ (found) |
| --- | --- | --- | --- |
| 332 | 1-{2-[3-(2-Methyl-1H-benzoimidazol-5-yl)- | Boc-D-Pipecolic Acid, N-Hydroxy-2-methyl-1H- | 418.5 |

-continued

| Example | Compound name | Starting materials | MH+ (found) |
|---|---|---|---|
| | [1,2,4]oxadiazol-5-yl]-piperidin-1-yl}-2-phenoxy-ethanone | benzoimidazole-5-carboxamidine and phenoxyacetyl chloride | |
| 333 | 1-{2-[3-(2-Amino-pyridin-4-yl)-[1,2,4]oxadiazol-5-yl]-piperidin-1-yl}-2-phenoxy-ethanone | Boc-D-Pipecolic Acid, 2-Amino-N-hydroxy-isonicotinamidine and phenoxyacetic acid | 380.5 |
| 334 | 1-{2-[3-(3-Hydroxy-phenyl)-[1,2,4]oxadiazol-5-yl]-piperidin-1-yl}-2-phenoxy-ethanone | Boc-D-Pipecolic Acid, 3-N-Dihydroxy-benzamidine and phenoxyacetic acid | 380.5 |
| 335 | 4-{5-[1-(2-Phenoxy-acetyl)-piperidin-2-yl]-[1,2,4]oxadiazol-3-yl}-1H-pyridin-2-one | Boc-D-Pipecolic Acid, 2,N-Dihydroxy-isonicotinamidine and phenoxyacetyl chloride | 381.4 |
| 336 | 1-{2-[3-(4-Hydroxy-phenyl)-[1,2,4]oxadiazol-5-yl]-piperidin-1-yl}-2-phenoxy-ethanone | Boc-D-Pipecolic Acid, 4-N-Dihydroxy-benzamidine and phenoxyacetic acid | 379.6 |
| 337 | 3-{5-[1-(2-Phenoxy-acetyl)-piperidin-2-yl]-[1,2,4]oxadiazol-3-yl}-phenylboronic acid | Boc-D-Pipecolic Acid, 3-(N-Hydroxycarbamidoyl)-phenylboronic acid and phenoxyacetyl chloride | 407.7 |
| 338 | 4-(2-Oxo-2-{2-[3-(2-oxo-2,3-dihydro-1H-indol-5-yl)-[1,2,4]oxadiazol-5-yl]-piperidin-1-yl}-ethoxy)-benzonitrile | Boc-D-Pipecolic Acid, N-Hydroxy-2-oxo-2,3-dihydro-1H-indole-5-carboxamidine and 4-cyanophenoxyacetic acid | 443.7 |
| 339 | 4-(2-{2-[3-(4-Methoxy-phenyl)-[1,2,4]oxadiazol-5-yl]-piperidin-1-yl}-2-oxo-ethoxy)-benzonitrile | Boc-D-Pipecolic Acid, N-Hydroxy-4-methoxy-benzamidine and 4-cyanophenoxyacetic acid | 419.3 |
| 340 | 2-Methyl-5-{5-[1-(2-phenoxy-acetyl)-piperidin-2-yl]-[1,2,4]oxadiazol-3-yl}-3H-pyrimidin-4-one | Boc-D-Pipecolic Acid, 4,N-Dihydroxy-2-methyl-pyrimidine-5-carboxamidine and phenoxyacetyl chloride | 396.2 |
| 341 | 1-[(R)-2-(3-Furan-2-yl-[1,2,4]oxadiazol-5-yl)-piperidin-1-yl]-2-phenoxy-ethanone | Boc-D-Pipecolic Acid, N-Hydroxy-furan-2-carboxamidine and phenoxyacetyl chloride | 354.2 |
| 342 | 1-[(R)-2-(3-Imidazo[1,2-a]pyridin-2-yl-[1,2,4]oxadiazol-5-yl)-piperidin-1-yl]-2-phenoxy-ethanone | Boc-D-Pipecolic Acid, N-Hydroxy-imidazo[1,2-a]pyridine-2-carboxamidine and phenoxyacetyl chloride | 404.2 |
| 343 | 1-{(R)-2-[3-(4-Methyl-[1,2,3]thiadiazol-5-yl)-[1,2,4]oxadiazol-5-yl]-piperidin-1-yl}-2-phenoxy-ethanone | Boc-D-Pipecolic Acid, N-Hydroxy-4-methyl-[1,2,3]thiadiazole-5-carboxamidine and phenoxyacetyl chloride | 386.2 |
| 344 | 1-{(R)-2-[3-(2,5-Dimethyl-2H-pyrazol-3-yl)-[1,2,4]oxadiazol-5-yl]-piperidin-1-yl}-2-phenoxy-ethanone | Boc-D-Pipecolic Acid, N-Hydroxy-2,5-dimethyl-2H-pyrazole-3-carboxamidine and phenoxyacetyl chloride | 382.2 |
| 345 | 2-Phenoxy-1-{(R)-2-[3-(1H-pyrazol-4-yl)-[1,2,4]oxadiazol-5-yl]-piperidin-1-yl}-ethanone | Boc-D-Pipecolic Acid, N-Hydroxy-1H-pyrazole-4-carboxamidine and phenoxyacetyl chloride | 354.2 |
| 346 | 1-{(R)-2-[3-(5-Methyl-isoxazol-3-yl)-[1,2,4]oxadiazol-5-yl]-piperidin-1-yl}-2-phenoxy-ethanone | Boc-D-Pipecolic Acid, N-Hydroxy-5-methyl-isoxazole-3-carboxamidine and phenoxyacetyl chloride | 369.2 |
| 347 | 2-Phenoxy-1-{(R)-2-[3-(1H-pyrazol-3-yl)-[1,2,4]oxadiazol-5-yl]-piperidin-1-yl}-ethanone | Boc-D-Pipecolic Acid, N-Hydroxy-1H-pyrazole-3-carboxamidine and phenoxyacetyl chloride | 354.2 |
| 348 | 5-{5-[(R)-1-(2-Phenoxy-acetyl)-piperidin-2-yl]-[1,2,4]oxadiazol-3-yl}-1H-pyrimidine-2,4-dione | Boc-D-Pipecolic Acid, 2,4,N-Trihydroxy-pyrimidine-5-carboxamidine and phenoxyacetyl chloride | 398.2 |
| 349 | 1-{(R)-2-[3-(6-Amino-pyridin-3-yl)-[1,2,4]oxadiazol-5-yl]-piperidin-1-yl}-2-phenoxy-ethanone | Boc-D-Pipecolic Acid, 6-Amino-N-hydroxy nicotinamidine and phenoxyacetyl chloride | 380.5 |

-continued

| Example | Compound name | Starting materials | MH+ (found) |
|---|---|---|---|
| 350 | 1-[(R)-2-(3-Imidazo[1,2-a]pyridin-6-yl-[1,2,4]oxadiazol-5-yl)-piperidin-1-yl]-2-phenoxy-ethanone | Boc-D-Pipecolic Acid, N-Hydroxy-imidazo[1,2-a]pyridine-6-carboxamidine and phenoxyacetyl chloride | 404.2 |
| 351 | 6-{5-[(R)-1-(2-Phenoxy-acetyl)-piperidin-2-yl]-[1,2,4]oxadiazol-3-yl}-4H-benzo[1,4]oxazin-3-one | Boc-D-Pipecolic Acid, N-Hydroxy-3-oxo-3,4-dihydro-2H-benzo[1,4]oxazine-6-carboxamidine and phenoxyacetyl chloride | 435.2 |
| 352 | 6-{5-[(R)-1-(2-Phenoxy-acetyl)-piperidin-2-yl]-[1,2,4]oxadiazol-3-yl}-1,4-dihydro-benzo[d][1,3]oxazin-2 one | Boc-D-Pipecolic Acid, N-Hydroxy-2-oxo-1,4-dihydro-2H-benzo[d][1,3]oxazine-6-carboxamidine and phenoxyacetyl chloride | 435.2 |
| 353 | 1-((R)-2-{3-[3-(1,1-Dioxo-1$$6-isothiazolidin-2-yl)-phenyl]-[1,2,4]oxadiazol-5-yl}-piperidin-1-yl)-2-phenoxy-ethanone | Boc-D-Pipecolic Acid, 3-(1,1-Dioxo-1$$6-isothiazolidin-2-yl)-N-hydroxy-benzamidine and phenoxyacetyl chloride | 483.3 |
| 354 | 1-(3-{5-[(R)-1-(2-Phenoxy-acetyl)-piperidin-2-yl]-[1,2,4]oxadiazol-3-yl}-phenyl)-pyrrolidin-2-one | Boc-D-Pipecolic Acid, N-Hydroxy-3-(2-oxo-pyrrolidin-1-yl)-benzamidine and phenoxyacetyl chloride | 447.3 |
| 355 | 1-(3-{5-[(R)-1-(2-Phenoxy-acetyl)-piperidin-2-yl]-[1,2,4]oxadiazol-3-yl}-phenyl)-imidazolidine-2,4-dione | Boc-D-Pipecolic Acid, 3-(2,4-Dioxo-imidazolidin-1-yl)-N-hydroxy-benzamidine and phenoxyacetyl chloride | 462.5 |
| 356 | 4-(3-{5-[(R)-1-(2-Phenoxy-acetyl)-piperidin-2-yl]-[1,2,4]oxadiazol-3-yl}-phenyl)-2,4-dihydro-[1,2,4]triazol-3-one | Boc-D-Pipecolic Acid, N-Hydroxy-3-(5-oxo-1,5-dihydro-[1,2,4]triazol-4-yl)-benzamidine and phenoxyacetyl chloride | 447.5 |
| 357 | 1-(3-Fluoro-5-{5-[(R)-1-(2-phenoxy-acetyl)-piperidin-2-yl]-[1,2,4]oxadiazol-3-yl}-phenyl)-pyrrolidine-2,5-dione | Boc-D-Pipecolic Acid, 3-(2,5-Dioxo-pyrrolidin-1-yl)-5-fluoro-N-hydroxy-benzamidine and phenoxyacetyl chloride | 479.2 |
| 358 | 5-{5-[(R)-1-(2-Phenoxy-acetyl)-piperidin-2-yl]-1H-[1,2,4]triazol-3-yl}-1,3-dihydro-indol-2-one | Boc-D-Pipecolic Acid, N-Amino-2-Oxo-2,3-dihydro-1H-indole-5-carboxamidine and phenoxyacetic acid | 418.5 |
| 359 | 1-{(R)-2-[5-(1H-Indazol-5-yl)-2H-[1,2,4]triazol-3-yl]-piperidin-1-yl}-2-phenoxy-ethanone | Boc-D-Pipecolic Acid, N-Amino-1H-Indazole-5-carboxamidine and phenoxyacetic acid | 403.5 |
| 360 | 1-{(R)-2-[5-(1H-Indol-5-yl)-2H-[1,2,4]triazol-3-yl]-piperidin-1-yl}-2-phenoxy-ethanone | Boc-D-Pipecolic Acid, N-Amino-1H-Indole-5-carboxamidine and phenoxyacetic acid | 402.5 |
| 361 | 1-{(R)-2-[5-(3H-Benzotriazol-5-yl)-2H-[1,2,4]triazol-3-yl]-piperidin-1-yl}-2-phenoxy-ethanone | Boc-D-Pipecolic Acid, N-Amino-3H-Benzotriazole-5-carboxamidine and phenoxyacetic acid | 402.5(M − H+) |
| 362 | 5-{5-[(R)-1-(2-Phenoxy-acetyl)-piperidin-2-yl]-1H-[1,2,4]triazol-3-yl}-1,3-dihydro-benzoimidazol-2-one | Boc-D-Pipecolic Acid, N-Amino-2-Oxo-2,3-dihydro-1H-benzoimidazole-5-carboxamidine and phenoxyacetic acid | 419.5 |
| 363 | 1-{(R)-2-[5-(2-Methyl-1H-benzoimidazol-5-yl)-2H-[1,2,4]triazol-3-yl]-piperidin-1-yl}-2-phenoxy-ethanone | Boc-D-Pipecolic Acid, N-Amino-2-Methyl-1H-benzoimidazole-5-carboxamidine and phenoxyacetic acid | 417.5 |
| 364 | 1-{(R)-2-[5-(2-Amino-pyridin-4-yl)-2H-[1,2,4]triazol-3-yl]-piperidin-1-yl}-2-phenoxy-ethanone | Boc-D-Pipecolic Acid, N-Amino-2-Amino-isonicotinamidine and phenoxyacetic acid | 379.5 |
| 365 | 5-(3-{5-[(R)-1-(2-Phenoxy-acetyl)-piperidin-2-yl]-1H-[1,2,4]triazol-3-yl}-phenyl)-3H-[1,3,4]oxadiazol-2-one | Boc-D-Pipecolic Acid, N-Amino-3-(5-Oxo-4,5-dihydro-[1,3,4]oxadiazol-2-yl)-benzamidine and phenoxyacetic acid | 446.7 |

| Example | Compound name | Starting materials | MH+ (found) |
|---|---|---|---|
| 366 | 1-{(R)-2-[5-(3-[1,3,4]Oxadiazol-2-yl-phenyl)-2H-[1,2,4]triazol-3-yl]-piperidin-1-yl}-2-phenoxy-ethanone | Boc-D-Pipecolic Acid, N-Amino-3-[1,3,4]Oxadiazol-2-yl-benzamidine and phenoxyacetic acid | 430.7 |
| 367 | 3-{5-[1-(2-Phenoxy-acetyl)-piperidin-2-yl]-1H-[1,2,4]triazol-3-yl}-phenylboronic acid | Boc-D-Pipecolic Acid, N-Amino-3-Carbamidoyl-phenylboronic acid and phenoxyacetic acid | 407.5 |

Example 368

6-{5-[(R)-1-(2-Phenoxy-acetyl)-piperidin-2-yl]-1H-[1,2,4]triazol-3-yl}-4H-benzo[1,4]oxazin-3-one

Step 1:

2-Hydrazinocarbonyl-piperidine-1-carboxylic acid tert-butyl ester 3 g of (R)-Piperidine-1,2-dicarboxylic acid 1-tert-butyl ester were dissolved in 30 ml DMF. 5 g HATU and 2.2 ml DIPEA were added and the reaction mixture cooled to 0° C. 4 eq. of Hydrazine-Monohydrate in 30 ml DMF were added and the reaction warmed to rt and stirred for 1 h. The crude product was extracted from ethylacetate/aq. NaHCO3.

MS(ISO): 244.3 (MH+)

Step 2:

6-(5-Piperidin-2-yl-1H-[1,2,4]triazol-3-yl)-4H-benzo[1,4]oxazin-3-one 1.5 mmol of 2-Hydrazinocarbonyl-piperidine-1-carboxylic acid tert-butyl ester were dissolved in 3 ml DMF. 1 eq of 3-Oxo-3,4-dihydro-2H-benzo[1,4]oxazine-6-carboxamidine and 90 ul acetic acid were added and the reaction mixture heated to 120° C. overnight. The solvent was evaporated and the crude extracted from ethylacetate/water. The resulting oil was taken up in 15 ml DCM and treated with 3 ml TFA. The reaction mixture was reduced to dryness.

Step 3:

6-{5-[(R)-1-(2-Phenoxy-acetyl)-piperidin-2-yl]-1H-[1,2,4]triazol-3-yl}-4H-benzo[1,4]oxazin-3-one Crude product from step 3 was taken up in DMF and cooled to 0° C. 4 eq. DIPEA and 1 eq of phenoxyacetyl chloride were added dropwise and the reaction mixture warmed to rt and stirred for additional 30 min. The product was isolated via preparative HPLC.

The following compounds were generated in analogy to example 368

| Example | Compound name | Starting materials | MH+ (found) |
|---|---|---|---|
| 369 | 1-[(R)-2-(5-Imidazo[1,2-a]pyridin-6-yl-2H-[1,2,4]triazol-3-yl)-piperidin-1-yl]-2-phenoxy-ethanone | Boc-D-Pipecolic Acid, Imidazo[1,2-a]pyridine-6-carboxamidine and phenoxyacetic acid | 443.7 |
| 370 | 1-{(R)-2-[5-(6-Amino-pyridin-3-yl)-2H-[1,2,4]triazol-3-yl]-piperidin-1-yl}-2-phenoxy-ethanone | Boc-D-Pipecolic Acid, 6-Amino-nicotinamidine and phenoxyacetic acid | 379.1 |
| 371 | 1-{(R)-2-[5-(1H-Benzoimidazol-5-yl)-2H-[1,2,4]triazol-3-yl]-piperidin-1-yl}-2-phenoxy-ethanone | Boc-D-Pipecolic Acid, 1H-Benzoimidazole-5-carboxamidine and phenoxyacetic acid | 403.2 |
| 372 | 2-Phenoxy-1-[(R)-2-(5-pyridin-3-yl-2H-[1,2,4]triazol-3-yl)-piperidin-1-yl]-ethanone | Boc-D-Pipecolic Acid, Nicotinamidine and phenoxyacetic acid | 364.2 |
| 373 | 1-{(R)-2-[5-(3,5-Dimethyl-isoxazol-4-yl)-2H-[1,2,4]triazol-3-yl]-piperidin-1-yl}-2-phenoxy-ethanone | Boc-D-Pipecolic Acid, 3,5-Dimethyl-isoxazole-4-carboxamidine and phenoxyacetic acid | 382.2 |
| 374 | 2-Phenoxy-1-[(R)-2-(5-thiophen-2-yl-2H-[1,2,4]triazol-3-yl)-piperidin-1-yl]-ethanone | Boc-D-Pipecolic Acid, Thiophene-2-carboxamidine and phenoxyacetic acid | 369.1 |

-continued

| Example | Compound name | Starting materials | MH+ (found) |
|---|---|---|---|
| 375 | 2-Phenoxy-1-[(R)-2-(5-pyrimidin-2-yl-2H-[1,2,4]triazol-3-yl)-piperidin-1-yl]-ethanone | Boc-D-Pipecolic Acid, Pyrimidine-2-carboxamidine and phenoxyacetic acid | 365.1 |
| 376 | 1-{(R)-2-[5-(4-Methyl-oxazol-5-yl)-2H-[1,2,4]triazol-3-yl]-piperidin-1-yl}-2-phenoxy-ethanone | Boc-D-Pipecolic Acid, 4-Methyl-oxazole-5-carboxamidine and phenoxyacetic acid | 368.1 |
| 377 | 2-Phenoxy-1-[(R)-2-(5-pyrazin-2-yl-2H-[1,2,4]triazol-3-yl)-piperidin-1-yl]-ethanone | Boc-D-Pipecolic Acid, Pyrazine-2-carboxamidine and phenoxyacetic acid | 365.1 |
| 378 | 1-{(R)-2-[5-(2-Fluoro-phenyl)-2H-[1,2,4]triazol-3-yl]-piperidin-1-yl}-2-phenoxy-ethanone | Boc-D-Pipecolic Acid, 2-Fluoro-benzamidine and phenoxyacetic acid | 381.1 |
| 379 | 1-{(R)-2-[5-(3,5-Difluoro-phenyl)-2H-[1,2,4]triazol-3-yl]-piperidin-1-yl}-2-phenoxy-ethanone | Boc-D-Pipecolic Acid, 3,5-Difluoro-benzamidine and phenoxyacetic acid | 399.1 |
| 380 | 1-{(R)-2-[5-(2-Methyl-pyridin-4-yl)-2H-[1,2,4]triazol-3-yl]-piperidin-1-yl}-2-phenoxy-ethanone | Boc-D-Pipecolic Acid, 2-Methyl-isonicotinamidine and phenoxyacetic acid | 378.1 |
| 381 | 1-{(R)-2-[5-(3-Fluoro-phenyl)-2H-[1,2,4]triazol-3-yl]-piperidin-1-yl}-2-phenoxy-ethanone | Boc-D-Pipecolic Acid, 3-Fluoro-benzamidine and phenoxyacetic acid | 381.1 |
| 382 | 1-{(R)-2-[5-(3,4-Difluoro-phenyl)-2H-[1,2,4]triazol-3-yl]-piperidin-1-yl}-2-phenoxy-ethanone | Boc-D-Pipecolic Acid, 3,4-Difluoro-benzamidine and phenoxyacetic acid | 399.1 |
| 383 | 6-{5-[(R)-1-(2-Phenoxy-acetyl)-piperidin-2-yl]-1H-[1,2,4]triazol-3-yl}-1,4-dihydro-benzo[d][1,3]oxazin-2-one | Boc-D-Pipecolic Acid, 2-Oxo-1,4-dihydro-2H-benzo[d][1,3]oxazine-6-carboxamidine and phenoxyacetic acid | 434.5 |
| 384 | 7-{5-[(R)-1-(2-Phenoxy-acetyl)-piperidin-2-yl]-1H-[1,2,4]triazol-3-yl}-3,4-dihydro-1H-quinazolin-2-one | Boc-D-Pipecolic Acid, 2-Oxo-1,2,3,4-tetrahydro-quinazoline-7-carboxamidine and phenoxyacetic acid | 433.5 |
| 385 | 1-(3-{5-[(R)-1-(2-Phenoxy-acetyl)-piperidin-2-yl]-1H-[1,2,4]triazol-3-yl}-phenyl)-imidazolidine-2,4-dione | Boc-D-Pipecolic Acid, 3-(2,4-Dioxo-imidazolidin-1-yl)-benzamidine and phenoxyacetic acid | 461.3 |

The following compounds were generated in analogy to example 1

| Example | Compound name | Starting materials | MH+ (found) |
|---|---|---|---|
| 386 | 1-{(R)-3-[3-(2-Amino-pyridin-4-yl)-[1,2,4]oxadiazol-5-yl]-morpholin-4-yl}-2-phenoxy-ethanone | (R)-Morpholine-3,4-dicarboxylic acid 4-tert-butyl ester, 2-Amino-N-hydroxy-isonicotinamidine and phenoxyacetyl chloride | 381.6 |
| 387 | 1-{(R)-3-[3-(1H-Benzoimidazol-5-yl)-[1,2,4]oxadiazol-5-yl]-morpholin-4-yl}-2-phenoxy-ethanone | (R)-Morpholine-3,4-dicarboxylic acid 4-tert-butyl ester, N-Hydroxy-1H-benzoimidazole-5-carboxamidine and phenoxyacetyl chloride | 406.2 |
| 388 | 1-{(R)-2-[3-(1H-Benzoimidazol-5-yl)-[1,2,4]oxadiazol-5-yl]-piperazin-1-yl}-2-phenoxy-ethanone | Piperazine-1,3-dicarboxylic acid 1-tert-butyl ester, N-Hydroxy-1H-benzoimidazole-5-carboxamidine and phenoxyacetic acid | 405.4 |

-continued

| Example | Compound name | Starting materials | MH+ (found) |
| --- | --- | --- | --- |
| 389 | 5-{5-[(R)-1-(2-Phenoxy-acetyl)-piperazin-2-yl]-[1,2,4]oxadiazol-3-yl}-1,3-dihydro-indol-2-one | Piperazine-1,3-dicarboxylic acid 1-tert-butyl ester, N-Hydroxy-2-oxo-2,3-dihydro-1H-indole-5-carboxamidine and phenoxyacetic acid | 420.4 |
| 390 | 1-{(R)-2-[3-(2-Amino-pyridin-4-yl)-[1,2,4]oxadiazol-5-yl]-piperazin-1-yl}-2-phenoxy-ethanone | Piperazine-1,3-dicarboxylic acid 1-tert-butyl ester, 2-Amino-N-hydroxy-isonicotinamidine and phenoxyacetic acid | 380.6 |

Example 391

(3-{5-[(R)-1-(2-Phenoxy-acetyl)-piperidin-2-yl]-[1,2,4]oxadiazol-3-yl}-phenoxy)-acetic acid The title compound was prepared in analogy to example 180 from (3-{5-[(R)-1-(2-Phenoxy-acetyl)-piperidin-2-yl]-[1,2,4]oxadiazol-3-yl}-phenoxy)-acetic acid methylester. MS: 436.5 (M–H+)

The following compounds were generated in analogy to example 194

| Example | Compound name | Starting materials | MH+ (found) |
| --- | --- | --- | --- |
| 392 | 2-Phenoxy-1-((R)-2-{5-[3-(piperidine-1-carbonyl)-phenyl]-2H-[1,2,4]triazol-3-yl}-piperidin-1-yl)-ethanone | 3-{5-[1-(2-Phenoxy-acetyl)-piperidin-2-yl]-1H-[1,2,4]triazol-3-yl}-benzoic acid and piperidine | 474.6 |
| 393 | 1-((R)-2-{5-[3-(Morpholine-4-carbonyl)-phenyl]-2H-[1,2,4]triazol-3-yl}-piperidin-1-yl)-2-phenoxy-ethanone | 3-{5-[1-(2-Phenoxy-acetyl)-piperidin-2-yl]-1H-[1,2,4]triazol-3-yl}-benzoic acid and morpholine | 476.6 |
| 394 | 1-((R-2-{5-[3-(4-Methyl-piperazine-1-carbonyl)-phenyl]-2H-[1,2,4]triazol-3-yl}-piperidin-1-yl)-2-phenoxy-ethanone | 3-{5-[1-(2-Phenoxy-acetyl)-piperidin-2-yl]-1H-[1,2,4]triazol-3-yl}-benzoic acid and N-methylpiperazine | 489.7 |
| 395 | 4-(3-{5-[(R)-1-(2-Phenoxy-acetyl)-piperidin-2-yl]-1H-[1,2,4]triazol-3-yl}-benzoyl)-piperazin-2-one | 3-{5-[1-(2-Phenoxy-acetyl)-piperidin-2-yl]-1H-[1,2,4]triazol-3-yl}-benzoic acid and Piperazin-2-one | 489.6 |
| 396 | N-(2-Methoxy-ethyl)-N-methyl-3-{5-[(R)-1-(2-phenoxy-acetyl)-piperidin-2-yl]-1H-[1,2,4]triazol-3-yl}-benzamide | 3-{5-[1-(2-Phenoxy-acetyl)-piperidin-2-yl]-1H-[1,2,4]triazol-3-yl}-benzoic acid and (2-Methoxy-ethyl)-methyl-amine | 478.6 |
| 397 | 1-((R)-2-{5-[3-(4-Acetyl-piperazine-1-carbonyl)-phenyl]-2H-[1,2,4]triazol-3-yl}-piperidin-1-yl)-2-phenoxy-ethanone | 3-{5-[1-(2-Phenoxy-acetyl)-piperidin-2-yl]-1H-[1,2,4]triazol-3-yl}-benzoic acid and 1-Piperazin-1-yl-ethanone | 517.7 |
| 398 | 1-(3-{5-[(R)-1-(2-Phenoxy-acetyl)-piperidin-2-yl]-1H-[1,2,4]triazol-3-yl}-benzoyl)-piperidine-4-carboxylic acid | 3-{5-[1-(2-Phenoxy-acetyl)-piperidin-2-yl]-1H [1,2,4]triazol-3-yl}-benzoic acid and Piperidine-4-carboxylic acid | 518.6 |
| 399 | 1-(3-{5-[(R)-1-(2-Phenoxy-acetyl)-piperidin-2-yl]-1H-[1,2,4]triazol-3-yl}-benzoyl)-piperidine-4-carboxylic acid amide | 3-{5-[1-(2-Phenoxy-acetyl)-piperidin-2-yl]-1H-[1,2,4]triazol-3-yl}-benzoic acid and Piperidine-4-carboxylic acid amide | 517.7 |
| 400 | 2-Phenoxy-1-((R)-2-{5-[3-(thiazolidine-3-carbonyl)-phenyl]-2H-[1,2,4]triazol-3-yl}-piperidin-1-yl)-ethanone | 3-{5-[1-(2-Phenoxy-acetyl)-piperidin-2-yl]-1H-[1,2,4]triazol-3-yl}-benzoic acid and Thiazolidine | 478.6 |

-continued

| Example | Compound name | Starting materials | MH+ (found) |
|---|---|---|---|
| 401 | N-(2-Dimethylamino-ethyl)-N-methyl-3-{5-[(R)-1-(2-phenoxy-acetyl)-piperidin-2-yl]-1H-[1,2,4]triazol-3-yl}-benzamide | 3-{5-[1-(2-Phenoxy-acetyl)-piperidin-2-yl]-1H-[1,2,4]triazol-3-yl}-benzoic acid and N,N,N'-Trimethyl-ethane-1,2-diamine | 491.7 |
| 402 | 2-Phenoxy-1-((R)-2-{5-[3-(thiomorpholine-4-carbonyl)-phenyl]-2H-[1,2,4]triazol-3-yl}-piperidin-1-yl)-ethanone | 3-{5-[1-(2-Phenoxy-acetyl)-piperidin-2-yl]-1H-[1,2,4]triazol-3-yl}-benzoic acid and thiomorpholine | 492.8 |
| 403 | 4-(3-{5-[(R)-1-(2-Phenoxy-acetyl)-piperidin-2-yl]-1H-[1,2,4]triazol-3-yl}-benzoyl)-piperazine-1-carboxylic acid ethyl ester | 3-{5-[1-(2-Phenoxy-acetyl)-piperidin-2-yl]-1H-[1,2,4]triazol-3-yl}-benzoic acid and Piperazine-1-carboxylic acid ethyl ester | 547.7 |
| 404 | N-(2-Hydroxy-ethyl)-3-{5-[(R)-1-(2-phenoxy-acetyl)-piperidin-2-yl]-1H-[1,2,4]triazol-3-yl}-benzamide | 3-{5-[1-(2-Phenoxy-acetyl)-piperidin-2-yl]-1H-[1,2,4]triazol-3-yl}-benzoic acid and aminoethanol | 450.6 |
| 405 | N-Methyl-3-{5-[(R)-1-(2-phenoxy-acetyl)-piperidin-2-yl]-1H-[1,2,4]triazol-3-yl}-N-(2-pyridin-2-yl-ethyl)-benzamide | 3-{5-[1-(2-Phenoxy-acetyl)-piperidin-2-yl]-1H-[1,2,4]triazol-3-yl}-benzoic acid and Methyl-(2-pyridin-2-yl-ethyl)-amine | 525.7 |
| 406 | N-(2-Cyano-ethyl)-N-cyclopropyl-3-{5-[(R)-1-(2-phenoxy-acetyl)-piperidin-2-yl]-1H-[1,2,4]triazol-3-yl}-benzamide | 3-{5-[1-(2-Phenoxy-acetyl)-piperidin-2-yl]-1H-[1,2,4]triazol-3-yl}-benzoic acid and 3-Cyclopropylamino-propionitrile | 499.6 |
| 407 | 1-(3-{5-[(R)-1-(2-Phenoxy-acetyl)-piperidin-2-yl]-1H-[1,2,4]triazol-3-yl}-benzoyl)-4-phenyl-piperidine-4-carbonitrile | 3-{5-[1-(2-Phenoxy-acetyl)-piperidin-2-yl]-1H-[1,2,4]triazol-3-yl}-benzoic acid and 4-Phenyl-piperidine-4-carbonitrile | 575.7 |
| 408 | 1-((R)-2-{5-[3-(4-Hydroxy-piperidine-1-carbonyl)-phenyl]-2H-[1,2,4]triazol-3-yl}-piperidin-1-yl)-2-phenoxy-ethanone | 3-{5-[1-(2-Phenoxy-acetyl)-piperidin-2-yl]-1H-[1,2,4]triazol-3-yl}-benzoic acid and Piperidin-4-ol | 490.6 |
| 409 | 8-(3-{5-[(R)-1-(2-Phenoxy-acetyl)-piperidin-2-yl]-1H-[1,2,4]triazol-3-yl}-benzoyl)-1,3,8-triaza-spiro[4.5]decane-2,4-dione | 3-{5-[1-(2-Phenoxy-acetyl)-piperidin-2-yl]-1H-[1,2,4]triazol-3-yl}-benzoic acid and 1,3,8-Triaza-spiro[4.5]decane-2,4-dione | 558.6 |
| 410 | 1-(2-{5-[3-(Spiro(1-Phtalan)-piperidine-4-carbonyl)-phenyl]-2H-[1,2,4]triazol-3-yl}-piperidin-1-yl)-2-phenoxy-ethanone | 3-{5-[1-(2-Phenoxy-acetyl)-piperidin-2-yl]-1H-[1,2,4]triazol-3-yl}-benzoic acid and 4-Spiro(1-Phtalan)-piperidine | 578.7 |
| 411 | 2-Phenoxy-1-((R)-2-{5-[3-(3-pyridin-4-yl-pyrrolidine-1-carbonyl)-phenyl]-2H-[1,2,4]triazol-3-yl}-piperidin-1-yl)-ethanone | 3-{5-[1-(2-Phenoxy-acetyl)-piperidin-2-yl]-1H-[1,2,4]triazol-3-yl}-benzoic acid and 4-Pyrrolidin-3-yl-pyridine | 537.7 |
| 412 | 1-((R)-2-{5-[3-(3-Methanesulfonyl-pyrrolidine-1-carbonyl)-phenyl]-2H-[1,2,4]triazol-3-yl}-piperidin-1-yl)-2-phenoxy-ethanone | 3-{5-[1-(2-Phenoxy-acetyl)-piperidin-2-yl]-1H-[1,2,4]triazol-3-yl}-benzoic acid and 3-Methanesulfonyl-pyrrolidine | 538.6 |
| 413 | 1-((R)-2-{5-[3-((S)-3-Ethoxy-pyrrolidine-1-carbonyl)-phenyl]-2H-[1,2,4]triazol-3-yl}-piperidin-1-yl)-2-phenoxy-ethanone | 3-{5-[1-(2-Phenoxy-acetyl)-piperidin-2-yl]-1H-[1,2,4]triazol-3-yl}-benzoic acid and (S)-3-Ethoxy-pyrrolidine | 504.6 |
| 414 | 1-((R)-2-{5-[3-((S)-3-Hydroxy-pyrrolidine-1-carbonyl)-phenyl]-2H-[1,2,4]triazol-3-yl}-piperidin-1-yl)-2-phenoxy-ethanone | 3-{5-[1-(2-Phenoxy-acetyl)-piperidin-2-yl]-1H-[1,2,4]triazol-3-yl}-benzoic acid and (S)-3-Hydroxy-pyrrolidine | 476.6 |

The following compounds were generated according to example 231

| Example | Compound name | Starting materials | MH+ (found) |
|---|---|---|---|
| 415 | 5-{5-[(R)-1-(2-Phenoxy-acetyl)-piperidin-2-yl]-1H-[1,2,4]triazol-3-yl}-nicotinamide | 5-{5-[1-(2-Phenoxy-acetyl)-piperidin-2-yl]-1H-[1,2,4]triazol-3-yl}-nicotinic acid and Rink resin | 407.5 |
| 416 | 2-(3-{5-[1-(2-Phenoxy-acetyl)-piperidin-2-yl]-[1,2,4]oxadiazol-3-yl}-phenoxy)-acetamide | (3-{5-[1-(2-Phenoxy-acetyl)-piperidin-2-yl]-[1,2,4]oxadiazol-3-yl}-phenoxy)-acetic acid and Rink resin | 437.5 |

The following compounds were generated according to example 242

| Example | Compound name | Starting materials | MH+ (found) |
|---|---|---|---|
| 417 | N-(3-Fluoro-5-{5-[(R)-1-(2-phenoxy-acetyl)-piperidin-2-yl]-[1,2,4]oxadiazol-3-yl}-phenyl)-acetamide | 1-{2-[3-(3-Amino-5-fluoro-phenyl)-[1,2,4]oxadiazol-5-yl]-piperidin-1-yl}-2-phenoxy-ethanone and acetyl chloride | 439.1 |
| 418 | N-(2-Fluoro-5-{5-[(R)-1-(2-phenoxy-acetyl)-piperidin-2-yl]-[1,2,4]oxadiazol-3-yl}-phenyl)-acetamide | Boc-D-Pipecolic Acid, N-[2-Fluoro-5-(N-hydroxycarbamidoyl)-phenyl]-acetamide and phenoxyacetyl chloride | 439.1 |
| 419 | N-(3-{5-[(R)-1-(2-Phenoxy-acetyl)-piperidin-2-yl]-1H-[1,2,4]triazol-3-yl}-phenyl)-propionamide | 1-{2-[5-(3-Amino-phenyl)-2H-[1,2,4]triazol-3-yl]-piperidin-1-yl}-2-phenoxy-ethanone and propionic acid chloride | 434.5 |
| 420 | N-(3-{5-[(R)-1-(2-Phenoxy-acetyl)-piperidin-2-yl]-1H-[1,2,4]triazol-3-yl}-phenyl)-isobutyramide | 1-{2-[5-(3-Amino-phenyl)-2H-[1,2,4]triazol-3-yl]-piperidin-1-yl}-2-phenoxy-ethanone and isobutyric acid chloride | 448.6 |

The following compounds were generated according to example 1

| Example | Compound name | Starting materials | MH+ (found) |
|---|---|---|---|
| 421 | N-(4-Fluoro-3-{5-[(R)-1-(2-phenoxy-acetyl)-piperidin-2-yl]-1H-[1,2,4]triazol-3-yl}-phenyl)-acetamide | 2-Hydrazinocarbonyl-piperidine-1-carboxylic acid tert-butyl ester, N-(3-Carbamidoyl-4-fluoro-phenyl)-acetamide and phenoxyacetic acid | 438.5 |
| 422 | N-(3-Fluoro-5-{5-[(R)-1-(2-phenoxy-acetyl)-piperidin-2-yl]-1H-[1,2,4]triazol-3-yl}-phenyl)-acetamide | 2-Hydrazinocarbonyl-piperidine-1-carboxylic acid tert-butyl ester, N-(3-Carbamimidoyl-5-fluoro-phenyl)-acetamide and phenoxyacetic acid | 348.5 |

-continued

| Example | Compound name | Starting materials | MH+ (found) |
|---------|---------------|--------------------|-------------|
| 423 | N-(2-Fluoro-5-{5-[(R)-1-(2-phenoxy-acetyl)-piperidin-2-yl]-1H-[1,2,4]triazol-3-yl}-phenyl)-acetamide | 2-Hydrazinocarbonyl-piperidine-1-carboxylic acid tert-butyl ester, N-(3-Carbamimidoyl-6-fluoro-phenyl)-acetamide and phenoxyacetic acid | 348.5 |

Example 424

N-(4-{5-[(R)-1-(2-Phenoxy-acetyl)-piperidin-2-yl]-1H-[1,2,4]triazol-3-yl}-pyridin-2-yl)-acetamide The title compound was generated in analogy to example 242 from 1-{2-[5-(2-Amino-pyridin-4-yl)-2H-[1,2,4]triazol-3-yl]-piperidin-1-yl}-2-phenoxy-ethanone and acetyl chloride.

MS 421.5 (MH+)

Example 425

1-(3-{5-[(R)-1-(2-Phenoxy-acetyl)-piperidin-2-yl]-1H-[1,2,4]triazol-3-yl}-phenyl)-azetidin-2-one 75 mg of 1-{2-[5-(3-Amino-phenyl)-2H-[1,2,4]triazol-3-yl]-piperidin-1-yl}-2-phenoxy-ethanone were dissolved in MDF and 40 ul DIPEA added. 34 mg of 3-Bromo-propionyl chloride were added at 0° C. and the reaction warmed up to rt and stirred for another 30 min. The reaction mixture was heated to 120° C. using microwave heating and the product was isolated via preparative HPLC.

MS(ISO): 432.5 (MH+)

Example 426

1-(3-{5-[1-(2-Phenoxy-acetyl)-piperidin-2-yl]-1H-[1,2,4]triazol-3-yl}-phenyl)-pyrrolidine-2,5-dione 0.1 mmol of 1-{2-[5-(3-Amino-phenyl)-2H-[1,2,4]triazol-3-yl]-piperidin-1-yl}-2-phenoxy-ethanone were dissolved in 1 ml DMF and 1 eq of succinic anhydride added. The reaction was stirred overnight and the intermediate (N-(3-{5-[1-(2-Phenoxy-acetyl)-piperidin-2-yl]-[1,2,4]oxadiazol-3-yl}-phenyl)-succinamic acid) isolated via preparative HPLC. The isolated material was redissolved in DMF and 1 eq of HATU was added. The reaction mixture was heated to 120° C. using microwave heating. The product was isolated via preparative HPLC.

MS(ISO): 460.5 (MH+)

Example 427

2-Phenoxy-1-[(R)-2-(5-pyridazin-4-yl-[1,2,4]oxadiazol-3-yl)-piperidin-1-yl]-ethanone Step 1:

(R)-2-(N-Hydroxycarbamidoyl)-piperidine-1-carboxylic acid tert-butyl ester 3 g of (R)-N-Boc-2-Cyanopiperidine (14 mmol) were treated with 70 mmol of hydrazine hydrochloride and 35 mmol sodium carbonate in a mixture of ethanol/water (7:3) and heated to 50° C. overnight. The solvent was evaporated and the crude extracted from ethylacetate/water. The organic layer was dried over sodium sulfate. After evaporation a white solid was obtained in quantitative yield.

MS(ISO): 244.5 (MH+)

Step 2:

(R)-2-(5-Pyridazin-4-yl-[1,2,4]oxadiazol-3-yl)-piperidine-1-carboxylic acid tert-butyl ester 0.2 mmol of pyridazine-4-carboxylic acid, HATU and Diisopropylethylamine were dissolved in 1 ml DMF and stirred for 15 min. 0.2 mmol of (R)-2-(N-Hydroxycarbamidoyl)-piperidine-1-carboxylic acid tert-butyl ester were added. The reaction was heated to 80° C. and stirred overnight. The DMF was evaporated and the crude extracted from ethylacetate/water. The crude product was not further characterized.

Step 3:

(R) 4-(3-Piperidin-2-yl-[1,2,4]oxadiazol-5-yl)-pyridazine trifluoroacetate

Crude material from step 3 was treated with neat TFA at room temperature for 1 h. The solvent was evaporated. The crude product was not further characterized.

Step 4:

2-Phenoxy-1-[(R)-2-(5-pyridazin-4-yl-[1,2,4]oxadiazol-3-yl)-piperidin-1-yl]-ethanone Crude material from step 3 was dissolved in 1 ml DMF and 0.1 mmol DIPEA. Either 0.1 mmol phenoxyacetyl chloride were added and the reaction stirred at room temperature for 30 min, or the corresponding phenoxyacetic acid derivatives were pre-activated with HATU/DIPEA in DMF for 10 min and added to the crude material from step 3. The product was isolated via preparative high performance liquid chromatography (HPLC).

MS(ISO): 366.5 (MH+)

The following compounds were generated in analogy to example 427

| Example | Compound name | Starting materials | MH+ (found) |
|---|---|---|---|
| 428 | 4-{3-[(R)-1-(2-Phenoxy-acetyl)-piperidin-2-yl]-[1,2,4]oxadiazol-yl}-benzonitrile | (R)-2-(N Hydroxycarbamidoyl)-piperidine-1-carboxylic acid tert-butyl ester, 4-Cyanobenzoic acid and Phenoxyacetyl chloride | 389.3 |
| 429 | 1-{(R)-2-[5-(3-Amino-pyrazin-2-yl)-[1,2,4]oxadiazol-3-yl]-piperidin-1-yl}-2-phenoxy-ethanone | (R)-2-(N Hydroxycarbamidoyl)-piperidine-1-carboxylic acid tert-butyl ester, 3-Amino-pyrazine-2-carboxylic acid and phenoxyacetyl chloride | 381.3 |
| 430 | 3-{3-[(R)-1-(2-Phenoxy-acetyl)-piperidin-2-yl]-[1,2,4]oxadiazol-5-yl}-benzonitrile | (R)-2-(N Hydroxycarbamidoyl)-piperidine-1-carboxylic acid tert-butyl ester, 3-Cyanobenzoic acid and phenoxyacetyl chloride | 389.3 |
| 431 | 1-{(R)-2-[5-(2-Hydroxy-pyridin-3-yl)-[1,2,4]oxadiazol-3-yl]-piperidin-1-yl}-2-phenoxy-ethanone | (R)-2-(N Hydroxycarbamidoyl)-piperidine-1-carboxylic acid tert-butyl ester, 2-Hydroxy-nicotinic and phenoxyacetyl chloride | 379.4 (M − H+) |
| 432 | 1-{(R)-2-[5-(5-Amino-pyridin-3-yl)-[1,2,4]oxadiazol-3-yl]-piperidin-1-yl}-2-phenoxy-ethanone | (R)-2-(N Hydroxycarbamidoyl)-piperidine-1-carboxylic acid tert-butyl ester, 5-Amino-nicotinic acid and phenoxyacetyl chloride | 380.3 |
| 433 | 1-{(R)-2-[5-(2-Hydroxy-pyridin-4-yl)-[1,2,4]oxadiazol-3-yl]-piperidin-1-yl}-2-phenoxy-ethanone | (R)-2-(N Hydroxycarbamidoyl)-piperidine-1-carboxylic acid tert-butyl ester, 2-Hydroxy-isonicotinic acid and phenoxyacetyl chloride | 381.2 |
| 434 | 1-{(R)-2-[5-(2-Hydroxy-6-methyl-pyridin-4-yl)-[1,2,4]oxadiazol-3-yl]-piperidin-1-yl}-2-phenoxy-ethanone | (R)-2-(N Hydroxycarbamidoyl)-piperidine-1-carboxylic acid tert-butyl ester, 2-Hydroxy-6-methyl-isonicotinic acid and phenoxyacetyl chloride | 395.2 |
| 435 | 1-{(R)-2-[5-(4-Hydroxy-pyridin-2-yl)-[1,2,4]oxadiazol-3-yl]-piperidin-1-yl}-2-phenoxy-ethanone | (R)-2-(N Hydroxycarbamidoyl)-piperidine-1-carboxylic acid tert-butyl ester, 4-Hydroxy-pyridine-2-carboxylic acid and phenoxyacetyl chloride | 381.2 |
| 436 | 1-{(R)-2-[5-(2-Amino-5-chloro-pyrimidin-4-yl)-[1,2,4]oxadiazol-3-yl]-piperidin-1-yl}-2-phenoxy-ethanone | (R)-2-(N Hydroxycarbamidoyl)-piperidine-1-carboxylic acid tert-butyl ester, 2-Amino-5-chloro-pyrimidine-4-carboxylic acid and phenoxyacetyl chloride | 415.2 |
| 437 | 2-Phenoxy-1-[(R)-2-(5-pyrazin-2-yl-[1,2,4]oxadiazol-3-yl)-piperidin-1-yl]-ethanone | (R)-2-(N Hydroxycarbamidoyl)-piperidine-1-carboxylic acid tert-butyl ester, Pyrazine-2-carboxylic acid and phenoxyacetyl chloride | 366.2 |
| 438 | 2-Phenoxy-1-{(R)-2-[5-(4-[1,2,4]triazol-1-yl-phenyl)-[1,2,4]oxadiazol-3-yl]-piperidin-1-yl}-ethanone | (R)-2-(N Hydroxycarbamidoyl)-piperidine-1-carboxylic acid tert-butyl ester, 4-[1,2,4]Triazol-1-yl-benzoic acid and phenoxyacetyl chloride | 431.2 |
| 439 | 2-Phenoxy-1-{(R)-2-[5-(4-tetrazol-1-yl-phenyl)-[1,2,4]oxadiazol-3-yl]-piperidin-1-yl}-ethanone | (R)-2-(N Hydroxycarbamidoyl)-piperidine-1-carboxylic acid tert-butyl ester, 4-Tetrazol-1-yl-benzoic acid and phenoxyacetyl chloride | 432.2 |
| 440 | 1-{(R)-2-[5-(1H-Benzoimidazol-4-yl)-[1,2,4]oxadiazol-3-yl]-piperidin-1-yl}-2-phenoxy-ethanone | (R)-2-(N Hydroxycarbamidoyl)-piperidine-1-carboxylic acid tert-butyl ester, 1H-Benzoimidazole-4-carboxylic acid and phenoxyacetyl chloride | 404.2 |

-continued

| Example | Compound name | Starting materials | MH+ (found) |
|---|---|---|---|
| 441 | 1-{(R)-2-[5-(4-Acetyl-phenyl)-[1,2,4]oxadiazol-3-yl]-piperidin-1-yl}-2-phenoxy-ethanone | (R)-2-(N Hydroxycarbamidoyl)-piperidine-1-carboxylic acid tert-butyl ester, 4-Acetyl-benzoic acid and phenoxyacetyl chloride | 406.2 |
| 442 | 1-{(R)-2-[5-(6-Hydroxy-pyridin-2-yl)-[1,2,4]oxadiazol-3-yl]-piperidin-1-yl}-2-phenoxy-ethanone | (R)-2-(N Hydroxycarbamidoyl)-piperidine-1-carboxylic acid tert-butyl ester, 6-Hydroxy-pyridine-2-carboxylic acid and phenoxyacetyl chloride | 381.2 |
| 443 | 1-{(R)-2-[5-(5-Methyl-pyrazin-2-yl)-[1,2,4]oxadiazol-3-yl]-piperidin-1-yl}-2-phenoxy-ethanone | (R)-2-(N Hydroxycarbamidoyl)-piperidine-1-carboxylic acid tert-butyl ester, 5-Methyl-pyrazine-2-carboxylic acid and phenoxyacetyl chloride | 380.2 |
| 444 | 2-Phenoxy-1-[(R)-2-(5-quinoxalin-2-yl-[1,2,4]oxadiazol-3-yl)-piperidin-1-yl]-ethanone | (R)-2-(N Hydroxycarbamidoyl)-piperidine-1-carboxylic acid tert-butyl ester, Quinoxaline-2-carboxylic acid and phenoxyacetyl chloride | 416.2 |
| 445 | 1-{(R)-2-[5-(3-Methanesulfonyl-phenyl)-[1,2,4]oxadiazol-3-yl]-piperidin-1-yl}-2-phenoxy-ethanone | (R)-2-(N Hydroxycarbamidoyl)-piperidine-1-carboxylic acid tert-butyl ester, 3-Methanesulfonyl-benzoic acid and phenoxyacetyl chloride | 442.2 |
| 446 | 1-{(R)-2-[5-(6-Chloro-pyridin-3-yl)-[1,2,4]oxadiazol-3-yl]-piperidin-1-yl}-2-phenoxy-ethanone | (R)-2-(N Hydroxycarbamidoyl)-piperidine-1-carboxylic acid tert-butyl ester, 6-Chloro-nicotinic acid and phenoxyacetyl chloride | 399.1 |
| 447 | 1-[(R)-2-(5-Benzothiazol-6-yl-[1,2,4]oxadiazol-3-yl)-piperidin-1-yl]-2-phenoxy-ethanone | (R)-2-(N Hydroxycarbamidoyl)-piperidine-1-carboxylic acid tert-butyl ester, Benzothiazole-6-carboxylic acid and phenoxyacetyl chloride | 421.2 |
| 448 | 2-Phenoxy-1-{(R)-2-[5-(2,4,5-trifluoro-phenyl)-[1,2,4]oxadiazol-3-yl]-piperidin-1-yl}-ethanone | (R)-2-(N Hydroxycarbamidoyl)-piperidine-1-carboxylic acid tert-butyl ester, 2,4,5-Trifluoro-benzoic acid and phenoxyacetyl chloride | 418.2 |
| 449 | 2-Phenoxy-1-{(R)-2-[5-(6-trifluoromethyl-pyridin-3-yl)-[1,2,4]oxadiazol-3-yl]-piperidin-1-yl}-ethanone | (R)-2-(N Hydroxycarbamidoyl)-piperidine-1-carboxylic acid tert-butyl ester, 6-Trifluoromethyl-nicotinic acid and phenoxyacetyl chloride | 433.2 |
| 450 | 1-[(R)-2-(5-Benzo[1,2,3]thiadiazol-5-yl-[1,2,4]oxadiazol-3-yl)-piperidin-1-yl]-2-phenoxy-ethanone | (R)-2-(N Hydroxycarbamidoyl)-piperidine-1-carboxylic acid tert-butyl ester, Benzo[1,2,3]thiadiazole-5-carboxylic acid and phenoxyacetyl chloride | 422.2 |
| 451 | 1-[(R)-2-(5-[1,8]Naphthyridin-2-yl-[1,2,4]oxadiazol-3-yl)-piperidin-1-yl]-2-phenoxy-ethanone | (R)-2-(N Hydroxycarbamidoyl)-piperidine-1-carboxylic acid tert-butyl ester, [1,8]Naphthyridine-2-carboxylic acid and phenoxyacetyl chloride | 416.2 |
| 452 | 1-[(R)-2-(5-[1,6]Naphthyridin-2-yl-[1,2,4]oxadiazol-3-yl)-piperidin-1-yl]-2-phenoxy-ethanone | (R)-2-N Hydroxycarbamidoyl)-piperidine-1-carboxylic acid tert-butyl ester, [1,6]Naphthyridine-2-carboxylic acid and phenoxyacetyl chloride | 416.2 |
| 453 | 1-[(R)-2-(5-Cinnolin-4-yl-[1,2,4]oxadiazol-3-yl)-piperidin-1-yl]-2-phenoxy-ethanone | (R)-2-(N Hydroxycarbamidoyl)-piperidine-1-carboxylic acid tert-butyl ester, Cinnoline-4-carboxylic acid and phenoxyacetyl chloride | 416.2 |
| 454 | 1-{(R)-2-[5-(1H-Benzotriazol-5-yl)-[1,2,4]oxadiazol-3-yl]-piperidin-1-yl}-2-phenoxy-ethanone | (R)-2-(N Hydroxycarbamidoyl)-piperidine-1-carboxylic acid tert-butyl ester, 1H-Benzotriazole-5-carboxylic acid and phenoxyacetyl chloride | 405.2 |

-continued

| Example | Compound name | Starting materials | MH+ (found) |
|---|---|---|---|
| 455 | 1-{(R)-2-[5-(1H-Benzoimidazol-5-yl)-[1,2,4]oxadiazol-3-yl]-piperidin-1-yl}-2-phenoxy-ethanone | (R)-2-(N Hydroxycarbamidoyl)-piperidine-1-carboxylic acid tert-butyl ester, 1H-Benzoimidazole-5-carboxylic acid and phenoxyacetyl chloride | 404.2 |
| 456 | 1-{(R)-2-[5-(3,6-Dichloro-pyridazin-4-yl)-[1,2,4]oxadiazol-3-yl]-piperidin-1-yl}-2-phenoxy-ethanone | (R)-2-(N Hydroxycarbamidoyl)-piperidine-1-carboxylic acid tert-butyl ester, 3,6-Dichloro-pyridazine-4-carboxylic acid and phenoxyacetyl chloride | 435.2 |
| 457 | 6-{3-[(R)-1-(2-Phenoxy-acetyl)-piperidin-2-yl]-[1,2,4]oxadiazol-5-yl}-4H-benzo[1,4]oxazin-3-one | (R)-2-(N Hydroxycarbamidoyl)-piperidine-1-carboxylic acid tert-butyl ester, 3-Oxo-3,4-dihydro-2H-benzo[1,4]oxazine-6-carboxylic acid and phenoxyacetyl chloride | 435.2 |
| 458 | 1-{(R)-2-[5-(3H-Imidazo[4,5-b]pyridin-6-yl)-[1,2,4]oxadiazol-3-yl]-piperidin-1-yl}-2-phenoxy-ethanone | (R)-2-(N Hydroxycarbamidoyl)-piperidine-1-carboxylic acid tert-butyl ester, 3H-Imidazo[4,5-b]pyridine-6-carboxylic acid and phenoxyacetyl chloride | 405.1 |
| 459 | N-(4-{3-[(R)-1-(2-Phenoxy-acetyl)-piperidin-2-yl]-[1,2,4]oxadiazol-5-yl}-pyridin-2-yl)-acetamide | (R)-2-(N Hydroxycarbamidoyl)-piperidine-1-carboxylic acid tert-butyl ester 2-Acetylamino-isonicotinic acid and phenoxyacetic acid | 422.2 |
| 460 | 1-{(R)-2-[5-(6-Chloro-3-hydroxy-pyridazin-4-yl)-[1,2,4]oxadiazol-3-yl]-piperidin-1-yl}-2-phenoxy-ethanone | (R)-2-(N Hydroxycarbamidoyl)-piperidine-1-carboxylic acid tert-butyl ester, 6-Chloro-3-hydroxy-pyridazine-4-carboxylic acid and phenoxyacetyl chloride | 416.1 |
| 461 | 6-{3-[(R)-1-(2-Phenoxy-acetyl)-piperidin-2-yl]-[1,2,4]oxadiazol-5-yl}-1,4-dihydro-quinoxaline-2,3-dione | (R)-2-(N Hydroxycarbamidoyl)-piperidine-1-carboxylic acid tert-butyl ester, 2,3-Dioxo-1,2,3,4-tetrahydro-quinoxaline-6-carboxylic acid and phenoxyacetyl chloride | 448.1 |
| 462 | 1-{(R)-2-[5-(6-Hydroxy-pyridin-3-yl)-[1,2,4]oxadiazol-3-yl]-piperidin-1-yl}-2-phenoxy-ethanone | (R)-2-(N Hydroxycarbamidoyl)-piperidine-1-carboxylic acid tert-butyl ester, 6-Hydroxy-nicotinic acid and phenoxyacetyl chloride | 381.1 |
| 463 | 7-{3-[(R)-1-(2-Phenoxy-acetyl)-piperidin-2-yl]-[1,2,4]oxadiazol-5-yl}-3,4-dihydro-1H-quinoxalin-2-one | (R)-2-(N Hydroxycarbamidoyl)-piperidine-1-carboxylic acid tert-butyl ester, 3-Oxo-1,2,3,4-tetrahydro-quinoxaline-6-carboxylic acid and phenoxyacetic acid | 434.2 |
| 464 | 1-{(R)-2-[5-(6-Amino-pyridin-2-yl)-[1,2,4]oxadiazol-3-yl]-piperidin-1-yl}-2-phenoxy-ethanone | (R)-2-(N Hydroxycarbamidoyl)-piperidine-1-carboxylic acid tert-butyl ester, 6-Amino-pyridine-2-carboxylic acid and phenoxyacetic acid | 380.2 |
| 465 | 6-{3-[(R)-1-(2-Phenoxy-acetyl)-piperidin-2-yl]-[1,2,4]oxadiazol-5-yl}-nicotinonitrile | (R)-2-(N Hydroxycarbamidoyl)-piperidine-1-carboxylic acid tert-butyl ester, 5-Cyano-pyridine-2-carboxylic acid and phenoxyacetic acid | 390.1 |
| 466 | 5-{3-[(R)-1-(2-Phenoxy-acetyl)-piperidin-2-yl]-[1,2,4]oxadiazol-5-yl}-pyridine-2-carbonitrile | (R)-2-(N Hydroxycarbamidoyl)-piperidine-1-carboxylic acid tert-butyl ester, 6-Cyano-nicotinic acid and phenoxyacetic acid | 390.1 |
| 467 | 4-{3-[(R)-1-(2-Phenoxy-acetyl)-piperidin-2-yl]-[1,2,4]oxadiazol-5-yl}-1,2-dihydro-indazol-3-one | (R)-2-(N Hydroxycarbamidoyl)-piperidine-1-carboxylic acid tert-butyl ester, 3-Oxo-2,3-dihydro-1H-indazole-4-carboxylic acid and phenoxyacetic acid | 420.2 |

-continued

| Example | Compound name | Starting materials | MH+ (found) |
|---|---|---|---|
| 468 | 1-{(R)-2-[5-(2-Amino-pyridin-4-yl)-[1,2,4]oxadiazol-3-yl]-piperidin-1-yl}-2-phenoxy-ethanone | (R)-2-(N Hydroxycarbamidoyl)-piperidine-1-carboxylic acid tert-butyl ester, 2-Amino-isonicotinic acid and phenoxyacetic acid | 380.1 |
| 469 | 1-{(R)-2-[5-(6-Hydroxy-pyrimidin-4-yl)-[1,2,4]oxadiazol-3-yl]-piperidin-1-yl}-2-phenoxy-ethanone | (R)-2-(N Hydroxycarbamidoyl)-piperidine-1-carboxylic acid tert-butyl ester, 6-Hydroxy-pyrimidine-4-carboxylic acid and phenoxyacetic acid | 382.1 |
| 470 | 4-(3-{3-[(R)-1-(2-Phenoxy-acetyl)-piperidin-2-yl]-[1,2,4]oxadiazol-5-yl}-phenyl)-2,4-dihydro-[1,2,4]triazol-3-one | (R)-2-(N Hydroxycarbamidoyl)-piperidine-1-carboxylic acid tert-butyl ester, 3-(5-Oxo-1,5-dihydro-[1,2,4]triazol-4-yl)-benzoic acid and phenoxyacetic acid | 447.2 |
| 471 | 1-(3-{3-[(R)-1-(2-Phenoxy-acetyl)-piperidin-2-yl]-[1,2,4]oxadiazol-5-yl}-phenyl)-imidazolidine-2,4-dione | (R)-2-(N Hydroxycarbamidoyl)-piperidine-1-carboxylic acid tert-butyl ester, 3-(2,4-Dioxo-imidazolidin-1-yl)-benzoic acid and phenoxyacetic acid | 462.2 |
| 472 | 1-((R)-2-{5-[3-(1,1-Dioxo-1$$6-isothiazolidin-2-yl)-phenyl]-[1,2,4]oxadiazol-3-yl}-piperidin-1-yl)-2-phenoxy-ethanone | (R)-2-(N Hydroxycarbamidoyl)-piperidine-1-carboxylic acid tert-butyl ester, 3-(1,1-Dioxo-1$$6-isothiazolidin-2-yl)-benzoic acid and phenoxyacetic acid | 483.2 |
| 473 | 1-(3-{3-[(R)-1-(2-Phenoxy-acetyl)-piperidin-2-yl]-[1,2,4]oxadiazol-5-yl}-phenyl)-pyrrolidin-2-one | (R)-2-(N Hydroxycarbamidoyl)-piperidine-1-carboxylic acid tert-butyl ester, 3-(2-Oxo-pyrrolidin-1-yl)-benzoic acid and phenoxyacetic acid | 447.2 |
| 474 | 1-(3-{3-[(R)-1-(2-Phenoxy-acetyl)-piperidin-2-yl]-[1,2,4]oxadiazol-5-yl}-phenyl)-1,3-dihydro-imidazol-2-one | (R)-2-(N Hydroxycarbamidoyl)-piperidine-1-carboxylic acid tert-butyl ester, 3-(2-Oxo-2,3-dihydro-imidazol-1-yl)-benzoic acid and phenoxyacetic acid | 446.2 |
| 475 | 3-(3-{3-[(R)-1-(2-Phenoxy-acetyl)-piperidin-2-yl]-[1,2,4]oxadiazol-5-yl}-phenyl)-imidazolidine-2,4-dione | (R)-2-(N Hydroxycarbamidoyl)-piperidine-1-carboxylic acid tert-butyl ester, 3-(2,5-Dioxo-imidazolidin-1-yl)-benzoic acid and phenoxyacetic acid | 462.2 |
| 476 | 1-{(R)-2-[5-(1-Methyl-1H-pyrazol-3-yl)-[1,2,4]oxadiazol-3-yl]-piperidin-1-yl}-2-phenoxy-ethanone | (R)-2-(N Hydroxycarbamidoyl)-piperidine-1-carboxylic acid tert-butyl ester, 1-Methyl-1H-pyrazole-3-carboxylic acid and phenoxyacetic acid | 368.2 |
| 477 | 2-Phenoxy-1-{(R)-2-[5-(1H-pyrazol-3-yl)-[1,2,4]oxadiazol-3-yl]-piperidin-1-yl}-ethanone | (R)-2-(N Hydroxycarbamidoyl)-piperidine-1-carboxylic acid tert-butyl ester, 1H-Pyrazole-3-carboxylic acid and phenoxyacetic acid | 354.1 |
| 478 | 1-{(R)-2-[5-(5-Methyl-isoxazol-3-yl)-[1,2,4]oxadiazol-3-yl]-piperidin-1-yl}-2-phenoxy-ethanone | (R)-2-(N Hydroxycarbamidoyl)-piperidine-1-carboxylic acid tert-butyl ester, 5-Methyl-isoxazole-3-carboxylic acid and phenoxyacetic acid | 369.1 |
| 479 | 1-{(R)-2-[5-(2,5-Dimethyl-2H-pyrazol-3-yl)-[1,2,4]oxadiazol-3-yl]-piperidin-1-yl}-2-phenoxy-ethanone | (R)-2-(N Hydroxycarbamidoyl)-piperidine-1-carboxylic acid tert-butyl ester, 2,5-Dimethyl-2H-pyrazole-3-carboxylic acid and phenoxyacetic acid | 382.2 |
| 480 | 1-{(R)-2-[5-(5-Methyl-2H-pyrazol-3-yl)-[1,2,4]oxadiazol-3-yl]-piperidin-1-yl}-2-phenoxy-ethanone | (R)-2-(N Hydroxycarbamidoyl)-piperidine-1-carboxylic acid tert-butyl ester, 5-Methyl-2H-pyrazole-3-carboxylic acid and phenoxyacetic acid | 368.2 |

| Example | Compound name | Starting materials | MH+ (found) |
|---|---|---|---|
| 481 | 1-{(R)-2-[5-(3-Methyl-isoxazol-5-yl)-[1,2,4]oxadiazol-3-yl]-piperidin-1-yl}-2-phenoxy-ethanone | (R)-2-(N Hydroxycarbamidoyl)-piperidine-1-carboxylic acid tert-butyl ester, 3-Methyl-isoxazole-5-carboxylic acid and phenoxyacetic acid | 369.1 |

The following intermediate compounds were prepared in analogy to example 256

| Example | Intermediate name | Starting materials |
|---|---|---|
| 482 | N-Hydroxy-2-imidazol-1-yl-isonicotinamidine | 2-Imidazol-1-yl-isonicotinonitrile and hydroxylamine |
| 483 | N-Hydroxy-4-(3H-imidazol-4-yl)-benzamidine | 4-(3H-Imidazol-4-yl)-benzonitrile and hydroxylamine |
| 484 | N-Hydroxy-4-(2-methyl-imidazol-1-yl)-benzamidine | 4-(2-Methyl-imidazol-1-yl)-benzonitrile and hydroxylamine |
| 485 | N-Hydroxy-2-pyrazol-1-yl-isonicotinamidine | 2-Pyrazol-1-yl-isonicotinonitrile and hydroxylamine |
| 486 | 5-(N-Hydroxycarbamidoyl)-nicotinic acid ethyl ester | 5-Cyano-nicotinic acid ethyl ester and hydroxylamine |
| 487 | N-Hydroxy-4-piperidin-1-yl-benzamidine | 4-Piperidin-1-yl-benzonitrile and hydroxylamine |
| 488 | N-Hydroxy-4-morpholin-1-yl-benzamidine | 4-Morpholin-1-yl-benzonitrile and hydroxylamine |
| 489 | N-Hydroxy-6-imidazol-1-yl-nicotinamidine | 6-Imidazol-1-yl-nicotinonitrile and hydroxylamine |
| 490 | N-[3-(N-Hydroxycarbamidoyl)-phenyl]-acetamide | N-(3-Cyano-phenyl)-acetamide and hydroxylamine |
| 491 | 4-(N-Hydroxycarbamidoyl)-benzoic acid benzyl ester | N-(3-Cyano-phenyl)-4-Cyano-benzoic acid benzyl ester and hydroxylamine |
| 492 | 5-(N-Hydroxycarbamidoyl)-pyridine-2-carboxylic acid methyl ester | 5-Cyano-pyridine-2-carboxylic acid methyl ester and hydroxylamine |
| 493 | 2-Fluoro-4-(N-hydroxycarbamidoyl)-benzoic acid ethyl ester | 4-Cyano-2-fluoro-benzoic acid ethyl ester and hydroxylamine |
| 494 | 4-(N-Hydroxycarbamidoyl)-benzoic acid methyl ester | 4-Cyano-benzoic acid methyl ester and hydroxylamine |
| 495 | [3-(N-Hydroxycarbamidoyl)-phenoxy]-acetic acid methyl ester | (3-Cyano-phenoxy)-acetic acid methyl ester and hydroxylamine |
| 496 | N-Hydroxy-2-methyl-1H-benzoimidazole-5-carboxamidine | 2-Methyl-1H-benzoimidazole-5-carbonitrile and hydroxylamine |
| 497 | 2-Amino-N-hydroxy-isonicotinamidine | 2-Amino-isonicotinonitrile and hydroxylamine |
| 498 | 3,N-Dihydroxy-benzamidine | 3-Hydroxy-benzonitrile and hydroxylamine |
| 499 | 4,N-Dihydroxy-benzamidine | 4-Hydroxy-benzonitrile and hydroxylamine |
| 500 | 4-(N-Hydroxycarbamimidoyl)-benzoic acid | 4-Cyano-phenylboronic acid and hydroxylamine |
| 501 | N-Hydroxy-furan-2-carboxamidine | Furan-2-carbonitrile and hydroxylamine |
| 502 | N-Hydroxy-4-methyl-[1,2,3]thiadiazole-5-carboxamidine | 4-Methyl-[1,2,3]thiadiazole-5-carbonitrile and hydroxylamine |
| 503 | N-Hydroxy-2,5-dimethyl-2H-pyrazole-3-carboxamidine | 2,5-Dimethyl-2H-pyrazole-3-carbonitrile and hydroxylamine |
| 504 | N-Hydroxy-1H-pyrazole-4-carboxamidine | 1H-Pyrazole-4-carbonitrile and hydroxylamine |
| 505 | N-Hydroxy-5-methyl-isoxazole-3-carboxamidine | 5-Methyl-isoxazole-3-carbonitrile and hydroxylamine |
| 506 | N-Hydroxy-1H-pyrazole-3-carboxamidine | 1H-Pyrazole-3-carbonitrile and hydroxylamine |
| 507 | N-Hydroxy-2,4-dioxo-1,2,3,4-tetrahydro-pyrimidine-5-carboxamidine | 2,4-Dioxo-1,2,3,4-tetrahydro-pyrimidine-5-carbonitrile and hydroxylamine |
| 508 | 6-Amino-N-hydroxy-nicotinamidine | 6-Amino-nicotinonitrile and hydroxylamine |
| 509 | N-Hydroxy-imidazo[1,2-a]pyridine-6-carboxamidine | Imidazo[1,2-a]pyridine-6-carbonitrile and hydroxylamine |

-continued

| Example | Intermediate name | Starting materials |
|---|---|---|
| 510 | N-[4-Fluoro-3-(N-hydroxycarbamimidoyl)-phenyl]-acetamide | N-(3-Cyano-4-fluoro-phenyl)-acetamide and hydroxylamine |
| 511 | N-[5-Fluoro-3-(N-hydroxycarbamimidoyl)-phenyl]-acetamide | N-(3-Cyano-5-fluoro-phenyl)-acetamide and hydroxylamine |
| 512 | N-[6-Fluoro-3-(N-hydroxycarbamimidoyl)-phenyl]-acetamide | N-(3-Cyano-6-fluoro-phenyl)-acetamide and hydroxylamine |
| 513 | N-Hydroxy-3-oxo-3,4-dihydro-2H-benzo[1,4]oxazine-6-carboxamidine | 3-Oxo-3,4-dihydro-2H-benzo[1,4]oxazine-6-carbonitrile and hydroxylamine |
| 514 | N-Hydroxy-2-oxo-1,4-dihydro-2H-benzo[d][1,3]oxazine-6-carboxamidine | 2-Oxo-1,4-dihydro-2H-benzo[d][1,3]oxazine-6-carbonitrile and hydroxylamine |
| 515 | N-Hydroxy-2-oxo-1,2,3,4-tetrahydro-quinazoline-7-carboxamidine | 2-Oxo-1,2,3,4-tetrahydro-quinazoline-7-carbonitrile and hydroxylamine |
| 516 | 3-(1,1-Dioxo-1□6-isothiazolidin-2-yl)-N-hydroxy-benzamidine | 3-(1,1-Dioxo-1□6-isothiazolidin-2-yl)-benzonitrile and hydroxylamine |
| 517 | N-Hydroxy-3-(2-oxo-pyrrolidin-1-yl)-benzamidine | 3-(2-Oxo-pyrrolidin-1-yl)-benzonitrile and hydroxylamine |
| 518 | 3-(2,4-Dioxo-imidazolidin-1-yl)-N-hydroxy-benzamidine | 3-(2,4-Dioxo-imidazolidin-1-yl)-benzonitrile and hydroxylamine |
| 519 | N-Hydroxy-3-(5-oxo-1,5-dihydro-[1,2,4]triazol-4-yl)-benzamidine | 3-(5-Oxo-1,5-dihydro-[1,2,4]triazol-4-yl)-benzonitrile and hydroxylamine |

The following compounds were generated according to example 312

| Example | Intermediate name | Starting materials |
|---|---|---|
| 520 | N-Amino-2-Oxo-2,3-dihydro-1H-indole-5-carboxamidine hydrochloride | 2-Oxo-2,3-dihydro-1H-indole-5-carbonitrile and hydrazine |
| 521 | N-Amino-1H-Indazole-5-carboxamidine hydrochloride | 1H-Indazole-5-carbonitrile and hydrazine |
| 522 | N-Amino-1H-Indole-5-carboxamidine hydrochloride | 1H-Indole-5-carbonitrile and hydrazine |
| 523 | N-Amino-1H-Benzotriazole-5-carboxamidine hydrochloride | 1H-Benzotriazole-5-carbonitrile and hydrazine |
| 524 | N-Amino-2-Oxo-2,3-dihydro-1H-benzoimidazole-5-carboxamidine hydrochloride | 2-Oxo-2,3-dihydro-1H-benzoimidazole-5-carbonitrile and hydrazine |
| 525 | N-Amino-N-Hydroxy-2-methyl-1H-benzoimidazole-5-carboxamidine hydrochloride | 2-Methyl-1H-benzoimidazole-5-carbonitrile and hydrazine |
| 526 | N-Amino-2-Amino-isonicotinamidine hydrochloride | 2-Amino-isonicotinonitrile and hydrazine |
| 527 | N-Amino-3-(5-Oxo-4,5-dihydro-[1,3,4]oxadiazol-2-yl)-benzamidine hydrochloride | 3-(5-Oxo-4,5-dihydro-[1,3,4]oxadiazol-2-yl)-benzonitrile and hydrazine |
| 528 | N-Amino-3-[1,3,4]Oxadiazol-2-yl-benzamidine hydrochloride | 3-[1,3,4]Oxadiazol-2-yl-benzonitrile and hydrazine |
| 529 | N-Amino-3-Carbamidoyl-phenylboronic acid hydrochloride | 3-Cyano-phenylboronic acid and hydrazine |
| 530 | N-Amino-2-fluoro-benzamidine hydrochloride | 2-Fluorobenzonitrile and hydrazine and hydrazine |
| 531 | N-Amino-6-Amino-nicotinamidine hydrochloride | 6-Amino-nicotinonitrile and hydrazine |
| 532 | N-Amino-4-Carbamimidoyl-benzoic acid methyl ester hydrochloride | 4-Cyano-benzoic acid methyl ester and hydrazine |
| 533 | N-Amino-4-Fluoro-benzamidine hydrochloride | 4-Fluoro-benzonitrile and hydrazine |
| 534 | N-Amino-3-Fluoro-benzamidine hydrochloride | 3-Fluoro-benzonitrile and hydrazine |

Example 535

N-(5-Cyano-2-fluoro-phenyl)-acetamide 10 mmol of 3-Amino-4-fluoro-benzonitrile were dissolved in 30 ml THF. 1.5 eq of DIPEA were added and the reaction mixture cooled to 0° C. 1.2 eq of acetylchloride were added dropwise, the reaction warmed up to rt and stirred for additional 30 min. The solvent was evaporated and the product isolated via extraction from ethylacetate and saturated $NaHCO_3$ solution.
MS(ISO): 179.2 (MH+)

Example 536

N-(3-Cyano-5-fluoro-phenyl)-acetamide

The title compound was prepared in analogy to example 535 from 3-Amino-5-Fluoro-benzonitril. MS(ISO): 179.2 (MH+)

Example 537

N-(3-Cyano-4-fluoro-phenyl)-acetamide

The title compound was prepared in analogy to example 535 from 5-Amino-2-Fluoro-benzonitril. MS(ISO): 179.2 (MH+)

Example 538

3-Oxo-3,4-dihydro-2H-benzo[1,4]oxazine-6-carbonitrile 24 mmol of 4-Hydroxy-3-nitrobenzonitrile were dissolved in DMF. 1.1 eq of Cs2CO3 were added and the reaction stirred at rt for 15 min. 1.5 eq of ethylbromo acetate were added and the reaction mixture heated to 50° C. for 2 h. The intermediate was isolated via extraction from ethylacetate/water. The organic layer was separated and dried over Na2SO4. After evaporation the resulting solid was redissolved in MeOH and sat. NH4Cl (1:1). 8 g of Zn powder were added and the suspension stirred at rt for 2 h. The solid was filtered off and the organic layer evaporated. Ethylacetate was added and the organic layer washed with sat. NaHCO3. The organic layer was separated again, dried over Na2SO4 and reduced resulting in a light brown solid. MS(ISO): 175.2 (MH+)

Example 539

2-Oxo-1,4-dihydro-2H-benzo[d][1,3]oxazine-6-carbonitrile 20 mmol of 4-Amino-3-hydroxymethyl-benzonitrile were dissolved in THF. 1.2 eq. of DIPEA were added and the reaction cooled to 0° C. 3.5 eq of ethyl chloroformate were added dropwise and the reaction warmed to rt and stirred for another 15 min. The crude material was extracted form etyhlacetate and sat. NaHCO3. After separation, and drying of the organic layer the solvent was evaporated and the crude taken up in toluene. 2.5 ml of DBU were added and the reaction mixture refluxed for 4 h. The organic layer was extracted with water and the organic layer separated and reduced resulting in a yellow oil. Crude material was not further characterized.

Example 540

2-Oxo-1,2,3,4-tetrahydro-quinazoline-7-carbonitrile 24 mmol of 2-Nitro-4-chloro-benzylamine hydrochloride were dissolved in THF. 2.2 eq of DIPEA were added and the reaction mixture cooled to 0° C. 3.5 eq. of ethyl chloroformte were added dropwise and the reaction stirred for 15 min. After extraction from ethylacetate/sat. NaHCO3 and evaporation of the organic layer a light brown solid resulted. This was taken up in MeOH/sat. NH4Cl (1:1). 6 g of Zn was added and the suspension stirred at rt for 4 h. The solid was filtered off, the methanol reduced and the product isolated via extraction with ethylacetate. After evaporation a light yellow solid resulted. MS(ISO): 174.2 (MH+)

Example 541

3-(5-Oxo-1,5-dihydro-[1,2,4]triazol-4-yl)-benzonitrile g of 3-Aminobenzonitril were dissolved in 20 ml MeOH. 1.8 ml of trimethyl orthoformate, hydrazinecarboxylic acid methyl ester and cat. para-toluenesulfonic acid were added. The reaction mixture was heated to 65° C. for 3 h. The suspension was cooled to rt and 9 ml of NaOMe solution were added and the reaction mixture stirred at rt for 2 h. Water was added and the pH adjusted to 1 using aq. HCl (25%). The resulting suspension was filtered off and dried under vacuum. MS(ISO): 187.2 (MH+)

Example 542

3-(2,4-Dioxo-imidazolidin-1-yl)-benzonitrile g of 3-Aminobenzonitril were dissolved in 60 ml Dioxan and 0.8 ml of Chloro-acetyl isocyanate added. The reaction mixture was stirred at rt for 2 h. 2.5 ml of DBU were added and the reaction mixture stirred at rt for 40 h. The product was extracted with DCM. MS(ISO): 202.2 (MH+)

Example 543

3-(1,1-Dioxo-1λ6-isothiazolidin-2-yl)-benzonitrile 1 g of 3-Aminobenzonitril were dissolved in 10 ml DCM and 2.2 ml of DIPEA. 1.3 ml of 3-Chloro-propane-1-sulfonyl chloride were added and the reaction mixture stirred at rt overnight. The organic layer was evaporated, the crude taken up in DMF and 1.5 ml DBU added. The reaction mixture was stirred at rt overnight. DCM was added and the organic phase washed with water. The organic layer was separated, dried over Na2SO4 and evaporated. MS(ISO): 232.2 (MH+)

Example 544

3-(2-Oxo-pyrrolidin-1-yl)-benzonitrile g of 3-Aminobenzonitril were dissolved in 20 ml DMF and 4.4 ml of DIPEA. The reaction mixture was cooled to 0° C. and 2 ml of 4-chloro-butyryl chloride added. The reaction mixture was stirred at rt for 1 h. 5 ml of DBU were added and the reaction mixture stirred at rt overnight. DCM was added and the organic phase washed with 1N HCL and water. The organic layer was separated, dried over Na2SO4 and evaporated. MS(ISO): 187.2 (MH+)

Example 545

6-Chloro-3-hydroxy-pyridazine-4-carboxylic acid 2 mmol of 3,6-Dichloropyridazine-4-carboxylic acid are treated with 8 ml of aqueous 2N NaOH and refluxed for 1 h. The reaction mixture was acidified to pH=1. The resulting white solid was filtered off and dried under vacuum. MS(ISO): 173.2 (M–H+)

Example 546

3-(5-Oxo-1,5-dihydro-[1,2,4]triazol-4-yl)-benzoic acid 13 mmol of methyl-3-aminobenzoate were dissolved in 20 ml MeOH. 12 mmol of trimethylorthoformiate, 12 mmol methyl hydrazinocarboxylate and 50 mg of p-toluenesulfonic acid were added. The suspension was heated for 48 h to 65° C. 37 mmol of sodium methanolate were added and stirred for additional 2 h. The organic layer was reduced and water was added. The solution was acidified to pH=1 and the resulting solid filtered off to result in 5.7 mmol of product. MS(ISO): 204.2 (M–H+)

Example 547

3-(2,4-Dioxo-imidazolidin-1-yl)-benzoic acid 12 mmol of ethyl-3-aminobenzoate were dissolved in 120 ml Dioxan. 1 eq of chloroacetyl isocyanate were added. The reaction mixture was stirred at rt for 1 h and then heated to 120° C. for an additional 2 h. The reaction was cooled to rt, 2 eq of DBU added and again stirred at rt overnight. The solvent was evaporated and the crude extracted from DCM. The crude material was dissolved in 20 ml MeOH and 4 ml of 4N NaOH were added. The reaction mixture was stirred at rt for 20 h. After evaporation of the organic layer the aqueous phase was acidified to pH=1 and the resulting white solid was filtered off and dried under vacuum. MS(ISO): 219.2 (M–H+)

Example 548

3-(1,1-Dioxo-1λ6-[1,2,5]thiadiazolidin-2-yl)-benzoic acid 13 mmol of methyl-3-aminobenzoate were dissolved in 20 ml DCM and 3 ml of TEA added. 1.6 ml of 3-chloropropane-sulfonyl chloride were added slowly under argon atmosphere. The reaction mixture was stirred at rt overnight and washed with 1N HCl. The organic layer was separated, dried over Na2SO4 and reduced under vacuum. The resulting crude was taken up in 16 ml DMF and 2.4 ml of DBU added. The reaction mixture was stirred at rt for 2 h and washed with 1N HCl. The crude material was dissolved in 20 ml MeOH and 4 ml of 2N NaOH were added. The reaction mixture was stirred at rt for 72 h and acidified with HCl to pH=1. The resulting white solid was filtered off and dried under vacuum. MS(ISO): 241.3 (M–H+)

Example 549

3-(2-Oxo-2,3-dihydro-imidazol-1-yl)-benzoic acid 12 mmol of ethyl-3-aminobenzoate were dissolved in 20 ml DCM and 2 ml of TEA added. The reaction mixture was cooled to ° C. and 1.5 ml Diphosgen were added slowly. The reaction mixture was warmed to rt and stirred for an additional 1 h under argon atmosphere. The reaction mixture was poured on ice and the organic layer separated, dried over Na2SO4 and reduced under vacuum. The crude material was taken up in 30 ml DCM and 1.3 ml of aminoacetaldehyde dimethylacetal were added. The reaction mixture was stirred for 3 h at rt. The organic layer was washed with sat. NaHCO3, separated and dried over Na2SO4. After evaporation of the solvent the resulting crude material was purified via Kieselgel chromatography. 200 mg of the product were dissolved in 5 ml MeOH and 2 ml of 2N NaOH added. The reaction mixture was stirred at rt for 2 h, acidified with HCl to pH=1 and the resulting white solid filtered off. MS(ISO): 203.2 (M–H+)

Example 550

3-(2,5-Dioxo-imidazolidin-1-yl)-benzoic acid 13 mmol of methyl-3-aminobenzoate were dissolved in 20 ml DCM and 1.7 ml of ethyl isocyanatoacetate added. The reaction mixture was stirred at rt for 1 h. The solvent was evaporated and the resulting crude taken up in 50 ml acetone. 50 ml of aq. HCl (25%) were added and heated to reflux for 8 h. After evaporation of the organic layer the resulting solid was filtered off, washed with water and dried under vacuum. MS(ISO): 219.2 (M–H+)

Example 551

3-Oxo-3,4-dihydro-2H-benzo[1,4]oxazine-6-carboxamidine 8.7 mmol of N-Hydroxy-3-oxo-3,4-dihydro-2H-benzo[1,4]oxazine-6-carboxamidine were dissolved in 25 ml acetic acid. 5 eq. of ammonium formiate and 0.05 eq. of Pd/C (10%) were added and the reaction mixture heated to reflux overnight. The reaction mixture was concentrated, cooled to 0° C. and the pH adjusted to 8 using aq. NaOH (28%). The resulting solid was filtered off and washed with water. MS(ISO): 192.2 (M–H+)

The following intermediate compounds were generated in analogy to example 551

| Example | Intermediate name | Starting material |
|---|---|---|
| 552 | Imidazo[1,2-a]pyridine-6-carboxamidine | N-Hydroxy-imidazo[1,2-a]pyridine-6-carboxamidine |
| 553 | 1H-Benzoimidazole-5-carboxamidine | N-Hydroxy-1H-benzoimidazole-5-carboxamidine |
| 554 | Nicotinamidine | N-Hydroxy-nicotinamidine |
| 555 | 3,5-Dimethyl-isoxazole-4-carboxamidine | N-Hydroxy-3,5-dimethyl-isoxazole-4-carboxamidine |

| Example | Intermediate name | Starting material |
|---|---|---|
| 556 | Thiophene-2-carboxamidine | N-Hydroxy-thiophene-2-carboxamidine |
| 556 | Pyrimidine-2-carboxamidine | N-Hydroxy-pyrimidine-2-carboxamidine |
| 557 | 4-Methyl-oxazole-5-carboxamidine | N-Hydroxy-4-methyl-oxazole-5-carboxamidine |
| 558 | Pyrazine-2-carboxamidine | N-Hydroxy-pyrazine-2-carboxamidine |
| 559 | 2-Methyl-isonicotinamidine | N-Hydroxy-2-methyl-isonicotinamidine |
| 560 | 2-Oxo-1,4-dihydro-2H-benzo[d][1,3]oxazine-6-carboxamidine | N-Hydroxy-2-oxo-1,4-dihydro-2H-benzo[d][1,3]oxazine-6-carboxamidine |
| 561 | 2-Oxo-1,2,3,4-tetrahydro-quinazoline-6-carboxamidine | N-Hydroxy-2-oxo-1,2,3,4-tetrahydro-quinazoline-6-carboxamidine |
| 562 | 3-(2,4-Dioxo-imidazolidin-1-yl)-benzamidine | 3-(2,4-Dioxo-imidazolidin-1-yl)-N-hydroxy-benzamidine |
| 563 | N-(3-Carbamidoyl-4-fluoro-phenyl)-acetamide | N-[4-Fluoro-3-(N-hydroxycarbamidoyl)-phenyl]-acetamide |
| 564 | N-(3-Carbamidoyl-5-fluoro-phenyl)-acetamide | N-[5-Fluoro-3-(N-hydroxycarbamidoyl)-phenyl]-acetamide |
| 565 | N-(3-Carbamidoyl-6-fluoro-phenyl)-acetamide | N-[6-Fluoro-3-(N-hydroxycarbamidoyl)-phenyl]-acetamide |

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidon in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene Glycol 400 | 150.0 mg |
| Acetic Acid | q.s. ad pH 5.0 |
| Water for injection solutions | ad 1.0 ml |

The active ingredient is dissolved in a mixture of Polyethylene Glycol 400 and water for injection (part). The pH is adjusted to 5.0 by Acetic Acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| Capsule contents | |
| --- | --- |
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
| --- | --- |
| Compound of formula (I) | 50.0 mg |
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K 30 | 10.0 mg |
| Magnesium stearate | 10.0 mg |
| Flavoring additives | 1.0 mg |

The active ingredient is mixed with lactose, microcristalline cellulose and sodium carboxymethyl cellulose and granulated with a mixture of polyvinylpyrrolidon in water. The granulate is mixed with magnesiumstearate and the flavouring additives and filled into sachets.

It is to be understood that the invention is not limited to the particular embodiments of the invention described above, as variations of the particular embodiments may be made and still fall within the scope of the appended claims.

What is claimed is:

1. A compound of formula (I):

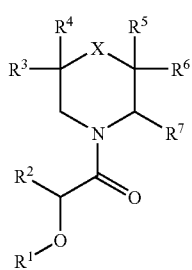

wherein:

X is $C(R^8R^9)$;

$R^1$ is phenyl optionally substituted with 1 to 3 substituents selected from the group consisting of halogen, hydroxy, lower-alkyl, hydroxy-lower-alkyl, fluoro-lower-alkyl, lower-alkoxy and CN;

$R^2$ is hydrogen or lower-alkyl;

$R^3$ and $R^4$ independently from each other are hydrogen, halogen, lower-alkyl or lower-alkoxy, or $R^3$ and $R^4$ together are =O to form a carbonyl group together with the carbon atom to which they are attached;

$R^5$ and $R^6$ independently from each other are hydrogen, halogen, lower-alkyl or lower-alkoxy, or $R^5$ and $R^6$ together are =O to form a carbonyl group together with the carbon atom to which they are attached;

$R^7$ is an oxadiazolyl or triazolyl, which oxadiazolyl or triazolyl is substituted with $R^{11}$ and optionally substituted with $R^{12}$;

$R^8$ and $R^9$ independently from each other are hydrogen, halogen, hydroxy, lower-alkyl, lower-alkoxy; or $R^8$ and $R^9$ are bound together and $-R^8-R^9-$ is $-(CH_2)_{2-7}-$ to form a ring together with the carbon atom to which they are attached;

$R^{11}$ is aryl or a heteroaryl selected from the group consisting of pyridinyl, pyrazinyl, pyrimidinyl, pyridinyl-2-one, oxadiazolyl, indazolyl, 1,3-dihydro-benzimidazol-2-one, 1,3-dihydro-indol-2-one, benztriazolyl, imidazopyridinyl, triazolepyridinyl, tetrazolepyridinyl, benzimidazolyl, 2-oxo-2,3-dihydro-1H-indol-5-yl, pyrimidin-4-one, furanyl, thiadiazolyl, pyrazolyl, isoxazolyl, pyrimidine-2,4-dione, benzooxazin-3-one, 1,4-dihydro-benzooxazin-2-one, indolyl, thiophenyl, oxazolyl, benzooxazin-2-one, 3,4-dihydro-quinazolin-2-one, pyridazinyl, quinoxalinyl, benzothiazolyl, benzothiadiazolyl, naphthyridinyl, cinnolinyl, 1,4-dihydro-quinoxaline-2,3-dione and 1,2-dihydro-indazol-3-one, which aryl or heteroaryl is optionally substituted with 1 to 3 substituents selected from the group consisting of lower-alkyl, hydroxy, $B(OH)_2$, carboxy-lower-alkoxy, carbamoyl-lower-alkoxy, cyano, hydroxy-lower-alkyl, fluoro-lower-alkyl, lower-alkoxy, halogen, $S(O_2)R^{13}$, $C(O)R^{14}$, $NO_2$, $NR^{15}R^{16}$, imidazolyl, pyrazolyl, tetrazolyl, pyrrolyl, phenyl-lower-alkoxy, [1,3,4]oxadiazol-2-one, oxadiazolyl, triazolyl and isoxazolyl, which imidazolyl is optionally substituted with lower-alkyl, and which phenyl-lower-alkoxy is optionally substituted with hydroxy, halogen, lower-alkyl, lower-alkoxy or fluoro-lower-alkyl, and which pyrazolyl is optionally substituted with lower-alkyl, and which isoxazolyl is optionally substituted with lower-alkyl;

$R^{12}$ is hydrogen or lower-alkyl;

$R^{13}$ is lower-alkyl, $NR^{17}R^{18}$ or fluoro-lower-alkyl;

$R^{14}$ is OH, $NR^{19}R^{20}$, lower-alkoxy, lower-alkenyl-oxy or lower-alkyl;

$R^{15}$ and $R^{16}$ independently from each other are hydrogen, lower-alkyl, lower-alkyl-carbonyl, lower-alkyl-$SO_2$, lower-alkenyl-oxy-carbonyl, $NH_2$-carbonyl, lower-alkyl-NH-carbonyl, (lower-alkyl)$_2$N-carbonyl or phenyl-lower-alkyl, which phenyl-lower-alkyl is optionally substituted with hydroxy, halogen, lower-alkyl, lower-alkoxy or fluoro-lower-alkyl; or $NR^{15}R^{16}$ is a heterocyclyl selected from the group consisting of morpholinyl, thiomorpholinyl, 1,1-dioxo-thiomorpholinyl, piperidinyl, piperidin-2-one, piperazin-2-one, 8-oxa-3-aza-bicyclo[3.2.1]octyl, piperazinyl, pyrrolidinyl, 1,1-dioxo-isothiazolidinyl, pyrrolidin-2- one, imidazolidine-2,4-dione, 2,4-dihydro[1,2,4]triazol-3-one, pyrrolidine-2,5-dione, azetidin-2-one and 1,3-dihydro-imidazol-2-one, which heterocyclyl is optionally substituted with hydroxy-lower-alkyl or lower-alkyl-carbonyl;

$R^{17}$ and $R^{18}$ independently from each other are hydrogen, lower-alkyl, hydroxy-lower-alkyl, lower-alkoxy-lower-alkyl; or $NR^{17}R^{18}$ is morpholinyl;

$R^{19}$ and $R^{20}$ independently from each other are hydrogen, lower-alkyl, cycloalkyl, hydroxy-lower-alkyl, lower-alkoxy-lower-alkyl, (lower-alkyl)$_2$N-lower-alkyl, pyridinyl-lower-alkyl or cyano-lower-alkyl; or $NR^{19}R^{20}$ is a heterocyclyl selected from the group consisting of morpholinyl, pyrrolidinyl, 8-oxa-3-aza-bicyclo[3.2.1]octyl, piperidinyl, piperazinyl, piperazin-2-one, thiazolidinyl, thiomorpholinyl, 1,3,8-triaza-spiro[4,5]decane-2,4-dione and spiro(1-phtalan)-piperidine-4-yl, which heterocyclyl is optionally substituted with hydroxy, lower-alkyl-S(O$_2$), lower-alkyl, lower-alkyl-carbonyl, carboxy, carbamoyl, lower-alkoxy-carbonyl, cyano, phenyl, pyridinyl or lower-alkoxy;

and pharmaceutically acceptable salts and esters thereof.

2. The compound according to claim 1, wherein
X is $C(R^8R^9)$;
$R^1$ is phenyl optionally substituted with 1 to 3 substituents selected from the group consisting of halogen, hydroxy, lower-alkyl, hydroxy-lower-alkyl, fluoro-lower-alkyl, lower-alkoxy and CN;
$R^2$ is hydrogen or lower-alkyl;
$R^3$ and $R^4$ independently from each other are hydrogen, halogen, lower-alkyl or lower-alkoxy, or
$R^3$ and $R^4$ together are =O to form a carbonyl group together with the carbon atom to which they are attached;
$R^5$ and $R^6$ independently from each other are hydrogen, halogen, lower-alkyl or lower-alkoxy, or
$R^5$ and $R^6$ together are =O to form a carbonyl group together with the carbon atom to which they are attached;
$R^7$ is an oxadiazolyl or triazolyl, which oxadiazolyl or triazolyl is substituted with $R^{11}$ and optionally substituted with $R^{12}$;
$R^8$ and $R^9$ independently from each other are hydrogen, halogen, hydroxy, lower-alkyl, lower-alkoxy; or
$R^8$ and $R^9$ are bound together and —$R^8$—$R^9$— is —(CH$_2$)$_{2-7}$— to form a ring together with the carbon atom to which they are attached;
$R^{11}$ is aryl or a heteroaryl selected from the group consisting of pyridinyl, pyrazinyl, pyrimidinyl, pyridinyl-2-one, oxadiazolyl, indazolyl, 1,3-dihydro-benzimidazol-2-one, 1,3-dihydro-indol-2-one, benztriazolyl, imidazopyridinyl, triazolepyridinyl, tetrazolepyridinyl and benzimidazolyl, which aryl or heteroaryl is optionally substituted with 1 to 3 substituents selected from the group consisting of lower-alkyl, hydroxy-lower-alkyl, fluoro-lower-alkyl, lower-alkoxy, halogen, S(O$_2$)$R^{13}$, C(O)$R^{14}$, NO$_2$, NR$^{15}$R$^{16}$, imidazolyl, pyrazolyl, tetrazolyl, pyrrolyl, and phenyl-lower-alkoxy, which imidazolyl is optionally substituted with lower-alkyl and which phenyl-lower-alkoxy is optionally substituted with hydroxy, halogen, lower-alkyl, lower-alkoxy or fluoro-lower-alkyl;
$R^{12}$ is hydrogen or lower-alkyl;
$R^{13}$ is lower-alkyl, NR$^{17}$R$^{18}$ or fluoro-lower-alkyl;
$R^{14}$ is OH, NR$^{19}$R$^{20}$, lower-alkoxy or lower-alkenyl-oxy;

$R^{15}$ and $R^{16}$ independently from each other are hydrogen, lower-alkyl, lower-alkyl-carbonyl, lower-alkyl-SO$_2$, lower-alkenyl-oxy-carbonyl, NH$_2$-carbonyl, lower-alkyl-NH-carbonyl, (lower-alkyl)$_2$N-carbonyl or phenyl-lower-alkyl, which phenyl-lower-alkyl is optionally substituted with hydroxy, halogen, lower-alkyl, lower-alkoxy or fluoro-lower-alkyl; or $NR^{15}R^{16}$ is a heterocyclyl selected from the group consisting of morpholinyl, thiomorpholinyl, 1,1-dioxo-thiomorpholinyl, piperidinyl, piperidin-2-one, piperazin-2-one, 8-oxa-3-aza-bicyclo[3.2.1]octyl, piperazinyl and pyrrolidinyl, which heterocyclyl is optionally substituted with hydroxy-lower-alkyl or lower-alkyl-carbonyl;

$R^{17}$ and $R^{18}$ independently from each other are hydrogen, lower-alkyl, hydroxy-lower-alkyl, lower-alkoxy-lower-alkyl; or $NR^{17}R^{18}$ is morpholinyl;

$R^{19}$ and $R^{20}$ independently from each other are hydrogen, lower-alkyl, cycloalkyl, hydroxy-lower-alkyl or lower-alkoxy-lower-alkyl; or $NR^{19}R^{20}$ is a heterocyclyl selected from the group consisting of morpholinyl, pyrrolidinyl and 8-oxa-3-aza-bicyclo[3.2.1]octyl, which heterocyclyl is optionally substituted with hydroxy or lower-alkyl-S(O$_2$);

and pharmaceutically acceptable salts and esters thereof.

3. The compound according to claim 1, wherein $R^1$ is phenyl optionally substituted with halogen, hydroxy, hydroxy-lower-alkyl or CN.

4. The compound according to claim 1, wherein $R^1$ is phenyl.

5. The compound according to claim 1, wherein $R^2$ is hydrogen.

6. The compound according to claim 1, wherein $R^3$ is hydrogen.

7. The compound according to claim 1, wherein $R^4$ is hydrogen.

8. The compound according to claim 1, wherein $R^5$ is hydrogen.

9. The compound according to claim 1, wherein $R^6$ is hydrogen.

10. The compound according to claim 1, wherein $R^7$ is

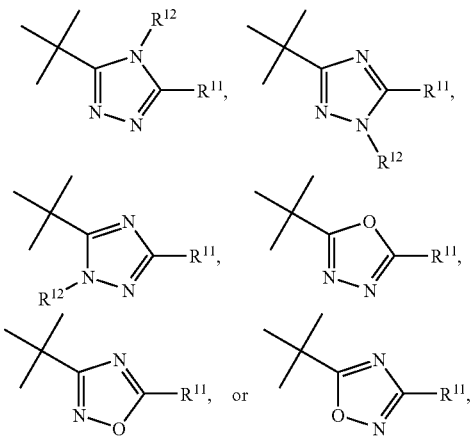

wherein $R^{11}$ and $R^{12}$ are as defined in claim 1.

11. The compound according to claim 1, wherein $R^7$ is

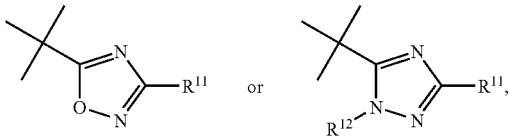

wherein $R^{11}$ and $R^{12}$ are as defined in claim 1.

12. The compound according to claim 1, wherein $R^7$ is

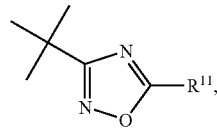

wherein $R^{11}$ is as defined in claim 1.

13. The compound according to claim 1, wherein $R^8$ is hydrogen.

14. The compound according to claim 1, wherein $R^9$ is hydrogen.

15. The compound according to claim 1, wherein $R^{11}$ is heteroaryl selected from the group consisting of pyridinyl, pyrazinyl, pyridinyl-2-one, indazolyl, 1,3-dihydro-benzimidazol-2-one, 1,3-dihydro-indol-2-one, benztriazolyl and benzimidazolyl, which phenyl or heteroaryl is optionally substituted with 1 to 2 substituents selected from the group consisting of lower-alkyl, hydroxy-lower-alkyl, fluoro-lower-alkyl, lower-alkoxy, halogen, $S(O_2)R^{13}$, $C(O)R^{14}$, $NO_2$, $NR^{15}R^{16}$, imidazolyl, pyrazolyl, tetrazolyl, pyrrolyl, and phenyl-lower-alkoxy, which imidazolyl is optionally substituted with lower-alkyl, wherein $R^{13}$, $R^{14}$, $R^{15}$ and $R^{16}$ are as defined in claim 1.

16. The compound according to claim 1, wherein $R^{11}$ is phenyl or a heteroaryl selected from the group consisting of pyridinyl, pyridinyl-2-one, indazolyl, 1,3-dihydro-benzimidazol-2-one, 1,3-dihydro-indol-2-one, benztriazolyl and benzimidazolyl, which phenyl or heteroaryl is optionally substituted with 1 to 2 substituents selected from the group consisting of fluoro-lower-alkyl, halogen, $C(O)R^{14}$ and $NR^{15}R^{16}$, wherein $R^{14}$, $R^{15}$ and $R^{16}$ are as defined in claim 1.

17. The compound according to claim 1, wherein $R^{11}$ is 1H-Indazol-5-yl, 1H-Indazol-6-yl, 1,3-dihydro-indol-2-one-6-yl, 1,3-dihydro-benzoimidazol-2-one-5-yl, 1,3-dihydro-indol-2-one-5-yl, 1H-Benzotriazol-5-yl, 1H-Benzoimidazol-5-yl, 1H-pyridin-2-one-4-yl, 4-Fluoro-phenyl, 3-trifluoromethyl-phenyl, 1H-Benzoimidazol-5-yl, 3-benzamide, 5-nicotinamide, 3-(N-acetamide)-phenyl or 3-(N-methanesulfonamide)-phenyl.

18. The compound according to claim 1, wherein $R^{11}$ is phenyl or a heteroaryl selected from the group consisting of 2-oxo-2,3-dihydro-1H-indol-5-yl, pyrimidin-4-one, furanyl, thiadiazolyl, pyrazolyl, isoxazolyl, pyrimidine-2,4-dione, benzooxazin-3-one, 1,4-dihydro-benzooxazin-2-one, indolyl, thiophenyl, oxazolyl, benzooxazin-2-one, 3,4-dihydro-quinazolin-2-one, pyridazinyl, quinoxalinyl, benzothiazolyl, benzothiadiazolyl, naphthyridinyl, cinnolinyl, 1,4-dihydro-quinoxaline-2,3-dione and 1,2-dihydro-indazol-3-one, which phenyl or heteroaryl is optionally substituted with 1 to 3 substituents selected from the group consisting of hydroxy, $B(OH)_2$, carboxy-lower-alkoxy, carbamoyl-lower-alkoxy, cyano, [1,3,4]oxadiazol-2-one, oxadiazolyl, triazolyl and isoxazolyl, which pyrazolyl is optionally substituted with lower-alkyl, and which isoxazolyl is optionally substituted with lower-alkyl.

19. The compound according to claim 1, wherein $R^{11}$ is phenyl or a heteroaryl selected from the group consisting of pyridinyl, 1,3-dihydro-indol-2-one, 1H-benzimidazolyl, 3H-pyrimidin-4-one, 1H-pyrazolyl, isoxazolyl and 4H-benzo[1,4]oxazin-3-one, which phenyl or heteroaryl is optionally substituted with 1 to 3 substituents selected from the group consisting of lower-alkyl, hydroxy, halogen and $NR^{15}R^{16}$, wherein $R^{14}$ and $R^{15}$ are as defined in claim 1.

20. The compound according to claim 1, wherein $R^{11}$ is 2-methyl-3H-pyrimidin-4-one, 5-methyl-isoxazol-3-yl, 1H-pyrazol-3-yl, 6-amino-pyridin-3-yl, 1,3-dihydro-indol-2-one, 2-amino-pyridin-4-yl, 4H-benzo[1,4]oxazin-3-one, 1H-benzimidazol-5-yl, 3-(N-acetamide)-4-fluoro-phenyl or 2-hydroxy-pyridin-4-yl.

21. The compound according to claim 1, wherein $R^{12}$ is hydrogen.

22. The compound according to claim 1, wherein $R^{13}$ is lower-alkyl.

23. The compound according to claim 1, wherein $R^{14}$ is $NR^{19}R^{20}$, wherein $R^{19}$ and $R^{20}$ are as defined in claim 1.

24. The compound according to claim 1, wherein $R^{14}$ is lower-alkyl.

25. The compound according to claim 1, wherein $R^{15}$ and $R^{16}$ independently from each other are hydrogen, lower-alkyl, lower-alkyl-carbonyl, lower-alkyl-$SO_2$, lower-alkanyl-oxy-carbonyl or lower-alkyl-NH-carbonyl; or $NR^{15}R^{16}$ is a heterocyclyl selected from the group consisting of morpholinyl, thiomorpholinyl, 1,1-dioxo-thiomorpholinyl, piperidinyl, piperidin-2-one, piperazin-2-one, piperazinyl and pyrrolidinyl, which heterocyclyl is optionally substituted with hydroxy-lower-alkyl or lower-alkyl-carbonyl.

26. The compound according to claim 1, wherein $R^{15}$ and $R^{16}$ independently from each other are hydrogen, lower-alkyl-carbonyl or lower-alkyl-$SO_2$.

27. The compound according to claim 1, wherein $NR^{15}R^{16}$ is a heterocyclyl selected from the group consisting of 1,1-dioxo-isothiazolidinyl, pyrrolidin-2-one, imidazolidine-2,4-dione, 2,4-dihydro[1,2,4]triazol-3-one, pyrrolidine-2,5-dione, azetidin-2-one and 1,3-dihydro-imidazol-2-one, which heterocyclyl is optionally substituted with hydroxy-lower-alkyl or lower-alkyl-carbonyl.

28. The compound according to claim 1, wherein $R^{17}$ and $R^{18}$ independently from each other are hydrogen or lower-alkyl; or $NR^{17}R^{18}$ is morpholinyl.

29. The compound according to claim 1, wherein $R^{19}$ and $R^{20}$ independently from each other are hydrogen, lower-alkyl, cycloalkyl, hydroxy-lower-alkyl, lower-alkoxy-lower-alkyl; or $NR^{19}R^{20}$ is a heterocyclyl selected from the group consisting of morpholinyl or pyrrolidinyl, which heterocyclyl is optionally substituted with hydroxy or lower-alkyl-$S(O_2)$.

30. The compound according to claim 1, wherein $R^{19}$ and $R^{20}$ are hydrogen.

31. The compound according to claim 1, wherein $R^{19}$ and $R^{20}$ independently from each other are (lower-alkyl)$_2$N-lower-alkyl, pyridinyl-lower-alkyl or cyano-lower-alkyl; or $NR^{19}R^{20}$ is a heterocyclyl selected from the group consisting of piperidinyl, piperazinyl, piperazin-2-one, thiazolidinyl, thiomorpholinyl, 1,3,8-triaza-spiro[4,5]decane-2,4-dione and spiro(1-phtalan)-piperidine-4-yl, which heterocyclyl is optionally substituted with hydroxy, lower-alkyl-$S(O_2)$, lower-alkyl, lower-alkyl-carbonyl, carboxy, carbamoyl, lower-alkoxy-carbonyl, cyano, phenyl, pyridinyl or lower-alkoxy.

32. The compound according to claim 1, which are R-isomers and which are characterised by formula (Ia)

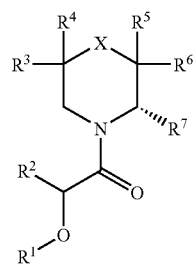

wherein $R^1$, $R^2$, $R^3$, $R^4$, $R^5$, $R^6$, $R^7$ and X are as defined in claim 1.

33. The compound according to claim 1, selected from the group consisting of (R)-1-{2-[3-(4-Methoxy-phenyl)-[1,2,4]oxadiazol-5-yl]-piperidin-1-yl}-2-phenoxy-ethanone,
(R)-3-(2-{2-[3-(4-Methoxy-phenyl)[1,2,4]oxadiazol-5-yl]-piperidin-1-yl}-2-oxo-ethoxy) benzonitrile,
(R)-1-{2-[3-(4-Methoxy-phenyl)-[1,2,4]oxadiazol-5-yl]-piperidin-1-yl}-2-phenoxy-propan-1-one,
(R)-1-{2-[3-(4-Bromo-phenyl)[1,2,4]oxadiazol-5-yl]-piperidin-1-yl}-2-phenoxy-ethanone,
(R)-2-(4-Hydroxy-phenoxy)-1-{2-[3-(4-methoxy-phenyl)-[1,2,4]oxadiazol-5-yl]-piperidin-1-yl}-ethanone,
(R)-2-(4-Chloro-phenoxy)-1-{2-[3-(4-methoxy-phenyl)-[1,2,4]oxadiazol-5-yl]-piperidin-1-yl}-ethanone,
(R)-2-(4-Hydroxymnethyl-phenoxy)-1-{2-[3-(4-methoxy-phenyl)-[1,2,4]oxadiazol-5-yl]-piperidin-1-yl}-ethanone,
(R)-2-(3-Chloro-phenoxy)-1-{2-[3-(4-methoxy-phenyl)-[1,2,4]oxadiazol-5-yl]-piperidin-1-yl}-ethanone,
(R)-2-(4-Fluoro-phenoxy)-1-{2-[3-(4-methoxy-phenyl)-[1,2,4]oxadiazol-5-yl]-piperidin-1-yl}-ethanone,
(R)-1-{2-[3-(4-Fluoro-phenyl)-[1,2,4]oxadiazol-5-yl]-piperidin-1-yl}-2-phenoxy-ethanone,
(R)-1-{2-[3-(4-Methane-sulfonyl-phenyl)-[1,2,4]oxadiazol-5-yl]-piperidin-1-yl}-2-phenoxy-ethanone,
(R)-4-{5-[1-(2-Phenoxy-acetyl)-piperidin-2-yl]-[1,2,4]oxadiazol-3-yl}-benzenesulfonamide,
(R)-2-(4-Fluoro-phenoxy)-1-[2-(3-pyridin-4-yl-[1,2,4]oxadiazol-5-yl)-piperidin-1-yl]-ethanone,
(R)-3-{5-[1-(2-Phenoxy-acetyl)-piperidin-2-yl]-[1,2,4]oxadiazol-3-yl}-benzoic acid methyl ester,
(R)-1-{2-[3-(3-Nitro-phenyl)-[1,2,4]oxadiazol-5-yl]-piperidin-1-yl}-2-phenoxy-ethanone,
(R)-1-{2-[3-(4-Nitro-phenyl)-[1,2,4]oxadiazol-5-yl]-piperidin-1-yl}-2-phenoxy-ethanone,
(R)-3-{5-[1-(2-Phenoxy-acetyl)-piperidin-2-yl]-[1,2,4]oxadiazol-3-yl}-benzenesulfonamide,
(R)-2-Phenoxy-1-[2-(3-pyrazin-2-yl-[1,2,4]oxadiazol-5-yl)-piperidin-1-yl]-ethanone,
(R)-1-(2-{3-[4-(Morpholine-4-sulfonyl)-phenyl]-[1,2,4]oxadiazol-5-yl}-piperidin-1-yl)-2-phenoxy-ethanone,
(R)-1-{2-[3-(6-Methoxy-pyridin-3-yl)-[1,2,4]oxadiazol-5-yl]-piperidin-1-yl}-2-phenoxy-ethanone,
(R)-1-{2-[3-(3-Hydroxymethyl-phenyl)-[1,2,4]oxadiazol-5-yl]-piperidin-1-yl}-2-phenoxy-ethanone,
(R)-6-{5-[1-(2-Phenoxy-acetyl)-piperidin-2-yl]-[1,2,4]oxadiazol-3-yl}-nicotinic acid allyl ester,
(R)-1-{2-[3-(4-Imidazol-1-yl-phenyl)-[1,2,4]oxadiazol-5-yl]-piperidin-1-yl}-2-phenoxy-ethanone, (R)-N-Methyl-4-{5-[1-(2-phenoxy-acetyl)-piperidin-2-yl]-[1,2,4]oxadiazol-3-yl}-benzenesulfonamide,
(R)-1-{2-[3-(6-Morpholin-4-yl-pyridin-3-yl)-[1,2,4]oxadiazol-5-yl]-piperidin-1-yl}-2-phenoxy-ethanone,
(R)-2-Phenoxy-1-{2-[3-(4-trifluoromethanesulfonyl-phenyl)-[1,2,4]oxadiazol-5-yl]-piperidin-1-yl}-ethanone,
(R)-2-Phenoxy-1-{2-[3-(4-trifluoromethyl-phenyl)-[1,2,4]oxadiazol-5-yl]-piperidin-1-yl}-ethanone,
(R)-1-{2-[3-(4-Chloro-phenyl)-[1,2,4]oxadiazol-5-yl]-piperidin-1-yl}-2-phenoxy-ethanone,
(R)-N-(4-{5-[1-(2-Phenoxy-acetyl)-piperidin-2-yl]-[1,2,4]oxadiazol-3-yl}-2-trifluoromethyl-phenyl)-acetamide,
(R)-1-{2-[3-(3-Methanesulfonyl-phenyl)-[1,2,4]oxadiazol-5-yl]-piperidin-1-yl}-2-phenoxy-ethanone,
(R)-1-{2-[3-(4-Methyl-3-nitro-phenyl)-[1,2,4]oxadiazol-5-yl]-piperidin-1-yl}-2-phenoxy-ethanone,
(R)-1-{2-[3-(4-Methoxy-3-nitro-phenyl)-[1,2,4]oxadiazol-5-yl]-piperidin-1-yl}-2-phenoxy-ethanone,
(R)-N-(2-Hydroxy-ethyl)-4-{5-[1-(2-phenoxy-acetyl)-piperidin-2-yl]-[1,2,4]oxadiazol-3-yl}-benzenesulfonamide,
(R)-N-(2-Methoxy-ethyl)-N-methyl-4-{5-[1-(2-phenoxy-acetyl)-piperidin-2-yl]-[1,2,4]oxadiazol-3-yl}-benzenesulfonamide,
(R)-N,N-Dimethyl-4-{5-[1-(2-phenoxy-acetyl)-piperidin-2-yl]-[1,2,4]oxadiazol-3-yl}-benzenesulfonamide,
(R)-N,N-Diethyl-4-{5-[1-(2-phenoxy-acetyl)-piperidin-2-yl]-[1,2,4]oxadiazol-3-yl}-benzenesulfonamide,
(R)-1-{2-[3-(2-Morpholin-4-yl-pyridin-4-yl)-[1,2,4]oxadiazol-5-yl]-piperidin-1-yl}-2-phenoxy-ethanone,
(R)-2-Phenoxy-1-{2-[3-(3,4,5,6-tetrahydro-2H-[1,2']bipyridinyl-4'-yl)-[1,2,4]oxadiazol-5-yl]-piperidin-1-yl}-ethanone,
(R)-2-Phenoxy-1-{2-[3-(2-thiomorpholin-4-yl-pyridin-4-yl)-[1,2,4]oxadiazol-5-yl]-piperidin-1-yl}-ethanone,
(R)-1-{2-[3-(2-Diethylamino-pyridin-4-yl)-[1,2,4]oxadiazol-5-yl]-piperidin-1-yl}-2-phenoxy-ethanone,
(R)-4-{5-[1-(2-Phenoxy-acetyl)-piperidin-2-yl]-[1,2,4]oxadiazol-3-yl}-pyridine-2-carboxylic acid ethyl ester,
(R)-1-(2-{3-[6-(4-Acetyl-piperazin-1-yl)-pyridin-3-yl]-[1,2,4]oxadiazol-5-yl}-piperidin-1-yl)-2-phenoxy-ethanone,
(R)-1-{2-[3-(2-Imidazol-1-yl-pyridin-4-yl)-[1,2,4]oxadiazol-5-yl]-piperidin-1-yl}-2-phenoxy-ethanone,
(R)-1-(3-{5-[1-(2-Phenoxy-acetyl)-piperidin-2-yl]-[1,2,4]oxadiazol-3-yl}-phenyl)-piperidin-2-one,
(R)-1-(2-{3-[4-(3H-Imidazol-4-yl)-phenyl]-[1,2,4]oxadiazol-5-yl}-piperidin-1-yl)-2-phenoxy-ethanone,
(R)-1-(2-{3-[4-(2-Methyl-imidazol-1-yl)-phenyl]-[1,2,4]oxadiazol-5-yl}-piperidin-1-yl)-2-phenoxy-ethanone,
(R)-2-Phenoxy-1-{2-[3-(2-pyrazol-1-yl-pyridin-4-yl)-[1,2,4]oxadiazol-5-yl]-piperidin-1-yl}-ethanone,
(R)-4-(5-{5-[1-(2-Phenoxy-acetyl)-piperidin-2-yl]-[1,2,4]oxadiazol-3-yl}-pyridin-2-yl)-piperazin-2-one,
(R)-2-Phenoxy-1-(2-{3-[4-(1H-tetrazol-5-yl)-phenyl]-[1,2,4]oxadiazol-5-yl}-piperidin-1-yl)-ethanone,
(R)-1-{2-[3-(1H-Indazol-5-yl)-[1,2,4]oxadiazol-5-yl]-piperidin-1-yl}-2-phenoxy-ethanone,
(R)-1-{2-[3-(1H-Indazol-6-yl)-[1,2,4]oxadiazol-5-yl]-piperidin-1-yl}-2-phenoxy-ethanone,
(R)-1-{2-[3-(4-Fluoro-3-trifluoromethyl-phenyl)-[1,2,4]oxadiazol-5-yl]-piperidin-1-yl}-2-phenoxy-ethanone,
(R)-6-{5-[1-(2-Phenoxy-acetyl)-piperidin-2-yl]-[1,2,4]oxadiazol-3-yl}-1,3-dihydro-indol-2-one,
(R)-5-{5-[1-(2-Phenoxy-acetyl)-piperidin-2-yl]-[1,2,4]oxadiazol-3-yl}-1,3-dihydro-benzoimidazol-2-one, (R)-5-{5-[1-(2-Phenoxy-acetyl)-piperidin-2-yl]-[1,2,4]
oxadiazol-3-yl}-1,3-dihydro-indol-2-one,
(R)-1-{2-[3-(1H-Benzotriazol-5-yl)-[1,2,4]oxadiazol-5-
yl]-piperidin-1-yl}-2-phenoxy-ethanone,
(R)-1-{2-[3-(1H-Benzoimidazol-5-yl)-[1,2,4]oxadiazol-
5-yl]-piperidin-1-yl}-2-phenoxy-ethanone,
(R)-1-(2-{3-[6-(1,1-Dioxo-thiomorpholin-4-yl)-pyridin-
3-yl]-[1,2,4]oxadiazol-5-yl}-piperidin-1-yl)-2-phe-
noxy-ethanone,
(R)-N-(4-{5-[1-(2-Phenoxy-acetyl)-piperidin-2-yl]-[1,2,
4]oxadiazol-3-yl}-pyridin-2-yl)-acetamide,
(R)-1-{2-[3-(6-Benzyloxy-pyridin-3-yl)-[1,2,4]oxadia-
zol-5-yl]-piperidin-1-yl}-2-phenoxy-ethanone,
(R)-5-{5-[1-(2-Phenoxy-acetyl)-piperidin-2-yl]-[1,2,4]
oxadiazol-3-yl}-nicotinic acid ethyl ester,
(R)-5-{5-[1-(2-Phenoxy-acetyl)-piperidin-2-yl]-[1,2,4]
oxadiazol-3-yl}-1H-pyridin-2-one,
(R)-2-Phenoxy-1-[2-(5-phenyl-2H-[1,2,4]triazol-3-yl)-
piperidin-1-yl]-ethanone,
(R)-1-{2-[5-(4-Methanesulfonyl-phenyl)-2H-[1,2,4]tria-
zol-3-yl]-piperidin-1-yl}-2-phenoxy-ethanone,
(R)-1-{2-[5-(3,4-Dimethoxy-phenyl)-2H-[1,2,4]triazol-
3-yl]-piperidin-1-yl}-2-phenoxy-ethanone,
(R)-1-{2-[5-(3,4-Dichloro-phenyl)-2H-[1,2,4]triazol-3-
yl]-piperidin-1-yl}-2-phenoxyethanone,
(R)-1-{2-[5-(4-Fluoro-phenyl)-2H-[1,2,4]triazol-3-yl]-
piperidin-1-yl}-2-phenoxy-ethanone,
(R)-2-Phenoxy-1-{2-[5-(3-trifluoromethyl-phenyl)-2H-
[1,2,4]triazol-3-yl]-piperidin-1-yl}-ethanone,
(R)-1-{2-[5-(4-Methoxy-phenyl)-2H-[1,2,4]triazol-3-yl]-
piperidin-1-yl}-2-phenoxy-ethanone,
(R)-1-{2-[5-(3-Nitro-phenyl)-2H-[1,2,4]triazol-3-yl]-pip-
eridin-1-yl}-2-phenoxy-ethanone,
(R)-3-{5-[1-(2-Phenoxy-acetyl)-piperidin-2-yl]-1H-[1,2,
4]triazol-3-yl}-benzoic acid methyl ester,
(R)-1-{2-[5-(4-Fluoro-3-trifluoromethyl-phenyl)-2H-[1,
2,4]triazol-3-yl]-piperidin-1-yl}-2-phenoxy-ethanone,
(R)-6-{5-[1-(2-Phenoxy-acetyl)-piperidin-2-yl]-1H-[1,2,
4]triazol-3-yl}-1,3-dihydro-indol-2-one,
1-{3-[3-(4-Methoxy-phenyl)-[1,2,4]oxadiazol-5-yl]-mor-
pholin-4-yl}-2-phenoxy-ethanone,
(R)-4-{5-[1-(2-Phenoxy-acetyl)-piperidin-2-yl]-[1,2,4]
oxadiazol-3-yl}-benzoic acid,
(R)-3-{5-[1-(2-Phenoxy-acetyl)-piperidin-2-yl]-[1,2,4]
oxadiazol-3-yl}-benzoic acid,
(R)-6-{5-[1-(2-Phenoxy-acetyl)-piperidin-2-yl]-[1,2,4]
oxadiazol-3-yl}-nicotinic acid,
(R)-2-Fluoro-4-{5-[1-(2-phenoxy-acetyl)-piperidin-2-
yl]-[1,2,4]oxadiazol-3-yl}-benzoic acid,
(R)-5-{5-[1-(2-Phenoxy-acetyl)-piperidin-2-yl]-[1,2,4]
oxadiazol-3-yl}-pyridine-2-carboxylic acid,
(R)-4-{5-[1-(2-Phenoxy-acetyl)-piperidin-2-yl]-[1,2,4]
oxadiazol-3-yl}-pyridine-2-carboxylic acid,
(R)-3-{5-[1-(2-Phenoxy-acetyl)-piperidin-2-yl]-1H-[1,2,
4]triazol-3-yl}-benzoic acid,
(R)-5-{5-[1-(2-Phenoxy-acetyl)-piperidin-2-yl]-[1,2,4]
oxadiazol-3-yl}-nicotinic acid,
1-(2-{3-[4-(Morpholine-4-carbonyl)-phenyl]-[1,2,4]oxa-
diazol-5-yl}-piperidin-1-yl)-2-phenoxy-ethanone,
(R)-1-(2-{3-[4-(3-Hydroxy-pyrrolidine-1-carbonyl)-phe-
nyl]-[1,2,4]oxadiazol-5-yl}-piperidin-1-yl)-2-phe-
noxy-ethanone,
(R)-N,N-Diethyl-4-{5-[1-(2-phenoxy-acetyl)-piperidin-
2-yl]-[1,2,4]oxadiazol-3-yl}-benzamide,
(R)-N-Methyl-4-{5-[1-(2-phenoxy-acetyl)-piperidin-2-
yl]-[1,2,4]oxadiazol-3-yl}-benzamide,
(R)-N,N-Dimethyl-4-{5-[1-(2-phenoxy-acetyl)-piperi-
din-2-yl]-[1,2,4]oxadiazol-3-yl}-benzamide,
(R)-N-Ethyl-4-{5-[1-(2-phenoxy-acetyl)-piperidin-2-yl]-
[1,2,4]oxadiazol-3-yl}-benzamide,
(R)-N-Cyclopropyl-4-{5-[1-(2-phenoxy-acetyl)-piperi-
din-2-yl]-[1,2,4]oxadiazol-3-yl}-benzamide,
(R)-N-(2-Hydroxy-ethyl)-4-{5-[1-(2-phenoxy-acetyl)-pi-
peridin-2-yl]-[1,2,4]oxadiazol-3-yl}-benzamide,
(R)-N-(2-Methoxy-ethyl)-N-methyl-4-{5-[1-(2-phenoxy-
acetyl)-piperidin-2-yl]-[1,2,4]oxadiazol-3-yl}-benza-
mide,
(R)-N-Methyl-3-{5-[1-(2-phenoxy-acetyl)-piperidin-2-
yl]-[1,2,4]oxadiazol-3-yl}-benzamide,
(R)-N,N-Dimethyl-3-{5-[1-(2-phenoxy-acetyl)-piperi-
din-2-yl]-[1,2,4]oxadiazol-3-yl}-benzamide,
(R)-N-Ethyl-3-{5-[1-(2-phenoxy-acetyl)-piperidin-2-yl]-
[1,2,4]oxadiazol-3-yl}-benzamide,
(R)-N-Cyclopropyl-3-{5-[1-(2-phenoxy-acetyl)-piperi-
din-2-yl]-[1,2,4]oxadiazol-3-yl}-benzamide,
(R)-N-(2-Hydroxy-ethyl)-3-{5-[1-(2-phenoxy-acetyl)-pi-
peridin-2-yl]-[1,2,4]oxadiazol-3-yl}-benzamide,
(R)-N-(2-Methoxy-ethyl)-N-methyl-3-{5-[1-(2-phenoxy-
acetyl)-piperidin-2-yl]-[1,2,4]oxadiazol-3-yl}-benza-
mide,
(R)-1-(2-{3-[3-(Morpholine-4-carbonyl)-phenyl]-[1,2,4]
oxadiazol-5-yl}-piperidin-1-yl)-2-phenoxy-ethanone,
(R)-1-(2-{3-[3-(3-Hydroxy-pyrrolidine-1-carbonyl)-phe-
nyl]-[1,2,4]oxadiazol-5-yl}-piperidin-1-yl)-2-phe-
noxy-ethanone,
(R)-N,N-Diethyl-3-{5-[1-(2-phenoxy-acetyl)-piperidin-
2-yl]-[1,2,4]oxadiazol-3-yl}-benzamide,
(R)-4-{5-[1-(2-Phenoxy-acetyl)-piperidin-2-yl]-[1,2,4]
oxadiazol-3-yl}-pyridine-2-carboxylic acid methyla-
mide,
(R)-4-{5-[1-(2-Phenoxy-acetyl)-piperidin-2-yl]-[1,2,4]
oxadiazol-3-yl}-pyridine-2-carboxylic acid dimethyla-
mide,
(R)-4-{5-[1-(2-Phenoxy-acetyl)-piperidin-2-yl]-[1,2,4]
oxadiazol-3-yl}-pyridine-2-carboxylic acid ethyla-
mide,
(R)-4-{5-[1-(2-Phenoxy-acetyl)-piperidin-2-yl]-[1,2,4]
oxadiazol-3-yl}-pyridine-2-carboxylic acid diethyla-
mide,
(R)-1-(2-{3-[2-(Morpholine-4-carbonyl)-pyridin-4-yl]-
[1,2,4]oxadiazol-5-yl}-piperidin-1-yl)-2-phenoxy-
ethanone,
(R)-1-(2-{3-[2-(3-Methanesulfonyl-pyrrolidine-1-carbo-
nyl)-pyridin-4-yl]-[1,2,4]oxadiazol-5-yl}-piperidin-1-
yl)-2-phenoxy-ethanone,
(R)-5-{5-[1-(2-Phenoxy-acetyl)-piperidin-2-yl]-[1,2,4]
oxadiazol-3-yl}-pyridine-2-carboxylic acid methyla-
mide,
(R)-N-Methyl-3-{5-[1-(2-phenoxy-acetyl)-piperidin-2-
yl]-1H-[1,2,4]triazol-3-yl}-benzamide,
(R)-N-Methyl-5-{5-[1-(2-phenoxy-acetyl)-piperidin-2-
yl]-[1,2,4]oxadiazol-3-yl}-nicotinamide,
(R)-N-Ethyl-5-{5-[1-(2-phenoxy-acetyl)-piperidin-2-yl]-
[1,2,4]oxadiazol-3-yl}-nicotinamide,
(R)-N-Diethyl-5-{5-[1-(2-phenoxy-acetyl)-piperidin-2-
yl]-[1,2,4]oxadiazol-3-yl}-nicotinamide,
(R)-N-Diethyl-5-{5-[1-(2-phenoxy-acetyl)-piperidin-2-
yl]-[1,2,4]oxadiazol-3-yl}-nicotinamide,
(R)-N-(2-Hydroxy-ethyl)-5-{5-[1-(2-phenoxy-acetyl)-pi-
peridin-2-yl]-[1,2,4]oxadiazol-3-yl}-nicotinamide,
(R)-N-(2-Methoxy-ethyl)-N-methyl-5-{5-[1-(2-phenoxy-
acetyl)-piperidin-2-yl]-[1,2,4]oxadiazol-3-yl}-nicoti-
namide, (R)-N-Cyclopropyl-5-{5-[1-(2-phenoxy-acetyl)-piperidin-2-yl]-[1,2,4]oxadiazol-3-yl}-nicotinamide,
(R)-1-(2-{3-[5-(3-Hydroxy-pyrrolidine-1-carbonyl)-pyridin-3-yl]-[1,2,4]oxadiazol-5-yl}-piperidin-1-yl)-2-phenoxy-ethanone,
(R)-4-{5-[1-(2-Phenoxy-acetyl)-piperidin-2-yl]-[1,2,4]oxadiazol-3-yl}-benzamide,
(R)-3-{5-[1-(2-Phenoxy-acetyl)-piperidin-2-yl]-[1,2,4]oxadiazol-3-yl}-benzamide,
(R)-4-{5-[1-(2-Phenoxy-acetyl)-piperidin-2-yl]-[1,2,4]oxadiazol-3-yl}-pyridine-2-carboxylic acid amide,
(R)-3-{5-[1-(2-Phenoxy-acetyl)-piperidin-2-yl]-1H-[1,2,4]triazol-3-yl}-benzamide,
5-{5-[1-(2-Phenoxy-acetyl)-piperidin-2-yl]-[1,2,4]oxadiazol-3-yl}-nicotinamide,
(R)-1-{2-[3-(3-Amino-phenyl)-[1,2,4]oxadiazol-5-yl]-piperidin-1-yl}-2-phenoxy-ethanone,
(R)-1-{2-[3-(4-Amino-phenyl)-[1,2,4]oxadiazol-5-yl]-piperidin-1-yl}-2-phenoxy-ethanone,
(R)-1-{2-[5-(3-Amino-phenyl)-2H-[1,2,4]triazol-3-yl]-piperidin-1-yl}-2-phenoxy-ethanone,
(R)-N-(3-{5-[1-(2-Phenoxy-acetyl)-piperidin-2-yl]-[1,2,4]oxadiazol-3-yl}-phenyl)-acetamide,
(R)-N-(4-{5-[1-(2-Phenoxy-acetyl)-piperidin-2-yl]-[1,2,4]oxadiazol-3-yl}-phenyl)-acetamide,
(R)-N-(5-{5-[1-(2-Phenoxy-acetyl)-piperidin-2-yl]-[1,2,4]oxadiazol-3-yl}-pyridin-2-yl)-acetamide,
(R)-N-(3-{5-[1-(2-Phenoxy-acetyl)-piperidin-2-yl]-1H-[1,2,4]triazol-3-yl}-phenyl)-acetamide,
(R)-N-(3-{5-[1-(2-Phenoxy-acetyl)-piperidin-2-yl]-[1,2,4]oxadiazol-3-yl}-phenyl)-methanesulfonamide,
(R)-N-(4-{5-[1-(2-Phenoxy-acetyl)-piperidin-2-yl]-[1,2,4]oxadiazol-3-yl}-phenyl)-methanesulfonamide,
(R)-(3-{5-[1-(2-Phenoxy-acetyl)-piperidin-2-yl]-[1,2,4]oxadiazol-3-yl}-phenyl)-carbamic acid allyl ester,
(R)-(4-{5-[1-(2-Phenoxy-acetyl)-piperidin-2-yl]-[1,2,4]oxadiazol-3-yl}-phenyl)-carbamic acid allyl ester,
(R)-N-(3-{5-[1-(2-Phenoxy-acetyl)-piperidin-2-yl]-1H-[1,2,4]triazol-3-yl}-phenyl)-methanesulfonamide,
(R)-1-Ethyl-3-(3-{5-[1-(2-phenoxy-acetyl)-piperidin-2-yl]-1H-[1,2,4]triazol-3-yl}-phenyl)-urea,
(R)-3-{5-[1-(2-Phenoxy-acetyl)-piperidin-2-yl]-1H-[1,2,4]triazol-3-yl}-benzonitrile, and
(R)-5-{5-[1-(2-Phenoxy-acetyl)-piperidin-2-yl]-[1,2,4]oxadiazol-3-yl}-nicotinonitrile,
and pharmaceutically acceptable salts and esters thereof.

34. The compound according to claim 1, selected from the group consisting of
(R)-1-{2-[3-(1H-Indazol-5-yl)-[1,2,4]oxadiazol-5-yl]-piperidin-1-yl}-2-phenoxy-ethanone,
(R)-1-{2-[3-(1H-Indazol-6-yl)-[1,2,4]oxadiazol-5-yl]-piperidin-1-yl}-2-phenoxy-ethanone,
(R)-6-{5-[1-(2-Phenoxy-acetyl)-piperidin-2-yl]-[1,2,4]oxadiazol-3-yl}-1,3-dihydro-indol-2-one,
(R)-5-{5-[1-(2-Phenoxy-acetyl)-piperidin-2-yl]-[1,2,4]oxadiazol-3-yl}-1,3-dihydro-benzoimidazol-2-one,
(R)-5-{5-[1-(2-Phenoxy-acetyl)-piperidin-2-yl]-[1,2,4]oxadiazol-3-yl}-1,3-dihydro-indol-2-one,
(R)-1-{2-[3-(1H-Benzotriazol-5-yl)-[1,2,4]oxadiazol-5-yl]-piperidin-1-yl}-2-phenoxy-ethanone,
(R)-1-{2-[3-(1H-Benzoimidazol-5-yl)-[1,2,4]oxadiazol-5-yl]-piperidin-1-yl}-2-phenoxy-ethanone,
(R)-1-{2-[5-(4-Fluoro-phenyl)-2H-[1,2,4]triazol-3-yl]-piperidin-1-yl}-2-phenoxy-ethanone,
(R)-2-Phenoxy-1-{2-[5-(3-trifluoromethyl-phenyl)-2H-[1,2,4]triazol-3-yl]-piperidin-1-yl}-ethanone,
(R)-3-{5-[1-(2-Phenoxy-acetyl)-piperidin-2-yl]-[1,2,4]oxadiazol-3-yl}-benzamide,
5-{5-[1-(2-Phenoxy-acetyl)-piperidin-2-yl]-[1,2,4]oxadiazol-3-yl}-nicotinamide,
(R)-N-(3-{5-[1-(2-Phenoxy-acetyl)-piperidin-2-yl]-1H-[1,2,4]triazol-3-yl}-phenyl)-acetamide, and
(R)-N-(3-{5-[1-(2-Phenoxy-acetyl)-piperidin-2-yl]-1H-[1,2,4]triazol-3-yl}-phenyl)-methanesulfonamide,
and pharmaceutically acceptable salts and esters thereof.

35. The compound according to claim 1, selected from the group consisting of
1-{(R)-2-[3-(2-Methyl-1H-benzoimidazol-5-yl)-[1,2,4]oxadiazol-5-yl]-piperidin-1-yl}-2-phenoxy-ethanone,
1-{(R)-2-[3-(2-Amino-pyridin-4-yl)-[1,2,4]oxadiazol-5-yl]-piperidin-1-yl}-2-phenoxy-ethanone,
1-{(R)-2-[3-(3-Hydroxy-phenyl)-[1,2,4]oxadiazol-5-yl]-piperidin-1-yl}-2-phenoxy-ethanone,
4-{5-[(R)-1-(2-Phenoxy-acetyl)-piperidin-2-yl]-[1,2,4]oxadiazol-3-yl}-1H-pyridin-2-one,
1-{(R)-2-[3-(4-Hydroxy-phenyl)-[1,2,4]oxadiazol-5-yl]-piperidin-1-yl}-2-phenoxy-ethanone,
3-{5-[1-(2-Phenoxy-acetyl)-piperidin-2-yl]-[1,2,4]oxadiazol-3-yl}-phenylboronic acid,
4-(2-Oxo-2-{(R)-2-[3-(2-oxo-2,3-dihydro-1H-indol-5-yl)-[1,2,4]oxadiazol-5-yl]-piperidin-1-yl}-ethoxy)-benzonitrile,
4-(2-{(R)-2-[3-(4-Methoxy-phenyl)-[1,2,4]oxadiazol-5-yl]-piperidin-1-yl}-2-oxo-ethoxy)-benzonitrile,
2-Methyl-5-{5-[(R)-1-(2-phenoxy-acetyl)-piperidin-2-yl]-[1,2,4]oxadiazol-3-yl}-3H-pyrimidin-4-one,
1-[(R)-2-(3-Furan-2-yl-[1,2,4]oxadiazol-5-yl)-piperidin-1-yl]-2-phenoxy-ethanone,
1-[(R)-2-(3-Imidazo[1,2-a]pyridin-2-yl-[1,2,4]oxadiazol-5-yl)-piperidin-1-yl]-2-phenoxy-ethanone,
1-{(R)-2-[3-(4-Methyl-[1,2,3]thiadiazol-5-yl)-[1,2,4]oxadiazol-5-yl]-piperidin-1-yl}-2-phenoxy-ethanone,
1-{(R)-2-[3-(2,5-Dimethyl-2H-pyrazol-3-yl)-[1,2,4]oxadiazol-5-yl]-piperidin-1-yl}-2-phenoxy-ethanone,
2-Phenoxy-1-{(R)-2-[3-(1H-pyrazol-4-yl)-[1,2,4]oxadiazol-5-yl]-piperidin-1-yl}-ethanone,
1-{(R)-2-[3-(5-Methyl-isoxazol-3-yl)-[1,2,4]oxadiazol-5-yl]-piperidin-1-yl}-2-phenoxy-ethanone,
2-Phenoxy-1-{(R)-2-[3-(1H-pyrazol-3-yl)-[1,2,4]oxadiazol-5-yl]-piperidin-1-yl}-ethanone,
5-{5-[(R)-1-(2-Phenoxy-acetyl)-piperidin-2-yl]-[1,2,4]oxadiazol-3-yl}-1H-pyrimidine-2,4-dione,
1-{(R)-2-[3-(6-Amino-pyridin-3-yl)-[1,2,4]oxadiazol-5-yl]-piperidin-1-yl}-2-phenoxy-ethanone,
1-[(R)-2-(3-Imidazo[1,2-a]pyridin-6-yl-[1,2,4]oxadiazol-5-yl)-piperidin-1-yl]-2-phenoxy-ethanone,
6-{5-[(R)-1-(2-Phenoxy-acetyl)-piperidin-2-yl]-[1,2,4]oxadiazol-3-yl}-4H-benzo[1,4]oxazin-3-one,
6-{5-[(R)-1-(2-Phenoxy-acetyl)-piperidin-2-yl]-[1,2,4]oxadiazol-3-yl}-1,4-dihydro-benzo[d][1,3]oxazin-2-one,
1-((R)-2-{3-[3-(1,1-Dioxo-1λ6-isothiazolidin-2-yl)-phenyl]-[1,2,4]oxadiazol-5-yl}-piperidin-1-yl)-2-phenoxy-ethanone,
1-(3-{5-[(R)-1-(2-Phenoxy-acetyl)-piperidin-2-yl]-[1,2,4]oxadiazol-3-yl}-phenyl)-pyrrolidin-2-one,
1-(3-{5-[(R)-1-(2-Phenoxy-acetyl)-piperidin-2-yl]-[1,2,4]oxadiazol-3-yl}-phenyl)-imidazolidine-2,4-dione,
4-(3-{5-[(R)-1-(2-Phenoxy-acetyl)-piperidin-2-yl]-[1,2,4]oxadiazol-3-yl}-phenyl)-2,4-dihydro-[1,2,4]triazol-3-one, 1-(3-Fluoro-5-{5-[(R)-1-(2-phenoxy-acetyl)-piperidin-2-yl]-[1,2,4]oxadiazol-3-yl}-phenyl)-pyrrolidine-2,5-dione,
5-{5-[(R)-1-(2-Phenoxy-acetyl)-piperidin-2-yl]-1H-[1,2,4]triazol-3-yl}-1,3-dihydro-indol-2-one,
1-{(R)-2-[5-(1H-Indazol-5-yl)-2H-[1,2,4]triazol-3-yl]-piperidin-1-yl}-2-phenoxy-ethanone,
1-{(R)-2-[5-(1H-Indol-5-yl)-2H-[1,2,4]triazol-3-yl]-piperidin-1-yl}-2-phenoxy-ethanone,
1-{(R)-2-[5-(3H-Benzotriazol-5-yl)-2H-[1,2,4]triazol-3-yl]-piperidin-1-yl}-2-phenoxy-ethanone,
5-{5-[(R)-1-(2-Phenoxy-acetyl)-piperidin-2-yl]-1H-[1,2,4]triazol-3-yl}-1,3-dihydro-benzoimidazol-2-one,
1-{(R)-2-[5-(2-Methyl-1H-benzoimidazol-5-yl)-2H-[1,2,4]triazol-3-yl]-piperidin-1-yl}-2-phenoxy-ethanone,
1-{(R)-2-[5-(2-Amino-pyridin-4-yl)-2H-[1,2,4]triazol-3-yl]-piperidin-1-yl}-2-phenoxy-ethanone,
5-(3-{5-[(R)-1-(2-Phenoxy-acetyl)-piperidin-2-yl]-1H-[1,2,4]triazol-3-yl}-phenyl)-3H-[1,3,4]oxadiazol-2-one,
1-{(R)-2-[5-(3-[1,3,4]Oxadiazol-2-yl-phenyl)-2H-[1,2,4]triazol-3-yl]-piperidin-1-yl}-2-phenoxy-ethanone,
3-{5-[1-(2-Phenoxy-acetyl)-piperidin-2-yl]-1H-[1,2,4]triazol-3-yl}-phenylboronic acid,
6-{5-[(R)-1-(2-Phenoxy-acetyl)-piperidin-2-yl]-1H-[1,2,4]triazol-3-yl}-4H-benzo[1,4]oxazin-3-one,
1-[(R)-2-(5-Imidazo[1,2-a]pyridin-6-yl-2H-[1,2,4]triazol-3-yl)-piperidin-1-yl]-2-phenoxy-ethanone,
1-{(R)-2-[5-(6-Amino-pyridin-3-yl)-2H-[1,2,4]triazol-3-yl]-piperidin-1-yl}-2-phenoxy-ethanone,
1-{(R)-2-[5-(1H-Benzoimidazol-5-yl)-2H-[1,2,4]triazol-3-yl]-piperidin-1-yl}-2-phenoxy-ethanone,
2-Phenoxy-1-[(R)-2-(5-pyridin-3-yl-2H-[1,2,4]triazol-3-yl)-piperidin-1-yl]-ethanone,
1-{(R)-2-[5-(3,5-Dimethyl-isoxazol-4-yl)-2H-[1,2,4]triazol-3-yl]-piperidin-1-yl}-2-phenoxy-ethanone,
2-Phenoxy-1-[(R)-2-(5-thiophen-2-yl-2H-[1,2,4]triazol-3-yl)-piperidin-1-yl]-ethanone,
2-Phenoxy-1-[(R)-2-(5-pyrimidin-2-yl-2H-[1,2,4]triazol-3-yl)-piperidin-1-yl]-ethanone,
1-{(R)-2-[5-(4-Methyl-oxazol-5-yl)-2H-[1,2,4]triazol-3-yl]-piperidin-1-yl}-2-phenoxy-ethanone,
2-Phenoxy-1-[(R)-2-(5-pyrazin-2-yl-2H-[1,2,4]triazol-3-yl)-piperidin-1-yl]-ethanone,
1-{(R)-2-[5-(2-Fluoro-phenyl)-2H-[1,2,4]triazol-3-yl]-piperidin-1-yl}-2-phenoxy-ethanone,
1-{(R)-2-[5-(3,5-Difluoro-phenyl)-2H-[1,2,4]triazol-3-yl]-piperidin-1-yl}-2-phenoxy-ethanone,
1-{(R)-2-[5-(2-Methyl-pyridin-4-yl)-2H-[1,2,4]triazol-3-yl]-piperidin-1-yl}-2-phenoxy-ethanone,
1-{(R)-2-[5-(3-Fluoro-phenyl)-2H-[1,2,4]triazol-3-yl]-piperidin-1-yl}-2-phenoxy-ethanone,
1-{(R)-2-[5-(3,4-Difluoro-phenyl)-2H-[1,2,4]triazol-3-yl]-piperidin-1-yl}-2-phenoxy-ethanone,
6-{5-[(R)-1-(2-Phenoxy-acetyl)-piperidin-2-yl]-1H-[1,2,4]triazol-3-yl}-1,4-dihydro-benzo[d][1,3]oxazin-2-one,
7-{5-[(R)-1-(2-Phenoxy-acetyl)-piperidin-2-yl]-1H-[1,2,4]triazol-3-yl}-3,4-dihydro-1H-quinazolin-2-one,
1-(3-{5-[(R)-1-(2-Phenoxy-acetyl)-piperidin-2-yl]-1H-[1,2,4]triazol-3-yl}-phenyl)-imidazolidine-2,4-dione,
(3-{5-[(R)-1-(2-Phenoxy-acetyl)-piperidin-2-yl]-[1,2,4]oxadiazol-3-yl}-phenoxy)-acetic acid,
2-Phenoxy-1-((R)-2-{5-[3-(piperidine-1-carbonyl)-phenyl]-2H-[1,2,4]triazol-3-yl}-piperidin-1-yl)-ethanone,
1-((R)-2-{5-[3-(Morpholine-4-carbonyl)-phenyl]-2H-[1,2,4]triazol-3-yl}-piperidin-1-yl)-2-phenoxy-ethanone,
1-((R)-2-{5-[3-(4-Methyl-piperazine-1-carbonyl)-phenyl]-2H-[1,2,4]triazol-3-yl}-piperidin-1-yl)-2-phenoxy-ethanone,
4-(3-{5-[(R)-1-(2-Phenoxy-acetyl)-piperidin-2-yl]-1H-[1,2,4]triazol-3-yl}-benzoyl)-piperazin-2-one,
N-(2-Methoxy-ethyl)-N-methyl-3-{5-[(R)-1-(2-phenoxy-acetyl)-piperidin-2-yl]-1H-[1,2,4]triazol-3-yl}-benzamide,
1-((R)-2-{5-[3-(4-Acetyl-piperazine-1-carbonyl)-phenyl]-2H-[1,2,4]triazol-3-yl}-piperidin-1-yl)-2-phenoxy-ethanone,
1-(3-{5-[(R)-1-(2-Phenoxy-acetyl)-piperidin-2-yl]-1H-[1,2,4]triazol-3-yl}-benzoyl)-piperidine-4-carboxylic acid,
1-(3-{5-[(R)-1-(2-Phenoxy-acetyl)-piperidin-2-yl]-1H-[1,2,4]triazol-3-yl}-benzoyl)-piperidine-4-carboxylic acid amide,
2-Phenoxy-1-((R)-2-{5-[3-(thiazolidine-3-carbonyl)-phenyl]-2H-[1,2,4]triazol-3-yl}-piperidin-1-yl)-ethanone,
N-(2-Dimethylamino-ethyl)-N-methyl-3-{5-[(R)-1-(2-phenoxy-acetyl)-piperidin-2-yl]-1H-[1,2,4]triazol-3-yl}-benzamide,
2-Phenoxy-1-((R)-2-{5-[3-(thiomorpholine-4-carbonyl)-phenyl]-2H-[1,2,4]triazol-3-yl}-piperidin-1-yl)-ethanone,
4-(3-{5-[(R)-1-(2-Phenoxy-acetyl)-piperidin-2-yl]-1H-[1,2,4]triazol-3-yl}-benzoyl)-piperazine-1-carboxylic acid ethyl ester,
N-(2-Hydroxy-ethyl)-3-{5-[(R)-1-(2-phenoxy-acetyl)-piperidin-2-yl]-1H-[1,2,4]triazol-3-yl}-benzamide,
N-Methyl-3-{5-[(R)-1-(2-phenoxy-acetyl)-piperidin-2-yl]-1H-[1,2,4]triazol-3-yl}-N-(2-pyridin-2-yl-ethyl)-benzamide,
N-(2-Cyano-ethyl)-N-cyclopropyl-3-{5-[(R)-1-(2-phenoxy-acetyl)-piperidin-2-yl]-1H-[1,2,4]triazol-3-yl}-benzamide,
1-(3-{5-[(R)-1-(2-Phenoxy-acetyl)-piperidin-2-yl]-1H-[1,2,4]triazol-3-yl}-benzoyl)-4-phenyl-piperidine-4-carbonitrile,
1-((R)-2-{5-[3-(4-Hydroxy-piperidine-1-carbonyl)-phenyl]-2H-[1,2,4]triazol-3-yl}-piperidin-1-yl)-2-phenoxy-ethanone,
8-(3-{5-[(R)-1-(2-Phenoxy-acetyl)-piperidin-2-yl]-1H-[1,2,4]triazol-3-yl}-benzoyl)-1,3,8-triaza-spiro[4.5]decane-2,4-dione,
1-(2-{5-[3-(Spiro(1-Phtalan)-piperidine-4-carbonyl)-phenyl]-2H-[1,2,4]triazol-3-yl}-piperidin-1-yl)-2-phenoxy-ethanone,
2-Phenoxy-1-((R)-2-{5-[3-(3-pyridin-4-yl-pyrrolidine-1-carbonyl)-phenyl]-2H-[1,2,4]triazol-3-yl}-piperidin-1-yl)-ethanone,
1-((R)-2-{5-[3-(3-Methanesulfonyl-pyrrolidine-1-carbonyl)-phenyl]-2H-[1,2,4]triazol-3-yl}-piperidin-1-yl)-2-phenoxy-ethanone,
1-((R)-2-{5-[3-((S)-3-Ethoxy-pyrrolidine-1-carbonyl)-phenyl]-2H-[1,2,4]triazol-3-yl}-piperidin-1-yl)-2-phenoxy-ethanone,
1-((R)-2-{5-[3-((S)-3-Hydroxy-pyrrolidine-1-carbonyl)-phenyl]-2H-[1,2,4]triazol-3-yl}-piperidin-1-yl)-2-phenoxy-ethanone,
5-{5-[(R)-1-(2-Phenoxy-acetyl)-piperidin-2-yl]-1H-[1,2,4]triazol-3-yl}-nicotinamide,
2-(3-{5-[1-(2-Phenoxy-acetyl)-piperidin-2-yl]-[1,2,4]oxadiazol-3-yl}-phenoxy)-acetamide,
N-(3-Fluoro-5-{5-[(R)-1-(2-phenoxy-acetyl)-piperidin-2-yl]-[1,2,4]oxadiazol-3-yl}-phenyl)-acetamide, N-(2-Fluoro-5-{5-[(R)-1-(2-phenoxy-acetyl)-piperidin-2-yl]-[1,2,4]oxadiazol-3-yl}-phenyl)-acetamide,
N-(3-{5-[(R)-1-(2-Phenoxy-acetyl)-piperidin-2-yl]-1H-[1,2,4]triazol-3-yl}-phenyl)-propionamide,
N-(3-{5-[(R)-1-(2-Phenoxy-acetyl)-piperidin-2-yl]-1H-[1,2,4]triazol-3-yl}-phenyl)-isobutyramide,
N-(4-Fluoro-3-{5-[(R)-1-(2-phenoxy-acetyl)-piperidin-2-yl]-1H-[1,2,4]triazol-3-yl}-phenyl)-acetamide,
N-(3-Fluoro-5-{5-[(R)-1-(2-phenoxy-acetyl)-piperidin-2-yl]-1H-[1,2,4]triazol-3-yl}-phenyl)-acetamide,
N-(2-Fluoro-5-{5-[(R)-1-(2-phenoxy-acetyl)-piperidin-2-yl]-1H-[1,2,4]triazol-3-yl}-phenyl)-acetamide,
N-(4-{5-[(R)-1-(2-Phenoxy-acetyl)-piperidin-2-yl]-1H-[1,2,4]triazol-3-yl}-pyridin-2-yl)-acetamide,
1-(3-{5-[(R)-1-(2-Phenoxy-acetyl)-piperidin-2-yl]-1H-[1,2,4]triazol-3-yl}-phenyl)-azetidin-2-one,
1-(3-{5-[1-(2-Phenoxy-acetyl)-piperidin-2-yl]-1H-[1,2,4]triazol-3-yl}-phenyl)-pyrrolidine-2,5-dione,
2-Phenoxy-1-[(R)-2-(5-pyridazin-4-yl-[1,2,4]oxadiazol-3-yl)-piperidin-1-yl]-ethanone,
4-{3-[(R)-1-(2-Phenoxy-acetyl)-piperidin-2-yl]-[1,2,4]oxadiazol-5-yl}-benzonitrile,
1-{(R)-2-[5-(3-Amino-pyrazin-2-yi)-[1,2,4]oxadiazol-3-yl]-piperidin-1-yl}-2-phenoxy-ethanone,
3-{3-[(R)-1-(2-Phenoxy-acetyl)-piperidin-2-yl]-[1,2,4]oxadiazol-5-yl}-benzonitrile,
1-{(R)-2-[5-(2-Hydroxy-pyridin-3-yl)-[1,2,4]oxadiazol-3-yl]-piperidin-1-yl}-2-phenoxy-ethanone,
1-{(R)-2-[5-(5-Amino-pyridin-3-yl)-[1,2,4]oxadiazol-3-yl]-piperidin-1-yl}-2-phenoxy-ethanone,
1-{(R)-2-[5-(2-Hydroxy-pyridin-4-yl)-[1,2,4]oxadiazol-3-yl]-piperidin-1-yl}-2-phenoxy-ethanone,
1-{(R)-2-[5-(2-Hydroxy-6-methyl-pyridin-4-yl)-[1,2,4]oxadiazol-3-yl]-piperidin-1-yl}-2-phenoxy-ethanone,
1-{(R)-2-[5-(4-Hydroxy-pyridin-2-yl)-[1,2,4]oxadiazol-3-yl]-piperidin-1-yl}-2-phenoxy-ethanone,
1-{(R)-2-[5-(2-Amino-5-chloro-pyrimidin-4-yl)-[1,2,4]oxadiazol-3-yl]-piperidin-1-yl}-2-phenoxy-ethanone,
2-Phenoxy-1-[(R)-2-(5-pyrazin-2-yl-[1,2,4]oxadiazol-3-yl)-piperidin-1-yl]-ethanone,
2-Phenoxy-1-{(R)-2-[5-(4-[1,2,4]triazol-1-yl-phenyl)-[1,2,4]oxadiazol-3-yl]-piperidin-1-yl}-ethanone,
2-Phenoxy-1-{(R)-2-[5-(4-tetrazol-1-yl-phenyl)-[1,2,4]oxadiazol-3-yl]-piperidin-1-yl}-ethanone,
1-{(R)-2-[5-(1H-Benzoimidazol-4-yl)-[1,2,4]oxadiazol-3-yl]-piperidin-1-yl}-2-phenoxy-ethanone,
1-{(R)-2-[5-(4-Acetyl-phenyl)-[1,2,4]oxadiazol-3-yl]-piperidin-1-yl}-2-phenoxy-ethanone,
1-{(R)-2-[5-(6-Hydroxy-pyridin-2-yl)-[1,2,4]oxadiazol-3-yl]-piperidin-1-yl}-2-phenoxy-ethanone,
1-{(R)-2-[5-(5-Methyl-pyrazin-2-yl)-[1,2,4]oxadiazol-3-yl]-piperidin-1-yl}-2-phenoxy-ethanone,
2-Phenoxy-1-[(R)-2-(5-quinoxalin-2-yl-[1,2,4]oxadiazol-3-yl)-piperidin-1-yl]-ethanone,
1-{(R)-2-[5-(3-Methanesulfonyl-phenyl)-[1,2,4]oxadiazol-3-yl]-piperidin-1-yl}-2-phenoxy-ethanone,
1-{(R)-2-[5-(6-Chloro-pyridin-3-yl)-[1,2,4]oxadiazol-3-yl]-piperidin-1-yl}-2-phenoxy-ethanone,
1-[(R)-2-(5-Benzothiazol-6-yl-[1,2,4]oxadiazol-3-yl)-piperidin-1-yl]-2-phenoxy-ethanone,
2-Phenoxy-1-{(R)-2-[5-(2,4,5-trifluoro-phenyl)-[1,2,4]oxadiazol-3-yl]-piperidin-1-yl}-ethanone,
2-Phenoxy-1-{(R)-2-[5-(6-trifluoromethyl-pyridin-3-yl)-[1,2,4]oxadiazol-3-yl]-piperidin-1-yl}-ethanone,
1-[(R)-2-(5-Benzo[1,2,3]thiadiazol-5-yl-[1,2,4]oxadiazol-3-yl)-piperidin-1-yl]-2-phenoxy-ethanone,
1-[(R)-2-(5-[1,8]Naphthyridin-2-yl-[1,2,4]oxadiazol-3-yl)-piperidin-1-yl]-2-phenoxy-ethanone,
1-[(R)-2-(5-[1,6]Naphthyridin-2-yl-[1,2,4]oxadiazol-3-yl)-piperidin-1-yl]-2-phenoxy-ethanone,
1-[(R)-2-(5-Cinnolin-4-yl-[1,2,4]oxadiazol-3-yl)-piperidin-1-yl]-2-phenoxy-ethanone,
1-{(R)-2-[5-(1H-Benzotriazol-5-yl)-[1,2,4]oxadiazol-3-yl]-piperidin-1-yl}-2-phenoxy-ethanone,
1-{(R)-2-[5-(1H-Benzoimidazol-5-yl)-[1,2,4]oxadiazol-3-yl]-piperidin-1-yl}-2-phenoxy-ethanone,
1-{(R)-2-[5-(3,6-Dichloro-pyridazin-4-yl)-[1,2,4]oxadiazol-3-yl]-piperidin-1-yl}-2-phenoxy-ethanone,
6-{3-[(R)-1-(2-Phenoxy-acetyl)-piperidin-2-yl]-[1,2,4]oxadiazol-5-yl}-4H-benzo[1,4]oxazin-3-one,
1-{(R)-2-[5-(3H-Imidazo[4,5-b]pyridin-6-yl)-[1,2,4]oxadiazol-3-yl]-piperidin-1-yl}-2-phenoxy-ethanone,
N-(4-{3-[(R)-1-(2-Phenoxy-acetyl)-piperidin-2-yl]-[1,2,4]oxadiazol-5-yl}-pyridin-2-yl)-acetamide,
1-{(R)-2-[5-(6-Chloro-3-hydroxy-pyridazin-4-yl)-[1,2,4]oxadiazol-3-yl]-piperidin-1-yl}-2-phenoxy-ethanone,
6-{3-[(R)-1-(2-Phenoxy-acetyl)-piperidin-2-yl]-[1,2,4]oxadiazol-5-yl}-1,4-dihydro-quinoxaline-2,3-dione,
1-{(R)-2-[5-(6-Hydroxy-pyridin-3-yl)-[1,2,4]oxadiazol-3-yl]-piperidin-1-yl}-2-phenoxy-ethanone,
7-{3-[(R)-1-(2-Phenoxy-acetyl)-piperidin-2-yl]-[1,2,4]oxadiazol-5-yl}-3,4-dihydro-1H-quinoxalin-2-one,
1-{(R)-2-[5-(6-Amino-pyridin-2-yl)-[1,2,4]oxadiazol-3-yl]-piperidin-1-yl}-2-phenoxy-ethanone,
6-{3-[(R)-1-(2-Phenoxy-acetyl)-piperidin-2-yl]-[1,2,4]oxadiazol-5-yl}-nicotinonitrile,
5-{3-[(R)-1-(2-Phenoxy-acetyl)-piperidin-2-yl]-[1,2,4]oxadiazol-5-yl}-pyridine-2-carbonitrile,
4-{3-[(R)-1-(2-Phenoxy-acetyl)-piperidin-2-yl]-[1,2,4]oxadiazol-5-yl}-1,2-dihydro-indazol-3-one,
1-{(R)-2-[5-(2-Amino-pyridin-4-yl)-[1,2,4]oxadiazol-3-yl]-piperidin-1-yl}-2-phenoxy-ethanone,
1-{(R)-2-[5-(6-Hydroxy-pyrimidin-4-yl)-[1,2,4]oxadiazol-3-yl]-piperidin-1-yl}-2-phenoxy-ethanone,
4-(3-{3-[(R)-1-(2-Phenoxy-acetyl)-piperidin-2-yl]-[1,2,4]oxadiazol-5-yl}-phenyl)-2,4-dihydro-[1,2,4]triazol-3-one,
1-(3-{3-[(R)-1-(2-Phenoxy-acetyl)-piperidin-2-yl]-[1,2,4]oxadiazol-5-yl}-phenyl)-imidazolidine-2,4-dione,
1-((R)-2-{5-[3-(1,1-Dioxo-1λ6-isothiazolidin-2-yl)-phenyl]-[1,2,4]oxadiazol-3-yl}-piperidin-1-yl)-2-phenoxy-ethanone,
1-(3-{3-[(R)-1-(2-Phenoxy-acetyl)-piperidin-2-yl]-[1,2,4]oxadiazol-5-yl}-phenyl)-pyrrolidin-2-one,
1-(3-{3-[(R)-1-(2-Phenoxy-acetyl)-piperidin-2-yl]-[1,2,4]oxadiazol-5-yl}-phenyl)-1,3-dihydro-imidazol-2-one,
3-(3-{3-[(R)-1-(2-Phenoxy-acetyl)-piperidin-2-yl]-[1,2,4]oxadiazol-5-yl}-phenyl)-imidazolidine-2,4-dione,
1-{(R)-2-[5-(1-Methyl-1H-pyrazol-3-yl)-[1,2,4]oxadiazol-3-yl]-piperidin-1-yl}-2-phenoxy-ethanone,
2-Phenoxy-1-{(R)-2-[5-(1H-pyrazol-3-yl)-[1,2,4]oxadiazol-3-yl]-piperidin-1-yl}-ethanone,
1-{(R)-2-[5-(5-Methyl-isoxazol-3-yl)-[1,2,4]oxadiazol-3-yl]-piperidin-1-yl}-2-phenoxy-ethanone,
1-{(R)-2-[5-(2,5-Dimethyl-2H-pyrazol-3-yl)-[1,2,4]oxadiazol-3-yl]-piperidin-1-yl}-2-phenoxy-ethanone,
1-{(R)-2-[5-(5-Methyl-2H-pyrazol-3-yl)-[1,2,4]oxadiazol-3-yl]-piperidin-1-yl}-2-phenoxy-ethanone, and
1-{(R)-2-[5-(3-Methyl-isoxazol-5-yl)-[1,2,4]oxadiazol-3-yl]-piperidin-1-yl}-2-phenoxy-ethanone,
and pharmaceutically acceptable salts and esters thereof.

36. The compound according to claim 1, selected from the group consisting of 2-Methyl-5-{5-[(R)-1-(2-phenoxy-acetyl)-piperidin-2-yl]-[1,2,4]oxadiazol-3-yl}-3H-pyrimidin-4-one,
1-{(R)-2-[3-(5-Methyl-isoxazol-3-yl)-[1,2,4]oxadiazol-5-yl]-piperidin-1-yl}-2-phenoxy-ethanone,
2-Phenoxy-1-{(R)-2-[3-(1H-pyrazol-3-yl)-[1,2,4]oxadiazol-5-yl]-piperidin-1-yl}-ethanone,
1-{(R)-2-[3-(6-Amino-pyridin-3-yl)-[1,2,4]oxadiazol-5-yl]-piperidin-1-yl}-2-phenoxy-ethanone,
5-{5-[(R)-1-(2-Phenoxy-acetyl)-piperidin-2-yl]-1H-[1,2,4]triazol-3-yl}-1,3-dihydro-indol-2-one,
1-{(R)-2-[5-(2-Amino-pyridin-4-yl)-2H-[1,2,4]triazol-3-yl]-piperidin-1-yl}-2-phenoxy-ethanone,
6-{5-[(R)-1-(2-Phenoxy-acetyl)-piperidin-2-yl]-1H-[1,2,4]triazol-3-yl}-4H-benzo[1,4]oxazin-3-one,
1-{(R)-2-[5-(6-Amino-pyridin-3-yl)-2H-[1,2,4]triazol-3-yl]-piperidin-1-yl}-2-phenoxy-ethanone,
1-{(R)-2-[5-(1H-Benzoimidazol-5-yl)-2H-[1,2,4]triazol-3-yl]-piperidin-1-yl}-2-phenoxy-ethanone,
N-(2-Fluoro-5-{5-[(R)-1-(2-phenoxy-acetyl)-piperidin-2-yl]-1H-[1,2,4]triazol-3-yl}-phenyl)-acetamide, and
1-{(R)-2-[5-(2-Hydroxy-pyridin-4-yl)-[1,2,4]oxadiazol-3-yl]-piperidin-1-yl}-2-phenoxy-ethanone, and pharmaceutically acceptable salts and esters thereof.

37. A process for the manufacture of a compound according to claim 1, comprising the step of reacting a compound of formula (II)

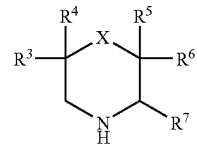

with a compound of formula (III)

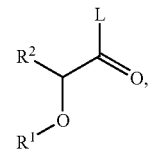

wherein $R^1$, $R^2$, $R^3$, $R^4$, $R^5$, $R^6$, $R^7$, and X are as defined in claim 1 and L is halogen.

38. A pharmaceutical composition, comprising a therapeutically effective amount of a compound according to claim 1 and a pharmaceutically acceptable carrier and/or adjuvant.

* * * * *

UNITED STATES PATENT AND TRADEMARK OFFICE
CERTIFICATE OF CORRECTION

PATENT NO.        : 7,645,776 B2
APPLICATION NO.   : 11/605904
DATED             : January 12, 2010
INVENTOR(S)       : Jean Ackermann It is certified that error appears in the above-identified patent and that said Letters Patent is hereby corrected as shown below:

In Column 115, Claim 15, Line 27, before the word -- heteroaryl -- insert -- phenyl or a --

Signed and Sealed this

Twenty-fifth Day of May, 2010

David J. Kappos
*Director of the United States Patent and Trademark Office*